United States Patent
Cai et al.

(10) Patent No.: US 7,618,975 B2
(45) Date of Patent: Nov. 17, 2009

(54) 4-ARYLAMINO-QUINAZOLINES AND ANALOGS AS ACTIVATORS OF CASPASES AND INDUCERS OF APOPTOSIS AND THE USE THEREOF

(75) Inventors: Sui Xiong Cai, San Diego, CA (US); Nilantha Sudath Sirisoma, San Diego, CA (US); Azra Pervin, Escondido, CA (US); John A. Drewe, Carlsbad, CA (US); Shailaja Kasibhatla, San Diego, CA (US); Songchun Jiang, San Diego, CA (US); Hong Zhang, San Diego, CA (US); Chris Pleiman, Holladay, UT (US)

(73) Assignees: Myriad Pharmaceuticals, Inc., Salt Lake City, UT (US); Cytovia, Inc., San Diego, CA (US)

( * ) Notice: Subject to any disclaimer, the term of this patent is extended or adjusted under 35 U.S.C. 154(b) by 865 days.

(21) Appl. No.: 10/885,903

(22) Filed: Jul. 6, 2004

(65) Prior Publication Data

US 2005/0137213 A1    Jun. 23, 2005

Related U.S. Application Data

(60) Provisional application No. 60/484,325, filed on Jul. 3, 2003, provisional application No. 60/493,006, filed on Aug. 7, 2003, provisional application No. 60/557,556, filed on Mar. 29, 2004, provisional application No. 60/571,288, filed on May 14, 2004.

(51) Int. Cl.
*A01N 43/90* (2006.01)
*A01N 43/54* (2006.01)
*A61K 31/519* (2006.01)
*A61K 31/517* (2006.01)
*C07D 413/00* (2006.01)
*C07D 473/00* (2006.01)
*C07D 401/00* (2006.01)
*C07D 403/00* (2006.01)
*C07D 417/00* (2006.01)
*C07D 419/00* (2006.01)
*C07D 239/72* (2006.01)

(52) U.S. Cl. .............. 514/262.1; 514/264.11; 514/266.4; 544/119; 544/264; 544/284; 544/293

(58) Field of Classification Search .......... None
See application file for complete search history.

(56) References Cited

U.S. PATENT DOCUMENTS

| | | |
|---|---|---|
| 2,883,382 A | 4/1959 | Elslager et al. |
| 3,031,450 A | 4/1962 | Fischer et al. |
| 3,213,090 A | 10/1965 | Roch |
| 3,502,681 A | 3/1970 | Allais et al. |
| 3,632,761 A | 1/1972 | Graham et al. |
| 3,769,410 A | 10/1973 | Bertrand |
| 3,971,783 A | 7/1976 | Barnish et al. |
| 4,025,629 A | 5/1977 | Coverdale |
| 4,322,420 A | 3/1982 | Kobayashi et al. |
| 4,421,920 A | 12/1983 | Baudouin et al. |
| 4,435,003 A | 3/1984 | Fletcher |
| 4,464,375 A | 8/1984 | Kobayashi et al. |
| 4,478,833 A | 10/1984 | Roch et al. |
| 4,480,096 A | 10/1984 | Fletcher |
| 4,510,307 A | 4/1985 | Hidaka et al. |
| 4,675,047 A | 6/1987 | Serban et al. |
| 4,714,698 A | 12/1987 | Roch et al. |
| 5,064,833 A | 11/1991 | Ife et al. |
| 5,114,939 A | 5/1992 | Dreikorn et al. |
| 5,145,843 A | 9/1992 | Arnold et al. |
| 5,187,168 A | 2/1993 | Primeau et al. |
| 5,223,505 A | 6/1993 | Hargreaves et al. |
| 5,236,925 A | 8/1993 | Primeau et al. |
| 5,240,940 A | 8/1993 | Arnold et al. |
| 5,256,781 A | 10/1993 | Primeau et al. |
| 5,270,466 A | 12/1993 | Haley |
| 5,276,148 A | 1/1994 | Siegel et al. |
| 5,294,622 A | 3/1994 | Dreikorn et al. |
| 5,330,989 A | 7/1994 | Soll et al. |
| 5,373,011 A | 12/1994 | Haley |
| 5,409,930 A | 4/1995 | Spada et al. |

(Continued)

FOREIGN PATENT DOCUMENTS

DE    1151806    7/1963

(Continued)

OTHER PUBLICATIONS

Dass, et. al.; 1952; Journal of Scientific and Industrial Research; 11B; 461-3.*

(Continued)

*Primary Examiner*—James O Wilson
*Assistant Examiner*—Jeffrey H Murray
(74) *Attorney, Agent, or Firm*—Kelly A. Echols; Herbert L. Ley, III; MPI IP Group

(57) ABSTRACT

Disclosed are 4-arylamino-quinazolines and analogs thereof effective as activators of caspases and inducers of apoptosis. The compounds of this invention are useful in the treatment of a variety of clinical conditions in which uncontrolled growth and spread of abnormal cells occurs.

48 Claims, 3 Drawing Sheets

U.S. PATENT DOCUMENTS

| | | |
|---|---|---|
| 5,436,233 A | 7/1995 | Lee et al. |
| 5,464,781 A | 11/1995 | Armitage et al. |
| 5,478,845 A | 12/1995 | Hansen et al. |
| 5,480,883 A | 1/1996 | Spada et al. |
| 5,565,472 A | 10/1996 | Hamanaka |
| 5,604,251 A | 2/1997 | Heitsch et al. |
| 5,618,814 A | 4/1997 | Heckel et al. |
| 5,618,829 A | 4/1997 | Takayanagi et al. |
| 5,646,153 A | 7/1997 | Spada et al. |
| 5,654,298 A | 8/1997 | Mills et al. |
| 5,654,307 A | 8/1997 | Bridges et al. |
| 5,656,643 A | 8/1997 | Spada et al. |
| 5,707,989 A | 1/1998 | Himmelsbach et al. |
| 5,710,158 A | 1/1998 | Myers et al. |
| 5,714,493 A | 2/1998 | Myers et al. |
| 5,721,237 A | 2/1998 | Myers et al. |
| 5,739,127 A | 4/1998 | Schohe-Loop et al. |
| 5,747,486 A | 5/1998 | Sohda et al. |
| 5,747,498 A | 5/1998 | Schnur et al. |
| 5,760,230 A | 6/1998 | Schohe-Loop et al. |
| 5,795,889 A | 8/1998 | Spada et al. |
| 5,874,438 A | 2/1999 | Schohe-Loop et al. |
| RE36,256 E | 7/1999 | Spada et al. |
| 5,948,819 A | 9/1999 | Ohtsuka et al. |
| 5,952,346 A | 9/1999 | Heitsch et al. |
| 5,965,740 A | 10/1999 | Kai et al. |
| 6,002,008 A | 12/1999 | Wissner et al. |
| 6,057,320 A | 5/2000 | Spada et al. |
| 6,080,747 A | 6/2000 | Uckun et al. |
| 6,080,748 A | 6/2000 | Uckun et al. |
| 6,084,095 A | 7/2000 | Bridges et al. |
| 6,124,330 A | 9/2000 | Venet et al. |
| 6,127,374 A | 10/2000 | Bridges |
| 6,136,837 A | 10/2000 | Kai et al. |
| 6,177,433 B1 | 1/2001 | Uckun et al. |
| 6,184,226 B1 | 2/2001 | Chakavarty et al. |
| 6,204,267 B1 | 3/2001 | Tang et al. |
| 6,232,312 B1 | 5/2001 | Pamukcu et al. |
| 6,242,196 B1 | 6/2001 | Spiegelman et al. |
| 6,251,912 B1 | 6/2001 | Wissner et al. |
| 6,265,410 B1 | 7/2001 | Bridges et al. |
| 6,265,425 B1 | 7/2001 | De Porre et al. |
| 6,277,989 B1 | 8/2001 | Chakavarty et al. |
| 6,284,764 B1 | 9/2001 | Kath et al. |
| 6,297,258 B1 | 10/2001 | Wissner et al. |
| 6,313,129 B1 | 11/2001 | Uckun et al. |
| 6,313,130 B1 | 11/2001 | Uckun et al. |
| 6,313,150 B1 | 11/2001 | Ohtsuka et al. |
| 6,316,454 B1 | 11/2001 | Uckun et al. |
| 6,326,373 B1 | 12/2001 | Uckun et al. |
| 6,329,371 B1 | 12/2001 | Kai et al. |
| 6,344,459 B1 | 2/2002 | Bridges et al. |
| RE37,650 E | 4/2002 | Spada et al. |
| 6,384,051 B1 | 5/2002 | Frost et al. |
| 6,391,874 B1 | 5/2002 | Cockerill et al. |
| 6,432,979 B1 | 8/2002 | Frost et al. |
| 6,452,005 B1 | 9/2002 | Uckun et al. |
| 6,455,534 B2 | 9/2002 | Bridges et al. |
| 6,469,013 B2 | 10/2002 | Uckun et al. |
| 6,476,031 B1 | 11/2002 | Chakravarty et al. |
| 6,476,040 B1 | 11/2002 | Lehner et al. |
| 6,486,187 B1 | 11/2002 | Venet et al. |
| 6,492,520 B1 | 12/2002 | Chen |
| 6,495,556 B2 | 12/2002 | Uckun et al. |
| 6,518,283 B1 | 2/2003 | Langham et al. |
| 6,521,620 B1 | 2/2003 | Bridges et al. |
| 6,541,481 B2 | 4/2003 | Kath et al. |
| 6,552,027 B2 | 4/2003 | Uckun et al. |
| 6,552,055 B1 | 4/2003 | Spiegelman et al. |
| 6,562,319 B2 | 5/2003 | Mishani et al. |
| 6,562,818 B1 | 5/2003 | Bridges |
| 6,602,863 B1 | 8/2003 | Bridges et al. |
| 6,617,329 B2 | 9/2003 | Himmelsbach et al. |
| 6,627,634 B2 | 9/2003 | Himmelsbach et al. |
| 6,635,651 B2 | 10/2003 | Uckun |
| 6,635,655 B1 | 10/2003 | Jayyosi et al. |
| 6,645,969 B1 | 11/2003 | Myers et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,664,247 B2 | 12/2003 | Bebbington et al. |
| 6,713,484 B2 | 3/2004 | Bridges et al. |
| 6,727,251 B2 | 4/2004 | Bebbington et al. |
| 6,740,651 B2 | 5/2004 | Himmelsbach et al. |
| 6,794,389 B2 | 9/2004 | Okano et al. |
| 6,828,320 B2 | 12/2004 | Cockerill et al. |
| 6,833,375 B2 | 12/2004 | Venet et al. |
| 6,864,255 B2 | 3/2005 | Geuns-Meyer et al. |
| 6,890,924 B2 | 5/2005 | Kath et al. |
| 2001/0014679 A1 | 8/2001 | Tang et al. |
| 2002/0048271 A1 | 4/2002 | Coffey et al. |
| 2002/0082270 A1 | 6/2002 | Himmelsbach et al. |
| 2002/0147198 A1 | 10/2002 | Chen et al. |
| 2002/0161010 A1 | 10/2002 | Chakravarty et al. |
| 2002/0165243 A1 | 11/2002 | Uckun et al. |
| 2002/0169180 A1 | 11/2002 | Himmelsbach et al. |
| 2002/0177601 A1 | 11/2002 | Himmelsbach et al. |
| 2003/0055068 A1 | 3/2003 | Bebbington et al. |
| 2003/0069248 A1 | 4/2003 | Chakravarty et al. |
| 2003/0087908 A1 | 5/2003 | Geuns-Meyer et al. |
| 2003/0087931 A1 | 5/2003 | Mailliet et al. |
| 2003/0105090 A1 | 6/2003 | Bebbington et al. |
| 2003/0134836 A1 | 7/2003 | Elbaum et al. |
| 2003/0144178 A1 | 7/2003 | Uckun |
| 2003/0144330 A1 | 7/2003 | Spiegelman et al. |
| 2003/0144506 A1 | 7/2003 | Brown |
| 2003/0149045 A1 | 8/2003 | Fatih |
| 2003/0149062 A1 | 8/2003 | Jung et al. |
| 2003/0162799 A1 | 8/2003 | Langham et al. |
| 2003/0165873 A1 | 9/2003 | Come et al. |
| 2003/0186995 A1 | 10/2003 | Kath et al. |
| 2003/0195230 A1 | 10/2003 | Chen et al. |
| 2003/0203922 A1 | 10/2003 | Patel et al. |
| 2003/0220336 A1 | 11/2003 | Jung et al. |
| 2003/0225089 A1 | 12/2003 | Jung et al. |
| 2003/0229051 A1 | 12/2003 | Bridges et al. |
| 2004/0014774 A1 | 1/2004 | Myers et al. |
| 2004/0034044 A1 | 2/2004 | Okano et al. |
| 2004/0034045 A1 | 2/2004 | Uckun |
| 2004/0038856 A1 | 2/2004 | Chakravarty et al. |
| 2004/0043388 A1 | 3/2004 | Come et al. |

FOREIGN PATENT DOCUMENTS

| | | |
|---|---|---|
| DE | 4132763 A1 | 4/1993 |
| DE | 19801438 A1 | 7/1999 |
| DE | 10040527 | 2/2002 |
| DE | 20204129 U1 | 8/2002 |
| FR | 1543405 | 10/1968 |
| FR | 1543448 | 10/1968 |
| FR | 1557928 | 2/1969 |
| FR | 2047882 | 3/1973 |
| FR | 2229413 A1 | 12/1974 |
| GB | 807826 | 1/1959 |
| GB | 971166 | 9/1964 |
| GB | 1195491 | 6/1970 |
| GB | 2033894 | 5/1980 |
| GB | 2052481 | 1/1981 |
| GB | 2230527 * | 9/1990 |
| GB | 2295387 A1 | 5/1996 |
| JP | 37007238 | 7/1962 |
| JP | 56020577 | 2/1981 |
| JP | 08003144 A2 | 1/1996 |
| JP | 09301933 | 11/1997 |

| | | |
|---|---|---|
| JP | 2003012631 | 1/2003 |
| WO | WO 8905297 A1 | 6/1989 |
| WO | WO 9012790 A1 | 11/1990 |
| WO | WO 9205158 A1 | 4/1992 |
| WO | WO 9214714 A1 | 9/1992 |
| WO | WO 9214716 A1 | 9/1992 |
| WO | WO 9220642 A1 | 11/1992 |
| WO | WO 9304048 A1 | 3/1993 |
| WO | WO 9308170 A1 | 4/1993 |
| WO | WO 9313097 A1 | 7/1993 |
| WO | WO 9313776 A1 | 7/1993 |
| WO | WO 9315058 A1 | 8/1993 |
| WO | WO 9317682 A1 | 9/1993 |
| WO | WO 9408975 A1 | 4/1994 |
| WO | WO 9414763 A1 | 7/1994 |
| WO | WO 9427994 A1 | 12/1994 |
| WO | WO 9515758 A1 | 6/1995 |
| WO | WO 9519774 A1 | 7/1995 |
| WO | WO 9527693 A1 | 10/1995 |
| WO | WO 9607657 A1 | 3/1996 |
| WO | WO 9609294 A1 | 3/1996 |
| WO | WO 9614319 A1 | 5/1996 |
| WO | WO 9630347 A1 | 10/1996 |
| WO | WO 9639145 A1 | 12/1996 |
| WO | WO 9712863 A1 | 4/1997 |
| WO | WO 9720820 A1 | 6/1997 |
| WO | WO 9720821 A1 | 6/1997 |
| WO | WO 9720822 A1 | 6/1997 |
| WO | WO 9720823 A2 | 6/1997 |
| WO | WO 9724328 A1 | 7/1997 |
| WO | WO 9728133 A1 | 8/1997 |
| WO | WO 9738963 A1 | 10/1997 |
| WO | WO 9749704 A1 | 12/1997 |
| WO | WO 9802434 A1 | 1/1998 |
| WO | WO 9805661 A1 | 2/1998 |
| WO | WO 9825598 A2 | 6/1998 |
| WO | WO 9843960 A1 | 10/1998 |
| WO | WO 9850370 A1 | 11/1998 |
| WO | WO 9906378 A1 | 2/1999 |
| WO | WO 9909016 A1 | 2/1999 |
| WO | WO 9909986 A1 | 3/1999 |
| WO | WO 9932098 A2 | 7/1999 |
| WO | WO 9961428 A1 | 12/1999 |
| WO | WO 0000202 A1 | 1/2000 |
| WO | WO 0010981 A1 | 3/2000 |
| WO | WO 0012497 A2 | 3/2000 |
| WO | WO 0018740 A1 | 4/2000 |
| WO | WO 0027819 A2 | 5/2000 |
| WO | WO 0032175 A2 | 6/2000 |
| WO | WO 0044728 A1 | 8/2000 |
| WO | WO 0051587 A2 | 9/2000 |
| WO | WO 0051991 A1 | 9/2000 |
| WO | WO 0055141 A1 | 9/2000 |
| WO | WO 0064888 A1 | 11/2000 |
| WO | WO 0073260 A1 | 12/2000 |
| WO | WO 0078735 A1 | 12/2000 |
| WO | WO 0112227 A1 | 2/2001 |
| WO | WO 0121594 A1 | 3/2001 |
| WO | WO 0121595 A1 | 3/2001 |
| WO | WO 0121596 A1 | 3/2001 |
| WO | WO 0125218 A1 | 4/2001 |
| WO | WO 0145641 A2 | 6/2001 |
| WO | WO 0168186 A2 | 9/2001 |
| WO | WO 0172710 A1 | 10/2001 |
| WO | WO 0177104 A1 | 10/2001 |
| WO | WO 0194341 A1 | 12/2001 |
| WO | WO 0198277 A2 | 12/2001 |
| WO | WO 0218370 A1 | 3/2002 |
| WO | WO 0218372 A1 | 3/2002 |
| WO | WO 0218376 A1 | 3/2002 |
| WO | WO 0224666 A2 | 3/2002 |
| WO | WO 0224667 A1 | 3/2002 |
| WO | WO 0230927 A1 | 4/2002 |
| WO | WO 0232872 A1 | 4/2002 |
| WO | WO 0236577 A1 | 5/2002 |
| WO | WO-02/47690 | 6/2002 |
| WO | WO 0243735 A1 | 6/2002 |
| WO | WO 02055501 A2 | 7/2002 |
| WO | WO 02059112 A2 | 8/2002 |
| WO | WO 02066461 A1 | 8/2002 |
| WO | WO 02068406 A2 | 9/2002 |
| WO | WO 02068415 A1 | 9/2002 |
| WO | WO 02073235 A2 | 9/2002 |
| WO | WO 02074341 A1 | 9/2002 |
| WO | WO 02076975 A1 | 10/2002 |
| WO | WO 02083654 A1 | 10/2002 |
| WO | WO 03005026 A2 | 1/2003 |
| WO | WO 03028641 A2 | 4/2003 |
| WO | WO 03040108 A1 | 5/2003 |
| WO | WO 03040109 A2 | 5/2003 |
| WO | WO 03045395 A1 | 6/2003 |
| WO | WO 03045939 A1 | 6/2003 |
| WO | WO 03066060 A2 | 8/2003 |
| WO | WO 03066602 A1 | 8/2003 |
| WO | WO 03082290 A1 | 10/2003 |
| WO | WO 03084503 A1 | 10/2003 |
| WO | WO 03084539 A2 | 10/2003 |
| WO | WO 03089439 A1 | 10/2003 |
| WO | WO 03091224 A1 | 11/2003 |
| WO | WO 03097615 A1 | 11/2003 |
| WO | WO 2004007457 A2 | 1/2004 |
| WO | WO 2004007481 A2 | 1/2004 |
| WO | WO 2004035543 A1 | 4/2004 |
| WO | WO-2004/078114 | 9/2004 |

OTHER PUBLICATIONS

Vippagunta et. al. Advanced Drug Delivery Reviews 48 (2001) 3-26.*
Dorwald F. A. Side Reactions in Organic Synthesis, 2005, Wiley: VCH, Weinheim p. IX of Preface.*
Doleschall, et. al., Tetrahedron (1968), 24(16), 5529-45.*
Abramovitch et al., "Direct acylamination of quinoline, isoquinoline, benzimidazole, pyridazine, and pyrimidine 1-oxides. Novel 1, 5-sigmatropic shift", Journal of Organic Chemistry, 1975, 40(1): 41-50.
Allais et al., "Analgesic compounds with no narcotic activity. Study of new 4- (2' -alkoxycarbonyl phenylamino) quinolines and related molecules", Chimica Therapeutica, 1973, 8(2):154-168.
Almog et al., "Mesomerism in N, N-dialkyl-N-(heteroaryl) amines", Tetrahedron, 1974, 30(4):549-552.
Anwar et al., "Some reactions of 4-cholorquinazoline, 6-nitro- and 6-amino- 4 (3H)—quinazolones", Revue Roumaine de Chimie, 1981, 26(11-12):1469-1478.
Apelt et al., "Development of a New Class of Nonimidazole Histmine H3 Receptor Ligands with Combined Inhibitory Histamine N-Methyltransferase Activity", Journal of Medicinal Chemistry, 2002, 45(5):1128-1141.
Assefa et al., "3D-QSAR and docking studies on 4-anilinoquinazoline and 4-anilinoquinoline epidermal growth factor receptor (EGFR) tyrosine kinase inhibitors", Journal of Computer-Aided Molecular Design, 2003, 17(8):475-493.
Bala et al., "Studies on the structure of 2-phenylquinoline-3-carboxylic acid derivatives", Zeszyty Naukowe Uniwersytetu Jagiellonskiego, Prace Chemiczne, 1976, 21:179-189.
Barluenga et al., "Reaction of 3-amlno-2-alkenimines with alkali metals: unexpected synthesis of substituted 4- (arylamino) quinolines", Journal of Organic Chemistry, 1989, 54(11):2596-2598.
Berlot et al., "Aminoquinolines. XI. Decomposition of tertiary 4-aminoquinolines and of related amines by hydrobromic acid in aqueous solution. Influence of the nature of the ring and of the hydrocarbon chain", Bulletin de la Societe Chimique de France, 1973, 11 Pt. 2:3175-3178.
Bethegnies et al., "7-Chloro (phenylthio)-4-phenylaminoquinolines. Study on the anti-inflammatory and analgesic activities", Farmaco, Edizione Scientifica, 1986, 41(6):471-477.

Boschelli et al., "Synthesis and Src kinase inhibitory activity of a series of 4-phenylamino-3-quinolinecarbonitriles", Journal of Medicinal Chemistry, 2001, 44(5):822-833.

Bouey-Bencteux et al., "Synthesis and antiproliferative properties of 4-aminoquinazoline derivatives as inhibitors of EGF receptor-associated tyrosine kinase activity", Anti-Cancer Drug Design, 1998, 13(8):893-922.

Bridges et al., "Tyrosine kinase inhibitors: unusually steep structure-activity relationship for analogs of 4- (3-bromoanilino)-6, 7-dimethoxyquinazoline (PD 153035), a potent inhibitor of the epidermal growth factor receptor", Journal of Medicinal Chemistry, 1996, 39(1):267-276.

Denny, William A., "The 4-anilinoquinazoline class of inhibitors of the erbB family of receptor tyrosine kinases", Farmaco, 2001, 56(1-2):51-56.

Desai et al., "Quinoline derivatives as antitubercular/antibacterial agents", Indian Journal of Chemistry, Section B: Organic Chemistry Including Medicinal Chemistry, 1996, 35B(8):871-873.

Doleschall et al., "4H-3, 1-Benzoxazin-4-ones. VII. Water elimination reactions of N-(2-ureidobenzoyl) anthranilic acids", Tetrahedron, 1968, 24(16):5529-5545.

Dymek et al., "Additional syntheses and transformations of compounds of the 2, 4-diarylaminoquinazoline type. III", Ann. Univ. Mariae Curie-Sklodowska, Lublin-Polonia Sect. AA, 1956, volume date 1954, 9:45-52.

Dymek et al., "Reactions of acetamide with aniline and phenyl isothiocyanate", Ann. Univ. Mariae Curie-Sklodowska, Lublin-Poloina Sect. AA 1956, volume date 1954, 9:35-43.

Elslager et al., "Amodiaquine N-oxides and other 7-chloro-4-aminoquinoline N-oxides", Journal of Heterocyclic Chemistry, 1964, 1(1):6-12.

Elslager et al., "Antifilarial agents. I. Effects of 4[(7-chloro-4-quinolyl)amino]-α-(mono-and dialkylamino)-o-cresols and related compounds against *Litomosoides camii* in gerbils", Journal of Medicinal Chemistry, 1969, 12(5):965-969.

Fusco et al., "Reactions of α-arylazo-α-cholroacetic acid esters with cyclic tertiary bases", Gazzetta Chimica Italiana, 1968, 98(5):511-534.

Galanakis et al., "Synthesis and Quantitative Structure-Activity Relationship of Dequalinim Analogs as K+ Channel Blockers: Investigations on the Role of the Substituent at Position 4 of the Quinoline Ring", Journal of Medicinal Chemistry, 1995, 38(18):3536-3546.

Gershuns et al., "Interaction of 2- (2' -benzimidazolyl) quinoline derivatives with Cu+ ions", Ukrainskii Khimicheskii Zhurnal (Russian Edition), 1971, 37(3):263-265.

Gfesser et al., "Synthesis and structure-activity relationships of 5-heteroatom-substituted pyridopyrimidines as adenosine kinase inhibitors", European Journal of Medicinal Chemistry, 2003, 38(3):245-252.

Gineinah et al., "Study on the synthesis of some new 1, 4-dihydro-4-oxoquinazoline derivatives", Zhonghua Yaoxue Zazhi, 1993, 45(1):7-14.

Girgis et al., "Phosphorus pentoxide in organic synthesis 25. New one-step synthesis of 4-aminoquinazolines. Comparison between mass spectra of 4-aminoquinazolines and 6-aminopurines", Chemica Scripta, 1986, 26(4):617-621.

Goossens et al., "DNA Interaction of the Tyrosine Protein Kinase Inhibitor PD153035 and Its N-Methyl Analogue", Biochemistry, 2001, 40(15):4663-4671.

Hamana et al., "Preparation of 2- and 4-substituted quinolines from 1-(2-quinolyl)—and 1- (4-quinolyl) pyridinium salts", Yakugaku Zasshi, 1964, 84:42-47.

Hassan et al., "Determination of glafenine in dosage forms and serum by thin-layer densitometry and high performance liquid chromatography", Journal of Pharmaceutical and Biomedical Analysis, 1997, 16(2):215-221.

Hidaka et al., "Selective inhibitors of three forms of cyclic nucleotide phosphodiesterase—basic and potential clinical applications", Advances in Cyclic Nucleotide and Protein Phosphorylation Research, 1984, 16:245-259.

Himbert et al., "Aminoethynyl metalations. 11. Reaction of silylated and stannylated ynamines with carbodiimides", Liebigs Annalen der Chemie, 1983, (7):1185-1193.

Himbert et al., "Aminoethynyl metalation. Part 3. 3-aminopropiolimidic acid derivatives-(aminoethynyl) stannylation of isocyanates, isothiocyanates, and carbodiimides", Tetrahedron Letters, 1978, (22):1951-1954.

Himbert et al., "Aminoethynyl metalations. 13. Synthesis and reactions of 3-aminopropiolamidines", Liebigs Annalen der Chemie, 1984, (1):85-97.

Hutchings et al., "Unusually high probability of second harmonic generation by some crystalline organic aldehydes", MCLC Section B: Nonlinear Optics, 1994, 7(1-2):157-166.

Ife et al., "Reversible Inhibitors of the Gastric (H+/K+)-ATPase. 5. Substituted 2, 4-Diaminoquinazolines and Thienopyrimidines", Journal of Medicinal Chemistry, 1995, 38(14):2763-2773.

Iida et al., "Fluorescence of 2, 4, 6, 8-substituted pyrimido [5, 4d] pyrimidines", Kogyo Kagaku Zasshi, 1967, 70(12):2308-2312.

Johannsen et al., "Reaction of 4-quinazolinamines with organolithium reagents", Chemica Scripta, 1987, 27(2):277-281.

Kappe et al., "Rearrangements of heterocycles. VIII. Mesoionic six-membered-ring heterocycles. XII. Ketenoid rearrangements of mesoionic pyrimidines", Chemische Berichte, 1979, 112(10):3424-3431.

Lee et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities", Journal of Medicinal Chemistry, 1995, 38(18):3547-3557.

Leiter, "Cancer chemotherapy screening data. VII", Cancer Research, 1960, 20(No. 7, Pt. 2):471-684.

Lin et al., "Some physicochemical parameters of 11H-indolo [3,2-c] quinoline", Heterocycles, 1989, 29(12):2353-2359.

McDonald et al., "Conversion of (2-chlorallyl) amines into heterocyclic compounds. I. 2-Methylindoles, 1,5,6,7-tetrahydro-3-methylindol-4-ones, and related heterocycles", Journal of the Chemical Society, Perkin Transactions, 1: Organic and Bio-Organic Chemistry (1972-1999), 1975, (15):1446-1450.

Moreau et al., "Autocorrelation of molecular structures. Application to SAR studies", Nouveau Journal de Chimie, 1980, 4(12):757-764.

Myers et al., "The preparation and SAR of 4- (anilino), 4- (phenoxy), and 4- (thiophenoxy)-quinazolines: inhibitors of p56lck and EGF-R tyrosine kinase activity", Bioorganic Medicinal Chemistry Letters, 1997, 7(4):417-420.

Myers et al., "The synthesis and SAR of new 4-(N-alkyl-N-phenyl) amino-6, 7-dimethoxyquinazolines and 4- (N-alkyl-N-phenyl) aminopyrazolo [3,4,d] pyrimidnes, inhibitors of CSF-1R tyrosine kinase activity", Bioorganic Medicinal Chemistry Letters, 1997, 7(4):421-424.

Rachid et al., "The Combi-Targeting Concept: Chemical Dissection of the Dual Targeting Properties of a Series of "Combi-Triazenes"", Journal of Medicinal Chemistry, 2003, 46(20):4313-4321.

Rewcastle et al., "Tyrosine kinase inhibitors. 5. Synthesis and structure-activity relationships for 4-[ (phenylmethyl) amino]—and 4-(phenylamino) quinazolines as potent adenosine 5'—triphosphate binding site inhibitors of the tyrosine kinase domain of the epidermal growth factor receptor", Journal of Medicinal Chemistry, 1995, 38(18):3482-3487.

Schaumann et al., "New synthesis and reaction behavior of aminoethynyl sulfides", Chemische Berichte, 1983, 116(2):509-513.

Tronchet et al., "C-Glycosyl derivatives. XLII. Synthesis of novel types of C-glycosyl derivatives from acetylenic sugars or their partial synthetic equivalents. Preliminary Communication", Helvetica Chimica Acta, 1981, 64(7):2322-2327.

Warhurst et al., "The chemotherapy of rodent malaria. XXXIII. The activity of chloroquine and related blood schizonticides and of some analogs in drug-induced pigment clumping", Annals of Tropical Medicine Parasitology, 1982, 76(3):257-264.

Wright et al., "Anilinoquinazoline Inhibitors of Fructose 1, 6-Bisphosphatase Bind at a Novel Allosteric Site: Synthesis, In Vitro Characterization, and X-ray Crystallography", Journal of Medicinal Chemistry, 2002, 45(18):3865-3877.

Yum et al., "Synthesis and pharmacological profile of 1-aryl-3-substituted pyrrolo [3,2-c] quinolines", Bioorganic Medicinal Chemistry Letters, 1999, 9(19):2819-2822.

Zankowska-Jasinska et al., "2-Benzhydrylmethyl-4-phenylaminoquinoline salts with dicarboxylic acids", Zeszyty Naukowe Uniwersytetu Jagiellonskiego, Prace Chemiczne, 1976, 21:127-132.

Zieba et al., "Azinyl sufides, part LXIII. 1-Alkyl-4- (arylamino) quinolinium-3-thiolates and 7-alkyl-12H-quino [3,4-b]-1,4-benzothiazinium salts", European Journal of Organic Chemistry, 2000, 16:2947-2953.

Database Beilstein 1992, XP002314667, Database Accession No. 636504.

Database Beilstein 1992, XP002314668, Database Accession No. 329732.

Database Caplus, Chemical Abstracts Services, XP002314666, Database Accession No. 1960:131417.

International Search Report. Mailed Feb. 15, 2005, International Application No. PCT/US2004/021631, Filed Jul. 6, 2004.

Kasibhatla et al., "MPC-6827: A Small-Molecule Inhibitor of Microtubule Formation That Is Not a Substrate for Multidrug Resistance Pumps", Cancer Research, Jun. 15, 2007, 67(12):5865-5871.

Rigby et al., "Preparation of Highly Substituted 4-Aminopyridones via the Reaction of 2-Methylene Dihydrobenzimidazole with Vinyl Isocyanates", Organic Letters, Mar. 14, 2003, 5(7):1151-1153.

* cited by examiner

4-ARYLAMINO-QUINAZOLINES AND ANALOGS AS ACTIVATORS OF CASPASES AND INDUCERS OF APOPTOSIS AND THE USE THEREOF

RELATED U.S. APPLICATIONS

This application claims the benefit of U.S. Provisional Application Ser. No. 60/484,325 filed Jul. 3, 2003, U.S. Provisional Application Ser. No. 60/493,006 filed Aug. 7, 2003, U.S. Provisional Application Ser. No. 60/557,556, filed Mar. 29, 2004, and U.S. Provisional Application Ser. No. 60/571,288, filed May 14, 2004, the contents of each of which are incorporated herein by reference in their entirety.

FIELD OF THE INVENTION

This invention is in the field of medicinal chemistry. In particular, the invention relates to compounds that are activators of caspases and inducers of apoptosis. The invention also relates to the use of these compounds as therapeutically effective anti-cancer agents.

TECHNICAL BACKGROUND

Organisms eliminate unwanted cells by a process variously known as regulated cell death, programmed cell death or apoptosis. Such cell death occurs as a normal aspect of animal development, as well as in tissue homeostasis and aging (Glucksmann, A., *Biol. Rev. Cambridge Philos. Soc.* 26:59-86 (1951); Glucksmann, A., *Archives de Biologie* 76:419-437 (1965); Ellis, et al., *Dev.* 112:591-603 (1991); Vaux, et al., *Cell* 76:777-779 (1994)). Apoptosis regulates cell number, facilitates morphogenesis, removes harmful or otherwise abnormal cells and eliminates cells that have already performed their function. Additionally, apoptosis occurs in response to various physiological stresses, such as hypoxia or ischemia (PCT published application WO96/20721).

There are a number of morphological changes shared by cells experiencing regulated cell death, including plasma and nuclear membrane blebbing, cell shrinkage (condensation of nucleoplasm and cytoplasm), organelle relocalization and compaction, chromatin condensation and production of apoptotic bodies (membrane enclosed particles containing intracellular material) (Orrenius, S., *J. Internal Medicine* 237: 529-536 (1995)).

Apoptosis is achieved through an endogenous mechanism of cellular suicide (Wyllie, A. H., in *Cell Death in Biology and Pathology*, Bowen and Lockshin, eds., Chapman and Hall (1981), pp. 9-34). A cell activates its internally encoded suicide program as a result of either internal or external signals. The suicide program is executed through the activation of a carefully regulated genetic program (Wyllie, et al., *Int. Rev. Cyt.* 68:251 (1980); Ellis, et al., *Ann. Rev. Cell Bio.* 7:663 (1991)). Apoptotic cells and bodies are usually recognized and cleared by neighboring cells or macrophages before lysis. Because of this clearance mechanism, inflammation is not induced despite the clearance of great numbers of cells (Orrenius, S., *J. Internal Medicine* 237:529-536 (1995)).

It has been found that a group of proteases are a key element in apoptosis (see, e.g., Thornberry, *Chemistry and Biology* 5:R97-R103 (1998); Thornberry, *British Med. Bull.* 53:478-490 (1996)). Genetic studies in the nematode *Caenorhabditis elegans* revealed that apoptotic cell death involves at least 14 genes, 2 of which are the pro-apoptotic (death-promoting) ced (for cell death abnormal) genes, ced-3 and ced-4. CED-3 is homologous to interleukin 1 beta-converting enzyme, a cysteine protease, which is now called caspase-1. When these data were ultimately applied to mammals, and upon further extensive investigation, it was found that the mammalian apoptosis system appears to involve a cascade of caspases, or a system that behaves like a cascade of caspases. At present, the caspase family of cysteine proteases comprises 14 different members, and more may be discovered in the future. All known caspases are synthesized as zymogens that require cleavage at an aspartyl residue prior to forming the active enzyme. Thus, caspases are capable of activating other caspases, in the manner of an amplifying cascade.

Apoptosis and caspases are thought to be crucial in the development of cancer (*Apoptosis and Cancer Chemotherapy*, Hickman and Dive, eds., Humana Press (1999)). There is mounting evidence that cancer cells, while containing caspases, lack parts of the molecular machinery that activates the caspase cascade. This makes the cancer cells lose their capacity to undergo cellular suicide and the cells become cancerous. In the case of the apoptosis process, Control points are known to exist that represent points for intervention leading to activation. These control points include the CED-9-BCL-like and CED-3-ICE-like gene family products, which are intrinsic proteins regulating the decision of a cell to survive or die and executing part of the cell death process itself, respectively (see, Schmitt, et al., *Biochem. Cell. Biol.* 75:301-314 (1997)). BCL-like proteins include BCL-xL and BAX-alpha, which appear to function upstream of caspase activation. BCL-xL appears to prevent activation of the apoptotic protease cascade, whereas BAX-alpha accelerates activation of the apoptotic protease cascade.

It has been shown that chemotherapeutic (anti-cancer) drugs can trigger cancer cells to undergo suicide by activating the dormant caspase cascade. This may be a crucial aspect of the mode of action of most, if not all, known anticancer drugs (Los, et al., *Blood* 90:3118-3129 (1997); Friesen, et al., *Nat. Med.* 2:574 (1996)). The mechanism of action of current antineoplastic drugs frequently involves an attack at specific phases of the cell cycle. In brief, the cell cycle refers to the stages through which cells normally progress during their lifetime. Normally, cells exist in a resting phase termed $G_o$. During multiplication, cells progress to a stage in which DNA synthesis occurs, termed S. Later, cell division, or mitosis occurs, in a phase called M. Antineoplastic drugs, such as cytosine arabinoside, hydroxyurea, 6-mercaptopurine, and methotrexate are S phase specific, whereas antineoplastic drugs, such as vincristine, vinblastine, and paclitaxel are M phase specific. M phase specific antineoplastic drugs, such as vinblastine and paclitaxel, are known to affect tubulin polymerization. The ability of cells to appropriately polymerize and depolymerize tubulin is thought to be an important activity for M phase cell division.

Many slow growing tumors, e.g. colon cancers, exist primarily in the $G_o$ phase, whereas rapidly proliferating normal tissues, for example bone marrow, exist primarily in the S or M phase. Thus, a drug like 6-mercaptopurine can cause bone marrow toxicity while remaining ineffective for a slow growing tumor. Further aspects of the chemotherapy of neoplastic diseases are known to those skilled in the art (see, e.g., Hardman, et al., eds., *Goodman and Gilman's The Pharmacological Basis of Therapeutics*, Ninth Edition, McGraw-Hill, New York (1996), pp. 1225-1287). Thus, it is clear that the possibility exists for the activation of the caspase cascade, although the exact mechanisms for doing so are not clear at this point. It is equally clear that insufficient activity of the caspase cascade and consequent apoptotic events are implicated in various types of cancer. The development of caspase cascade activators and inducers of apoptosis is a highly desirable goal in the development of therapeutically effective antineoplastic agents. Moreover, since autoimmune disease and certain degenerative diseases also involve the proliferation of abnormal cells, therapeutic treatment for these diseases could also involve the enhancement of the apoptotic process through the administration of appropriate caspase cascade activators and inducers of apoptosis.

EP520722 discloses derivatives of 4-anilino-quinazolines as inhibitors of the EGFR tyrosine kinase with antitumor activity:

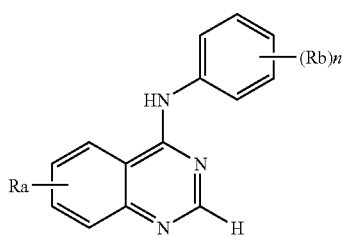

wherein, for example, $R^a$ is hydrogen, trifluoromethyl, or nitro, n is 1; and $R^b$ is halogen, trifluoromethyl or nitro.

EP602851 discloses quinazolines as inhibitors of the EGFR tyrosine kinase:

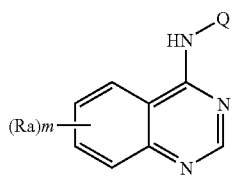

wherein, for example $R^a$ is hydroxy, amino, ureido, or trifluoromethoxy, m is 1, 2 or 3; Q is a 9 or 10-membered bicyclic heterocyclic moiety.

EP635498 discloses 4-anilino-quinazolines as inhibitors of the EGFR tyrosine kinase:

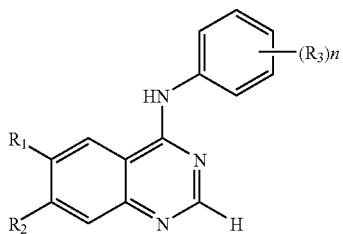

wherein, for example $R_1$ includes hydroxy, amino or $C_{1-4}$ alkoxy, $R_2$ is hydrogen, hydroxy, or halogen, $R_3$ is halogen, n is 1, 2 or 3.

EP635507 discloses tricyclic derivatives as inhibitors of the EGFR tyrosine kinase:

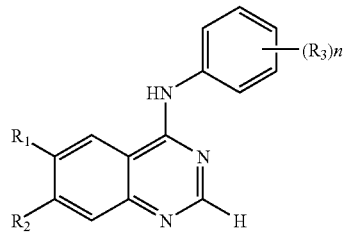

wherein, $R_1$ and $R_2$ together form an optionally substituted 5 or 6 membered ring containing at least one heteroatom; $R_3$ includes hydrogen, hydroxy, or halogen, m is 1, 2 or 3.

WO9609294 discloses substituted heteroaromatic compounds as inhibitors of protein tyrosine kinase:

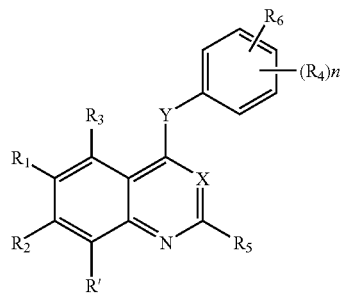

wherein, for example X is N or CH; Y is O, S, or $NR^a$ wherein $R^a$ is H or $C_{1-8}$ alkyl; $R_1$, $R_2$, $R_3$ and $R_{3'}$ includes amino, hydrogen, hydroxy, or halogen; $R_4$ includes amino, hydrogen, hydroxy, or halogen; n is 1, 2 or 3; $R_5$ is selected from the group comprising hydrogen, halogen, trifluoromethyl, $C_{1-4}$ alkyl and $C_{1-4}$ alkoxy; $R_6$ is a group $ZR_7$ wherein Z includes O, S or NH and $R_7$ is an optionally substituted $C_{3-6}$ cycloalkyl, or an optionally substituted 5,6,7,8,9,10-membered carbocyclic or heterocyclic moiety.

WO9713771 discloses substituted heteroaromatic compounds as inhibitors of protein tyrosine kinase:

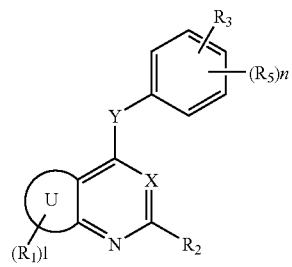

wherein, for example X is N or CH; U represents a fused 5,6,7-membered heterocyclic ring; Y is O, S, or $NR^a$ wherein $R^a$ is H or $C_{1-8}$ alkyl; $R_1$ included 5,6-membered heterocyclic ring, or amino, hydrogen, hydroxy, or halogen; n is 0, 1, 2 or 3. $R_2$ is selected from the group comprising hydrogen, halogen, trifluoromethyl, $C_{1-4}$ alkyl and $C_{1-4}$ alkoxy; $R_3$ is a group $ZR_4$ wherein Z includes O, S or NH and $R_4$ is an optionally substituted $C_{3-6}$ cycloalkyl, or an optionally substituted 5,6,7,8,9,10-membered carbocyclic or heterocyclic moiety. $R_5$ includes hydrogen, hydroxy, or halogen; n is 1, 2 or 3.

WO9802438 discloses bicyclic heteroaromatic compounds as inhibitors of protein tyrosine kinase:

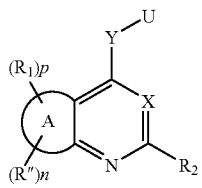

wherein, for example X is N or CH; Y is O, S, or NR$^a$ wherein R$^a$ is H or C$_{1-8}$ alkyl; R" represents a phenyl group or a 5- or 6-membered heterocyclic ring, or amino, hydrogen, hydroxy, or halogen; n is 0 or 1. R$_1$ includes amino, hydrogen, hydroxy, or halogen; p is 0 to 3. R$_2$ is selected from the group comprising hydrogen, halogen, trifluoromethyl, C$_{1-4}$ alkyl and C$_{1-4}$ alkoxy; U represents a 5 to 10-membered mono or bicyclic ring system; A represents a fused 5, 6, or 7-membered heterocyclic ring.

Myers et al. (*Bioorg. Med. Chem. Lett.* 7:421-424 (1997)) reported 4-(N-methyl-N-phenyl)amino-6,7-dimethoxyquinazoline as inhibitor of CSF-1R tyrosine kinase. It was reported that substitutions on the phenyl ring resulted in reduced activity. Replacement of the 6,7-dimethoxy groups by hydrogen resulted in more than 40-fold reduction in potency. Substitution in the 2-position of quinazoline by a Cl or methoxy group resulted in inactive compounds (IC$_{50}$>50 μM).

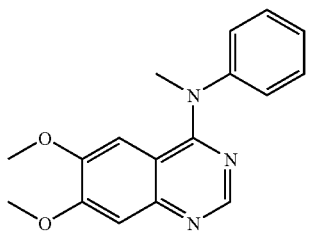

Rewcastle et al. (*J. Med. Chem.* 38:3482-3487 (1995)) reported 4-(phenylamino)-quinazolines as inhibitors of tyrosine kinase of Epidermal Growth Factor Receptor. It was reported that N-methylation of the amino group (R$_1$=Me, R$_2$=R$_3$=R$_4$=H) completely abolished activity (IC$_{50}$>100,000 nM). The 6,7-dimethoxy compound (R$_1$=H, R$_2$=R$_3$=OMe, R$_4$=Br, IC$_{50}$=0.029 nM) was almost 1000-fold more potent than the corresponding non-substituted analog (R$_1$=H, R$_2$=R$_3$=H, R$_4$=Br, IC$_{50}$=27 nM).

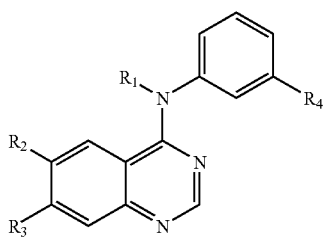

Bridges et al. (*J. Med. Chem.* 39:267-276 (1996)) reported analogs of 4-(3-bromoanilino)-6,7-dimethoxyquinazoline as inhibitors of tyrosine kinase of Epidermal Growth Factor Receptor. It was reported that introduction of a methyl group to the 2-position (R$_1$=Me, R$_2$=3'-Br, R$_3$=H) resulted in at least 400,000-fold loss of potency (IC$_{50}$>10,000 nM) vs the hydrogen analog. Introduction of an amino group to the 2-position (R$_1$=NH$_2$, R$_2$=3'-Br, R$_3$=H) also resulted in over 18,000-fold loss of potency (IC$_{50}$>10,000 nM). Methylation of the anilino nitrogen (R$_3$=Me) led to 6,000-fold drop in activity. The 4'-Br analog (IC$_{50}$=0.96 nM) was almost 40-fold less active than the 3'-Br analog (IC$_{50}$=0.025 nM), and the 2'-Br analog (IC$_{50}$=128 nM) was at least 5,000-fold less active than the 3'-Br analog.

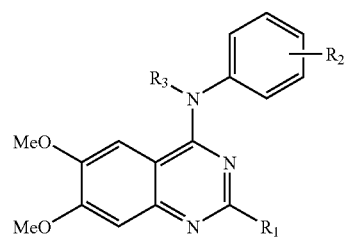

SUMMARY OF THE INVENTION

The present invention is related to the discovery that 4-arylamino-quinazolines and analogs, as represented in Formula I-VIb below, are potent tubulin inhibitors and active in inhibiting topoisomerase, particularly topoisomerase II. They are activators of the caspase cascade leading to the activation of caspase-3 and inducers or promoters of apoptosis. Thus, they are useful in treating or delaying the onset of diseases and disorders that are responsive to the inhibition of tubulin or topoisomerase, or to the induction of apoptosis.

Accordingly, one aspect of the present invention is directed to the use of compounds of the present invention in inhibiting tubulin, in inducing capase activities, particularly caspase-3 activities, in inhibiting topoisomerase I or II, and inducing or promoting apoptosis, by administering the compounds to cells in vitro or in vivo in warm-blood animals, particularly mammals.

Another aspect of the present invention is to provide a method for treating or delaying the onset of diseases and disorders that are responsive to inhibition of tubulin or topoisomerase II, including but not limited to neoplastic diseases (such as cancer), psoriasis, autoimmune diseases, and fungi infection. The method comprises administering to a subject mammal in need of the treatment a therapeutically effective amount of a compound of the present invention.

Many of the compounds as represented by Formula I-VIb below are novel compounds. Therefore, another aspect of the present invention is to provide novel compounds, and to also provide for the use of these novel compounds for treating, preventing or ameliorating neoplasia and cancer.

Yet another aspect of the present invention is to provide a pharmaceutical composition useful for treating disorders responsive to the inhibition of tubulin or topoisomerase II, and the induction of apoptosis, containing an effective amount of a compound of the present invention, preferably in admixture with one or more pharmaceutically acceptable carriers or diluents.

In yet another aspect of the present invention, methods are provided for the preparation of the novel compounds of the present invention.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

Figure 1:
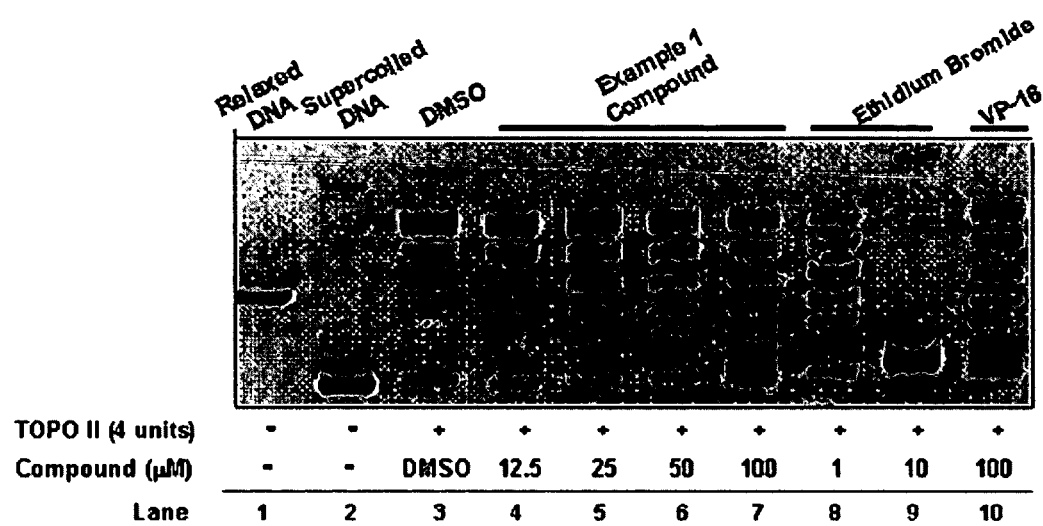
FIG. 1 depicts the results of a Topoisomerase II activity assay testing Example 1 compound.

It has been discovered that compounds of the present invention are potent inhibitors of tubulin. It is also discovered that the compounds can also inhibit topoisomerase activities, such as topoisomerase II-dependent conversion of supercoiled DNA to topoisomers. The compounds are potent and highly efficacious activators of the caspase cascade particularly caspase-3, and inducers of apoptosis. Therefore, the compounds are useful for treating diseases and disorders responsive to induction of apoptosis, inhibition of tubulin and/or inhibition of topoisomerase II.

Thus, the present invention provides a method of inhibiting tubulin in cells in vitro or in warm-blood animals, particularly mammals, more particularly humans. As used herein, the term "inhibiting tubulin" means inhibiting the polymerization (or assembly) of tubulin monomers or promoting depolymerization of microtubules (i.e., tubulin disassembly). Inhibition of tubulin can be assayed, e.g., by the method described in Example 145 below. The present invention also provides a method for inhibiting topoisomerase II in cells in vitro or in warm-blood animals, particularly mammals, more particularly humans. As used herein, the term "inhibiting topoisomerase II" means inhibiting the activities of the enzyme topoisomerase II in topoisomerase II-dependent conversion of supercoiled DNA to topoisomers. Inhibition of topoisomerase II activities can be assayed by, e.g., a method described in Example 151. In addition, the present invention also provides a method of activating caspase, particularly caspase-3 and inducing apoptosis in cells in vitro or in warm-blood animals, particularly mammals, more particularly humans. The term "activating caspase" as used herein means activating or enhancing the enzymatic (protease) activity of a caspase (e.g., caspase-3), which, if occurring inside cells, results in promoted apoptosis or cell death. The ability of a compound in activating caspase, particularly caspase-3, can be assayed in a method as provided in Example 143 below. The term "inducing apoptosis" as used herein means inducing apoptosis in cells so as to cause cell death. The ability of a compound to induce apoptosis can be tested in a method as described in Example 147 below. Also provided are methods for treating or delaying the onset of diseases and disorders responsive to inhibiting tubulin, inhibiting topoisomerase II, activating caspase-3, or inducing apoptosis. Specific examples of such diseases and disorders are provided in details below.

The above various methods of the present invention can be practiced by or comprise treating cells in vitro or a warm-blood animal, particularly mammal, more particularly a human with an effective amount of a compound according to the present invention. As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human a pharmaceutical composition comprising an effective amount of a compound according to the present invention.

Specifically, the methods of the present invention comprise treating cells in vitro or a warm-blood animal, particularly mammal, more particularly a human with an effective amount of a compound according to Formula I:

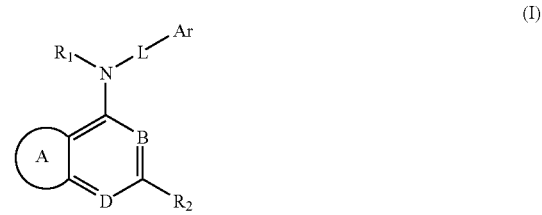

(I)

or pharmaceutically acceptable salts or solvates thereof, wherein:

Ar is aryl or heteroaryl; each of which is optionally substituted by one or more substituents wherein each substituent is independently halo, hydroxy, hydroxy-$C_{1-6}$ alkyl-, $C_{1-6}$ alkyl-C(O)O—, amino, nitro, cyano, $C_{1-6}$ alkyl, $C_{2-4}$ alkenyl, $C_{2-4}$ alkynyl, $C_{1-6}$ acylamino, $C_{1-6}$ acyloxy, $C_{1-6}$ alkoxy, or $C_{1-6}$ alkylthiol-;

$R_1$ is $C_{1-6}$ alkyl, preferably methyl or ethyl, more preferably methyl;

A is an aromatic, heteroaromatic, heterocyclic, or carbocyclic ring; each of which is optionally substituted by one or more substituents wherein each substituent is as defined for Ar;

$R_2$ is H, halo, nitro, cyano, azido, hydroxy, thiol, or a member of the group consisting of: amino, alkoxy, $C_{1-6}$ alkyl, halo-$C_{1-6}$ alkyl, $C_{2-6}$ alkenyl, $C_{2-6}$ alkynyl, hydroxyalkyl, amino-$C_{1-6}$ alkyl, carboxy-$C_{1-6}$ alkyl, nitro, cyano, acylamido, acyloxy, carboxy, carbonylamido, alkylthiol; each of which is optionally substituted by one or more substituents wherein each substituent is as defined for Ar;

L is $(CR_{11}R_{12})_n$ or $NR_{11}CO$ wherein $R_{11}$, and $R_{12}$ independently are hydrogen or alkyl optionally substituted by $R_{1a}$, $R_{1b}$, or $R_{1c}$; wherein $R_{1a}$, $R_{1b}$, and $R_{1c}$ are as defined for Ar;

n is 0, 1 or 2;

B and D are independently nitrogen or $CR_{13}$, wherein $R_{13}$ is hydrogen, halo, nitro, cyano, azido, hydroxy, thiol, or a member of the group consisting of amino, alkoxy, $C_{1-6}$ alkyl, halo-$C_{1-6}$ alkyl, $C_{2-6}$ alkenyl, $C_{2-6}$ alkynyl, hydroxyalkyl, amino-$C_{1-6}$ alkyl, carboxy-$C_{1-6}$ alkyl, nitro, cyano, acylamido, acyloxy, carboxy, carbonylamido, alkylthiol; each of which is optionally substituted by one or more substituents wherein each substituent is as defined for Ar; and with the proviso that at least one of B and D is nitrogen.

Preferred compounds of Formula I include compounds wherein D is nitrogen, and B is $CR_{13}$. Other preferred compounds of Formula I include those having Formula Ia:

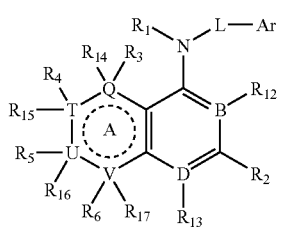

(Ia)

or pharmaceutically acceptable salts or solvates thereof, wherein:

A ring is a 6-membered aryl, heteroaryl or carbocycle;

L is $[C(R_{L1})(R_{L2})]_n$ or $-N(R_{L1})C(O)-$, wherein $R_{L1}$ and $R_{L2}$ independently are H or $C_{1-6}$ alkyl, n is 0, 1 or 2;

$R_1$ is methyl or ethyl;

Ar is aryl or heteroaryl, each of which is optionally substituted by one or more substituents wherein each substituent is independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

$R_2$-$R_6$, and $R_{12}$-$R_{17}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, with the proviso that when A is aryl or heteroaryl, then there are no substituents $R_{14}$-$R_{17}$; and B, D, Q, T, U and V, are independently carbon or nitrogen, wherein at least one of B and D is nitrogen; wherein when B or D is nitrogen, then there is no substituent at the nitrogen; and wherein when A is heteroaryl and Q, T, U or V is nitrogen, then there is no substituent at the nitrogen.

Preferably, when the A ring is aryl or heteroaryl and U is carbon, then $R_5$ is hydrogen or flourine, preferably hydrogen.

Other preferred compounds include compounds wherein ring A is benzo or fused cyclohexyl. Another group of preferred compounds include compounds wherein Ar is phenyl, naphthyl, pyridyl, pyridazyl, pyrimidyl, pyrazyl, quinolyl, isoquinolyl, isoxazolyl, pyrazolyl, imidazolyl, thienyl, furyl or pyrrolyl; each of which is optionally substituted by one or more substituents wherein each substituent is independently halo, hydroxy, hydroxy$C_{1-6}$ alkyl-, $C_{1-6}$ alkyl-C(O)O—, amino, nitro, cyano, $C_1$-$C_6$ alkyl, $C_2$-$C_4$ alkenyl, $C_2$-$C_4$ alkynyl, $C_1$-$C_6$ acylamino, $C_1$-$C_6$ acyloxy, $C_1$-$C_6$ alkoxy, or $C_{1-6}$ alkylthiol-More preferably, Ar is phenyl, pyridyl, pyridazyl, pyrimidyl or pyrazyl, each of which is optionally substituted by one or more substituents wherein each substituent is as defined immediately above.

Another group of preferred compounds of Formula Ia include compounds wherein $R_2$ is H, halo, or a member of the group consisting of $N_3$, $C_{1-4}$ alkoxy, $C_{1-4}$ alkylthiol, hydroxy$C_{1-4}$ alkyl, $C_{1-4}$ alkyl and —N($R^a$)($R^b$) wherein $R^a$ and $R^b$ are independently H, OH ($R^a$ and $R^b$ are not both OH), $C_{2-4}$ hydroxyalkyl, or $C_{1-4}$ alkyl or $R^a$ and $R^b$ together with the nitrogen atom to which they are both linked form a 3, 4, 5 or 6-membered heterocycle; each of the member is optionally substituted by 1-4 substituents wherein each substituent is independently halo, OH, or $C_{1-4}$ alkyl.

In preferred embodiments of the compounds of Formula Ia, one or two of Q, T, U and V are nitrogen, and both B and D are nitrogen.

Other compounds of Formula I for use in the methods of the present invention include those having Formula Ib:

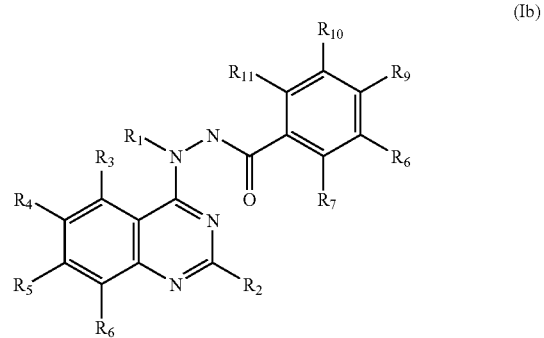

(Ib)

or pharmaceutically acceptable salts or solvates thereof, wherein:

$R_1$ is $C_{1-4}$ alkyl, preferably methyl or ethyl, more preferably methyl;

$R_2$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; wherein optionally two adjacent $R_7$-$R_{11}$ groups may together form a 3, 4, 5 or 6-membered aryl, heteroaryl, carbocycle, or heterocycle.

Preferably, $R_5$ is H or F, more preferably H. Also preferably $R_2$ is $R_2$ is H, halo, or a member of the group consisting of: $N_3$, $C_{1-4}$ alkoxy, $C_{1-4}$ alkylthiol, hydroxy-$C_{1-4}$ alkyl, $C_{1-4}$ alkyl and —N($R^a$)($R^b$) wherein $R^a$ and $R^b$ are independently H, OH ($R^a$ and $R^b$ are not both OH), $C_{2-4}$ hydroxyalkyl, or $C_{1-4}$ alkyl or $R^a$ and $R^b$ together with the nitrogen atom to which they are both linked form a 3, 4, 5 or 6-membered heterocycle (e.g., morpholino); each of the member is optionally substituted by 1-4 substituents wherein each substituent is independently halo, OH, or $C_{1-4}$ alkyl.

Other preferred compounds of Formula I for the methods of the invention include those having Formula Ic:

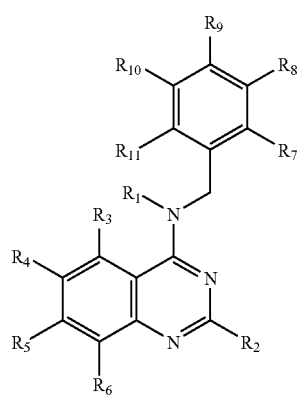

(Ic)

or pharmaceutically acceptable salts or solvates thereof, wherein:

$R_1$ is $C_{1-4}$ alkyl, preferably methyl or ethyl, more preferably methyl;

$R_2$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), $C_{1-6}$ alkyl-C(O)N($R^a$)($R^b$), C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; wherein optionally two adjacent $R_7$-$R_{11}$ groups may together form a 3, 4, 5 or 6-membered aryl, heteroaryl, carbocycle, or heterocycle.

Preferably, $R_5$ is H or F, more preferably H. Also preferably $R_2$ is H, halo, or a member of the group consisting of: $N_3$, $C_{1-4}$ alkoxy, $C_{1-4}$ alkylthiol, hydroxy-$C_{1-4}$ alkyl, $C_{1-4}$ alkyl and —N($R^a$)($R^b$) wherein $R^a$ and $R^b$ are independently H, OH ($R^a$ and $R^b$ are not both OH), $C_{2-4}$ hydroxyalkyl, or $C_{1-4}$ alkyl or $R^a$ and $R^b$ together with the nitrogen atom to which they are both linked form a 3, 4, 5 or 6-membered heterocycle (e.g., morpholino); each of the member is optionally substituted by 1-4 substituents wherein each substituent is independently halo, OH, or $C_{1-4}$ alkyl.

Another group of compounds useful in the various methods of the present invention are those represented by Formula II:

(II)

or pharmaceutically acceptable salts or solvates thereof, wherein:

Ar is as defined in Formula Ia above;

$R_1$ is a $C_{1-3}$ alkyl, preferably methyl or ethyl;

$R_2$-$R_6$, $R_{12}$ and $R_{13}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N $(R^a)(R^b)$, —C(O)N$(R^a)(R^b)$, N$(R^a)(R^b)$—C$_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), C$_{2-6}$ hydroxyalkyl, or C$_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, N$_3$, OH, thiol, nitro, CN, C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyl-O—, C$_{2-6}$ alkynyl-O—, hydroxy-C$_{1-6}$ alkyl, C$_{1-6}$ alkoxy-C$_{1-6}$ alkyl, C$_{1-6}$ acyl, C$_{1-6}$ acyloxy, C$_{1-6}$ alkyl-C(O)O—C$_{1-6}$ alkyl, —C(O)O—C$_{1-6}$ alkyl, C$_{1-6}$ alkyl-C(O)O—C$_{1-6}$ alkyl-, C$_{1-6}$ acylamido, —N$(R^a)(R^b)$, —C$_{1-6}$ alkyl-C(O)N$(R^a)(R^b)$, —C(O)N$(R^a)(R^b)$, N$(R^a)(R^b)$—C$_{1-6}$ alkyl-, wherein $R^a$ and $R^b$ are independently H, OH ($R^a$ and $R^b$ are not both OH), C$_{2-6}$ hydroxyalkyl, or C$_{1-6}$ alkyl or $R^a$ and $R^b$ together with the nitrogen atom to which they are both linked form a 3, 4, 5 or 6-membered heterocycle; preferably, when U is C, R$_5$ is H or F, preferably H; and B, D, Q, T, U and V are independently C or N, wherein at least one of B and D is nitrogen. In some embodiments, at least one of Q, T, U and V is N. In one embodiment, D is N and B is C. In another embodiment, B is N and D is C. In another specific embodiment, both B and D are N. In all embodiments, preferably when B, D, Q, T, U or V is N, there is no substituent at the N.

Other preferred compounds include compounds wherein Ar is phenyl, naphthyl, pyridyl, pyridazyl, pyrimidyl, pyrazyl, quinolyl, isoquinolyl, isoxazolyl, pyrazolyl, imidazolyl, thienyl, furyl or pyrrolyl; each of which is optionally substituted by one or more substituents wherein each substituent is as defined immediately above. More preferably, Ar is phenyl, pyridyl or pyridazyl, pyrimidyl, pyrazyl, each of which is optionally substituted by one or more substituents wherein each substituent is as defined immediately above. Another group of preferred compounds of Formula II include compounds wherein R$_2$ is a member of the group consisting of H, halo, N$_3$, C$_{1-4}$ alkoxy, C$_{1-4}$ alkylthiol, hydroxyC$_{1-4}$ alkyl, C$_{1-4}$ alkyl, and —N$(R^a)(R^b)$ wherein $R^a$ and $R^b$ are independently H, OH ($R^a$ and $R^b$ are not both OH), C$_{2-4}$ hydroxyalkyl, or C$_{1-4}$ alkyl or $R^a$ and $R^b$ together with the nitrogen atom to which they are both linked form a 3, 4, 5 or 6-membered heterocycle; each of the member being optionally substituted by 1-4 substituents wherein each substituent is independently halo, OH, or C$_{1-4}$ alkyl.

In preferred embodiments of the compounds of Formula II, one or two of Q, T, U and V are N, and both B and D are N.

Another group of preferred compounds that may be employed in the methods of the present invention are represented by Formula III:

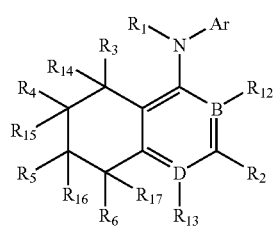

(III)

or pharmaceutically acceptable salts or solvates thereof, wherein:

Ar is as defined above in Formula Ia and II;
R$_1$ is a C$_{1-3}$ alkyl, preferably methyl or ethyl, more preferably methyl;
R$_2$-R$_6$ and R$_{12}$-R$_{17}$ are independently H, halo, N$_3$, OH, thiol, nitro, CN, NH$_2$, C$_{1-6}$ alkyl, C$_{2-6}$ alkenyl, C$_{2-6}$ alkynyl, C$_{1-6}$ alkoxy, C$_{1-6}$ alkylthiol, halo-C$_{1-6}$ alkyl, C$_{2-6}$ alkenyl-O—, C$_{2-6}$ alkynyl-O—, hydroxy-C$_{1-6}$ alkyl, C$_{1-6}$ alkoxy-C$_{1-6}$ alkyl, C$_{1-6}$ acyl, C$_{1-6}$ acyloxy, —C$_{1-6}$ alkyl-C(O)O—C$_{1-6}$ alkyl, —C(O)O—C$_{1-6}$ alkyl, C$_{1-6}$ alkyl-C(O)O—C$_{1-6}$ alkyl-, C$_{1-6}$ acylamido, —N$(R^a)(R^b)$, —C$_{1-6}$ alkyl-C(O)N$(R^a)(R^b)$, —C(O)N$(R^a)(R^b)$, N$(R^a)(R^b)$—C$_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), C$_{2-6}$ hydroxyalkyl, or C$_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, N$_3$, OH, thiol, nitro, CN, C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyl-O—, C$_{2-6}$ alkynyl-O—, hydroxy-C$_{1-6}$ alkyl, C$_{1-6}$ alkoxy-C$_{1-6}$ alkyl, C$_{1-6}$ acyl, C$_{1-6}$ acyloxy, —C$_{1-6}$ alkyl-C(O)O—C$_{1-6}$ alkyl, —C(O)O—C$_{1-6}$ alkyl, C$_{1-6}$ alkyl-C(O)O—C$_{1-6}$ alkyl-, C$_{1-6}$ acylamido, —N$(R^a)(R^b)$, —C$_{1-6}$ alkyl-C(O)N$(R^a)(R^b)$, —C(O)N$(R^a)(R^b)$, N$(R^a)(R^b)$—C$_{1-6}$ alkyl-, wherein $R^a$ and $R^b$ are independently H, OH ($R^a$ and $R^b$ are not both OH), C$_{2-6}$ hydroxyalkyl, or C$_{1-6}$ alkyl or $R^a$ and $R^b$ together with the nitrogen atom to which they are both linked form a 3, 4, 5 or 6-membered heterocycle; and B and D are independently C or N, wherein at least one of B and D is N, and when B or D is N, then there is no substituent at the nitrogen atom.

Other preferred compounds according to Formula III include compounds wherein Ar is phenyl, naphthyl, pyridyl, pyridazyl, pyrimidyl, pyrazyl, quinolyl, isoquinolyl, isoxazolyl, pyrazolyl, imidazolyl, thienyl, furyl or pyrrolyl; each of which is optionally substituted by one or more substituents wherein each substituent is as defined immediately above. More preferably, Ar is phenyl, pyridyl pyridazyl, pyrimidyl, or pyrazyl, each of which is optionally substituted by one or more substituents wherein each substituent is as defined immediately above. In one embodiment, Ar is pyridyl pyridazyl, pyrimidyl, or pyrazyl, each of which is optionally substituted by one or more substituents as defined above for Ar. Also preferably R$_2$ is a member of the group consisting of H, halo, N$_3$, C$_{1-4}$ alkoxy, C$_{1-4}$ alkylthiol, hydroxyC$_{1-4}$ alkyl, C$_{1-4}$ alkyl, and —N$(R^a)(R^b)$ wherein $R^a$ and $R^b$ are independently H, OH ($R^a$ and $R^b$ are not both OH), C$_{2-4}$ hydroxyalkyl, or C$_{1-4}$ alkyl or $R^a$ and $R^b$ together with the nitrogen atom to which they are both linked form a 3, 4, 5 or 6-membered heterocycle; each of the member being optionally substituted by 1-4 substituents wherein each substituent is independently halo, OH, or C$_{1-4}$ alkyl. In preferred embodiments of the compounds of Formula III, both B and D are N.

Preferably a compound according to Formula III is other than (5,6,7,8-tetrahydro-quinazolin-4-yl)-phenyl-ethylamine.

More preferably, the methods of inhibiting tubulin, inhibiting topoisomerase II, activating caspase-3, inducing apoptosis and treating or delaying the onset of diseases and disorders responsive to the inhibition of tubulin or topoisomerase II or to the activation of caspase-3 or induction of apoptosis comprise administering an effective amount of a compound or a pharmaceutical composition containing an effective amount of the compound, which compound is represented by any one of Formulae IV, IVa, IVb, V, Va, Vb, Vc, VI, VIa and VIb, and each and all embodiments thereof and salts or solvates thereof, as provided below.

Additional compounds useful in such methods, particularly the methods of inhibiting tubulin, inhibiting topoisomerase II, activating caspase-3 and inducing apoptosis, and treating diseases and disorders responsive to the inhibition of tubulin or topoisomerase II, or activating caspase-3 and inducing apoptosis include compounds according to Formula IV:

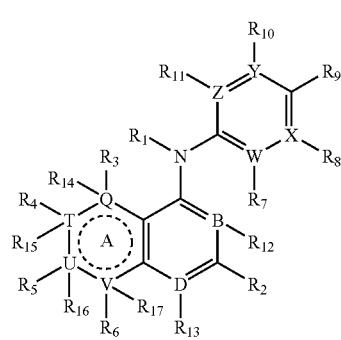

(IV)

and pharmaceutically acceptable salts and solvates thereof, wherein:

$R_1$ is methyl or ethyl, preferably methyl;

A ring is a carbocycle, aryl or heteroaryl;

$R_2$-$R_{17}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle, with the proviso that when A is aryl or heteroaryl, then there are no substituents $R_{14}$-$R_{17}$; and B, D, Q, T, U, V, W, X, Y, and Z are independently C or N, wherein at least one of B and D is N; wherein when B, D, W, X, Y, or Z is N, then there is no substituent at the N; and wherein when A is heteroaryl and Q, T, U or V is N, then there is no substituent at the N.

Preferably when the A ring is aryl or heteroaryl and U is C, $R_5$ is not alkoxy. More preferably, when the A ring is aryl or heteroaryl and U is C, then $R_5$ is H or F, preferably H.

In some embodiments of the compounds of Formula IV, one of W, X, Y and Z is N. In other embodiments of the compounds of Formula IV, two of W, X, Y and Z are N. In any of the embodiments, preferably one or two of Q, T, U and V are N. In preferred embodiments, B and D both are N.

Further additional compounds in addition to the compounds represented by Formulae IV, IVa, IVb, V, Va, Vb, Vc, VI, VIa and VIb, and all embodiments thereof, which are useful in the methods of the present invention, particularly the methods of inhibiting tubulin, inhibiting topoisomerase II, activating caspase-3 and inducing apoptosis, and treating diseases and disorders responsive to the inhibition of tubulin or topoisomerase II, activating caspase-3 and inducing apoptosis, include compounds according to Formula VI:

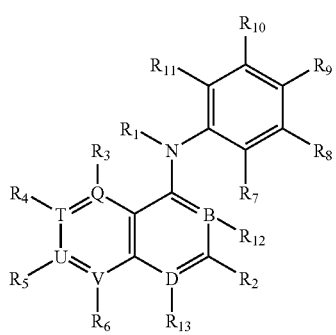

(VI)

or pharmaceutically acceptable salts or solvates thereof, wherein:

$R_1$ is methyl or ethyl, preferably methyl;

$R_5$ is H or F, preferably H;

$R_2$-$R_4$, $R_6$-$R_{13}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$, groups together form a 3, 4, 5 or 6-membered carbocycle or heterocycle; and B, D, Q, T, U and V are independently C or N, provided that at least one of B and D is N; wherein when B, D, Q, T, U or V is N, then there is no substituent at the N.

In some embodiments of the compounds according to Formula VI, one or two of Q, T, U and V are N. In preferred embodiments, both B and D are N.

Further additional compounds useful in such methods, particularly the methods of inhibiting tubulin, inhibiting topoisomerase II, activating caspase-3 and inducing apoptosis, and treating diseases and disorders responsive to the inhibition of tubulin or topoisomerase II, activating caspase-3 and inducing apoptosis, include compounds according to Formula VIa:

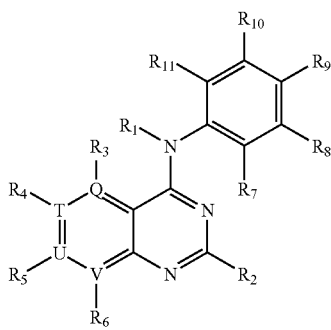

(VIa)

or pharmaceutically acceptable salts or solvates thereof, wherein:

$R_1$ is methyl or ethyl, preferably methyl;

$R_5$ is H or F, preferably H;

$R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H. OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle; and Q, T, U and V are independently C or N, wherein when Q, T, U or V is N, then there is no substituent at the N.

In some embodiments of the compounds according to Formula VIa, one or two of Q, T, U and V are N.

Still further additional compounds useful in such methods, particularly the methods of inhibiting tubulin or topoisomerase II, activating caspase-3 and inducing apoptosis, and treating diseases and disorders responsive to the inhibition of tubulin or topoisomerase II, activating caspase-3 and inducing apoptosis, include compounds according to Formula VIb:

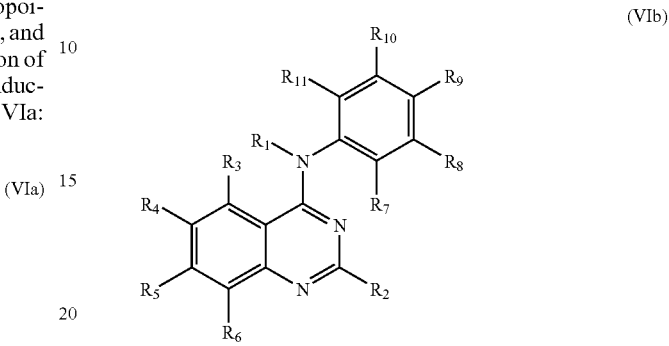

(VIb)

or pharmaceutically acceptable salts or solvates thereof, wherein:

$R_1$ is methyl or ethyl, more preferably methyl;

$R_5$ is H or F, preferably H;

$R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —C alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H. OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$, groups together form a 3, 4, 5 or 6-membered carbocycle or heterocycle.

In the various embodiments of the above methods of the present invention, preferably the compounds administered in the methods of the invention are able to induce caspase activation as determined by the method and under conditions (measurement at 24 hours) described in Example 143, preferably at an $EC_{50}$ no greater than 1,000 nM, more preferably at an $EC_{50}$ no greater than about 500 nM, more preferably at an $EC_{50}$ no greater than about 200 nM, more preferably at an $EC_{50}$ no greater than about 100 nM, even more preferably at an $EC_{50}$ no greater than about 50 nM, and most preferably at an $EC_{50}$ no greater than about 10 nM. Also preferred in the above methods of the invention are compounds of Formula I-VIb, and pharmaceutically acceptable salts or solvates thereof, that are able to inhibit tubulin at an $IC_{50}$ of no greater than about 2,000 nM, more preferably no greater than about 1,000 nM, most preferably less than about 500 nM, as determined by the method and under conditions described in Example 145.

Exemplary compounds useful in the methods of the invention include, but are not limited to, compounds in Examples 1-142; and pharmaceutically acceptable salts or solvates thereof, and:
(2-Chloro-quinazolin-4-yl)-(4-methoxy-phenyl)-methyl-amine;
(2-Chloro-quinazolin-4-yl)-(4-methyl-phenyl)-methyl-amine;
(2-Chloro-quinazolin-4-yl)-(4-chloro-phenyl)-methyl-amine;
(2-Chloro-quinazolin-4-yl)-(4-nitro-phenyl)-methyl-amine;
(2-Chloro-quinazolin-4-yl)-(4-trifluoromethoxy-phenyl)-methyl-amine;
(2-Chloro-quinazolin-4-yl)-phenyl-methyl-amine;
$N^2$-Hydroxyl-$N^4$-(4-methoxy-phenyl)-$N^4$-methyl-quinazoline-2,4-diamine;
$N^2$-(2-Hydroxylethyl)-$N^4$-(4-methoxy-phenyl)-$N^4$-methyl-quinazoline-2,4-diamine;
$N^4$-(4-methoxy-phenyl)-$N^4$-methyl-quinazoline-2,4-diamine;
$N^2$-(3,7-Dimethyl-octa-2,6-dienyl)-$N^4$-(4-methoxy-phenyl)-$N^4$-methyl-quinazoline-2,4-diamine;
$N^4$-(4-Methoxy-phenyl)-$N^4$-methyl-N-2-(2-morpholin-4-yl-ethyl)-quinazoline-2,4-diamine;
(4-Methoxy-phenyl)-methyl-(2-morpholin-4-yl-quinazolin-4-yl)-amine;
$N^2$-(3,7-Dimethyl-octa-2,6-dienyl)-$N^4$-(4-methyl-phenyl)-$N^4$-methyl-quinazoline-2,4-diamine;
(2-Chloro-6,7-dimethoxyquinazolin-4-yl)-(4-methoxy-phenyl)-methyl-amine;
(5,6,7,8-Tetrahydro-quinazolin-4-yl)-(4-methoxy-phenyl)-methyl-amine;
(2-Chloro-quinazolin-4-yl)-(4-methoxy-benzyl)-methyl-amine;
(4-Methoxy-phenyl)-methyl-quinazolin-4-yl-amine;
(4-Methyl-phenyl)-methyl-quinazolin-4-yl-amine;
(2-Chloro-quinazolin-4-yl)-(6-methoxy-pyridin-3-yl)-methyl-amine;
(2-Chloro-quinazolin-4-yl)-isopropyl-(4-methoxy-phenyl)-amine;
(2-Chloro-quinazolin-4-yl)-cyclohexyl-(4-methoxy-phenyl)-amine;
(2-Chloro-quinazolin-4-yl)-(2,3-dimethoxy-phenyl)-methyl-amine;
(2-Chloro-quinazolin-4-yl)-ethyl-4-methoxy-phenyl)-amine;
(2-Chloro-quinazolin-4-yl)-2,4-dimethoxy-phenyl)-methyl-amine;
(2-Chloro-quinazolin-4-yl)-2,5-dimethoxy-phenyl)-methyl-amine;
(2-Chloro-quinazolin-4-yl)-3-methoxy-phenyl)-methyl-amine;
(2-Chloro-quinazolin-4-yl)-2-methoxy-phenyl)-methyl-amine;
4-Chloro-benzoic acid N'-methyl-N'-2-methylthio-quinazolin-4-yl)-hydrazide;
Benzoic acid N'-methyl-N'-2-methylthio-quinazolin-4-yl)-hydrazide;
Thiophene-2-carboxylic acid N'-methyl-N'-2-methylthio-quinazolin-4-yl)-hydrazide;
$N^2$-[2-(1H-Imidazol-4-yl)-ethyl]-$N^4$-(4-methoxy-phenyl)-$N^4$-methyl-quinazoline-2,4-diamine;
$N^2$-(3-Dimethylamino-propyl)-$N^4$-(4-methoxy-phenyl)-$N^4$-methyl-quinazoline-2,4-diamine;
$N^2$-(2-Hydroxyethyl)-$N^4$-(6-methoxypyridin-3-yl)-$N^4$-methyl-quinazoline-2,4-diamine;
$N^4$-(6-methoxypyridin-3-yl)-$N^4$-methyl-quinazoline-2,4-diamine;
(2-Chloro-quinazolin-4-yl)-(4-methylcarboxyphenyl)-methyl-amine;
(2-methoxy-quinazolin-4-yl)-(4-methoxyphenyl)-methylamine;
(2-Chloro-quinazolin-4-yl)-(4-hydroxyphenyl)-methylamine;
(2-Fluoromethyl-quinazolin-4-yl)-(4-methoxy-phenyl)-methyl-amine;
(2-Chloro-6-methyl-quinazolin-4-yl)-(4-methoxy-phenyl)-methyl-amine;
(2-Chloro-7-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(2,7-Dichloro-quinazolin-4-yl)-(4-methoxy-phenyl)-methyl-amine;
(5-Chloro-2-isopropoxy-quinazolin-4-yl)-(4-methoxy-phenyl)-methyl-amine;
(Isoquinolin-1-yl)-(4-methoxy-phenyl)-methyl-amine;
(4-Methoxy-phenyl)-methyl-(quinolin-4-yl)-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-phenoxy-phenyl)-methyl-amine;
(2-Chloro-quinazolin-4-yl)-(4-propoxy-phenyl)-methyl-amine;
(4-Methoxy-phenyl)-methyl-(2-methyl-quinazolin-4-yl)-amine;
4-Methoxy-benzoic acid N'-methyl-N'-(2-trifluoromethyl-quinazolin-4-yl)-hydrazide;
3-Methyl-benzoic acid N'-methyl-N'-(2-methylthio-quinazolin-4-yl)-hydrazide;
4-Fluoro-benzoic acid N'-methyl-N'-(2-methylthio-quinazolin-4-yl)-hydrazide; and
2-Fluoro-benzoic acid N'-methyl-N'-(2-trifluoromethyl-quinazolin-4-yl)-hydrazide;
(2-Chloro-quinazolin-4-yl)-(2,5-dimethoxy-phenyl)-amine;
5-Chloro-$N^2$,$N^4$-bis-(4-methoxy-phenyl)-$N^2$,$N^4$-dimethyl-quinazoline-2,4-diamine;
(2-Chloromethyl-quinazolin-4-yl)-(4-methoxy-phenyl)-methyl-amine;
(2-Ethyl-quinazolin-4-yl)-(4-methoxy-phenyl)-methyl-amine;
(2-Hydroxymethyl-quinazolin-4-yl)-4-methoxy-phenyl)-methyl-amine;
(2-Dimethylaminomethyl-quinazolin-4-yl)-(4-methoxy-phenyl)-methyl-amine;
(4-Methoxy-phenyl)-(2-phenyl-quinazolin-4-yl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;

(4-Isopropoxy-phenyl)-(2-methyl-quinazolin-4-yl)-methyl-amine;
(4-Ethyl-phenyl)-(2-methyl-quinazolin-4-yl)-methyl-amine;
(2-Methyl-quinazolin-4-yl)-(2,4,6-trimethoxy-phenyl)-methyl-amine;
(2,8-Dichloro-quinazolin-4-yl)-(4-methoxy-phenyl)-methyl-amine;
(2,5-Dichloro-quinazolin-4-yl)-(4-methoxy-phenyl)-methyl-amine;
(5-Methoxy-2-methyl-quinazolin-4-yl)-(4-methoxy-phenyl)-methyl-amine;
(4-Methoxy-phenyl)-(2-methyl-pyrido[2,3-d]pyrimidin-4-yl)-methyl-amine;
(4-Hydroxy-phenyl)-(2-methyl-quinazolin-4-yl)-methyl-amine;
(2-Chloro-quinazolin-4-yl)-(4-ethoxy-phenyl)-methylamine;
(2-Methyl-quinazolin-4-yl)-(6-methoxy-pyridin-3-yl)-methyl-amine;
(2-Fluoro-4-methoxy-phenyl)-(2-methyl-quinazolin-4-yl)-methyl-amine;
(2-Methyl-quinazolin-4-yl)-(4-nitro-phenyl)-methyl-amine;
(4-Amino-phenyl)-(2-methyl-quinazolin-4-yl)-methyl-amine;
(4-Azido-phenyl)-(2-methyl-quinazolin-4-yl)-methyl-amine;
(4-Amino-2,6-dibromo-phenyl)-(2-methyl-quinazolin-4-yl)-methyl-amine;
(4-Amino-2-bromo-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;
(4-Methoxy-phenyl-2,3,5,6-d$_4$)-(2-methyl-quinazolin-4-yl)-methyl-amine;
(4-Methoxy-phenyl)-(2-methyl-6-nitro-quinazolin-4-yl)-methyl-amine;
(6-Amino-2-methyl-quinazolin-4-yl)-(4-methoxy-phenyl)-methyl-amine;
(6-Azido-2-methyl-quinazolin-4-yl)-(4-methoxy-phenyl)-methyl-amine;
(7-Amino-2-methyl-quinazolin-4-yl)-(4-methoxy-phenyl)-methyl-amine;
(7-Azido-2-methyl-quinazolin-4-yl)-(4-methoxy-phenyl)-methyl-amine;
Ethyl 4-(N-4-Methoxy-phenyl)-N-methylamino)quinazoline-2-carboxylate;
Succinimidyl 4-(N-Methyl-N-2-methylquinazolin-4-yl)amino)benzoic Acid Ester;
(2-Methylthio-quinazolin-4-yl)-(4-methoxy-phenyl)-methyl-amine;
(2-Azido-quinazolin-4-yl)-(4-methoxy-phenyl)-methyl-amine;
(2-Dimethylamino-quinazolin-4-yl)-(4-methoxy-phenyl)-methyl-amine;
(2-Methylamino-quinazolin-4-yl)-(4-methoxy-phenyl)-methyl-amine;
(4-Fluoro-phenyl)-(2-methyl-quinazolin-4-yl)-methyl-amine;
(6-Methoxy-pyridazin-3-yl)-(2-methyl-quinazolin-4-yl)-methyl-amine;
(5-Methoxy-pyrazin-2-yl)-(2-methyl-quinazolin-4-yl)-methyl-amine;
(2-Dimethylamino-quinazolin-4-yl)-(6-methoxy-pyridin-3-yl)-methyl-amine;
(2-Methylamino-quinazolin-4-yl)-(6-methoxy-pyridin-3-yl)-methyl-amine;
(5-Methoxy-pyridin-2-yl)-(2-methyl-quinazolin-4-yl)-methyl-amine;
Difluoromethyl-4-methoxy-phenyl)-(2-methyl-quinazolin-4-yl)-amine;
(4-Methoxy-phenyl)-(2-methyl-pteridin-4-yl)-methyl-amine;
(5-Methoxy-pyrimidin-2-yl)-(2-methyl-quinazolin-4-yl)-methyl-amine;
and pharmaceutically acceptable salts or solvates thereof.

The present invention also provides novel compounds, which are potent tubulin inhibitors, topoisomerase II inhibitors, caspase-3 activators and/or apoptosis inducers/promoters. Specifically, the novel compounds of the present invention are represented by Formula IV and pharmaceutically acceptable salts or solvates thereof:

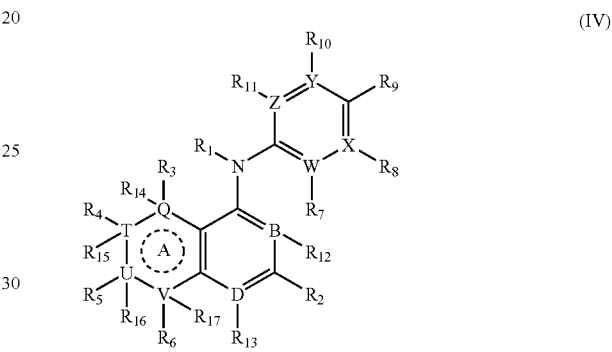

(IV)

wherein
$R_1$ is methyl or ethyl, and preferably methyl;
A ring is a carbocycle, aryl or heteroaryl;
$R_2$-$R_{17}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O, $C_{2-6}$ alkynyl-O, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$) (10), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle, with the proviso that when A ring is aryl or heteroaryl, then there are no substituents $R_{14}$-$R_{17}$; and with the proviso that when A ring is aryl or heteroaryl and U is C, then $R_5$ is H or F, preferably H; and B, D, Q, T, U, V, W, X, Y and Z are independently C or N, wherein at least one of B and D is N; wherein when B, D, W, X, Y or Z is N, then there is no substituent at the N; and wherein when A is heteroaryl and Q, T, U or V is N, then there is no substituent at the N; and wherein when A is carbocycle and W, X, Y and Z are all carbon atoms, then the compound is not 2-amino-4-(N-ethylanilino)-5,6,7,8-tetrahydro-quinazoline; and wherein when A is benzo and W, X, Y and Z are all C, then (1) $R_9$ is not ($C_{1-3}$ alkyl)OC(O)alkoxy-; and (2) when $R_9$ is H, then at least one of $R_8$ and $R_{10}$ are not H or $C_{1-6}$ alkyl, or halo; and wherein when A is heteroaryl and W, X, Y and Z are all C, when $R_9$ is H, then at least one of $R_8$ and $R_{10}$ is not H or alkyl, provided that $R_8$ and $R_{10}$ may be both alkyl.

Preferably when $R_9$ is H then $R_8$ or $R_{10}$ or both are independently selected from the group OH; $N_3$; —$XR_{2a}$ wherein X is S or O and $R_{2a}$ is $C_{1-6}$ alkyl (preferably $C_{1-3}$ alkyl, more preferably $CH_3$) optionally substituted with OH or halo; —$NH(R_{2b})$ or $N(R_{2b})(R_{2c})$ wherein $R_{2b}$ and $R_{2c}$ are independently $C_{1-6}$ alkyl (preferably $C_{1-3}$ alkyl, more preferably $CH_3$) optionally substituted with OH or halo (preferably F, and wherein optionally $R_{2b}$ and $R_{2c}$ may together form a 3-6 membered heterocycle; and —$C(O)OR_{2d}$ wherein $R_{2d}$ is $C_{1-6}$ alkyl (preferably $C_{1-3}$ alkyl); and more preferably $R_9$ is not H.

In some embodiments of the compounds of Formula IV, one of W, X, Y and Z is N. In other embodiments of the compounds of Formula IV, two of W, X, Y and Z are N. In any of the embodiments, preferably one or two of Q, T, U and V are N. In preferred embodiments, B and D both are N.

One group of the compounds of the present invention are represented by Formula IVa:

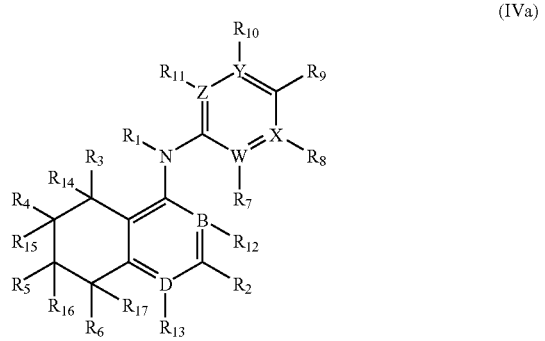

(IVa)

or a pharmaceutically acceptable salt or solvate thereof, wherein:

$R_1$ is methyl, ethyl, preferably methyl;

$R_2$-$R_{17}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), —C(O)N($R^a$)($R^b$), $N(R^a)(R^b)$—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), —C(O)N($R^a$)($R^b$), $N(R^a)(R^b)$—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle; and B, D, W, X, Y, and Z are independently C or N, provided that at least one of B and D is N, at least one of W, X, Y, and Z is N, and when B, D, W, X, Y, or Z is N then there is no substituent at the N.

In some embodiments, one of X, Y, W and Z is N. In other embodiments, two of X, Y, W and Z are N. Preferably D is nitrogen, and more preferably both B and D are N.

In a preferred embodiment, compounds of the present invention have Formula IVa, or a pharmaceutically acceptable salt or solvate thereof, wherein:

$R_1$ is methyl or ethyl, preferably methyl;

$R_2$ is a member of the group consisting of H, halo, $N_3$, $C_{1-4}$ alkoxy, $C_{1-4}$ alkylthiol, hydroxy$C_{1-4}$ alkyl, $C_{1-4}$ alkyl, and —$N(R^a)(R^b)$ wherein $R^a$ and $R^b$ are independently H, OH ($R^a$ and $R^b$ are not both OH), $C_{2-4}$ hydroxyalkyl, or $C_{1-4}$ alkyl or $R^a$ and $R^b$ together with the nitrogen atom to which they are both linked form a 3, 4, 5 or 6-membered heterocycle; each of the member being optionally substituted by 1-4 substituents wherein each substituent is independently halo, OH, or $C_{1-4}$ alkyl;

$R_7$ and $R_{11}$ are independently H, halo (preferably F), $CH_3$, or $OCH_3$;

$R_8$ and $R_{10}$ are independently H, halo (preferably F or Cl), $C_{1-3}$ alkyl (preferably $CH_3$) optionally substituted with halo (preferably 1-3 F), $C_{1-3}$ alkoxy (preferably $OCH_3$), or $C_{1-3}$ alkylthiol (preferably —S—$CH_3$);

$R_9$ is H, OH, $C_1$, $N_3$, $C_{1-4}$ alkoxy, $C_{1-4}$ alkylthiol, hydroxy$C_{1-4}$ alkyl, $C_{1-4}$ alkyl, —COOR$^c$ wherein R$^c$ is $C_{1-3}$ alkyl, or —$N(R^a)(R^b)$ wherein $R^a$ and $R^b$ are independently H, OH ($R^a$ and $R^b$ are not both OH), $C_{2-4}$ hydroxyalkyl, or $C_{1-4}$ alkyl or $R^a$ and $R^b$ together with the nitrogen atom to which they are both linked form a 3, 4, 5 or 6-membered heterocycle; each of the member being optionally substituted by 1-4 substituents wherein each substituent is independently halo, OH, or $C_{1-4}$ alkyl; and optionally two adjacent $R_8$, $R_9$, and $R_{10}$ groups may together form a 3, 4, 5, or 6-membered carbocycle, heterocycle, preferably heterocyle; and B, D, W, X, Y, and Z are independently C or N, and at least one of B and D is N, at least one of W, X, Y and Z is N, and when B, D, W, X, Y, or Z is N then there is no substituent at the N. Preferably D is N. In some embodiments, both B and D are N.

In specific embodiments, only one of W, X, Y and Z is N. In other specific embodiments, two of W, X, Y and Z are N.

In preferred embodiments of the compound of Formula IVa, $R_9$ is selected from the group:

—$OR_{9a}$, wherein $R_{9a}$ is methyl, ethyl, fluoromethyl ($CH_2F$, $CHF_2$, $CF_3$), or fluoroethyl;

—$N_3$;

—$N(CH_3)_2$;

—NHCH$_3$; and

—COOR$_{9b}$, wherein R$_{9b}$ is H or C$_{1-2}$ alkyl.

Another group of compounds of the present invention are represented by Formula IVb:

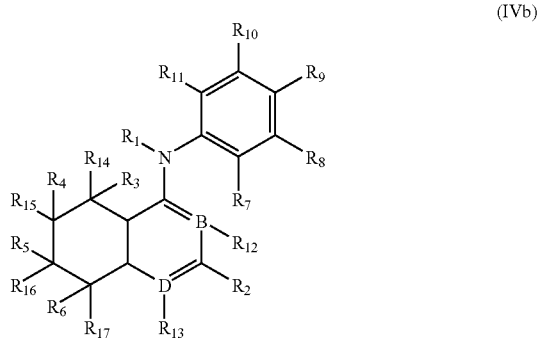

or pharmaceutically acceptable salts or solvates thereof, wherein:

R$_2$-R$_{17}$ are independently H, halo, N$_3$, OH, thiol, nitro, CN, NH$_2$, C$_{1-6}$ alkyl, C$_{2-6}$ alkenyl, C$_{2-6}$ alkynyl, C$_{1-6}$ alkoxy, C$_{1-6}$ alkylthiol, halo-C$_{1-6}$ alkyl, C$_{2-6}$ alkenyl-O—, C$_{2-6}$ alkynyl-O—, hydroxy-C$_{1-6}$ alkyl, C$_{1-6}$ alkoxy-C$_{1-6}$ alkyl, C$_{1-6}$ acyl, C$_{1-6}$ acyloxy, —C$_{1-6}$ alkyl-C(O)O—C$_{1-6}$ alkyl, —C(O)O—C$_{1-6}$ alkyl, C$_{1-6}$ alkyl-C(O)O—C$_{1-6}$ alkyl-, C$_{1-6}$ acylamido, —N(R$^a$)(R$^b$), —C$_{1-6}$ alkyl-C(O)N(R$^a$)(R$^b$), —C(O)N(R$^a$)(R$^b$), N(R$^a$)(R$^b$)—C$_{1-6}$ alkyl-, 3, 4, 5, or 6-membered carbocycle, heterocycle, aryl, or heteroaryl, wherein R$^a$ and R$^b$ are independently H, OH (R$^a$ and R$^b$ are not both OH), C$_{2-6}$ hydroxyalkyl, or C$_{1-6}$ alkyl, or R$^a$ and R$^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, N$_3$, OH, thiol, nitro, CN, C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyl-O—, C$_{2-6}$ alkynyl-O—, hydroxy-C$_{1-6}$ alkyl, C$_{1-6}$ alkoxy-C$_{1-6}$ alkyl, C$_{1-6}$ acyl, C$_{1-6}$ acyloxy, —C$_{1-6}$ alkyl-C(O)O—C$_{1-6}$ alkyl, —C(O)O—C$_{1-6}$ alkyl, C$_{1-6}$ alkyl-C(O)O—C$_{1-6}$ alkyl-, C$_{1-6}$ acylamido, —N(R$^a$)(R$^b$), —C$_{1-6}$ alkyl-C(O)N(R$^a$)(R$^b$), —C(O)N(R$^a$)(R$^b$), N(R$^a$)(R$^b$)—C$_{1-6}$ alkyl-, wherein R$^a$ and R$^b$ are independently H, OH (R$^a$ and R$^b$ are not both OH), C$_{2-6}$ hydroxyalkyl, or C$_{1-6}$ alkyl or R$^a$ and R$^b$ together with the nitrogen atom to which they are both linked form a 3, 4, 5 or 6-membered heterocycle, wherein optionally any two adjacent R$_7$-R$_{11}$ groups together form a 3, 4, 5 or 6-membered carbocycle or heterocycle; and B and D are independently C or N, provided that at least one of B and D is N, and when B or D is N then there is no substituent at the N; with the proviso that said compound is not 2-amino-4-(N-ethylanilino)-5,6,7,8-tetrahydro-quinazoline.

Preferably, in the compounds of Formula IVb, D is N, and more preferably both B and D are N.

In preferred embodiments, when R$_1$ is ethyl then at least one of R$_8$, R$_9$, and R$_{10}$ is not H; preferably R$_9$ is not H. Also preferably, when R$_9$ is H then R$_8$ or R$_{10}$ or both are independently selected from the group OH; N$_3$; amido; N-dimethylamido; —XR$_{9a}$ wherein X is S or O and R$_{9a}$ is C$_{1-6}$ alkyl (preferably C$_{1-3}$ alkyl, more preferably CH$_3$) optionally substituted with OH or halo; C$_{1-3}$ alkyl optionally substituted with halo (preferably F); —N(R$^a$)(R$^b$) wherein R$^a$ and R$^b$ are independently H, OH (R$^a$ and R$^b$ are not both OH), or C$_{1-6}$ alkyl (preferably C$_{1-3}$ alkyl, more preferably CH$_3$) optionally substituted with OH or halo (preferably F, and wherein optionally R$_{2b}$ and R$_{2c}$ may together form a 3-6 membered heterocycle; and —C(O)OR$^c$ wherein R$^c$ is C$_{1-6}$ alkyl (preferably C$_{1-3}$ alkyl).

In a preferred embodiment of the compound of Formula IVb:

R$_1$ is methyl or ethyl, preferably methyl;

R$_3$-R$_6$, R$_{12}$-R$_{17}$ are as defined above;

R$_2$ is a member of the group consisting of H, halo, N$_3$, C$_{1-4}$ alkoxy, C$_{1-4}$ alkylthiol, hydroxyC$_{1-4}$ alkyl, C$_{1-4}$ alkyl, and —N(R$^a$)(R$^b$) wherein R$^a$ and R$^b$ are independently H, OH (R$^a$ and R$^b$ are not both OH), C$_{2-4}$ hydroxyalkyl, or C$_{1-4}$ alkyl or R$^a$ and R$^b$ together with the nitrogen atom to which they are both linked form a 3, 4, 5 or 6-membered heterocycle; each of the member being optionally substituted by 1-4 substituents wherein each substituent is independently halo, OH, or C$_{1-4}$ alkyl;

R$_7$ and R$_{11}$ are independently H, halo (preferably F), CH$_3$, or OCH$_3$;

R$_8$ and R$_{10}$ are independently H, halo (preferably F or Cl), C$_{1-3}$ alkyl (preferably CH$_3$) optionally substituted with halo (preferably 1-3 F), C$_{1-3}$ alkoxy (preferably OCH$_3$), or C$_{1-3}$ alkylthiol (preferably —S—CH$_3$);

R$_9$ is OH, C$_1$, N$_3$, C$_{1-4}$ alkoxy, C$_{1-4}$ alkylthiol, hydroxyC$_{1-4}$ alkyl, C$_{1-4}$ alkyl, —COOR$^c$ wherein R$^c$ is C$_{1-3}$ alkyl, or —N(R$^a$)(R$^b$) wherein R$^a$ and R$^b$ are independently H, OH (R$^a$ and R$^b$ are not both OH), C$_{2-4}$ hydroxyalkyl, or C$_{1-4}$ alkyl or R$^a$ and R$^b$ together with the nitrogen atom to which they are both linked form a 3, 4, 5 or 6-membered heterocycle; each of the member being optionally substituted by 1-4 substituents wherein each substituent is independently halo, OH, or C$_{1-4}$ alkyl; and optionally two adjacent R$_8$, R$_9$, and R$_{10}$ groups may together form a 3, 4, 5, or 6-membered carbocycle, heterocycle, preferably heterocycle; and B and D are independently C or N, and at least one of B and D is N.

In more preferred embodiments of the compound of Formula IVa, R$_9$ is selected from the group:

—OR$_{9a}$, wherein R$_{9a}$ is methyl, ethyl, fluoromethyl (e.g., CH$_2$F, CHF$_2$, CF$_3$), fluoroethyl;

—N$_3$;

—N(CH$_3$)$_2$;

—NHCH$_3$; and

—COOR$_{9b}$, wherein R$_{9b}$ is H or C$_{1-2}$ alkyl.

Other novel compounds of the present invention are those represented by Formula V:

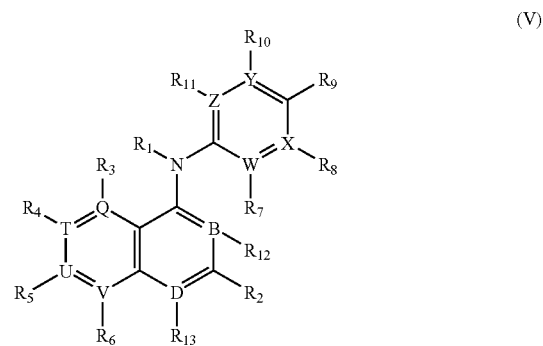

or a pharmaceutically acceptable salt or solvate thereof, wherein:

$R_1$ is methyl or ethyl, preferably methyl;

$R_5$ is H, F, Cl, $N_3$, methyl, methoxy or $NH_2$, with the proviso that when $R_5$ is methoxy, $R_1$ is methyl; Preferably $R_5$ is H, F or $N_3$, more preferably H or F, and most preferably H;

$R_2$-$R_4$, and $R_6$-$R_{13}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), (O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle; and B, D, Q, T, U, V, W, X, Y and Z are independently C or N; provided that at least one of B and D is N, and at least one of W, X, Y and Z is N, and wherein when B, D, Q, T, U, V, W, X, Y or Z is N, then there is no substituent at the N.

In a specific embodiment, preferably when $R_9$ is H, at least one of $R_8$ and $R_{10}$ is not H, more preferably $R_9$ is other than H.

In some specific embodiments, B is C and D is N. In other specific embodiments, B is N and D is C. In preferred embodiments, both B and D are N.

In one embodiment of the compounds of Formula V, $R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl).

In another embodiment of the compound of Formula V, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In preferred embodiment, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, $R_9$ is selected from the group consisting of H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —N($R^a$)($R^b$) wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

In another embodiment, $R_9$ is —$OCH_3$, —$OC_2H_5$, —$N(CH_3)_2$, —$CO_2CH_3$, —$OCHF_2$, or $N_3$.

In yet another embodiment, when $R_9$ is H, at least one of $R_8$ and $R_{10}$ is not H. In another embodiment, when $R_9$ is alkyl, $R_2$ is not H.

In a specific embodiment, compounds of the invention include compounds of Formula V or pharmaceutically acceptable salts or solvates thereof, wherein:

$R_1$ is $C_{1-2}$ alkyl, and preferably $R_1$ is methyl;

$R_5$ is H or F, preferably H;

$R_2$-$R_4$, $R_6$, $R_8$-$R_{10}$, $R_{12}$ and $R_{13}$ are independently H; halo; $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo) $C_{1-3}$ alkoxy, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, $C_2$-$C_4$ alkenyl, $C_2$-$C_4$ alkynyl, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; or —N($R^a$)($R^b$) where $R^a$ and $R^b$ are independently H; OH ($R^a$ and $R^b$ are not both OH); $C_{2-6}$ hydroxyalkyl; $C_{1-6}$ alkyl; or $C_{1-6}$ alkyl substituted with —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together, and/or $R^e$ and $R^f$ together, with the nitrogen atom to which they are linked form a 3, 4, 5 or 6-membered heterocycle; preferably when $R_9$ is H, at least one of $R_8$ and $R_{10}$ is not H, more preferably $R_9$ is other than H.

$R_7$ and $R_{11}$ are independently H, halo (preferably F or Cl, more preferably F), $C_{1-3}$ alkyl (preferably $CH_3$), or $C_{1-4}$ alkoxy (preferably $OCH_3$); and B, D, Q, T, U, V, W, X, Y, and Z are as defined above, provided that when B, D, Q, T, U, V, W, X, Y or Z is N there is no substituent at the N.

In another preferred embodiment of the compounds of Formula V, $R_1$ is methyl or ethyl, more preferably methyl;

$R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ with N together may form a 3, 4, 5 or 6-membered heterocycle (e.g., piperidinyl, pyrrolidinyl, and morpholinyl);

$R_3$ and $R_{12}$ are independently H; halo; $C_{1-3}$ alkyl; or $C_{1-13}$ alkoxy;

$R_4$, $R_6$, and $R_{13}$ are independently H; halo (preferably F or Cl); $N_3$; $C_{1-3}$ alkyl (preferably $CH_3$); $C_{1-3}$ alkoxy (preferably $OCH_3$); or —$N(R^a)(R^b)$ wherein $R^a$ and $R^b$ are independently H, OH, $C_{1-3}$ alkyl, (hydroxy)$C_{1-3}$ alkyl, and optionally $R^a$ and $R^b$ together may form a 3, 4, 5 or 6-membered heterocycle (e.g., piperidinyl, pyrrolidinyl, and morpholinyl), and wherein $R^a$ and $R^b$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group: H; OH; Cl; $N_3$; $C_{1-3}$ alkyl (preferably methyl or ethyl) or $C_{1-3}$ haloalkyl (preferably monofluoromethyl, difluoromethyl, trifluoromethyl);

—$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);

—$N(R^a)(R^b)$ wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and B, D, Q, T, U, V, W, X, Y, and Z are independently C or N, provided that at least one of B and D is N, and at least one of W, X, Y, and Z is N, wherein when B, D, Q, T, U, V, W, X, Y, or Z is nitrogen, then there is no substituent at the N.

In more preferred embodiment, compounds of the invention include compounds of Formula V or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$;

$R_3$ and $R_{12}$ are independently H, $CH_3$, $OCH_3$, F, or Cl;

$R_4$, $R_6$, and $R_{13}$ are independently H, $CH_3$, $NH_2$, $N_3$, F, or Cl;

$R_5$ is H;

$R_7$ and $R_{11}$ are independently H, F, or $OCH_3$;

$R_8$ and $R_{10}$ are independently H, F, Cl, or $OCH_3$;

$R_9$ is selected from the group of consisting of H; OH; Cl; $N_3$; $C_{1-3}$ alkyl (preferably methyl or ethyl); $C_{1-3}$ haloalkyl (preferably monofluoromethyl, difluoromethyl, trifluoromethyl); —$OR_{9a}$ where $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —$N(R^a)(R^b)$ wherein $R^a$ and $R^b$ are independently H or $C_{1-3}$ alkyl; and —$COOR_{9b}$, wherein $R_{9b}$ is $C_{1-3}$ alkyl (preferably methyl or ethyl), and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and B, D, Q, T, U, V, W, X, Y and Z are as defined above, provided that when B, D, Q, T, U, V, W, X, Y or Z is N, then there is no substituent at the N. Preferably in this embodiment, when $R_9$ is alkyl, $R_2$ not H.

In a even more preferred embodiment, compounds of the invention include compounds of Formula V or pharmaceutically acceptable salts or solvates thereof, wherein $R_1$ is methyl; $R_2$ is H, methyl, Cl, —$CH_2OH$, —$NH_2$, —$NHCH_3$, —$NHCH_2CH_2OH$, —$OCH_3$, —$SCH_3$, or —$CH_2F$; $R_3$ and $R_{12}$ are independently H, methyl, —$OCH_3$, or Cl; $R_4$ is H, methyl, or $NH_2$; $R_5$ is H; $R_6$ and $R_{13}$ are independently H or methyl; $R_7$ and $R_{11}$ are independently H or F; $R_8$ and $R_{10}$ are independently H, or F or $OCH_3$; and $R_9$ is —$OCH_3$, —$OC_2H_5$, —$N(CH_3)_2$, —$CO_2CH_3$, —$OCHF_2$, or $N_3$; and B, D, Q, T, U, V, W, X, Y, and Z are as defined above, provided that when B, D, Q, T, U, V, W, X, Y, or Z is N, then there is no substituent at the N.

In all embodiments of the compounds of Formula V, it is preferred that one of W, X, Y and Z is N, or two of W, X, Y and Z are N. In any of the embodiments, preferably one or two of Q, T, U and V are N. For example, Q and V can be both N and T and U are C.

Other preferred compounds of the present invention are those represented by Formula V, with the proviso that Q, T, U, and V are all carbon. Specifically, such compounds are represented by Formula Va:

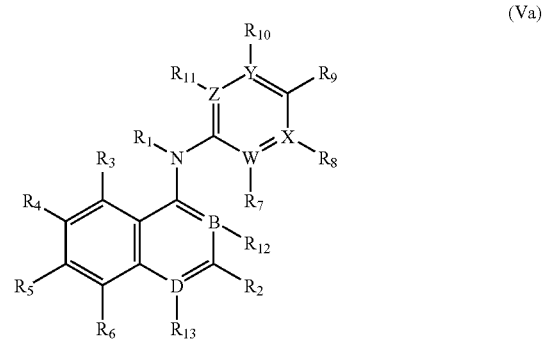

(Va)

or pharmaceutically acceptable salts or solvates thereof, wherein:

$R_1$ is methyl or ethyl, preferably methyl;

$R_5$ is H, F, Cl, $N_3$, methyl, methoxy or $NH_2$, with the proviso that when $R_5$ is methoxy, $R_1$ is methyl; Preferably $R_5$ is H, F or $N_3$, more preferably H or F, and most preferably H;

$R_2$-$R_4$, and $R_6$-$R_{13}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$, groups together form a 3, 4, 5 or 6-membered carbocycle or heterocycle; and B, D, W, X, Y and Z are independently C or N, provided that at least one of B and D is N, and at least one of W, X, Y and Z is N, and wherein when B, D, W, X, Y or Z is N, then there is no substituent at the N.

In a specific embodiment, preferably when $R_9$ is H, then at least one of $R_8$ and $R_{10}$ is not H, more preferably $R_9$ is other than H.

In some specific embodiments, B is C and D is N. In other specific embodiments, B is N and D is C. In preferred embodiments, both B and D are N.

In one embodiment of the compounds of Formula Va, $R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH (Re and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl).

In another embodiment of the compound of Formula Va, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In preferred embodiment, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, $R_9$ is selected from the group consisting of H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —N($R^a$)($R^b$) wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

In another embodiment, $R_9$ is —$OCH_3$, —$OC_2H_5$, —$N(CH_3)_2$, —$CO_2CH_3$, —$OCHF_2$, or $N_3$.

In yet another embodiment, when $R_9$ is H, then at least one of $R_8$ and $R_{10}$ is not H.

In another embodiment, when $R_9$ is alkyl, then $R_2$ is not H.

In a specific embodiment, compounds of the invention include compounds of Formula Va or pharmaceutically acceptable salts or solvates thereof, wherein:

$R_1$ is $C_{1-2}$ alkyl, and preferably $R_1$ is methyl;

$R_5$ is H or F, preferably H;

$R_2$-$R_4$, $R_6$, $R_8$-$R_{10}$, $R_{12}$ and $R_{13}$ are independently H; halo; $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo) $C_{1-3}$ alkoxy, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, $C_2$-$C_4$ alkenyl, $C_2$-$C_4$ alkynyl, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; or —N($R^a$)($R^b$) where $R^a$ and $R^b$ are independently H; OH ($R^a$ and $R^b$ are not both OH); $C_{2-6}$ hydroxyalkyl; $C_{1-6}$ alkyl; or $C_{1-6}$ alkyl substituted with —N($R^e$)($R^f$) where Re and $R^f$ are independently H, OH ($R^e$ and $R^f$ are not both OH), or $C_{1-3}$ alkyl; wherein optionally $R^a$ and $R^b$ together, and/or $R^e$ and $R^f$ together, with the nitrogen atom to which they are linked form a 3, 4, 5 or 6-membered heterocycle; preferably when $R_9$ is H, at least one of $R_8$ and $R_{10}$ is not H, more preferably $R_9$ is other than H.

$R_7$ and $R_{11}$ are independently H, halo (preferably F or Cl, more preferably F), $C_{1-3}$ alkyl (preferably $CH_3$), or $C_{1-4}$ alkoxy (preferably OCH3); and B, D, W, X, Y, and Z are as defined above, provided that when B, D, W, X, Y or Z is N there is no substituent at the N.

In another preferred embodiment of the compounds of Formula Va, $R_1$ is methyl or ethyl, more preferably methyl;

$R_2$ is H; halo; $N_3$;
- $C_{1-6}$ alkyl (preferably $C_{1-3}$ alkyl, more preferably $CH_3$) optionally substituted with OH or halo (preferably F, e.g., monofluoro, difluoro, or trifluoro);
- —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
- —$CO_2R^d$, wherein $R^d$ is $C_{1-3}$ alkyl, preferably methyl or ethyl; or
- —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl);

$R_3$ and $R_{12}$ are independently H; halo; $C_{1-3}$ alkyl; or $C_{1-3}$ alkoxy;

$R_4$, $R_6$, and $R_{13}$ are independently H; halo (preferably F or Cl); $N_3$; $C_{1-3}$ alkyl (preferably $CH_3$); $C_{1-3}$ alkoxy (preferably $OCH_3$); or —$N(R^a)(R^b)$ wherein $R^a$ and $R^b$ are independently H, OH, $C_{1-3}$ alkyl, hydroxy-$C_{1-3}$ alkyl, and optionally $R^a$ and $R^b$ together may form a 3, 4, 5 or 6-membered heterocycle (e.g., piperidinyl, pyrrolidinyl, and morpholinyl), and wherein $R^a$ and $R^b$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group: H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —$N(R^a)(R^b)$ wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and B, D, W, X, Y, and Z are independently C or N, provided that at least one of B and D is N, and at least one of W, X, Y, and Z is N, wherein when B, D, W, X, Y, or Z is nitrogen, then there is no substituent at the N.

In more preferred embodiment, compounds of the invention include compounds of Formula Va or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$;

$R_3$ and $R_{12}$ are independently H, $CH_3$, $OCH_3$, F, or Cl;

$R_4$, $R_6$, and $R_{13}$ are independently H, $CH_3$, $NH_2$, $N_3$, F, or Cl;

$R_5$ is H;

$R_7$ and $R_{11}$ are independently H, F, or $OCH_3$;

$R_8$ and $R_{10}$ are independently H, F, Cl, or $OCH_3$;

$R_9$ is selected from the group of consisting of H; OH; Cl; $N_3$; $C_{1-3}$ alkyl (preferably methyl or ethyl); $C_{1-3}$ haloalkyl (preferably monofluoromethyl, difluoromethyl, trifluoromethyl); —$OR_{9a}$ where $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —$N(R^a)(R^b)$ wherein $R^a$ and $R^b$ are independently H or $C_{1-3}$ alkyl; and —$COOR_{9b}$, wherein $R_{9b}$ is $C_{1-3}$ alkyl (preferably methyl or ethyl), and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and B, D, W, X, Y and Z are as defined above, provided that when B, D, W, X, Y or Z is N, then there is no substituent at the N. Preferably in this embodiment, when $R_9$ is alkyl, $R_2$ not H.

In a even more preferred embodiment, compounds of the invention include compounds of Formula Va or pharmaceutically acceptable salts or solvates thereof, wherein $R_1$ is methyl; $R_2$ is H, methyl, Cl, —$CH_2OH$, —$NH_2$, —$NHCH_3$, —$NHCH_2CH_2OH$, —$OCH_3$, —$SCH_3$, or —$CH_2F$; $R_3$ and $R_{12}$ are independently H, methyl, —$OCH_3$, or Cl; $R_4$ is H, methyl, or $NH_2$; $R_5$ is H; $R_6$ and $R_{13}$ are independently H or methyl; $R_7$ and $R_{11}$ are independently H or F; $R_8$ and $R_{10}$ are independently H, or F or $OCH_3$; and $R_9$ is —$OCH_3$, —$OC_2H_5$, —$N(CH_3)_2$, —$CO_2CH_3$, —$OCHF_2$, or $N_3$; and B, D, W, X, Y, and Z are as defined above, provided that when B, D, W, X, Y, or Z is N, then there is no substituent at the N.

In all embodiments of the compounds of Formula Va, it is preferred that one of W, X, Y and Z is N, or two of W, X, Y and Z are N.

Another group of preferred compounds of the present invention are those represented by Formula V with the proviso that both B and D are nitrogen. Specifically such compounds are represented by Formula Vb:

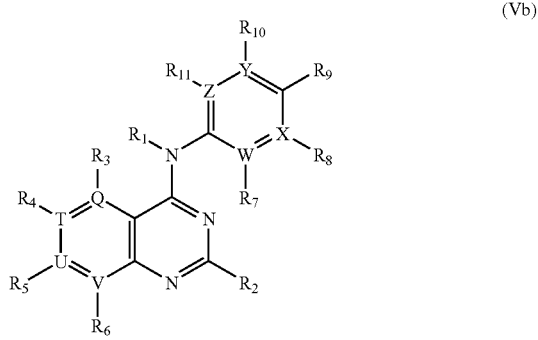

(Vb)

or pharmaceutically acceptable salts or solvates thereof, wherein:

$R_1$ is methyl or ethyl, preferably methyl;

$R_5$ is H, F, Cl, $N_3$, methyl, methoxy or $NH_2$, with the proviso that when $R_5$ is methoxy, $R_1$ is methyl; Preferably $R_5$ is H, F or $N_3$, more preferably H or F, and most preferably H;

$R_2$-$R_4$, and $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle; and Q, T, U, V, W, X, Y and Z are independently C or N, provided that at least one of W, X, Y and Z is N, and wherein when Q, T, U, V, W, X, Y or Z is N, then there is no substituent at the N.

In a specific embodiment, preferably when $R_9$ is H, then at least one of $R_8$ and $R_{10}$ is not H, more preferably $R_9$ is other than H.

In one embodiment of the compounds of Formula Vb, $R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl).

In another embodiment of the compound of Formula V, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In preferred embodiment, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, $R_9$ is selected from the group consisting of H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —N($R^a$)($R^b$) wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

In another embodiment, $R_9$ is —$OCH_3$, —$OC_2H_5$, —$N(CH_3)_2$, —$CO_2CH_3$, —$OCHF_2$, or $N_3$.

In yet another embodiment, when $R_9$ is H, then at least one of $R_8$ and $R_{10}$ is not H. In another embodiment, when $R_9$ is alkyl, then $R_2$ is not H.

In a specific embodiment, compounds of the invention include compounds of Formula Vb or pharmaceutically acceptable salts or solvates thereof, wherein:

$R_1$ is $C_{1-2}$ alkyl, and preferably $R_1$ is methyl;

$R_5$ is H or F, preferably H;

$R_2$-$R_4$, $R_6$, $R_8$-$R_{10}$ are independently H; halo; $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo) $C_{1-3}$ alkoxy, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, $C_2$-$C_4$ alkenyl, $C_2$-$C_4$ alkynyl, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; or —N($R^a$)($R^b$) where $R^a$ and $R^b$ are independently H; OH ($R^a$ and $R^b$ are not both OH); $C_{2-6}$ hydroxyalkyl; $C_{1-6}$ alkyl; or $C_{1-6}$ alkyl substituted with —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together, and/or $R^e$ and $R^f$ together, with the nitrogen atom to which they are linked to form a 3, 4, 5 or 6-membered heterocycle; preferably when $R_9$ is H, at least one of $R_8$ and $R_{10}$ is not H, more preferably $R_9$ is other than H.

$R_7$ and $R_{11}$ are independently H, halo (preferably F or Cl, more preferably F), $C_{1-3}$ alkyl (preferably $CH_3$), or $C_{1-4}$ alkoxy (preferably OCH3); and Q, T, U, V, W, X, Y, and Z are as defined above, provided that when Q, T, U, V, W, X, Y or Z is N there is no substituent at the N.

In another preferred embodiment of the compounds of Formula Vb, $R_1$ is methyl or ethyl, more preferably methyl;

$R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably $H_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$, and $R_6$ are independently H; halo (preferably F or Cl); $N_3$; $C_{1-3}$ alkyl (preferably $CH_3$); $C_{1-3}$ alkoxy (preferably $OCH_3$); or —$N(R^a)(R^b)$ wherein $R^a$ and $R^b$ are independently H, OH, $C_{1-13}$ alkyl, hydroxy-$C_{1-3}$ alkyl, and optionally $R^a$ and $R^b$ together may form a 3, 4, 5 or 6-membered heterocycle (e.g., piperidinyl, pyrrolidinyl, and morpholinyl), and wherein $R^a$ and $R^b$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group: H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —$N(R^a)(R^b)$ wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and Q, T, U, V, W, X, Y, and Z are independently C or N, provided that at least one of W, X, Y, and Z is N, wherein when Q, T, U, V, W, X, Y, or Z is nitrogen, then there is no substituent at the N.

In more preferred embodiment, compounds of the invention include compounds of Formula Vb or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$;

$R_3$ is H, $CH_3$, $OCH_3$, F, or Cl;

$R_4$, and $R_6$ are independently H, $CH_3$, $NH_2$, $N_3$, F, or Cl;

$R_5$ is H;

$R_7$ and $R_{11}$ are independently H, F, or $OCH_3$;

$R_8$ and $R_{10}$ are independently H, F, Cl, or $OCH_3$;

$R_9$ is selected from the group of consisting of H; OH; Cl; $N_3$; $C_{1-3}$ alkyl (preferably methyl or ethyl); $C_{1-3}$ haloalkyl (preferably monofluoromethyl, difluoromethyl, trifluoromethyl); —$OR_{9a}$ where $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —$N(R^a)(R^b)$ wherein $R^a$ and $R^b$ are independently H or $C_{1-3}$ alkyl; and —$COOR_{9b}$, wherein $R_{9b}$ is $C_{1-3}$ alkyl (preferably methyl or ethyl), and optionally $R_9$ and one of $R_8$ and $R_{10}$ together form a 3, 4, 5, or 6-membered heterocycle; preferably when $R_9$ is H, at least one of $R_8$ and $R_{10}$ is not H, more preferably $R_9$ is other than H; and Q, T, U, V, W, X, Y and Z are as defined above, provided that when Q, T, U, V, W, X, Y or Z is N, then there is no substituent at the N. Preferably in this embodiment, when $R_9$ is alkyl, then $R_2$ is not H.

In an even more preferred embodiment, compounds of the invention include compounds of Formula Vb or pharmaceutically acceptable salts or solvates thereof, wherein $R_1$ is methyl; $R_2$ is H, methyl, Cl, —$CH_2OH$, —$NH_2$, —$NHCH_3$, —$NHCH_2CH_2OH$, —$OCH_3$, —$SCH_3$, or —$CH_2F$; $R_3$ is H, methyl, —$OCH_3$, or Cl; $R_4$ is H, methyl, or $NH_2$; $R_5$ is H; $R_6$ is H or methyl; $R_7$ and $R_{11}$ are independently H or F; $R_8$ and $R_{10}$ are independently H, or F or $OCH_3$; and $R_9$ is —$OCH_3$, —$OC_2H_5$, —$N(CH_3)_2$, —$CO_2CH_3$, —$OCHF_2$, or $N_3$; and Q, T, U, V, W, X, Y, and Z are as defined above, provided that when Q, T, U, V, W, X, Y, or Z is N, then there is no substituent at the N.

In all embodiments of the compounds of Formula Vb, it is preferred that one of W, X, Y and Z is N, or two of W, X, Y and Z are N. In any of the embodiments, preferably one or two of Q, T, U and V are N. For example, Q and V can be both N, and T and U are C.

Another specific group of compounds of Formula V include those represented by Formula Vc:

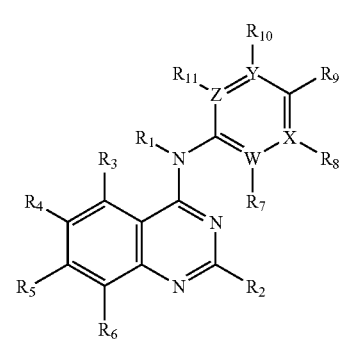

(Vc)

or pharmaceutically acceptable salts or solvates thereof, wherein:

$R_1$ is methyl or ethyl, preferably methyl;

$R_5$ is H, F, Cl, $N_3$, methyl, methoxy or $NH_2$, with the proviso that when $R_5$ is methoxy, $R_1$ is methyl; preferably $R_5$ is H, F or $N_3$, more preferably H or F, and most preferably H;

$R_2$-$R_4$, and $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N $(R^a)(R^b)$, —$C(O)N(R^a)(R^b)$, $N(R^a)(R^b)$—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$, groups together form a 3, 4, 5 or 6-membered carbocycle or heterocycle; and W, X, Y and Z are independently C or N, provided that at least one of W, X, Y and Z is N, and wherein when W, X, Y or Z is N, then there is no substituent at the N.

In a specific embodiment, preferably when $R_9$ is H, then at least one of $R_8$ and $R_{10}$ is not H, more preferably $R_9$ is other than H.

In one embodiment of the compounds of Formula Vc, $R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl).

In another embodiment of the compound of Formula Vc, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In preferred embodiment, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, $R_9$ is selected from the group consisting of H; OH; Cl; $N_3$; $C_{1-3}$ alkyl (preferably methyl or ethyl) or $C_{1-3}$ haloalkyl (preferably monofluoromethyl, difluoromethyl, trifluoromethyl); —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —N($R^a$)($R^b$) wherein $R^a$ and $R^b$ are independently H or $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle.

In another embodiment, $R_9$ is —$OCH_3$, —$OC_2H_5$, —$N(CH_3)_2$, —$CO_2CH_3$, —$OCHF_2$, or $N_3$.

In yet another embodiment, when $R_9$ is H, then at least one of $R_8$ and $R_{10}$ is not H. In another embodiment, when $R_9$ is alkyl, then $R_2$ is not H.

In a specific embodiment, compounds of the invention include compounds of Formula Vc or pharmaceutically acceptable salts or solvates thereof, wherein:
$R_1$ is $C_{1-2}$ alkyl, and preferably $R_1$ is methyl;
$R_5$ is H or F, preferably H;
$R_2$-$R_4$, $R_6$, $R_8$-$R_{10}$ are independently H; halo; $N_3$;
$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo) $C_{1-3}$ alkoxy, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, $C_2$-$C_4$ alkenyl, $C_2$-$C_4$ alkynyl, —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle;

—($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle; or —N($R^a$)($R^b$) where $R^a$ and $R^b$ are independently H; OH ($R^a$ and $R^b$ are not both OH); $C_{2-6}$ hydroxyalkyl; $C_{1-6}$ alkyl; or $C_{1-6}$ alkyl substituted with —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together, and/or $R^e$ and $R^f$ together, with the nitrogen atom to which they are linked form a 3, 4, 5 or 6-membered heterocycle;

—($C_{0-3}$ alkyl)C(O)N($R^a$)($R^b$) wherein $R^a$ and $R^b$ are independently $C_{1-3}$ alkyl, $C_{2-3}$ hydroxyalkyl or $C_{1-3}$ haloalkyl; preferably when $R_9$ is H, then at least one of $R_8$ and $R_{10}$ is not H, more preferably $R_9$ is other than H;

$R_7$ and $R_{11}$ are independently H, halo (preferably F or Cl, more preferably F), $C_{1-3}$ alkyl (preferably $CH_3$), or $C_{1-4}$ alkoxy (preferably $OCH_3$); and W, X, Y, and Z are as defined above, provided that when W, X, Y or Z is N there is no substituent at the N.

In another preferred embodiment of the compounds of Formula Vc,
$R_1$ is methyl or ethyl, more preferably methyl;
$R_2$ is H; halo; $N_3$;
$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together may form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$, $R_6$ are independently H; halo (preferably F or Cl); $N_3$; $C_{1-3}$ alkyl (preferably $CH_3$); $C_{1-3}$ alkoxy (preferably $OCH_3$); or $-N(R^a)(R^b)$ wherein $R^a$ and $R^b$ are independently H, OH, $C_{1-3}$ alkyl, (hydroxy)$C_{1-3}$ alkyl, and optionally $R^a$ and $R^b$ together may form a 3, 4, 5 or 6-membered heterocycle (e.g., piperidinyl, pyrrolidinyl, and morpholinyl), and wherein $R^a$ and $R^b$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group: H; OH; Cl; $N_3$; $C_{1-3}$ alkyl (preferably methyl or ethyl) or $C_{1-3}$ haloalkyl (preferably monofluoromethyl, difluoromethyl, trifluoromethyl); $-OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); $-N(R^a)(R^b)$ wherein $R^a$ and $R^b$ are independently H or $C_{1-3}$ alkyl; $-C_{0-3}$ alkyl)$COOR_{9b}$, wherein $R_{9b}$ is $C_{1-3}$ alkyl (preferably methyl or ethyl); or $-C_{0-3}$ alkyl)$C(O)N(R^a)(R^b)$ wherein $R^a$ and $R^b$ are independently $C_{1-3}$ alkyl; and optionally $R_9$ and one of $R_8$ and $R_{10}$ together form a 3, 4, 5, or 6-membered heterocycle; preferably when $R_9$ is H, then at least one of $R_8$ and $R_{10}$ is not H, more preferably $R_9$ is other than H; and W, X, Y, and Z are independently C or N, provided that at least one of W, X, Y, and Z is N, wherein when W, X, Y, or Z is nitrogen, then there is no substituent at the N.

In more preferred embodiment, compounds of the invention include compounds of Formula Vc or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, $-NHCH_2CH_2OH$, $NHCH_3$, $N(CH_3)_2$, $N_3$, morpholino, $OCH_3$, $OC_2H_5$, or $SCH_3$;

$R_3$ is H, $CH_3$, $OCH_3$, F, or Cl;

$R_4$ and $R_6$ are independently H, $CH_3$, $NH_2$, $N_3$, F, or Cl;

$R_5$ is H;

$R_7$ and $R_{11}$ are independently H, F, or $OCH_3$;

$R_8$ and $R_{10}$ are independently H, F, Cl, or $OCH_3$;

$R_9$ is selected from the group of consisting of H; OH; Cl; $N_3$; $C_{1-3}$ alkyl (preferably methyl or ethyl); $C_{1-3}$ haloalkyl (preferably monofluoromethyl, difluoromethyl, trifluoromethyl); $-OR_{9a}$ where $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); $-N(R^a)(R^b)$ wherein $R^a$ and $R^b$ are independently H or $C_{1-3}$ alkyl; and $-COOR_{9b}$, wherein $R_{9b}$ is $C_{1-3}$ alkyl (preferably methyl or ethyl), and optionally $R_9$ and one of $R_8$ and $R_{10}$ together form a 3, 4, 5, or 6-membered heterocycle; preferably when $R_9$ is H, then at least one of $R_8$ and $R_{10}$ is not H, more preferably $R_9$ is other than H; and W, X, Y and Z are as defined above, provided that when W, X, Y or Z is N, then there is no substituent at the N. Preferably in this embodiment, when $R_9$ is alkyl, $R_2$ not H.

In a even more preferred embodiment, compounds of the invention include compounds of Formula Vc or pharmaceutically acceptable salts or solvates thereof, wherein $R_1$ is methyl; $R_2$ is H, methyl, Cl, $-CH_2OH$, $-NH_2$, $-NHCH_3$, $-NHCH_2CH_2OH$, $-OCH_3$, $-SCH_3$, or $-CH_2F$; $R_3$ and $R_{12}$ are independently H, methyl, $-OCH_3$, or Cl; $R_4$ is H, methyl, or $NH_2$; $R_5$ is H; $R_6$ and $R_{13}$ are independently H or methyl; $R_7$ and $R_{11}$ are independently H or F; $R_5$ and $R_{10}$ are independently H, or F or $OCH_3$; and $R_9$ is $-OCH_3$, $-OC_2H_5$, $-N(CH_3)_2$, $-CO_2CH_3$, $-OCHF_2$, or $N_3$; and W, X, Y, and Z are as defined above, provided that when W, X, Y, or Z is N, then there is no substituent at the N.

In all embodiments of the compounds of Formula Vc, it is preferred that one of W, X, Y and Z is N, or two of W, X, Y and Z are N.

Other preferred compounds of the present invention are those represented by Formula VI:

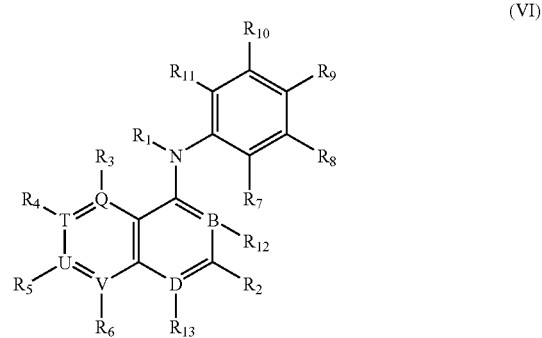

(VI)

or pharmaceutically acceptable salts or solvates thereof, wherein:

$R_1$ is methyl or ethyl, preferably methyl;

$R_5$ is H or F, preferably H;

$R_2$-$R_4$, and $R_6$-$R_{13}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $-C_{1-6}$ alkyl-C(O)O—$C_{1-6}$ alkyl, $-C(O)O-C_{1-6}$ alkyl, $C_{1-6}$ alkyl-C(O)O—$C_{1-6}$ alkyl-, $C_{1-6}$ acylamido, $-N(R^a)(R^b)$, $-C_{1-6}$ alkyl-C(O)N$(R^a)(R^b)$, $-C(O)N(R^a)(R^b)$, $N(R^a)(R^b)-C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $C_{1-6}$ alkyl-C(O)O—$C_{1-6}$ alkyl, $-C(O)O-C_{1-6}$ alkyl, $C_{1-6}$ alkyl-C(O)O—$C_{1-6}$ alkyl-, $C_{1-6}$ acylamido, $-N(R^a)(R^b)$, $-C_{1-6}$ alkyl-C(O)N$(R^a)(R^b)$, $-C(O)N(R^a)(R^b)$, $N(R^a)(R^b)-C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked to form a 3, 4, 5 or 6-membered heterocycle, wherein optionally any two adjacent $R_7$-$R_{11}$ groups together form a 3, 4, 5 or 6-membered carbocycle or heterocycle; and B, D, Q, T, U and V are independently C or N, provided that at least one of B and D is N, and when B, D, Q, T, U or V is N, then there is no substituent at the N;

wherein when Q, T, U and V are all C, then $R_9$ is not carboxyalkoxy or an ester thereof (preferably $R_9$ is not —O($C_{1-6}$ alkyl)C(O)O($C_{1-6}$ alkyl); wherein when $R_9$ is H then at least one of $R_8$ and $R_{10}$ is not H or halo or alkyl; and wherein when $R_9$ is alkyl, then $R_2$ is not aryl.

In one embodiment, compounds of the invention include compounds of Formula VI or pharmaceutically acceptable salts or solvates thereof, wherein:

$R_1$ is methyl or ethyl, preferably methyl;

$R_5$ is H or F, preferably H;

$R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked to form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, Cl 6 alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), $C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$, groups together form a 3, 4, 5 or 6-membered carbocycle or heterocycle; exactly one of B and D is N; and Q, T, U and V are independently C or N, wherein at least one of Q, T, U and V is N, and when Q, T, U or V is N there is no substituent at the N, provided that when $R_9$ is H then $R_2$ is not optionally substituted aryl or heteroaryl. Preferably, $R_8$ and $R_{10}$ are not both H, or one H and the other alkyl. Preferably when $R_9$ is H then at least one of $R_8$ and $R_{10}$ is not H or alkyl. More preferably, when $R_9$ is H then at least one of $R_8$ and $R_{10}$ is not H, alkyl, or halo.

In one embodiment, $R_9$ is selected from the group consisting of H, OH, $C_1$, $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo)$C_{1-3}$ alkoxy, —N($R^a$)($R^b$) where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked to form a 3, 4, 5 or 6-membered heterocycle;

—XR$^c$ wherein X is S or O and R$^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;

—($C_{0-3}$ alkyl)CO$_2$R$^d$, wherein R$^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they both are linked form a 3, 4, 5 or 6-membered heterocycle;

—N($R^a$)($R^b$) where $R^a$ and $R^b$ are independently H, OH ($R^a$ and $R^b$ are not both OH), $C_{2-4}$ hydroxyalkyl, $C_{1-3}$ alkyl, or $C_{1-3}$ alkyl substituted with —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle; or —$C_{0-3}$ alkyl)C(O)N($R^a$)($R^b$) where $R^a$ and $R^b$ are independently H or $C_{1-3}$ alkyl; and optionally $R_9$ and one of $R_8$ and $R_{10}$ together form a 3, 4, 5, or 6-membered heterocycle; preferably $R_9$ is selected from the group outlined above except $R_9$ is not H and $C_{1-6}$alkyl.

In another embodiment, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —OR$_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$); —N($R^a$)($R^b$) where $R^a$ and $R^b$ are independently $C_{1-3}$ alkyl; or —COOR$_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle; preferably $R_9$ is selected from the group outlined above except $R_9$ is not H or $C_{1-3}$alkyl.

In a preferred embodiment, $R_9$ is $N_3$, —OR$_{9a}$ wherein $R_{9a}$ is $C_{1-3}$ alkyl optionally substituted with 1-7 F, —N($R^a$)($R^b$) where $R^a$ and $R^b$ are independently $C_{1-3}$ alkyl, —COOR$_{9b}$ where $R_{9b}$ is $C_{1-3}$ alkyl.

In a more preferred embodiment, $R_9$ is —OCH$_3$, —OC$_2$H$_5$, —N(CH$_3$)$_2$, —CO$_2$CH$_3$, —OCHF$_2$, or $N_3$.

In the various embodiments of the compounds according to Formula VI preferably when $R_9$ is H, $R_8$ or $R_{10}$ or both are independently OH; Cl; $N_3$; —XR$_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$) or —N($R^a$)($R^b$) where $R^a$ and $R^b$ are independently $C_{1-3}$ alkyl; or —COOR$_{9b}$, wherein $R_{9b}$ is $C_{1-3}$ alkyl (preferably methyl or ethyl). More preferably, when $R_9$ is H, $R_8$ or $R_{10}$ or both are independently $N_3$, —OR$_{9a}$, wherein $R_{9a}$ is $C_{1-4}$ alkyl or $C_{1-3}$ haloalkyl; —N($R^a$)($R^b$) where $R^a$ and $R^b$ are independently $C_{1-3}$ alkyl; or —COOR$_{9b}$, wherein $R_{9b}$ is $C_{1-3}$ alkyl (preferably methyl or ethyl). Even more preferably when $R_9$ is H, $R_5$ or $R_{10}$ or both are $C_{1-3}$ alkoxy or $C_{1-3}$ haloalkoxy.

Also preferably in the various embodiments, when $R_9$ is H then $R_2$ is not H, and preferably $R_2$ is halo; $C_{1-3}$ alkyl optionally substituted with OH or halo (preferably F, e.g., monofluoro, difluoro, or trifluoro); —XR$_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —N($R^a$)($R^b$) wherein $R^a$ and Rb are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —NHCH$_2$CH$_2$OH, NHCH$_3$, N(CH$_3$)$_2$, $N_3$, morpholino, OCH$_3$, OC$_2$H$_5$, or SCH$_3$.

Also preferably, when $R_9$ is $C_{1-6}$ alkyl or $C_{1-6}$ haloalkyl, $R_2$ is not H, and preferably is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —NHCH$_2$CH$_2$OH, NHCH$_3$, N(CH$_3$)$_2$, $N_3$, morpholino, OCH$_3$, OC$_2$H$_5$, or SCH$_3$.

In one embodiment, $R_2$ is H; halo; $N_3$; $C_{1-6}$ alkyl (preferably $C_{1-3}$ alkyl, more preferably $CH_3$) optionally substituted with OH or halo (preferably F, e.g., monofluoro, difluoro, or trifluoro); —XR$_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted); —$CO_2R^d$, wherein $R^d$ is $C_{1-3}$ alkyl, preferably methyl or ethyl; or —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably $CH_2CH_2OH$), and wherein optionally $R^a$ and $R^b$ together with the N they are both linked to may form a 3, 4, 5 or 6-membered heterocycle.

In a preferred embodiment, $R_2$ is H; halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl.

In preferred embodiments, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In more preferred embodiments, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In all embodiments of the compound of Formula VI, it is preferred that one or two of Q, T, U and V are N. For example Q and V are N and T and U are C.

In one embodiment, compounds of the invention include compounds of Formula VI or pharmaceutically acceptable salts or solvates thereof, wherein:

$R_1$ is methyl or ethyl, preferably methyl;
$R_2$ is H; halo; $N_3$;
  $C_{1-6}$ alkyl (preferably $C_{1-3}$ alkyl, more preferably $CH_3$) optionally substituted with OH or halo (preferably F, e.g., monofluoro, difluoro, or trifluoro);
  —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
  —$CO_2R^d$, wherein $R^d$ is $C_{1-3}$ alkyl, preferably methyl or ethyl; or
  —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together with the N they are both linked to may form a 3, 4, 5 or 6-membered heterocycle (e.g., piperidinyl, pyrrolidinyl, and morpholinyl);
$R_3$ is H; halo; $C_{1-3}$ alkyl; or $C_{1-3}$ alkoxy;
$R_4$ and $R_6$ are independently H; halo (preferably F or Cl); $N_3$; $C_{1-6}$ alkyl (preferably $C_{1-3}$, more preferably $CH_3$); $C_{1-3}$ alkoxy (preferably $OCH_3$); or —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$) or $C_{2-3}$ hydroxyalkyl (preferably —$CH_2CH_2OH$), wherein $R_{2b}$ and $R_{2c}$ together with the N they are both linked to may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;
$R_5$ is H or F, preferably H;
$R_7$ and $R_{11}$ are independently H; halo (preferably F or Cl, more preferably F); $CH_3$; or $OCH_3$;
$R_8$ and $R_{10}$ are independently H; halo (preferably F or Cl, more preferably Cl); OH; $N_3$; $C_{1-3}$ alkyl (preferably $CH_3$); $C_{1-3}$ alkoxy (preferably $OCH_3$); $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl);
$R_9$ is selected from the group consisting of H, OH, $C_1$, $N_3$;
  $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo)$C_{1-3}$ alkoxy, —$N(R^a)(R^b)$ where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked form a 3, 4, 5 or 6-membered heterocycle;
  —$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;
  —($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —$N(R^a)(R^b)$ where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they both are linked form a 3, 4, 5 or 6-membered heterocycle;
  —$N(R^a)(R^b)$ where $R^a$ and $R^b$ are independently H, OH ($R^a$ and $R^b$ are not both OH), $C_{2-4}$ hydroxyalkyl, $C_{1-3}$ alkyl, or $C_{1-3}$ alkyl substituted with —$N(R^e)(R^f)$ where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle; or
  —$C_{0-3}$ alkyl)$C(O)N(R^a)(R^b)$ where $R^a$ and $R^b$ are independently H or $C_{1-3}$ alkyl; and optionally $R_9$ and one of $R_8$ and $R_{10}$ together form a 3, 4, 5, or 6-membered heterocycle; provided that when $R_9$ is H, at least one of $R_8$ and $R_{10}$ is not hydrogen or alkyl;
exactly one of B and D is N; and
Q, T, U and V are independently C or N, provided that at least one of Q, T, U and V is N, wherein when Q, T, U or V is N, then there is no substituent at the N. In some specific embodiments, one or two of Q, T, U and V are N.

Preferably when $R_9$ is H, $R_8$ or $R_{10}$ or both are independently OH; Cl; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, $R_{9a}$, wherein $R_{9a}$ is $C_{1-4}$ alkyl or $C_{1-3}$ haloalkyl, or —N($R^a$)($R^b$) where $R^a$ and $R^b$ are independently $C_{1-3}$ alkyl; or —COOR$_{9b}$, wherein R$_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ haloalkoxy.

Also preferably, when $R_9$ is $C_{1-6}$ alkyl or $C_{1-6}$ haloalkyl, $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In another preferred embodiment, compounds of the invention include compounds of Formula VI or pharmaceutically acceptable salts or solvates thereof, wherein:

$R_1$ is methyl or ethyl, and preferably methyl;

$R_2$ is H; halo; $N_3$;
  $C_{1-6}$ alkyl (preferably $C_{1-3}$ alkyl, more preferably $CH_3$) optionally substituted with OH or halo (preferably F, e.g., monofluoro, difluoro, or trifluoro);
  —XR$_{2a}$ wherein X is S or O, and R$_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
  —$CO_2$-R$_{2f}$, wherein R$_{2f}$ is $C_{1-6}$ alkyl (preferably $C_{1-3}$ alkyl, more preferably methyl or ethyl); or
  —N(R$_{2b}$)(R$_{2c}$) wherein R$_{2b}$ and R$_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N(R$_{2d}$)(R$_{2e}$) wherein R$_{2d}$ and R$_{2e}$ are independently H, OH, $C_{1-3}$ alkyl (preferably $CH_3$), or $C_{2-3}$ hydroxyalkyl (preferably —$CH_2CH_2OH$), and wherein optionally R$_{2b}$ and R$_{2c}$ together with the N they are both linked to may form a 3, 4, 5 or 6-membered heterocycle (e.g., piperidinyl, pyrrolidinyl, and morpholinyl), and wherein R$_{2b}$ and R$_{2c}$ are not both OH, R$_{2d}$ and R$_{2e}$ are not both OH;

$R_3$ is H; halo; $C_{1-3}$ alkyl; or $C_{1-3}$ alkoxy;

$R_4$ and $R_6$ are independently H; halo (preferably F or Cl); $N_3$; $C_{1-3}$ alkyl (preferably $CH_3$); $C_{1-3}$ alkoxy (preferably $OCH_3$); or —N(R$_{2b}$)(R$_{2c}$) wherein R$_{2b}$ and R$_{2c}$ are independently H, OH, $CH_3$, or ethyl, and optionally R$_{2b}$ and R$_{2c}$ together with the N they are both linked to may form a 3, 4, 5 or 6-membered heterocycle (e.g., piperidinyl, pyrrolidinyl, and morpholinyl), and wherein R$_{2b}$ and R$_{2c}$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group:
  hydrogen; hydroxy; Cl; $N_3$;
  $C_{1-3}$ alkyl (preferably methyl or ethyl) or $C_{1-3}$ haloalkyl (preferably monofluoromethyl, difluoromethyl, trifluoromethyl);
    —OR$_{9a}$, wherein R$_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);
    —N($R^a$)($R^b$), wherein $R^a$ and $R^b$ are independently H, $C_{1-3}$ alkyl, or halo $C_{1-3}$alkyl; or
    —COOR$_{9b}$, wherein R$_{9b}$ is $C_{1-3}$ alkyl (preferably methyl or ethyl); and optionally $R_9$ and one of $R_8$ and $R_{10}$ together form a 3, 4, 5, or 6-membered carbocycle or heterocycle;

exactly one of B and D is N; and

Q, T, U and V are independently C or N, wherein at least one of Q, T, U and V are N, wherein when Q, T, U or V is N, then the there is no substituent at the N; with the proviso that when $R_9$ is H then $R_8$ and $R_{10}$ are not both H or one H and the other alkyl. Preferably when $R_9$ is H then at least one of $R_8$ or $R_{10}$ is not H or alkyl. More preferably when $R_9$ is H then at least one of $R_8$ or $R_{10}$ is not H, alkyl, or halo.

In some specific embodiments, one or two of Q, T, U and V are N.

Preferably in this embodiment, when $R_9$ is H, $R_8$ or $R_{10}$ or both are independently OH; Cl; $N_3$; $C_{1-3}$ haloalkyl (preferably monofluoromethyl, difluoromethyl, trifluoromethyl); —XR$_{9a}$, where X is O or S, and R$_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$) or —N($R^a$)($R^b$) where $R^a$ and $R^b$ are independently $C_{1-3}$ alkyl; or —COOR$_{9b}$, wherein R$_{9b}$ is $C_{1-3}$ alkyl (preferably methyl or ethyl). More preferably, when $R_9$ is H, $R_8$ or $R_{10}$ or both are independently $N_3$, —OR$_{9a}$, wherein R$_{9a}$ is $C_{1-4}$ alkyl or $C_{1-3}$ haloalkyl, or —N($R^a$)($R^b$) where $R^a$ and $R^b$ are independently $C_{1-3}$ alkyl; or —COOR$_{9b}$, wherein R$_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably, when $R_9$ is $C_{1-6}$ alkyl or $C_{1-6}$ haloalkyl, $R_2$ is not H and preferably $R_2$ is halo; $C_{1-3}$ alkyl optionally substituted with OH or halo (preferably F, e.g., monofluoro, difluoro, or trifluoro); —XR$_{2a}$ wherein X is S or O and R$_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —N($R^a$)($R^b$) wherein $R^a$ and Rb are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VI or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$; $R_3$ is H, $CH_3$, $OCH_3$, F, or Cl; $R_4$ and $R_6$ are independently H, $CH_3$, $NH_2$, $N_3$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
  hydrogen; hydroxy; Cl;
  $C_{1-3}$ alkyl (preferably methyl or ethyl) or $C_{1-3}$ haloalkyl (preferably monofluoromethyl, difluoromethyl, trifluoromethyl);
    —OR$_{9a}$, wherein R$_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); $C_{1-3}$ alkyl substituted amino (preferably —$NHCH_3$ or —$N(CH_3)_2$);

$N_3$; or

- —$COOR_{9b}$, wherein $R_{9b}$ is $C_{1-3}$ alkyl (preferably methyl or ethyl), and optionally $R_8$ and $R_9$ together form a 3, 4, 5, or 6-membered carbocycle or heterocycle;

exactly one of B and D is N; and

Q, T, U and V are independently C or N, and at least one of Q, T, U and V is N, wherein when Q, T, U or V is N, then there is no substituent at the N. In some specific embodiments, one or two of Q, T, U and V are nitrogen.

Preferably in this embodiment, when $R_9$ is H, $R_8$ or $R_{10}$ or both are independently OH; Cl; $N_3$; $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably, when $R_9$ is $C_{1-6}$ alkyl or $C_{1-6}$ haloalkyl, $R_2$ is not H and preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VI or pharmaceutically acceptable salts or solvates thereof, wherein:

$R_1$ is methyl;

$R_2$ is H, methyl, ethyl, Cl, F, fluoromethyl ($CH_2F$, $CHF_2$, $CF_3$), $CH_2OH$, $NH_2$, $NHCH_3$, $N(CH_3)_2$, —$NHCH_2CH_2OH$, $OCH_3$, or $SCH_3$; $R_3$ is H, $CH_3$, $OCH_3$, F, or Cl; $R_4$ and $R_6$ are independently H, $CH_3$, $NH_2$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:

- —$OR_{9a}$, wherein $R_{9a}$ is selected from the group of methyl, ethyl, fluoromethyl (e.g., $CH_2F$, $CHF_2$, $CF_3$), and fluoroethyl;
- —$NHCH_3$;
- —$N(CH_3)_2$;
- $N_3$; and
- —$COOR_{9b}$, wherein $R_{9b}$ is H or methyl or ethyl;

exactly one of B and D is N; and

Q, T, U and V are independently C or N, and at least one of Q, T, U and V is N, wherein when Q, T, U or V is N, then there is no substituent at the N. In some specific embodiments, one or two of Q, T, U and V are nitrogen.

In a more preferred embodiment, compounds of the invention include compounds of Formula VI or pharmaceutically acceptable salts or solvates thereof, wherein:

$R_1$ is $CH_3$;

$R_2$ is H, methyl, Cl, —$CH_2OH$, —$NH_2$, —$NHCH_3$, —$NHCH_2CH_2OH$, —$OCH_3$, —$SCH_3$, or —$CH_2F$;

$R_3$ is H, —$CH_3$, —$OCH_3$, or Cl;

$R_4$ is H, $CH_3$, or $NH_2$;

$R_5$ is H;

$R_6$ is H, or $CH_3$;

$R_7$ and $R_{11}$ are independently H, or F;

$R_8$ and $R_{10}$ are independently H, or F or $OCH_3$;

$R_9$ is —$OCH_3$ or —$OC_2H_5$, —$N(CH_3)_2$, —$CO_2CH_3$, —$OCHF_2$, or $N_3$;

exactly one of B and D is N; and

Q, T, U and V are independently C or N, and at least one of Q, T, U and V is N, wherein when Q, T, U or V is N, then there is no substituent at the N. In some specific embodiments, one or two of Q, T, U and V are nitrogen.

In a more preferred embodiment, the present invention provides compounds of Formula VI or pharmaceutically acceptable salts or solvates thereof, wherein $R_1$ is $CH_3$; $R_2$ is Cl, methyl, or $CH_2F$; $R_3$ is H, $CH_3$, F, or Cl; $R_4$, $R_5$ and $R_6$ are H; $R_7$, $R_8$, $R_{10}$ and $R_{11}$ are independently H or F; $R_9$ is —$OCH_3$ or —$N(CH_3)_2$; and Q, T, U and V are independently C or N, and at least one of Q, T, U and V is N, wherein when Q, T, U or V is N, then there is no substituent at the N. In some specific embodiments, one or two of Q, T, U and V are nitrogen.

In another embodiment, compounds of the invention include compounds of Formula VI or pharmaceutically acceptable salts or solvates thereof, wherein:

$R_1$ is methyl or ethyl, preferably methyl;

$R_5$ is H or F, preferably H; and $R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, (O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), —C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle;

exactly one of B and D is N provided that when B or D is N there is no substituent at the N; and all of Q, T, U, and V are C;

provided that: (1) when $R_9$ is H then $R_8$ and $R_{10}$ are not both H or one H and the other halo; and (2) when $R_9$ is alkyl then $R_2$ is not optionally substituted aryl or heteroaryl. Preferably when $R_9$ is H then $R_8$ and $R_{10}$ are not both H or one H and the other halo or alkyl or haloalkyl.

In one embodiment, $R_9$ is selected from the group consisting of H, $C_1$, $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo) $C_{1-3}$ alkoxy, —$N(R^a)(R^b)$ where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;

—$(C_{0-3}$ alkyl)$CO_2R^d$, wherein $R^d$ is an $C_{1-6}$ alkyl, preferably $C_{1-3}$ alkyl;

—$N(R^a)(R^b)$ where $R^a$ and $R^b$ are independently H, OH ($R^a$ and $R^b$ are not both OH), $C_{2-4}$ hydroxyalkyl, $C_{1-3}$ alkyl, or —$N(R^e)(R^f)$ where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle; or —$C_{0-3}$ alkyl)$C(O)N(R^a)(R^b)$ where $R^a$ and $R^b$ are independently H or $C_{1-3}$ alkyl; and optionally $R_9$ and one of $R_8$ and $R_{10}$ together form a 3, 4, 5, or 6-membered heterocycle. Preferably $R_9$ is selected from such groups except $R_9$ is not H or chloro.

In another embodiment, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —$OR_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle. Preferably $R_9$ is selected from such groups except $R_9$ is not H or chloro.

In a preferred embodiment, $R_9$ is $N_3$; $OR_{9a}$, wherein $R_{9a}$ is $C_{1-3}$ alkyl optionally substituted with 1-7 F; —$N(R^a)(R^b)$ where $R^a$ and $R^b$ are independently $C_{1-3}$ alkyl; or —$COOR_{9b}$ where $R_{9b}$ is $C_{1-3}$ alkyl.

In more preferred embodiment, $R_9$ is —$OCH_3$, —$OC_2H_5$, —$N(CH_3)_2$, —$CO_2CH_3$, $OCHF_2$, or $N_3$.

Preferably when $R_9$ is H, $R_8$ or $R_{10}$ or both are independently OH; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably in the various embodiments, when $R_9$ is H, $R_8$ and $R_{10}$ are not H or one H and the other halo, and $R_2$ is not H, and preferably $R_2$ is halo; $N_3$, $C_{1-3}$ alkyl optionally substituted with OH or halo (preferably F, e.g., monofluoro-, difluoro-, or trifluoro); —$XR_{2a}$ wherein X is S or O and $R_{2a}$ is $C_{1-3}$ alkyl (more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, when $R_9$ is $C_{1-6}$ alkyl, halo, or $C_{1-6}$ haloalkyl, $R_2$ is not H, and preferably $R_2$ is halo; $N_3$, $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In one embodiment, $R_2$ is H; halo; $N_3$; $C_{1-6}$ alkyl (preferably $C_{1-3}$ alkyl, more preferably $CH_3$) optionally substituted with OH or halo (preferably F, e.g., monofluoro, difluoro, or trifluoro); —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted); —$CO_2R^d$, wherein $R^d$ is $C_{1-3}$ alkyl, preferably methyl or ethyl; or —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together with the nitrogen they both are linked to may form a 3, 4, 5 or 6-membered heterocycle.

In a preferred embodiment, $R_2$ is H; halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl.

In preferred embodiments, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In more preferred embodiments, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, compounds of the invention include compounds of Formula VI or pharmaceutically acceptable salts or solvates thereof, wherein:

$R_1$ is methyl or ethyl, preferably methyl;

$R_2$ is H; halo; $N_3$;
  $C_{1-6}$ alkyl (preferably $C_{1-3}$ alkyl, more preferably $CH_3$) optionally substituted with OH or halo (preferably F, e.g., monofluoro, difluoro, or trifluoro);
  —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
  —$CO_2R^d$, wherein $R^d$ is $C_{1-3}$ alkyl, preferably methyl or ethyl; or
  —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —CH$_2$CH$_2$OH), and wherein optionally R$^a$ and R$^b$ together may form a 3, 4, 5 or 6-membered heterocycle (e.g., piperidinyl, pyrrolidinyl, and morpholinyl);

R$_3$ is H; halo; C$_{1-3}$ alkyl; or C$_{1-3}$ alkoxy;

R$_4$ and R$_6$ are independently H; halo (preferably F or Cl); N$_3$; C$_{1-6}$ alkyl (preferably C$_{1-3}$, more preferably CH$_3$); C$_{1-3}$ alkoxy (preferably OCH$_3$); or —N(R$_{2b}$)(R$_{2c}$) wherein R$_{2b}$ and R$_{2c}$ are independently H, OH, C$_{1-6}$ alkyl (preferably C$_{1-3}$ alkyl, more preferably CH$_3$), C$_{1-6}$ hydroxyalkyl (preferably C$_{2-3}$ hydroxyalkyl, more preferably —CH$_2$CH2OH), or C$_{1-6}$ alkyl (preferably C$_{1-3}$ alkyl, more preferably CH$_3$) that is optionally substituted with —N(R$_{2d}$)(R$_{2e}$) wherein R$_{2d}$ and R$_{2e}$ are independently H, OH, C$_{1-3}$ alkyl (preferably CH$_3$) or C$_{2-3}$ hydroxyalkyl (preferably —CH$_2$CH2OH), wherein R$_{2b}$ and R$_{2c}$ together may form a 3, 4, 5 or 6-membered heterocycle (e.g., piperidinyl, pyrrolidinyl, and morpholinyl), and wherein R$_{2b}$ and R$_{2c}$ are not both OH, R$_{2d}$ and R$_{2e}$ are not both OH;

R$_5$ is H or F, preferably H;

R$_7$ and R$_{11}$ are independently H; halo (preferably F or Cl, more preferably F); CH$_3$; or OCH$_3$;

R$_8$ and R$_{10}$ are independently H; halo (preferably F or Cl, more preferably Cl); OH; N$_3$; C$_{1-3}$ alkyl (preferably CH$_3$); C$_{1-3}$ alkoxy (preferably OCH$_3$); C$_{1-3}$ haloalkyl (preferably monofluoromethyl, difluoromethyl, trifluoromethyl); —XR$_{9a}$, where X is O or S, and R$_{9a}$ is C$_{1-4}$ alkyl or C$_{1-3}$ haloalkyl (e.g., fluoroalkyl, preferably fluoromethyl, i.e., CH$_2$F, CHF$_2$, CF$_3$); —NH(R$^a$) or —N(R$^a$)(R$^e$) where R$^a$ and R$^b$ are independently C$_{1-3}$ alkyl; or —COOR$_{9b}$, wherein R$_{9b}$ is C$_{1-3}$ alkyl (preferably methyl or ethyl). and R$_9$ is H; OH; N$_3$; halo;

C$_{1-3}$ alkyl (preferably methyl or ethyl) or C$_{1-3}$ haloalkyl (preferably monofluoromethyl, difluoromethyl, trifluoromethyl);

—(C$_{0-3}$ alkyl)C(O)N(R$^a$)(R$^b$) where R$^a$ and R$^b$ are independently H, C$_{2-4}$ hydroxyalkyl, C$_{1-3}$ alkyl, or C$_{1-3}$ alkyl optionally substituted with —N(R$^e$)(R$^f$) where R$^e$ and R$^f$ are independently H, OH (R$^a$ and R$^b$ are not both OH), or C$_{1-3}$ alkyl; wherein optionally R$^a$ and R$^b$ together with the N form a 3, 4, 5 or 6-membered heterocycle, and optionally R$^e$ and R$^f$ together with the nitrogen atom to which they both are linked form a 3, 4, 5 or 6-membered heterocycle;

—CO$_2$-R$_{2f}$, wherein R$_{2f}$ is an optionally substituted C$_{1-6}$ alkyl (preferably C$_{1-3}$ alkyl, more preferably methyl or ethyl), the alkyl may be optionally substituted with OH, halo, C$_{1-3}$ alkoxy, amino, and C$_{1-3}$ alkylamino;

—XR$_{2a}$ wherein X is S or O and R$_{2a}$ is C$_{1-6}$ alkyl (preferably C$_{1-3}$ alkyl, more preferably CH$_3$) optionally substituted with a moiety selected from the group OH, halo, C$_{1-3}$ alkoxy, amino, and C$_{1-3}$ alkylamino; or —N(R$_{2b}$)(R$_{2c}$) wherein R$_{2b}$ and R$_{2c}$ are independently H, OH, C$_{1-6}$ alkyl (preferably C$_{1-3}$ alkyl, more preferably CH$_3$), C$_{1-6}$ haloalkyl, C$_{1-6}$ hydroxyalkyl (preferably C$_{2-3}$ hydroxyalkyl, more preferably —CH$_2$CH$_2$OH), or C$_{1-6}$ alkyl (preferably C$_{1-3}$ alkyl, more preferably CH$_3$) that is optionally substituted with —N(R$_{2d}$)(R$_{2e}$) wherein R$_{2d}$ and R$_{2e}$ are independently H, OH, C$_{1-3}$ alkyl (preferably CH$_3$) or C$_{2-3}$ hydroxyalkyl (preferably —CH$_2$CH$_2$OH), wherein optionally R$_{2b}$ and R$_{2c}$ together with the nitrogen they both are linked to may form a 3, 4, 5 or 6-membered heterocycle (e.g., piperidinyl, pyrrolidinyl, and morpholinyl), and wherein R$_{2b}$ and R$_{2c}$ are not both OH, R$_{2d}$ and R$_{2e}$ are not both OH; optionally, R$_9$ and one of R$_8$ and R$_{10}$ together form a 3, 4, 5 or 6-membered carbocycle or heterocycle;

exactly one of B and D is N provided that when B or D is N there is no substituent at the N; and all of Q, T, U, and V are C;

provided that when R$_9$ is H then R$_8$ and R$_{10}$ are not both H or one H and the other halo.

Preferably when R$_9$ is H, R$_8$ or R$_{10}$ or both are independently OH; N$_3$; —XR$_{9a}$, where X is O or S, and R$_{9a}$ is C$_{1-4}$ alkyl or C$_{1-3}$ haloalkyl (e.g., fluoroalkyl, preferably fluoromethyl, i.e., CH$_2$F, CHF$_2$, CF$_3$); —NH(R$^a$) or —N(R$^a$)(R$^b$) where R$^a$ and R$^b$ are independently C$_{1-3}$ alkyl; or —COOR$_{9b}$, wherein R$_{9b}$ is C$_{1-3}$ alkyl (preferably methyl or ethyl). More preferably, when R$_9$ is H, R$_8$ or R$_{10}$ or both are independently N$_3$, —OR$_{9a}$, wherein R$_{9a}$ is C$_{1-4}$ alkyl or C$_{1-3}$ haloalkyl, or —N(R$^a$)(R$^b$) where R$^a$ and R$^b$ are independently C$_{1-3}$ alkyl; or —COOR$_{9b}$, wherein R$_{9b}$ is C$_{1-3}$ alkyl (preferably methyl or ethyl). Even more preferably when R$_9$ is H, R$_8$ or R$_{10}$ or both are C$_{1-3}$ alkoxy or C$_{1-3}$ halo alkoxy.

Also preferably, when R$_9$ is C$_{1-6}$ alkyl, halo, or C$_{1-6}$ haloalkyl, then R$_2$ is not H and preferably R$_2$ is methyl, ethyl, Cl, F, fluoromethyl (CH$_2$F, CHF$_2$, CF$_3$), C$_{1-3}$ hydroxyalkyl (preferably CH$_2$OH or CH$_2$CH$_2$OH), NH$_2$, NH$_2$OH, —NHCH$_2$CH$_2$OH, NHCH$_3$, N(CH$_3$)$_2$, N$_3$, morpholino, OCH$_3$, OC$_2$H$_5$, or SCH$_3$.

In another preferred embodiment, compounds of the invention include compounds of Formula VI or pharmaceutically acceptable salts or solvates thereof, wherein:

R$_1$ is methyl or ethyl, and preferably methyl;

R$_2$ is H; halo; N$_3$;

C$_{1-6}$ alkyl (preferably C$_{1-3}$ alkyl, more preferably CH$_3$) optionally substituted with 1-4 substituents which are independently OH or halo (preferably F, e.g., monofluoro, difluoro, or trifluoro);

—XR$_{2a}$ wherein X is S or O, and R$_{2a}$ is C$_{1-6}$ alkyl (preferably C$_{1-3}$ alkyl, more preferably CH$_3$) optionally substituted with OH or halo (preferably F, e.g., monofluoro-, difluoro-, or trifluoro-substituted);

—CO$_2$-R$_{2f}$, wherein R$_{2f}$ is C$_{1-6}$ (preferably C$_{1-3}$, more preferably methyl or ethyl); or —N(R$_{2b}$)(R$_{2c}$) wherein R$_{2b}$ and R$_{2c}$ are independently H, OH, C$_{1-6}$ alkyl (preferably C$_{1-3}$ alkyl, more preferably CH$_3$), C$_{1-6}$ hydroxyalkyl (preferably C$_{2-3}$ hydroxyalkyl, more preferably —CH$_2$CH2OH), or C$_{1-6}$ alkyl (preferably C$_{1-3}$ alkyl, more preferably CH$_3$) that is optionally substituted with —N(R$_{2d}$)(R$_{2e}$) wherein R$_{2d}$ and R$_{2e}$ are independently H, OH, C$_{1-3}$ alkyl (preferably CH$_3$), or C$_{2-3}$ hydroxyalkyl (preferably —CH$_2$CH$_2$OH), and wherein optionally R$_{2b}$ and R$_{2c}$ together with the nitrogen they both are linked to may form a 3, 4, 5 or 6-membered heterocycle (e.g., piperidinyl, pyrrolidinyl, and morpholinyl), and wherein R$_{2b}$ and R$_{2c}$ are not both OH, R$_{2d}$ and R$_{2e}$ are not both OH;

R$_3$ is H; halo; C$_{1-3}$ alkyl; or C$_{1-3}$ alkoxy;

R$_4$ and R$_6$ are independently H; halo (preferably F or Cl); N$_3$; C$_{1-3}$ alkyl (preferably CH$_3$); C$_{1-3}$ alkoxy (preferably OCH$_3$); or —N(R$_{2b}$)(R$_{2c}$) wherein R$_{2b}$ and R$_{2c}$ are independently H, OH, CH$_3$, and optionally R$_{2b}$ and R$_{2c}$ together with the nitrogen they both are linked to may form a 3, 4, 5 or 6-membered heterocycle (e.g., piperidinyl, pyrrolidinyl, and morpholinyl), and wherein R$_{2b}$ and R$_{2c}$ are not both OH;

R$_5$ is H;

R$_7$ and R$_{11}$ are independently H, halo (preferably F), CH$_3$, or OCH$_3$;

R$_8$ and R$_{10}$ are independently H; halo (preferably F or Cl, more preferably F); C$_{1-3}$ alkyl (preferably CH$_3$); C$_{1-3}$ alkoxy (preferably OCH$_3$); —XR$_{9a}$, where X is O or S, and R$_{9a}$ is C$_{1-4}$ alkyl or C$_{1-3}$ haloalkyl (e.g., fluoroalkyl, preferably fluoromethyl, i.e., $CH_2F$, $CHF_2$, $CF_3$); —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl); and $R_9$ is selected from the group:

hydrogen; hydroxy; $N_3$;

$C_{1-3}$ alkyl (preferably methyl or ethyl) or $C_{1-3}$ haloalkyl (preferably monofluoromethyl, difluoromethyl, trifluoromethyl);

—$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);

—$N(R_{2b})(R_{2c})$ wherein $R_{2b}$ and $R_{2c}$, are independently H, $C_{1-3}$ alkyl, or $C_{1-3}$ haloalkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle;

exactly one of B and D is N provided that when B or D is N there is no substituent at the N; and all of Q, T, U, and V are C;

provided that when $R_9$ is H at least one of $R_8$ and $R_{10}$ is not H or halo, preferably at least one of $R_8$ and $R_{10}$ is not H or halo or $C_{1-3}$ alkyl.

Preferably in this embodiment, when $R_9$ is H, $R_8$ or $R_{10}$ or both are independently —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR^{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably in this embodiment, when $R_9$ is H then $R_8$ and $R_{10}$ are not both H or one H and the other halo, and $R_2$ is not H.

Also preferably, in this embodiment, when $R_9$ is $C_{1-6}$ alkyl, halo, or $C_{1-6}$ haloalkyl, then $R_2$ is not H and preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VI or pharmaceutically acceptable salts or solvates thereof, wherein:

$R_1$ is methyl or ethyl, and preferably methyl;

$R_2$ is H; halo; $N_3$;

$C_{1-6}$ alkyl (preferably $C_{1-3}$ alkyl, more preferably $CH_3$) optionally substituted with 1-4 substituents which are OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$N(R_{2b})(R_{2c})$ wherein $R_{2b}$ and $R_{2c}$ are independently H, OH, $C_{1-6}$ alkyl (preferably $C_{1-3}$ alkyl), $C_{1-6}$ hydroxyalkyl (preferably $C_{2-3}$ hydroxyalkyl, more preferably —$CH_2CH_2OH$), or $R_{2b}$ and $R_{2c}$ together form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$ and $R_6$ are independently H; halo (preferably F or Cl); $N_3$; $C_{1-3}$ alkyl (preferably $CH_3$); $C_{1-3}$ alkoxy (preferably $OCH_3$); or —$N(R_{2b})(R_{2c})$ wherein $R_{2b}$ and $R_{2c}$ are independently H, OH ($R_{2b}$ and $R_{2c}$ are not both OH), $CH_3$, or $R_{2b}$ and $R_{2c}$ together form a 3, 4, 5 or 6-membered heterocycle (e.g., piperidinyl, pyrrolidinyl, and morpholinyl);

$R_5$ is H or F, preferably H;

$R_7$ and $R_{11}$ are independently H, halo (preferably F), $C_{1-3}$ alkyl (preferably $CH_3$), $C_{1-3}$ alkoxy (preferably $OCH_3$), or $C_{1-3}$ alkylthiol; Preferably $R_7$ and $R_{11}$ are independently H, halo or methoxy;

$R_8$ and $R_{10}$ are independently H; halo (preferably F or Cl); $C_{1-3}$ alkyl (preferably $CH_3$); $C_{1-3}$ alkoxy (preferably $OCH_3$) or $C_{1-3}$ alkylthiol; and $R_9$ is selected from the group:

hydrogen; hydroxy; Cl; $N_3$;

$C_{1-3}$ alkyl (preferably methyl or ethyl) or $C_{1-3}$ haloalkyl (preferably monofluoromethyl, difluoromethyl, trifluoromethyl);

—$OR_{9a}$, wherein $R_{12}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);

—$N(R_{2b})(R_{2c})$ wherein $R_{2b}$ and $R_{2c}$ are independently $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle;

exactly one of B and D is N provided that when B or D is N there is no substituent at the N; and all of Q, T, U, and V are C;

provided that when $R_9$ is H at least one of $R_8$ and $R_{10}$ is not H or halo, preferably at least one of $R_8$ and $R_{10}$ is not H or halo or $C_{1-3}$ alkyl.

Preferably in this embodiment, when $R_9$ is H, $R_8$ or $R_{10}$ or both are independently $C_{1-3}$ alkoxy (preferably $OCH_3$) or $C_{1-3}$ alkylthiol, each being optionally substituted with 1-4 F. Even more preferably when $R_9$ is H, $R_8$ or $R_{10}$ or both are methoxy or ethoxy. Also preferably $R_2$ is not H.

Also preferably, when $R_9$ is $C_{1-3}$ alkyl, halo, or $C_{1-3}$ haloalkyl, then $R_2$ is not H, preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VI or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$; $R_3$ is H, $CH_3$, $OCH_3$, F, or Cl; $R_4$ and $R_6$ are independently H, $CH_3$, $NH_2$, $N_3$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
H; OH; $N_3$;
$C_{1-3}$ alkyl (preferably methyl or ethyl) or $C_{1-3}$ haloalkyl (preferably monofluoromethyl, difluoromethyl, trifluoromethyl);
—$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);
—$N(R_{2b})(R_{2c})$ wherein $R_{2b}$ and $R_{2c}$ are independently $C_{1-3}$ alkyl; or
—$COOR_{9b}$, wherein $R_{9b}$ is $C_{1-3}$ alkyl (preferably methyl or ethyl), and optionally $R_8$ and $R_9$ together form a 3, 4, 5, or 6-membered heterocycle;
exactly one of B and D is N provided that when B or D is N there is no substituent at the N; and
all of Q, T, U, and V are C;
provided that when $R_9$ is H, at least one of $R_8$ and $R_{10}$ is $OCH_3$, and when $R_9$ is $C_{1-3}$ alkyl or $C_{1-3}$ haloalkyl or Cl then $R_2$ is Cl or methyl or ethyl.

Preferably in this embodiment, when $R_9$ is H, $R_8$ or $R_{10}$ or both are independently $C_{1-3}$ alkoxy (preferably $OCH_3$) or $C_{1-3}$ alkylthiol, each being optionally substituted with 1-4 F. Even more preferably when $R_9$ is H, $R_8$ or $R_{10}$ or both are methoxy or ethoxy. Also preferably $R_2$ is not H.

Also preferably, when $R_9$ is $C_{1-3}$ alkyl, halo, or $C_{1-3}$ haloalkyl, then $R_2$ is not H, preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VI or pharmaceutically acceptable salts or solvates thereof, wherein:
$R_1$ is $CH_3$;
$R_2$ is H, methyl, ethyl, Cl, F, fluoromethyl ($CH_2F$, $CHF_2$, $CF_3$), $CH_2OH$, $NH_2$, $NHCH_3$, $N(CH_3)_2$, —$NHCH_2CH_2OH$, $OCH_3$, or $SCH_3$; $R_3$ is H, $CH_3$, $OCH_3$, F, or Cl; $R_4$ and $R_6$ are independently H, $CH_3$, $NH_2$, F, or Cl;
$R_5$ is H; $R_7$ and $R_{11}$ are independently H, F, or $OCH_3$; $R_8$ and $R_{10}$ are independently H, F, Cl, or $OCH_3$; and
$R_9$ is selected from the group:
—$OR_{12}$, wherein $R_{12}$ is selected from the group of methyl, ethyl, fluoromethyl (e.g., $CH_2F$, $CHF_2$, $CF_3$), and fluoroethyl;
—$NHCH_3$;
—$N(CH_3)_2$;
—$N_3$; and
—$COOR_{13}$, wherein $R_{13}$ is methyl or ethyl;
exactly one of B and D is N provided that when B or D is N there is no substituent at the N; and
all of Q, T, U, and V are C.

In a more preferred embodiment, compounds of the invention include compounds of Formula VI or pharmaceutically acceptable salts or solvates thereof, wherein:
$R_1$ is $CH_3$;
$R_2$ is H, methyl, Cl, —$CH_2OH$, —$NH_2$, —$NHCH_3$, —$NHCH_2CH_2OH$, —$OCH_3$, —$SCH_3$, or —$CH_2F$;
$R_3$ is H, —$CH_3$, —$OCH_3$, or Cl;
$R_4$ is H, $CH_3$, or $NH_2$;
$R_5$ is H;
$R_6$ is H, or $CH_3$;
$R_7$ and $R_{11}$ are independently H, or F;
$R_8$ and $R_{10}$ are independently H, or F or $OCH_3$; and
$R_9$ is —$OCH_3$ or —$OC_2H_5$, —$N(CH_3)_2$, —$CO_2CH_3$, —$OCHF_2$, or $N_3$;
exactly one of B and D is N provided that when B or D is N there is no substituent at the N; and
all of Q, T, U, and V are C.

In a more preferred embodiment, the present invention provides compounds of Formula VI or pharmaceutically acceptable salts or solvates thereof, wherein $R_1$ is $CH_3$; $R_2$ is Cl, methyl, or $CH_2F$; $R_3$ is H, $CH_3$, F, or Cl; $R_4$, $R_5$ and $R_6$ are H; $R_7$, $R_8$, $R_{10}$ and $R_{11}$ are independently H or F; and $R_9$ is —$OCH_3$ or —$N(CH_3)_2$; exactly one of B and D is N provided that when B or D is N there is no substituent at the N; and all of Q, T, U, and V are C.

Specifically, one group of the compounds of Formula VI are those represented by Formula VIa:

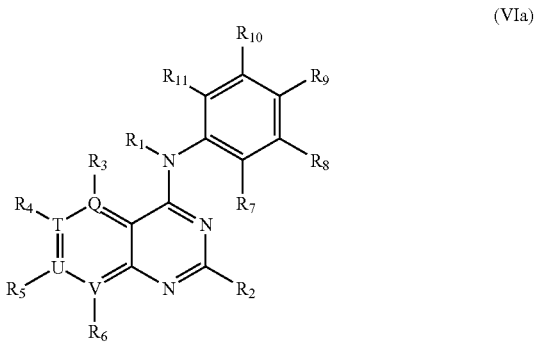

(VIa)

or pharmaceutically acceptable salts or solvates thereof, wherein:
$R_1$ is methyl or ethyl, preferably methyl;
$R_5$ is H or F, preferably H;
$R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), C(O)N($R^a$)($R^b$), N($R^a$)($R^b$)—$C_{1-6}$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked to form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —$N(R^a)(R^b)$, —$C_{1-6}$ alkyl-C(O)N($R^a$)($R^b$), —C(O)N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle; and Q, T, U and V are independently C or N, wherein at least one of Q, T, U and V is N, and when Q, T, U or V is N there is no substituent at the N, provided that when $R_9$ is H then $R_8$ and $R_{10}$ are not both H, or one H and the other alkyl. Preferably when $R_9$ is H then at least one of $R_8$ and $R_{10}$ is not H or alkyl. More preferably, when $R_9$ is H then at least one of $R_8$ and $R_{10}$ is not H, alkyl, or halo.

In one embodiment, $R_9$ is selected from the group consisting of H, OH, $C_1$, $N_3$;

- $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo)$C_{1-3}$ alkoxy, —N($R^a$)($R^b$) where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked to form a 3, 4, 5 or 6-membered heterocycle;
- —$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;
- —($C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —N($R^a$)($R^b$) where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they both are linked form a 3, 4, 5 or 6-membered heterocycle;
- —N($R^a$)($R^b$) where $R^a$ and $R^b$ are independently H, OH ($R^a$ and $R^b$ are not both OH), $C_{2-4}$ hydroxyalkyl, $C_{1-3}$ alkyl, or $C_{1-3}$ alkyl substituted with —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they are both linked form a 3, 4, 5 or 6-membered heterocycle; or
- —$C_{0-3}$ alkyl)C(O)N($R^a$)($R^b$) where $R^a$ and $R^b$ are independently H or $C_{1-3}$ alkyl; and optionally $R_9$ and one of $R_8$ and $R_{10}$ together form a 3, 4, 5, or 6-membered heterocycle; preferably $R_9$ is selected from the group outlined above except $R_9$ is not H and $C_{1-6}$alkyl.

In another embodiment, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —$OR_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$); —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle; preferably $R_9$ is selected from the group outlined above except $R_9$ is not H or $C_{1-3}$alkyl.

In a preferred embodiment, $R_9$ is $N_3$, —$OR_{9a}$ wherein $R_{9a}$ is $C_{1-3}$ alkyl optionally substituted with 1-7 F, —N($R^a$)($R^b$) where $R^a$ and $R^b$ are independently $C_{1-3}$ alkyl, —$COOR_{9b}$ where $R_{9b}$ is $C_{1-3}$ alkyl.

In a more preferred embodiment, $R_9$ is —$OCH_3$, —$OC_2H_5$, —N($CH_3$)$_2$, —$CO_2CH_3$, —$OCHF_2$, or $N_3$.

In the various embodiments of the compounds according to Formula VIa preferably when $R_9$ is H, $R_8$ or $R_{10}$ or both are independently OH; Cl; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —NH($R^a$) or —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl; —N($R^a$)($R^b$) where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ haloalkoxy.

Also preferably in the various embodiments, when $R_9$ is H then $R_2$ is not H, and preferably $R_2$ is halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —N($R^a$)($R^b$) wherein $R^a$ and Rb are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, N($CH_3$)$_2$, $N_3$, morpholino, $OCH_3$, $OC_2H_5$, or $SCH_3$.

Also preferably, when $R_9$ is $C_{1-6}$ alkyl or $C_{1-6}$ haloalkyl, $R_2$ is not H, and preferably is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, N($CH_3$)$_2$, $N_3$, morpholino, $OCH_3$, $OC_2H_5$, or $SCH_3$.

In one embodiment, $R_2$ is H; halo; $N_3$; $C_{1-6}$ alkyl (preferably $C_{1-3}$ alkyl, more preferably $CH_3$) optionally substituted with OH or halo (preferably F, e.g., monofluoro, difluoro, or trifluoro); —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted); —$CO_2R^d$, wherein $R^d$ is $C_{1-3}$ alkyl, preferably methyl or ethyl; or —N($R^a$)($R^b$) wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —N($R^e$)($R^f$) wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH_2OH$), and wherein optionally $R^a$ and $R^b$ together with the N they are both linked to may form a 3, 4, 5 or 6-membered heterocycle.

In a preferred embodiment, $R_2$ is H; halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —N($R^a$)($R^b$) wherein $R^a$ and $R^b$ are independently H, OH ($R^a$ and $R^b$ are not both OH), $C_{1-3}$ alkyl (preferably $CH_3$), $C_{2-3}$ hydroxyalkyl.

In preferred embodiments, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, N($CH_3$)$_2$, $N_3$, morpholino, $OCH_3$, $OC_2H_5$, or $SCH_3$.

In more preferred embodiments, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In all embodiments of the compound of Formula VIa, it is preferred that one or two of Q, T, U and V are N. For example Q and V are N and T and U are C.

In one embodiment, compounds of the invention include compounds of Formula VIa or pharmaceutically acceptable salts or solvates thereof, wherein:

$R_1$ is methyl or ethyl, preferably methyl;

$R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2R^d$, wherein $R^d$ is $C_{1-3}$ alkyl, preferably methyl or ethyl; or

—$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH2OH$), and wherein optionally $R^a$ and $R^b$ together with the N they are both linked to may form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$ and $R_6$ are independently H; halo (preferably F or Cl); $N_3$; $C_{1-6}$ alkyl (preferably $C_{1-3}$, more preferably $CH_3$); $C_{1-3}$ alkoxy (preferably $OCH_3$); or —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$) or $C_{2-3}$ hydroxyalkyl (preferably —$CH_2CH_2OH$), wherein $R_{2b}$ and $R_{2c}$ together with the N they are both linked to may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F, preferably H;

$R_7$ and $R_{11}$ are independently H; halo (preferably F or Cl, more preferably F); $CH_3$; or $OCH_3$;

$R_8$ and $R_{10}$ are independently H; halo (preferably F or Cl, more preferably Cl); OH; $N_3$; $C_{1-3}$ alkyl (preferably $CH_3$); $C_{1-3}$ alkoxy (preferably $OCH_3$); $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl);

$R_9$ is selected from the group consisting of H, OH, $C_1$, $N_3$;

$C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo)$C_{1-3}$ alkoxy, —$N(R^a)(R^b)$ where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked form a 3, 4, 5 or 6-membered heterocycle;

—$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;

—$(C_{0-3}$ alkyl)$CO_2R^d$, wherein $R^d$ is an $C_{1-6}$ alkyl (preferably $C_{1-3}$ alkyl, more preferably methyl or ethyl) optionally substituted with 1, 2 or 3 substituents, each substituent being independently OH, halo, $C_{1-3}$ alkoxy (e.g., fluoroalkoxy), —$N(R^a)(R^b)$ where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they both are linked form a 3, 4, 5 or 6-membered heterocycle;

—$N(R^a)(R^b)$ where $R^a$ and $R^b$ are independently H, OH ($R^a$ and $R^b$ are not both OH), $C_{2-4}$ hydroxyalkyl, $C_{1-3}$ alkyl, or $C_{1-3}$ alkyl substituted with —$N(R^e)(R^f)$ where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle; or —$C_{0-3}$ alkyl)$C(O)N(R^a)(R^b)$ where $R^a$ and $R^b$ are independently H or $C_{1-3}$ alkyl; and optionally $R_9$ and one of $R_8$ and $R_{10}$ together form a 3, 4, 5, or 6-membered heterocycle; provided that when $R_9$ is H, at least one of $R_8$ and $R_{10}$ is not hydrogen or alkyl; and Q, T, U and V are independently C or N, provided that at least one of Q, T, U and V is N, wherein when Q, T, U or V is N, then there is no substituent at the N. In some specific embodiments, one or two of Q, T, U and V are N.

Preferably when $R_9$ is H, $R_8$ or $R_{10}$ or both are independently OH; Cl; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_9$ or $R_{10}$ or both are $C_{1-3}$ alkoxy or $C_{1-3}$ haloalkoxy.

Also preferably, when $R_9$ is $C_{1-6}$ alkyl or $C_{1-6}$ haloalkyl, $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In another preferred embodiment, compounds of the invention include compounds of Formula VIa or pharmaceutically acceptable salts or solvates thereof, wherein:

$R_1$ is methyl or ethyl, and preferably methyl;

$R_2$ is H; halo; $N_3$;

$C_{1-6}$ alkyl (preferably $C_{1-3}$ alkyl, more preferably $CH_3$) optionally substituted with OH or halo (preferably F, e.g., monofluoro, difluoro, or trifluoro);

—$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);

—$CO_2$-$R_{2f}$ wherein $R_{2f}$ is $C_{1-6}$ alkyl (preferably $C_{1-3}$ alkyl, more preferably methyl or ethyl); or —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$), or $C_{2-3}$ hydroxyalkyl (preferably —$CH_2CH_2OH$), and wherein optionally $R_{2b}$ and $R_{2c}$ together with the N they are both linked to may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_3$ is H; halo; $C_{1-3}$ alkyl; or $C_{1-3}$ alkoxy;

$R_4$ and $R_6$ are independently H; halo (preferably F or Cl); $N_3$; $C_{1-3}$ alkyl (preferably $CH_3$); $C_{1-3}$ alkoxy (preferably $OCH_3$); or —$N(R_{2b})(R_{2c})$ wherein $R_{2b}$ and $R_{2c}$ are independently H, OH, $CH_3$, or ethyl, and optionally $R_{2b}$ and $R_{2c}$ together with the N they are both linked to may form a 3, 4, 5 or 6-membered heterocycle (e.g., piperidinyl, pyrrolidinyl, and morpholinyl), and wherein $R_{2b}$ and $R_{2c}$ are not both OH);

$R_5$ is H;

$R_7$ and $R_{11}$, are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); and $R_9$ is selected from the group:
  hydrogen; hydroxy; Cl; $N_3$;
  $C_{1-3}$ alkyl (preferably methyl or ethyl) or $C_{1-3}$ haloalkyl (preferably monofluoromethyl, difluoromethyl, trifluoromethyl);
  $OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); —N(Ra)(Rb), wherein Ra and Rb are independently H, C1-3 alkyl, or halo C1-3alkyl; or
  —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered carbocycle or heterocycle;

Q, T, U and V are independently C or N, wherein at least one of, T, U and V are N, wherein when Q, T, U or V is nitrogen, then the there is no substituent at the N; with the proviso that when $R_9$ is H then $R_8$ and $R_9$ are not both H or one H and the other alkyl. Preferably when $R_9$ is H then at least one of $R_8$ or $R_{10}$ is not H or alkyl. More preferably when $R_9$ is H then at least one of $R_8$ or $R_{10}$ is not H, alkyl, or halo.

In some specific embodiments, one or two of Q, T, U and V are N.

Preferably in this embodiment, when $R_9$ is H, $R_8$ or $R_{10}$ or both are independently OH; Cl; $N_3$; $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably, when $R_9$ is $C_{1-6}$ alkyl or $C_{1-6}$ haloalkyl, $R_2$ is not H and preferably $R_2$ is halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VIa or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$; $R_3$ is H, $CH_3$, $OCH_3$, F, or Cl; $R_4$ and $R_6$ are independently H, $CH_3$, $NH_2$, $N_3$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
  hydrogen; hydroxy; Cl;
  $C_{1-3}$ alkyl (preferably methyl or ethyl) or $C_{1-3}$ haloalkyl (preferably monofluoromethyl, difluoromethyl, trifluoromethyl);
  —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$); $C_{1-3}$ alkyl substituted amino (preferably —$NHCH_3$ or —$N(CH_3)_2$);
  $N_3$; or
  —$COOR_{9b}$, wherein $R_{9b}$ is $C_{1-3}$ alkyl (preferably methyl or ethyl), and optionally $R_8$ and $R_9$ together form a 3, 4, 5, or 6-membered carbocycle or heterocycle; and Q, T, U and V are independently C or N, and at least one of Q, T, U and V is N, wherein when Q, T, U or V is N, then there is no substituent at the N. In some specific embodiments, one or two of Q, T, U and V are nitrogen.

Preferably in this embodiment, when $R_9$ is H, $R_8$ or $R_{10}$ or both are independently OH; Cl; $N_3$; $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably, when $R_9$ is $C_{1-6}$ alkyl or $C_{1-6}$ haloalkyl, $R_2$ is not H and preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VIa or pharmaceutically acceptable salts or solvates thereof, wherein:

$R_1$ is methyl;

$R_2$ is H, methyl, ethyl, Cl, F, fluoromethyl ($CH_2F$, $CHF_2$, $CF_3$), $CH_2OH$, $NH_2$, $NHCH_3$, $N(CH_3)_2$, —$NHCH_2CH_2OH$, $OCH_3$, or $SCH_3$; $R_3$ is H, $CH_3$, $OCH_3$, F, or Cl; $R_4$ and $R_6$ are independently H, $CH_3$, $NH_2$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
- —$OR_{9a}$, wherein $R_{9a}$ is selected from the group of methyl, ethyl, fluoromethyl (e.g., $CH_2F$, $CHF_2$, $CF_3$), and fluoroethyl;
- —$NHCH_3$;
- —$N(CH_3)_2$;
- $N_3$; and
- —$COOR_{9b}$, wherein $R_{9b}$ is H or methyl or ethyl; and Q, T, U and V are independently C or N, and at least one of Q, T, U and V is N, wherein when Q, T, U or V is N, then there is no substituent at the N. In some specific embodiments, one or two of Q, T, U and V are nitrogen.

In a more preferred embodiment, compounds of the invention include compounds of Formula VIa or pharmaceutically acceptable salts or solvates thereof, wherein:
$R_1$ is $CH_3$;
$R_2$ is H, methyl, Cl, —$CH_2OH$, —$NH_2$, —$NHCH_3$, —$NHCH_2CH_2OH$, —$OCH_3$, —$SCH_3$, or —$CH_2F$;
$R_3$ is H, —$CH_3$, —$OCH_3$, or Cl;
$R_4$ is H, $CH_3$, or $NH_2$;
$R_5$ is H;
$R_6$ is H, or $CH_3$;
$R_7$ and $R_{11}$ are independently H, or F;
$R_8$ and $R_{10}$ are independently H, or F or $OCH_3$;
$R_9$ is —$OCH_3$ or —$OC_2H_5$, —$N(CH_3)_2$, —$CO_2CH_3$, —$OCHF_2$, or $N_3$; and Q, T, U and V are independently C or N, and at least one of Q, T, U and V is N, wherein when Q, T, U or V is N, then there is no substituent at the N. In some specific embodiments, one or two of Q, T, U and V are nitrogen.

In a more preferred embodiment, the present invention provides compounds of Formula VIa or pharmaceutically acceptable salts or solvates thereof, wherein $R_1$ is $CH_3$; $R_2$ is Cl, methyl, or $CH_2F$; $R_3$ is H, $CH_3$, F, or Cl; $R_4$, $R_5$ and $R_6$ are H; $R_7$, $R_8$, $R_{10}$ and $R_{11}$ are independently H or F; $R_9$ is —$OCH_3$ or —$N(CH_3)_2$; and Q, T, U and V are independently C or N, and at least one of Q, T, U and V is N, wherein when Q, T, U or V is N, then there is no substituent at the N. In some specific embodiments, one or two of Q, T, U and V are nitrogen.

Other compounds of the invention include those of Formula VIb:

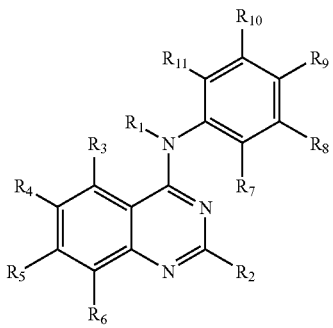

(VIb)

or pharmaceutically acceptable salts, or solvates thereof, wherein:
$R_1$ is methyl or ethyl, preferably methyl;
$R_5$ is H or F, preferably H; and $R_2$-$R_4$, $R_6$-$R_{11}$ are independently H, halo, $N_3$, OH, thiol, nitro, CN, $NH_2$, $C_{1-6}$ alkyl, $C_{2-6}$ alkenyl, $C_{2-6}$ alkynyl, $C_{1-6}$ alkoxy, $C_{1-6}$ alkylthiol, halo-$C_{1-6}$ alkyl, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, —$C_{1-6}$ alkyl-C(O)O—$C_{1-6}$ alkyl, —C(O)O—$C_{1-6}$ alkyl, $C_{1-6}$ alkyl-C(O)O—$C_{1-6}$ alkyl-, $C_{1-6}$ acylamido, —N($R^a$)($R^b$), —C alkyl-C(O)N($R^a$)($R^b$),
—C(O)N($R^a$)($R^b$), N($R^a$)($R^b$)—$C_1$ alkyl-, 3, 4, 5, or 6-membered carbocycle, heterocycle, aryl, or heteroaryl, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 3, 4, 5 or 6-membered heterocycle (e.g., piperidinyl, pyrrolidinyl, and morpholinyl); wherein any of the groups is optionally substituted with 1-3 substituents wherein each substituent is independently halo, $N_3$, OH, thiol, nitro, CN, $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyl-O—, $C_{2-6}$ alkynyl-O—, hydroxy-$C_{1-6}$ alkyl, $C_{1-6}$ alkoxy-$C_{1-6}$ alkyl, $C_{1-6}$ acyl, $C_{1-6}$ acyloxy, $C_{1-6}$ alkyl-C(O)O—$C_{1-6}$ alkyl-, $C_{1-6}$ acylamido, —N($R^a$)($R^b$), —$C_{1-6}$ alkyl-C(O)N($R^a$)($R^b$), —C(O)N($R^a$)($R^b$), N($R^a$)($R^b$)—$C_{1-6}$alkyl-, wherein $R^a$ and $R^b$ are independently H, OH ($R^a$ and $R^b$ are not both OH), $C_{2-6}$ hydroxyalkyl, or $C_{1-6}$ alkyl or $R^a$ and $R^b$ together with the nitrogen atom to which they are both linked form a 3, 4, 5 or 6-membered heterocycle, wherein optionally any two adjacent $R_7$-$R_{11}$ groups together form a 3, 4, 5 or 6-membered carbocycle or heterocycle;

provided that $R_9$ is not —O($C_{1-6}$ alkyl)C(O)O($C_{1-6}$ alkyl), and when $R_9$ is H then $R_8$ and $R_{10}$ are not both H or one H and the other halo. Preferably when $R_9$ is H then $R_5$ and $R_{10}$ are not both H or one H and the other halo or alkyl or haloalkyl.

In one embodiment, $R_9$ is selected from the group consisting of H, $C_1$, $N_3$;
- $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, (halo)$C_{1-3}$ alkoxy, —N($R^a$)($R^b$) where $R^a$ and $R^b$ are independently H, OH ($R^a$ and $R^b$ are not both OH), $C_{2-4}$ hydroxyalkyl, or $C_{1-3}$ alkyl or $R^a$ and $R^b$ together with the nitrogen atom to which they are both linked form a 3, 4, 5 or 6-membered heterocycle;
- —$XR^c$ wherein X is S or O and $R^c$ is $C_{1-6}$ alkyl (preferably $C_{1-3}$ alkyl, more preferably $CH_3$) optionally substituted with 1, 2 or 3 substituents, each substituent being independently OH, halo, $C_{1-3}$ alkoxy, or (halo)$C_{1-3}$ alkoxy;
- —($C_{0-3}$ alkyl)$CO_2R^d$, wherein $R^d$ is an $C_{1-6}$ alkyl, preferably $C_{1-3}$ alkyl;
- —N($R^a$)($R^b$) where $R^a$ and $R^b$ are independently H, OH ($R^a$ and $R^b$ are not both OH), $C_{2-4}$ hydroxyalkyl, $C_{1-3}$ alkyl, or —N($R^e$)($R^f$) where $R^e$ and $R^f$ are independently H, OH ($R^e$ and $R^f$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle; or
- —$C_{0-3}$ alkyl)C(O)N($R^a$)($R^b$) where $R^a$ and $R^b$ are independently H or $C_{1-3}$ alkyl; and optionally $R_9$ and one of $R_8$ and $R_{10}$ together form a 3, 4, 5, or 6-membered heterocycle. Preferably $R_9$ is selected from such groups except $R_9$ is not H or chloro.

In another embodiment, $R_9$ is H; OH; Cl; $N_3$; $C_{1-3}$ alkyl (preferably methyl; $C_{1-3}$ haloalkyl (preferably monofluoromethyl, difluoromethyl, trifluoromethyl); —$OR_{9a}$, wherein $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle. Preferably $R_9$ is selected from such groups except $R_9$ is not H or chloro.

In a preferred embodiment, $R_9$ is $N_3$; —$OR_{9a}$, wherein $R_{9a}$ is $C_{1-3}$ alkyl optionally substituted with 1-7 F; —$N(R^a)(R^b)$ where $R^a$ and $R^b$ are independently $C_{1-3}$ alkyl; or —$COOR_{9b}$ where $R_{9b}$ is $C_{1-3}$ alkyl.

In more preferred embodiment, $R_9$ is —$OCH_3$, —$OC_2H_5$, —$N(CH_3)_2$, —$CO_2CH_3$, —$OCHF_2$, or $N_3$.

Preferably when $R_9$ is H, $R_8$ or $R_{10}$ or both are independently OH; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably in the various embodiments, when $R_9$ is H, $R_8$ and $R_{10}$ are not H or one H and the other halo, and $R_2$ is not H, and preferably $R_2$ is halo; $N_3$, $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, when $R_9$ is $C_{1-6}$ alkyl, halo, or $C_{1-6}$ haloalkyl, $R_2$ is not H, and preferably $R_2$ is halo; $N_3$, $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl. More preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In one embodiment, $R_2$ is H; halo; $N_3$; $C_{1-6}$ alkyl (preferably $C_{1-3}$ alkyl, more preferably $CH_3$) optionally substituted with OH or halo (preferably F, e.g., monofluoro, difluoro, or trifluoro); —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted); —$CO_2R^d$, wherein $R^d$ is $C_{1-3}$ alkyl, preferably methyl or ethyl; or —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxy-alkyl (preferably —$CH_2CH2OH$), and wherein optionally $R^a$ and $R^b$ together with the nitrogen they both are linked to may form a 3, 4, 5 or 6-membered heterocycle.

In a preferred embodiment, $R_2$ is H; halo; $C_{1-3}$ alkyl optionally substituted with OH or halo (preferably F, e.g., monofluoro, difluoro, or trifluoro); —$XR_{2a}$ wherein X is S or O and $R_{2a}$ is $C_{1-3}$ alkyl (preferably $C_{1-3}$ alkyl, more preferably $CH_3$) optionally substituted with halo (preferably F, e.g., monofluoro-, difluoro-, or trifluoro-substituted); or —$N(R^a)(R^b)$ wherein $R^a$ and $R^b$ are independently H, OH ($R^a$ and $R^b$ are not both OH), $C_{1-3}$ alkyl (preferably $CH_3$), $C_{2-3}$ hydroxyalkyl.

In preferred embodiments, $R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In more preferred embodiments, $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

In one embodiment, compounds of the invention include compounds of Formula VIb or pharmaceutically acceptable salts or solvates thereof, wherein:

$R_1$ is methyl or ethyl, preferably methyl;

$R_2$ is H; halo; $N_3$;
  $C_{1-6}$ alkyl (preferably $C_{1-3}$ alkyl, more preferably $CH_3$) optionally substituted with OH or halo (preferably F, e.g., monofluoro, difluoro, or trifluoro);
  —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
  —$CO_2R^d$, wherein $R^d$ is $C_{1-3}$ alkyl, preferably methyl or ethyl; or
  —$N(R^a)(R^b)$ wherein $R^a$ and $R^b$ are independently H, OH ($R^a$ and $R^b$ are not both OH), $C_{1-3}$ alkyl (preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R^e)(R^f)$ wherein $R^e$ and $R^f$ are independently H, OH ($R^e$ and $R^f$ are not both OH), $C_{1-3}$ alkyl (preferably $CH_3$), or $C_{2-3}$ hydroxyalkyl (preferably —$CH_2CH2OH$), and wherein optionally $R^a$ and $R^b$ together may form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$ and $R_6$ are independently H; halo (preferably F or Cl); $N_3$; $C_{1-6}$ alkyl (preferably $C_{1-3}$, more preferably $CH_3$); $C_{1-3}$ alkoxy (preferably $OCH_3$); or —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$) or $C_{2-3}$ hydroxyalkyl (preferably —$CH_2CH2OH$), wherein $R_{2b}$ and $R_{2c}$ together may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_5$ is H or F, preferably H;

$R_7$ and $R_{11}$ are independently H; halo (preferably F or Cl, more preferably F); $CH_3$; or $OCH_3$;

$R_8$ and $R_{10}$ are independently H; halo (preferably F or Cl, more preferably Cl); OH; $N_3$; $C_{1-3}$ alkyl (preferably $CH_3$); $C_{1-3}$ alkoxy (preferably $OCH_3$); $C_{1-3}$ haloalkyl (preferably monofluoromethyl, difluoromethyl, trifluoromethyl); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). and $R_9$ is H; OH; $N_3$; halo;

- $C_{1-3}$ alkyl (preferably methyl or ethyl) or $C_{1-3}$ haloalkyl (preferably monofluoromethyl, difluoromethyl, trifluoromethyl);
- —$(CO_{0-3}$ alkyl$)C(O)N(R^a)(R^b)$ where $R^a$ and $R^b$ are independently H, $C_{2-4}$ hydroxyalkyl, $C_{1-3}$ alkyl, or $C_{1-3}$ alkyl optionally substituted with —$N(R^e)(R^f)$ where $R^e$ and $R^f$ are independently H, OH ($R^a$ and $R^b$ are not both OH), or $C_{1-3}$ alkyl; wherein optionally $R^a$ and $R^b$ together with the N form a 3, 4, 5 or 6-membered heterocycle, and optionally $R^e$ and $R^f$ together with the nitrogen atom to which they both are linked form a 3, 4, 5 or 6-membered heterocycle;
- —$CO_2$-$R_{2f}$, wherein $R_{2f}$ is an optionally substituted $C_{1-6}$ alkyl (preferably $C_{1-3}$ alkyl, more preferably methyl or ethyl), the alkyl may be optionally substituted with OH, halo, $C_{1-3}$ alkoxy, amino, and $C_{1-3}$ alkylamino;
- —$XR_{2a}$ wherein X is S or O and $R_{2a}$ is $C_{1-6}$ alkyl (preferably $C_{1-3}$ alkyl, more preferably $CH_3$) optionally substituted with a moiety selected from the group OH, halo, $C_{1-3}$ alkoxy, amino, and $C_{1-3}$ alkylamino; or
- —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ haloalkyl, $C_{1-6}$ hydroxyalkyl (preferably $C_{2-3}$ hydroxyalkyl, more preferably —$CH_2CH2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$) or $C_{2-3}$ hydroxyalkyl (preferably —$CH_2CH_2OH$), wherein optionally $R_{2b}$ and $R_{2c}$ together with the nitrogen they both are linked to may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;
- optionally, $R_9$ and one of $R_8$ and $R_{10}$ together form a 3, 4, 5 or 6-membered carbocycle or heterocycle;

provided that when $R_9$ is H then $R_8$ and $R_{10}$ are not both H or one H and the other halo.

Preferably when $R_9$ is H, $R_8$ or $R_{10}$ or both are independently OH; $N_3$; —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$NH(R^a)$ or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$alkoxy or $C_{1-3}$ halo alkoxy.

Also preferably, when $R_9$ is $C_{1-6}$ alkyl, halo, or $C_{1-6}$ haloalkyl, then $R_2$ is not H and preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

In another preferred embodiment, compounds of the invention include compounds of Formula VIb or pharmaceutically acceptable salts or solvates thereof, wherein:

$R_1$ is methyl or ethyl, and preferably methyl;

$R_2$ is H; halo; $N_3$;

- $C_{1-6}$ alkyl (preferably $C_{1-3}$ alkyl, more preferably $CH_3$) optionally substituted with 1-4 substituents which are independently OH or halo (preferably F, e.g., monofluoro, difluoro, or trifluoro);
- —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted);
- —$CO_2$-$R_{2f}$, wherein $R_{2f}$ is $C_{1-6}$ (preferably $C_{1-3}$, more preferably methyl or ethyl); or
- —$N(R_{2b})(R_{2c})$ wherein $R_{2b}$ and $R_{2c}$ are independently H, OH, $C_{1-6}$ alkyl (preferably $C_{1-3}$ alkyl, more preferably $CH_3$), $C_{1-6}$ hydroxyalkyl (preferably $C_{2-3}$ hydroxyalkyl, more preferably —$CH_2CH_2OH$), or $C_{1-6}$ alkyl (preferably $C_{1-3}$ alkyl, more preferably $CH_3$) that is optionally substituted with —$N(R_{2d})(R_{2e})$ wherein $R_{2d}$ and $R_{2e}$ are independently H, OH, $C_{1-3}$ alkyl (preferably $CH_3$), or $C_{2-3}$ hydroxyalkyl (preferably —$CH_2CH_2OH$), and wherein optionally $R_{2b}$ and $R_{2c}$ together with the nitrogen they both are linked to may form a 3, 4, 5 or 6-membered heterocycle (e.g., piperidinyl, pyrrolidinyl, and morpholinyl), and wherein $R_{2b}$ and $R_{2c}$ are not both OH, $R_{2d}$ and $R_{2e}$ are not both OH;

$R_3$ is H; halo; $C_{1-3}$ alkyl; or $C_{1-3}$ alkoxy;

$R_4$ and $R_6$ are independently H; halo (preferably F or Cl); $N_3$; $C_{1-3}$ alkyl (preferably $CH_3$); $C_{1-3}$ alkoxy (preferably $OCH_3$); or —$N(R_{2b})(R_{2c})$ wherein $R_{2b}$ and $R_{2c}$ are independently H, OH, $CH_3$, and optionally $R_{2b}$ and $R_{2c}$ together with the nitrogen they both are linked to may form a 3, 4, 5 or 6-membered heterocycle (e.g., piperidinyl, pyrrolidinyl, and morpholinyl), and wherein $R_{2b}$ and $R_{2c}$ are not both OH;

$R_5$ is H;

$R_7$ and $R_{11}$ are independently H, halo (preferably F), $CH_3$, or $OCH_3$;

$R_8$ and $R_{10}$ are independently H; halo (preferably F or Cl, more preferably F); $C_{1-3}$ alkyl (preferably $CH_3$); $C_{1-3}$ alkoxy (preferably $OCH_3$); —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl); and $R_9$ is selected from the group:

hydrogen; hydroxy; $N_3$;

- $C_{1-3}$ alkyl (preferably methyl or ethyl) or $C_{1-3}$ haloalkyl (preferably monofluoromethyl, difluoromethyl, trifluoromethyl);
- —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);
- —$N(R_{2b})(R_{2c})$ wherein $R_{2b}$ and $R_{2c}$ are independently H, $C_{1-3}$ alkyl, or $C_{1-3}$ haloalkyl; or
- —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle;

provided that when $R_9$ is H at least one of $R_8$ and $R_{10}$ is not H or halo, preferably at least one of $R_8$ and $R_{10}$ is not H or halo or $C_{1-3}$ alkyl.

Preferably in this embodiment, when $R_9$ is H, $R_8$ or $R_{10}$ or both are independently —$XR_{9a}$, where X is O or S, and $R_{9a}$ is $C_{1-4}$ alkyl or $C_{1-3}$ haloalkyl (e.g., fluoroalkyl, preferably fluoromethyl, i.e., $CH_2F$, $CHF_2$, $CF_3$); —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). More preferably, when $R_9$ is H, $R_8$ or $R_{10}$ or both are independently $N_3$, —$OR_{9a}$, wherein $R_{9a}$ is $C_{1-4}$ alkyl or $C_{1-3}$ haloalkyl, or —$N(R^a)(R^b)$ where $R^a$ and $R^b$ are independently $C_{1-3}$ alkyl; or —$COOR_{9b}$, wherein $R_{9b}$ is $C_{1-3}$ alkyl (preferably methyl or ethyl). Even more preferably when $R_9$ is H, $R_8$ or $R_{10}$ or both are $C_{1-3}$ alkoxy or $C_{1-3}$ halo alkoxy.

Also preferably in this embodiment, when $R_9$ is H then $R_8$ and $R_{10}$ are not both H or one H and the other halo, and $R_2$ is not H.

Also preferably, in this embodiment, when $R_9$ is $C_{1-6}$ alkyl, halo, or $C_{1-6}$ haloalkyl, then $R_2$ is not H and preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VIb or pharmaceutically acceptable salts or solvates thereof, wherein:

$R_1$ is methyl or ethyl, and preferably methyl;

$R_2$ is H; halo; $N_3$;
- $C_{1-6}$ alkyl (preferably $C_{1-3}$ alkyl, more preferably $CH_3$) optionally substituted with 1-4 substituents which are OH or halo (preferably F, e.g., monofluoro, difluoro, or trifluoro);
- —$XR_{2a}$ wherein X is S or O, and $R_{2a}$ is $C_{1-6}$ alkyl (preferably $C_{1-3}$ alkyl, more preferably $CH_3$) optionally substituted with OH or halo (preferably F, e.g., monofluoro-, difluoro-, or trifluoro-substituted); or
- —$N(R_{2b})(R_{2c})$ wherein $R_{2b}$ and $R_{2c}$ are independently H, OH, $C_{1-6}$ alkyl (preferably $C_{1-3}$ alkyl), $C_{1-6}$ hydroxyalkyl (preferably $C_{2-3}$ hydroxyalkyl, more preferably —$CH_2CH_2OH$), or $R_{2b}$ and $R_{2c}$ together form a 3, 4, 5 or 6-membered heterocycle (e.g., piperidinyl, pyrrolidinyl, and morpholinyl);

$R_3$ is H; halo; $C_{1-3}$ alkyl; or $C_{1-3}$ alkoxy;

$R_4$ and $R_6$ are independently H; halo (preferably F or Cl); $N_3$; $C_{1-3}$ alkyl (preferably $CH_3$); $C_{1-3}$ alkoxy (preferably $OCH_3$); or —$N(R_{2b})(R_{2c})$ wherein $R_{2b}$ and $R_{2c}$ are independently H, OH ($R_{2b}$ and $R_{2c}$ are not both OH), $CH_3$, or $R_{2b}$ and $R_{2c}$ together form a 3, 4, 5 or 6-membered heterocycle (e.g., piperidinyl, pyrrolidinyl, and morpholinyl);

$R_5$ is H or F, preferably H;

$R_7$ and $R_{11}$ are independently H, halo (preferably F), $C_{1-3}$ alkyl (preferably $CH_3$), $C_{1-3}$ alkoxy (preferably $OCH_3$), or $C_{1-3}$ alkylthiol; Preferably $R_7$ and $R_{11}$ are independently H, halo or methoxy;

$R_8$ and $R_{10}$ are independently H; halo (preferably F or Cl); $C_{1-3}$ alkyl (preferably $CH_3$); $C_{1-3}$ alkoxy (preferably $OCH_3$) or $C_{1-3}$ alkylthiol; and $R_9$ is selected from the group:
- hydrogen; hydroxy; Cl; $N_3$;
- $C_{1-3}$ alkyl (preferably methyl or ethyl) or $C_{1-3}$ haloalkyl (preferably monofluoromethyl, difluoromethyl, trifluoromethyl);
- —$OR_{9a}$, wherein $R_{12}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);
- —$N(R_{2b})(R_{2c})$ wherein $R_{2b}$ and $R_{2c}$ are independently $C_{1-3}$ alkyl; or
- —$COOR_{9b}$, wherein $R_{9b}$ is $C_{1-3}$ alkyl (preferably methyl or ethyl); and optionally $R_9$ and one of $R_8$ and $R_{10}$ together form a 3, 4, 5, or 6-membered heterocycle;

provided that when $R_9$ is H at least one of $R_8$ and $R_{10}$ is not H or halo, preferably at least one of $R_8$ and $R_{10}$ is not H or halo or $C_{1-3}$ alkyl.

Preferably in this embodiment, when $R_9$ is H, $R_8$ or $R_{10}$ or both are independently $C_{1-3}$ alkoxy (preferably $OCH_3$) or $C_{1-3}$ alkylthiol, each being optionally substituted with 1-4 F. Even more preferably when $R_9$ is H, $R_8$ or $R_{10}$ or both are methoxy or ethoxy. Also preferably $R_2$ is not H.

Also preferably, when $R_9$ is $C_{1-3}$ alkyl, halo, or $C_{1-3}$ haloalkyl, then $R_2$ is not H, preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VIb or pharmaceutically acceptable salts or solvates thereof, wherein:

$R_1$ is methyl or ethyl, preferably methyl;

$R_2$ is H, methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$; $R_3$ is H, $CH_3$, $OCH_3$, F, or Cl; $R_4$ and $R_6$ are independently H, $CH_3$, $NH_2$, $N_3$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
- H; OH; $N_3$;
- $C_{1-3}$ alkyl (preferably methyl or ethyl) or $C_{1-3}$ haloalkyl (preferably monofluoromethyl, difluoromethyl, trifluoromethyl);
- —$OR_{9a}$, wherein $R_{9a}$ is $C_{1-3}$ alkyl (i.e., methyl, ethyl, propyl, isopropyl) or $C_{1-3}$ haloalkyl (e.g., fluoroalkyl, preferably fluoromethyl, i.e., $CH_2F$, $CHF_2$, $CF_3$);
- —$N(R_{2b})(R_{2c})$ wherein $R_{2b}$ and $R_{2c}$ are independently $C_{1-3}$ alkyl; or
- —$COOR_{9b}$, wherein $R_{9b}$ is $C_{1-3}$ alkyl (preferably methyl or ethyl), and optionally $R_8$ and $R_9$ together form a 3, 4, 5, or 6-membered heterocycle; provided that when $R_9$ is H, at least one of $R_8$ and $R_{10}$ is $OCH_3$, and when $R_9$ is $C_{1-3}$ alkyl or $C_{1-3}$ haloalkyl or Cl then $R_2$ is Cl or methyl or ethyl.

Preferably in this embodiment, when $R_9$ is H, $R_8$ or $R_{10}$ or both are independently $C_{1-3}$ alkoxy (preferably $OCH_3$) or $C_{1-3}$ alkylthiol, each being optionally substituted with 1-4 F. Even more preferably when $R_9$ is H, $R_8$ or $R_{10}$ or both are methoxy or ethoxy. Also preferably $R_2$ is not H.

Also preferably, when $R_9$ is $C_{1-3}$ alkyl, halo, or $C_{1-3}$ haloalkyl, then $R_2$ is not H, preferably $R_2$ is methyl, ethyl, Cl, F, fluoromethyl ($CH_2F$, $CHF_2$, $CF_3$), $C_{1-3}$ hydroxyalkyl (preferably $CH_2OH$ or $CH_2CH_2OH$), $NH_2$, $NH_2OH$, —$NHCH_2CH_2OH$, $NHCH_3$, $N(CH_3)_2$, $N_3$, morpholino, $OCH_3$, $OC_2H_5$, or $SCH_3$.

Also preferably, in this embodiment, when $R_9$ is H, $R_8$ or $R_{10}$ or both are $OCH_3$ and preferably $R_7$ and $R_{11}$ are H, and also preferably $R_2$ is not hydrogen and preferably $R_2$ is methyl or chloro. Also preferably in this embodiment, when $R_9$ is alkyl or haloalkyl or chloro, $R_2$ is not hydrogen and preferably $R_2$ is methyl or chloro.

In another preferred embodiment, compounds of the invention include compounds of Formula VIb or pharmaceutically acceptable salts or solvates thereof, wherein:

$R_1$ is $CH_3$;
$R_2$ is H, methyl, ethyl, Cl, F, fluoromethyl ($CH_2F$, $CHF_2$, $CF_3$), $CH_2OH$, $NH_2$, $NHCH_3$, $N(CH_3)_2$, —$NHCH_2CH_2OH$, $OCH_3$, or $SCH_3$; $R_3$ is H, $CH_3$, $OCH_3$, F, or Cl; $R_4$ and $R_6$ are independently H, $CH_3$, $NH_2$, F, or Cl; $R_5$ is H; $R_7$ and $R_{11}$ are independently H, F, or $OCH_3$; $R_8$ and $R_{10}$ are independently H, F, Cl, or $OCH_3$; and $R_9$ is selected from the group:
  —$OR_{12}$, wherein $R_{12}$ is selected from the group of methyl, ethyl, fluoromethyl (e.g., $CH_2F$, $CHF_2$, $CF_3$), and fluoroethyl;
  —$NHCH_3$;
  —$N(CH_3)_2$;
  $N_3$; and
  —$COOR_{13}$, wherein $R_{13}$ is methyl or ethyl.

In a more preferred embodiment, compounds of the invention include compounds of Formula VIb or pharmaceutically acceptable salts or solvates thereof, wherein:
$R_1$ is $CH_3$;
$R_2$ is H, methyl, Cl, —$CH_2OH$, —$NH_2$, —$NHCH_3$, —$NHCH_2CH_2OH$, —$OCH_3$, —$SCH_3$, or —$CH_2F$;
$R_3$ is H, —$CH_3$, —$OCH_3$, or Cl;
$R_4$ is H, $CH_3$, or $NH_2$;
$R_5$ is H;
$R_6$ is H, or $CH_3$;
$R_7$ and $R_{11}$ are independently H, or F;
$R_8$ and $R_{10}$ are independently H, or F or $OCH_3$; and
$R_9$ is —$OCH_3$ or —$OC_2H_5$, —$N(CH_3)_2$, —$CO_2CH_3$, —$OCHF_2$, or $N_3$.

In a more preferred embodiment, the present invention provides compounds of Formula VIb or pharmaceutically acceptable salts or solvates thereof, wherein $R_1$ is $CH_3$; $R_2$ is Cl, methyl, or $CH_2F$; $R_3$ is H, $CH_3$, F, or Cl; $R_4$, $R_5$ and $R_6$ are H; $R_7$, $R_8$, $R_{10}$ and $R_{11}$ are independently H or F; and $R_9$ is —$OCH_3$ or —$N(CH_3)_2$.

In another embodiment, compounds of Formula VIb include compounds wherein:
$R_1$ is methyl or ethyl;
$R_2$ is methyl, ethyl, fluoromethyl, trifluoromethyl, methoxy, chloro, hydrogen, morpholino, hydroxymethane, methylthiol, or an amino optionally substituted with hydroxyethyl, or hydroxy;
$R_3$ is hydrogen, chloro, methyl, or methoxy;
$R_4$ and $R_6$ are independently hydrogen, chloro, or methyl;
$R_5$ is hydrogen;
$R_7$, $R_8$, $R_{10}$, and $R_{11}$ are independently hydrogen, fluoro, methyl, or methoxy; and
$R_9$ is methyl, ethyl, methoxy, ethoxy, propoxy, isopropoxy, trifluoromethoxy, difluoromethoxy, azido, dimethylamino, methylcarboxy, chloro, hydrogen, or hydroxyl; or pharmaceutically acceptable salts or solvates thereof.

Preferably, the compounds of this embodiment are not selected form the group consisting of:
6-amino-4-[(N-methyl-N-phenyl)amino]quinazoline;
1-{4-[(N-methyl-N-phenyl)amino]-6-quinazolinyl}-3-methyltriazene;
1-{4-[(N-methyl-N-phenyl)amino]-6-quinazolinyl}-3,3-dimethyltriazene;
4-(N-methylanilino)-6-sulfonylquinazoline;
4-(N-methylanilino)-6-halosulfonylquinazoline;
8-Chloro-4-(N-methylanilino)quinazoline;
4-(N-methylanilino)-8-trifluoromethylquinazoline;
2-butyl-N-methyl-N-phenylquinazolin-4-amine;
4-(N-methylanilino)-6,8-dimethylquinazoline;
4-(N-methylanilino)-quinazoline;
4-(N-methylanilino)-6-methoxyquinazoline;
4-(N-methylanilino)-6-chloroquinazoline;
N-(3-chlorophenyl)-N-(quinazolin-4-yl)-N-methyl-amine;
4-(N-methylanilino)-2-chloroquinazoline;
4-(N-methylanilino)-2-chloro-8-methoxyquinazoline;
4-(N-ethylanilino)-2-chloroquinazoline;
4-(N-methylanilino)-2-chloro-6-methoxyquinazoline;
4-(N-methylanilino)-2-chloro-8-fluoroquinazoline;
2-amino-4-(N-methylphenylamino)quinazoline hydrochloride; or
2-amino-4-(N-methylphenylamino)-8-methoxyquinazoline hydrochloride.

In another embodiment, compounds of Formula VIb include compounds wherein:
$R_1$ is methyl;
$R_2$ is methyl, chloro, fluoromethyl, hydroxymethyl, amino, hydrogen, or hydroxyethylamino;
$R_3$ is hydrogen, methyl, methoxy, or chloro;
$R_4$ and $R_6$ are independently hydrogen or methyl;
$R_5$ is hydrogen;
$R_7$ and $R_{11}$ are independently hydrogen or fluoro;
$R_8$ and $R_{10}$ are independently hydrogen or fluoro; and
$R_9$ is methoxy, ethoxy, dimethylamino, methylcarboxy, difluoromethoxy, or azido;

or pharmaceutically acceptable salts or solvates thereof.

Among all the compounds of the present invention as disclosed above, preferred are those that can induce caspase activation as determined by the method and under conditions (measurement at 24 hours) described in Example 143, preferably at an $EC_{50}$ of no greater than about 1,000 nM, more preferably at an $EC_{50}$ of no greater than about 500 nM, more preferably at an $EC_{50}$ of no greater than about 200 nM, even more preferably at an $EC_{50}$ of no greater than about 100 nM, and most preferably at an $EC_{50}$ of no greater than about 10 nM. Also preferred compounds are those of Formula I-VIb, and pharmaceutically acceptable salts or solvates thereof, that are able to inhibit tubulin at an $IC_{50}$ of no greater than about 2,000 nM, preferably no greater than about 1,000 nM, more preferably less than about 500 nM, as determined by the method and under conditions described in Example 145.

Exemplary compounds of the present invention are compounds provided in Examples 1-142; and pharmaceutically acceptable salts or prodrugs thereof, including but not limited to:
(2-Chloro-quinazolin-4-yl)-(4-methoxy-phenyl)-methyl-amine;
(2-Chloro-quinazolin-4-yl)-(4-methyl-phenyl)-methyl-amine;
(2-Chloro-quinazolin-4-yl)-(4-chloro-phenyl)-methyl-amine;
(2-Chloro-quinazolin-4-yl)-(4-nitro-phenyl)-methyl-amine;
(2-Chloro-quinazolin-4-yl)-(4-trifluoromethoxy-phenyl)-methyl-amine;
$N^2$-Hydroxyl-$N^4$-(4-methoxy-phenyl)-$N^4$-methyl-quinazoline-2,4-diamine;
$N^2$-(2-Hydroxylethyl)-$N^4$-(4-methoxy-phenyl)-$N^4$-methyl-quinazoline-2,4-diamine;
$N^4$-(4-methoxy-phenyl)-$N^4$-methyl-quinazoline-2,4-diamine;
$N^2$-(3,7-Dimethyl-octa-2,6-dienyl)-$N^4$-(4-methoxy-phenyl)-$N^4$-methyl-quinazoline-2,4-diamine;
$N^4$-(4-Methoxy-phenyl)-$N^4$-methyl-N-2-(2-morpholin-4-yl-ethyl)-quinazoline-2,4-diamine;
(4-Methoxy-phenyl)-methyl-(2-morpholin-4-yl-quinazolin-4-yl)-amine;
$N^2$-(3,7-Dimethyl-octa-2,6-dienyl)-$N^4$-(4-methyl-phenyl)-$N^4$-methyl-quinazoline-2,4-diamine;

(2-Chloro-6,7-dimethoxyquinazolin-4-yl)-(4-methoxy-phenyl)-methyl-amine;
(5,6,7,8-Tetrahydro-quinazolin-4-yl)-(4-methoxy-phenyl)-methyl-amine;
(2-Chloro-quinazolin-4-yl)-(4-methoxy-benzyl)-methyl-amine;
(4-Methoxy-phenyl)-methyl-quinazolin-4-yl-amine;
(4-Methyl-phenyl)-methyl-quinazolin-4-yl-amine;
(2-Chloro-quinazolin-4-yl)-(6-methoxy-pyridin-3-yl)-methyl-amine;
(2-Chloro-quinazolin-4-yl)-isopropyl-(4-methoxy-phenyl)-amine;
(2-Chloro-quinazolin-4-yl)-cyclohexyl-(4-methoxy-phenyl)-amine;
(2-Chloro-quinazolin-4-yl)-(2,3-dimethoxy-phenyl)-methyl-amine;
(2-Chloro-quinazolin-4-yl)-ethyl-(4-methoxy-phenyl)-amine;
(2-Chloro-quinazolin-4-yl)-(2,4-dimethoxy-phenyl)-methyl-amine;
(2-Chloro-quinazolin-4-yl)-(2,5-dimethoxy-phenyl)-methyl-amine;
(2-Chloro-quinazolin-4-yl)-(3-methoxy-phenyl)-methyl-amine;
(2-Chloro-quinazolin-4-yl)-(2-methoxy-phenyl)-methyl-amine;
$N^2$[2-(1H-Imidazol-4-yl)-ethyl]-$N^4$-(4-methoxy-phenyl)-$N^4$-methyl-quinazoline-2,4-diamine;
$N^2$-(3-Dimethylamino-propyl)-$N^4$-(4-methoxy-phenyl)-$N^4$-methyl-quinazoline-2,4-diamine;
$N^2$-(2-Hydroxyethyl)-$N^4$-(6-methoxypyridin-3-yl)-$N^4$-methyl-quinazoline-2,4-diamine;
$N^4$-(6-methoxypyridin-3-yl)-$N^4$-methyl-quinazoline-2,4-diamine;
(2-Chloro-quinazolin-4-yl)-(4-methylcarboxyphenyl)-methyl-amine;
(2-methoxy-quinazolin-4-yl)-(4-methoxyphenyl)-methylamine;
(2-Chloro-quinazolin-4-yl)-(4-hydroxyphenyl)-methylamine;
(2-Fluoromethyl-quinazolin-4-yl)-(4-methoxy-phenyl)-methyl-amine;
(2-Chloro-6-methyl-quinazolin-4-yl)-(4-methoxy-phenyl)-methyl-amine;
(2-Chloro-7-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(2,7-Dichloro-quinazolin-4-yl)-(4-methoxy-phenyl)-methyl-amine;
(5-Chloro-2-isopropoxy-quinazolin-4-yl)-(4-methoxy-phenyl)-methyl-amine;
(Isoquinolin-1-yl)-(4-methoxy-phenyl)-methyl-amine;
(4-Methoxy-phenyl)-methyl-(quinolin-4-yl)-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-phenoxy-phenyl)-methyl-amine;
(2-Chloro-quinazolin-4-yl)-(4-propoxy-phenyl)-methyl-amine; and
(4-Methoxy-phenyl)-methyl-(2-methyl-quinazolin-4-yl)-amine;
(2-Chloro-quinazolin-4-yl)-(2,5-dimethoxy-phenyl)-amine;
5-Chloro-$N^2$,$N^4$-bis-(4-methoxy-phenyl)-$N^2$,$N^4$-dimethyl-quinazoline-2,4-diamine;
(2-Chloromethyl-quinazolin-4-yl)-(4-methoxy-phenyl)-methyl-amine;
(2-Ethyl-quinazolin-4-yl)-(4-methoxy-phenyl)-methyl-amine;
(2-Hydroxymethyl-quinazolin-4-yl)-4-methoxy-phenyl)-methyl-amine;
(2-Dimethylaminomethyl-quinazolin-4-yl)-(4-methoxy-phenyl)-methyl-amine;
(4-Methoxy-phenyl)-(2-phenyl-quinazolin-4-yl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;
(4-Isopropoxy-phenyl)-(2-methyl-quinazolin-4-yl)-methyl-amine;
(4-Ethyl-phenyl)-(2-methyl-quinazolin-4-yl)-methyl-amine;
(2-Methyl-quinazolin-4-yl)-(2,4,6-trimethoxy-phenyl)-methyl-amine;
(2,8-Dichloro-quinazolin-4-yl)-(4-methoxy-phenyl)-methyl-amine;
(2,5-Dichloro-quinazolin-4-yl)-(4-methoxy-phenyl)-methyl-amine;
(5-Methoxy-2-methyl-quinazolin-4-yl)-(4-methoxy-phenyl)-methyl-amine;
(4-Methoxy-phenyl)-(2-methyl-pyrido[2,3-d]pyrimidin-4-yl)-methyl-amine;
(4-Hydroxy-phenyl)-(2-methyl-quinazolin-4-yl)-methyl-amine;
(2-Chloro-quinazolin-4-yl)-(4-ethoxy-phenyl)-methylamine;
(2-Methyl-quinazolin-4-yl)-(6-methoxy-pyridin-3-yl)-methyl-amine;
(2-Fluoro-4-methoxy-phenyl)-(2-methyl-quinazolin-4-yl)-methyl-amine;
(2-Methyl-quinazolin-4-yl)-(4-nitro-phenyl)-methyl-amine;
(4-Amino-phenyl)-(2-methyl-quinazolin-4-yl)-methyl-amine;
(4-Azido-phenyl)-(2-methyl-quinazolin-4-yl)-methyl-amine;
(4-Amino-2,6-dibromo-phenyl)-(2-methyl-quinazolin-4-yl)-methyl-amine;
(4-Amino-2-bromo-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;
(4-Methoxy-phenyl-2,3,5,6-$d_4$)-(2-methyl-quinazolin-4-yl)-methyl-amine;
(4-Methoxy-phenyl)-(2-methyl-6-nitro-quinazolin-4-yl)-methyl-amine;
(6-Amino-2-methyl-quinazolin-4-yl)-(4-methoxy-phenyl)-methyl-amine;
(6-Azido-2-methyl-quinazolin-4-yl)-(4-methoxy-phenyl)-methyl-amine;
(7-Amino-2-methyl-quinazolin-4-yl)-(4-methoxy-phenyl)-methyl-amine;
(7-Azido-2-methyl-quinazolin-4-yl)-(4-methoxy-phenyl)-methyl-amine;
Ethyl 4-(N-(4-Methoxy-phenyl)-N-methylamino)quinazoline-2-carboxylate;

Succinimidyl 4-(N-Methyl-N-(2-methylquinazolin-4-yl)amino)benzoic Acid Ester;
(2-Methylthio-quinazolin-4-yl)-(4-methoxy-phenyl)-methyl-amine;
(2-Azido-quinazolin-4-yl)-(4-methoxy-phenyl)-methyl-amine;
(2-Dimethylamino-quinazolin-4-yl)-(4-methoxy-phenyl)-methyl-amine;
(2-Methylamino-quinazolin-4-yl)-(4-methoxy-phenyl)-methyl-amine;
(4-Fluoro-phenyl)-(2-methyl-quinazolin-4-yl)-methyl-amine;
(6-Methoxy-pyridazin-3-yl)-(2-methyl-quinazolin-4-yl)-methyl-amine;
(5-Methoxy-pyrazin-2-yl)-(2-methyl-quinazolin-4-yl)-methyl-amine;
(2-Dimethylamino-quinazolin-4-yl)-(6-methoxy-pyridin-3-yl)-methyl-amine;
(2-Methylamino-quinazolin-4-yl)-(6-methoxy-pyridin-3-yl)-methyl-amine;
(5-Methoxy-pyridin-2-yl)-(2-methyl-quinazolin-4-yl)-methyl-amine;
Difluoromethyl-(4-methoxy-phenyl)-(2-methyl-quinazolin-4-yl)-amine;
(4-Methoxy-phenyl)-(2-methyl-pteridin-4-yl)-methyl-amine;
(5-Methoxy-pyrimidin-2-yl)-(2-methyl-quinazolin-4-yl)-methyl-amine;
and pharmaceutically acceptable salts or prodrugs thereof.

In one embodiment, exemplary compounds of the invention include:
(2-Chloro-quinazolin-4-yl)-(6-methoxy-pyridin-3-yl)-methyl-amine;
$N^2$-(2-Hydroxyethyl)-$N^4$-(6-methoxypyridin-3-yl)-$N^4$-methyl-quinazoline-2,4-diamine;
$N^4$-(6-Methoxypyridin-3-yl)-$N^4$-methyl-quinazoline-2,4-diamine;
(2-Methyl-quinazolin-4-yl)-(6-methoxy-pyridin-3-yl)-methyl-amine;
(6-Methoxy-pyridazin-3-yl)-(2-methyl-quinazolin-4-yl)-methyl-amine;
(5-Methoxy-pyrazin-2-yl)-(2-methyl-quinazolin-4-yl)-methyl-amine;
(2-Dimethylamino-quinazolin-4-yl)-(6-methoxy-pyridin-3-yl)-methyl-amine;
(2-Methylamino-quinazolin-4-yl)-(6-methoxy-pyridin-3-yl)-methyl-amine;
(2-Methyl-quinazolin-4-yl)-(pyrazin-2-yl)-methyl-amine;
(5-Methoxy-pyridin-2-yl)-(2-methyl-quinazolin-4-yl)-methyl-amine; and
(5-Methoxy-pyrimidin-2-yl)-(2-methyl-quinazolin-4-yl)-methyl-amine;
or a pharmaceutically acceptable salt or solvate thereof.

In another embodiment, exemplary compounds of the invention include:
(4-Methoxy-phenyl)-(2-methyl-pyrido[2,3-d]pyrimidin-4-yl)-methyl-amine; and
(4-Methoxy-phenyl)-(2-methyl-pteridin-4-yl)-methyl-amine;
or a pharmaceutically acceptable salt or solvate thereof.

In another embodiment, exemplary compounds of the invention include:
$N^2$-Hydroxyl-$N^4$-(4-methoxy-phenyl)-$N^4$-methyl-quinazoline-2,4-diamine;
$N^2$-(2-Hydroxylethyl)-$N^4$-(4-methoxy-phenyl)-$N^4$-methyl-quinazoline-2,4-diamine;
$N^4$-(4-methoxy-phenyl)-$N^4$-methyl-quinazoline-2,4-diamine;
$N^2$-(3,7-Dimethyl-octa-2,6-dienyl)-$N^4$-(4-methoxy-phenyl)-$N^4$-methyl-quinazoline-2,4-diamine;
$N^4$-(4-Methoxy-phenyl)-$N^4$-methyl-$N^2$-(2-morpholin-4-yl-ethyl)-quinazoline-2,4-diamine;
(4-Methoxy-phenyl)-methyl-(2-morpholin-4-yl-quinazolin-4-yl)-amine;
$N^2$-(3,7-Dimethyl-octa-2,6-dienyl)-$N^4$-(4-methyl-phenyl)-$N^4$-methyl-quinazoline-2,4-diamine;
$N^2$-[2-(1H-Imidazol-4-yl)-ethyl]-$N^4$-(4-methoxy-phenyl)-$N^4$-methyl-quinazoline-2,4-diamine;
$N^2$-(3-Dimethylamino-propyl)-$N^4$-(4-methoxy-phenyl)-$N^4$-methyl-quinazoline-2,4-diamine;
5-Chloro-$N^2$,$N^4$-bis-(4-methoxy-phenyl)-$N^2$,$N^4$-dimethyl-quinazoline-2,4-diamine;
6-Chloro-$N^2$,$N^4$-bis-(4-methoxy-phenyl)-$N^2$,$N^4$-dimethyl-quinazoline-2,4-diamine;
(2-Dimethylamino-quinazolin-4-yl)-(4-methoxy-phenyl)-methyl-amine; and
(2-Methylamino-quinazolin-4-yl)-(4-methoxy-phenyl)-methyl-amine;
or a pharmaceutically acceptable salt or solvate thereof.

In yet another embodiment, exemplary compounds of the invention include:
(2-Fluoromethyl-quinazolin-4-yl)-(4-methoxy-phenyl)-methyl-amine;
(4-Methoxy-phenyl)-methyl-(2-methyl-quinazolin-4-yl)-amine; (2-Chloromethyl-quinazolin-4-yl)-(4-methoxy-phenyl)-methyl-amine;
(2-Ethyl-quinazolin-4-yl)-(4-methoxy-phenyl)-methyl-amine;
(4-carboxy-phenyl)-(2-methyl-quinazolin-4-yl)-methyl-amine;
Ethyl 4-(N-(4-methoxy-phenyl)-N-methylamino)quinazoline-2-carboxylate;
(2-hydroxymethyl-quinazolin-4-yl)-(4-methoxy-phenyl)-methyl-amine;
(2-Dimethylaminomethyl-quinazolin-4-yl)-(4-methoxy-phenyl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;
(4-Isopropoxy-phenyl)-(2-methyl-quinazolin-4-yl)-methyl-amine;
(4-Ethyl-phenyl)-(2-methyl-quinazolin-4-yl)-methyl-amine;
(5-Methoxy-2-methyl-quinazolin-4-yl)-(4-methoxy-phenyl)-methyl-amine;
(4-Hydroxy-phenyl)-(2-methyl-quinazolin-4-yl)-methyl-amine;
(2-Fluoro-4-methoxy-phenyl)-(2-methyl-quinazolin-4-yl)-methyl-amine;
(2-Methyl-quinazolin-4-yl)-(4-nitro-phenyl)-methyl-amine;
(4-Amino-phenyl)-(2-methyl-quinazolin-4-yl)-methyl-amine;
(4-Azido-phenyl)-(2-methyl-quinazolin-4-yl)-methyl-amine;
(4-Amino-2,6-dibromo-phenyl)-(2-methyl-quinazolin-4-yl)-methyl-amine;
(4-Amino-2-bromo-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;

(4-Methoxy-phenyl-2,3,5,6-d$_4$)-(2-methyl-quinazolin-4-yl)-methyl-amine;
(4-Methoxy-phenyl)-(2-methyl-6-nitro-quinazolin-4-yl)-methyl-amine;
(6-Amino-2-methyl-quinazolin-4-yl)-(4-methoxy-phenyl)-methyl-amine;
(6-Azido-2-methyl-quinazolin-4-yl)-(4-methoxy-phenyl)-methyl-amine;
(4-Methoxy-phenyl)-(2-methyl-7-nitro-quinazolin-4-yl)-methyl-amine;
(2,4,6-Trimethoxy-phenyl)-(2-methyl-quinazolin-4-yl)-methyl-amine;
(7-Amino-2-methyl-quinazolin-4-yl)-(4-methoxy-phenyl)-methyl-amine;
(7-Azido-2-methyl-quinazolin-4-yl)-(4-methoxy-phenyl)-methyl-amine;
(3,5-Dibromo-4-methoxyphenyl)-(2-methyl-6-nitro-quinazolin-4-yl)-methyl-amine;
(4-Fluoro-phenyl)-(2-methyl-quinazolin-4-yl)-methyl-amine; and
Difluoromethyl-(4-methoxy-phenyl)-(2-methyl-quinazolin-4-yl)-amine;
or a pharmaceutically acceptable salt or solvate thereof.

In another embodiment, exemplary compounds of the invention include:
(2-Chloro-quinazolin-4-yl)-(4-methoxy-phenyl)-methyl-amine;
(2-Chloro-quinazolin-4-yl)-(4-methyl-phenyl)-methyl-amine;
(2-Chloro-quinazolin-4-yl)-(4-chloro-phenyl)-methyl-amine;
(2-Chloro-quinazolin-4-yl)-(4-nitro-phenyl)-methyl-amine;
(2-Chloro-quinazolin-4-yl)-(4-trifluoromethoxy-phenyl)-methyl-amine;
(2-Chloro-6,7-dimethoxyquinazolin-4-yl)-(4-methoxy-phenyl)-methyl-amine;
(2-Chloro-quinazolin-4-yl)-(6-methoxy-pyridin-3-yl)-methyl-amine;
(2-Chloro-quinazolin-4-yl)-isopropyl-(4-methoxy-phenyl)-amine;
(2-Chloro-quinazolin-4-yl)-cyclohexyl-(4-methoxy-phenyl)-amine;
(2-Chloro-quinazolin-4-yl)-(2,3-dimethoxy-phenyl)-methyl-amine;
(2-Chloro-quinazolin-4-yl)-ethyl-(4-methoxy-phenyl)-amine;
(2-Chloro-quinazolin-4-yl)-(2,4-dimethoxy-phenyl)-methyl-amine;
(2-Chloro-quinazolin-4-yl)-(2,5-dimethoxy-phenyl)-methyl-amine;
(2-Chloro-quinazolin-4-yl)-(3-methoxy-phenyl)-methyl-amine;
(2-Chloro-quinazolin-4-yl)-(2-methoxy-phenyl)-methyl-amine;
(2-Chloro-quinazolin-4-yl)-(4-methylcarboxyphenyl)-methyl-amine;
(2-Chloro-quinazolin-4-yl)-(4-hydroxyphenyl)-methylamine;
(2-Chloro-6-methyl-quinazolin-4-yl)-(4-methoxy-phenyl)-methyl-amine;
(2-Chloro-7-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(2,7-Dichloro-quinazolin-4-yl)-(4-methoxy-phenyl)-methyl-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-phenoxy-phenyl)-methyl-amine;
(2-Chloro-quinazolin-4-yl)-(4-propoxy-phenyl)-methyl-amine;
(2-Chloro-quinazolin-4-yl)-(4-ethoxy-phenyl)-methyl-amine;
(2,8-Dichloro-quinazolin-4-yl)-(4-methoxy-phenyl)-methyl-amine; and
(2,5-Dichloro-quinazolin-4-yl)-(4-methoxy-phenyl)-methyl-amine;
or a pharmaceutically acceptable salt or solvate thereof.

In yet another embodiment, exemplary compounds of the invention include:
(4-Methoxy-phenyl)-methyl-quinazolin-4-yl-amine; and
(4-Methyl-phenyl)-methyl-quinazolin-4-yl-amine;
or a pharmaceutically acceptable salt or solvate thereof.

In another embodiment, exemplary compounds useful in the methods of the invention include:
(2-methoxy-quinazolin-4-yl)-(4-methoxyphenyl)-methylamine; and
(5-Chloro-2-isopropoxy-quinazolin-4-yl)-(4-methoxy-phenyl)-methyl-amine;
or a pharmaceutically acceptable salt or solvate thereof.

The term "alkyl" as employed herein by itself or as part of another group refers to both straight and branched chain radicals of up to ten carbons. Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups, which may be optionally substituted.

The term "alkenyl" as employed herein by itself or as part of another group means a straight or branched chain radical of 2-10 carbon atoms, unless the chain length is limited thereto, including at least one double bond between two of the carbon atoms in the chain. Typical alkenyl groups include ethenyl, 1-propenyl, 2-propenyl, 2-methyl-1-propenyl, 1-butenyl and 2-butenyl.

The term "alkynyl" is used herein to mean a straight or branched chain radical of 2-10 carbon atoms, unless the chain length is limited thereto, wherein there is at least one triple bond between two of the carbon atoms in the chain. Typical alkynyl groups include ethynyl, 1-propynyl, 1-methyl-2-propynyl, 2-propynyl, 1-butynyl and 2-butynyl.

Useful alkoxy groups include oxygen substituted by one of the $C_{1-10}$ alkyl groups mentioned above, which may be optionally substituted. Alkoxy substituents include, without limitation, halo, morpholino, amino including alkylamino and dialkylamino, and carboxy including esters thereof.

Useful alkylthio groups include sulfur substituted by one of the $C_{1-10}$ alkyl groups mentioned above, which may be optionally substituted. Also included are the sulfoxides and sulfones of such alkylthio groups.

Useful amino groups include —$NH_2$, —$NHR_{18}$ and —$NR_{18}R_{19}$, wherein $R_{18}$ and $R_{18}$ are $C_{1-10}$ alkyl or cycloalkyl groups, or $R_{18}$ and $R_{19}$ are combined with the N to form a ring structure, such as a piperidine, or $R_{18}$ and $R_{19}$ are combined with the N and other group to form a ring, such as a piperazine. The alkyl group may be optionally substituted.

Optional substituents on the alkyl, alkenyl, alkynyl, cycloalkyl, carbocyclic and heterocyclic groups include one or more halo, hydroxy, carboxyl, amino, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_2$-$C_6$)alkenyl, $C_6$-$C_{10}$ aryl($C_2$-$C_6$)alkynyl, saturated and unsaturated heterocyclic or heteroaryl.

Optional substituents on the aryl, arylalkyl, arylalkenyl, arylalkynyl and heteroaryl and heteroarylalkyl groups include one or more halo, $C_1$-$C_6$ haloalkyl, $C_6$-$C_{10}$ aryl, $C_4$-$C_7$ cycloalkyl, $C_1$-$C_6$ alkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl($C_2$-$C_6$)alkenyl, $C_6$-$C_{10}$ aryl($C_2$-$C_6$)alkynyl, $C_1$-$C_6$ hydroxyalkyl, nitro, amino, ureido, cyano, $C_1$-$C_6$ acylamino, hydroxy, thiol, $C_1$-$C_6$ acyloxy, azido, $C_1$-$C_6$ alkoxy, carboxy or $C_{1-2}$ alkylenedioxy (e.g., methylenedioxy).

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, azulenyl, biphenyl, biphenylenyl and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful saturated or partially saturated carbocyclic groups are cycloalkyl groups as described above, as well as cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups substituted by any of the above-mentioned $C_{6-14}$ aryl groups.

The term "arylalkynyl" is used herein to mean any of the above-mentioned $C_{2-10}$ alkynyl groups substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl groups substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido, and pentafluorobenzoylamido.

Useful acyloxy groups are any $C_{1-6}$ acyl (alkanoyl) attached to an oxy (—O—) group, e.g., formyloxy, acetoxy, propionyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, pyrazolinyl, tetronoyl and tetramoyl groups.

The term "heteroaryl" as employed herein refers to groups having 5 to 14 ring atoms; 6, 10 or 14 π electrons shared in a cyclic array; and containing carbon atoms and 1, 2 or 3 oxygen, nitrogen or sulfur heteroactoms.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, phosphate, sulphate, citrate, lactate, tartrate, maleate, fumarate, mandelate and oxalate; and inorganic and organic base addition salts with bases, such as sodium hydroxy, Tris(hydroxymethyl)aminomethane (TRIS, trometsane) and N-methyl-glucamine.

Examples of prodrugs of the compounds of the invention include the simple esters of carboxylic acid containing compounds (e.g., those obtained by condensation with a C, 4 alcohol according to methods known in the art); esters of hydroxy containing compounds (e.g., those obtained by condensation with a $C_{1-4}$ carboxylic acid, $C_{3-6}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (*J. Med. Chem.* 42:3623-3628 (1999)) and Greenwald, et. al., (*J. Med. Chem.* 42:3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formulae I-VIb can be prepared as illustrated by the exemplary reaction in Scheme 1. Reaction of optionally substituted quinazoline-2,4-dione with phosphorylchloride produces the corresponding 2,4-dichloroquinazoline, which is reacted with an optionally substituted aniline, such as N-methyl-4-methoxy-aniline, to produce the substituted 2-chloro-4-anilino-quinazoline.

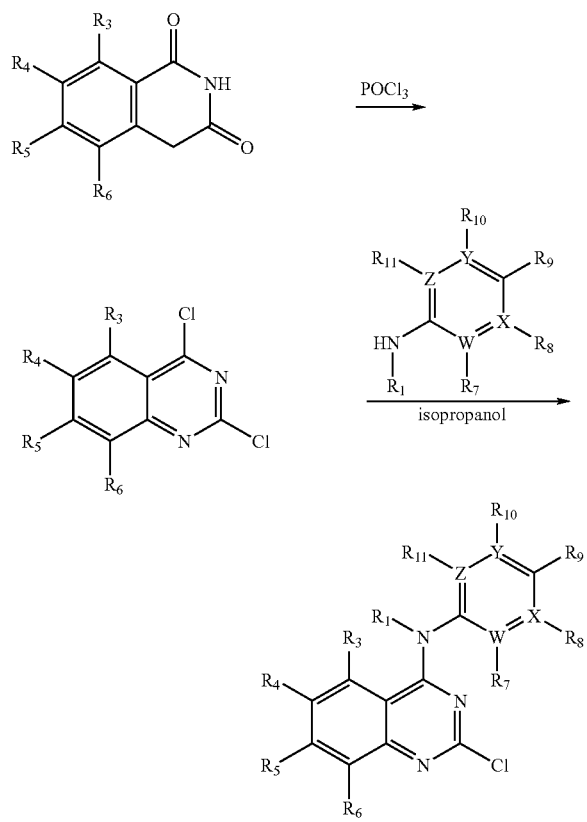

Compounds of this invention with Formulae I-VIb also could be prepared as illustrated by the exemplary reaction in Scheme 2. Reaction of the substituted 2-chloro-4-anilino-quinazoline with a nucleophile ($R_2$), such as hydroxylamine, in isopropanol heated by microwave produces the 2-nucleophile substituted-4-anilino-quinazoline, such as substituted hydroxylamino. Other nucleophiles that can be used in the reaction include NaOMe, NaN₃, NaSMe, NH₃, NH₂Me, or NHMe₂, and the reaction can be run at room temperature or elevated temperature.

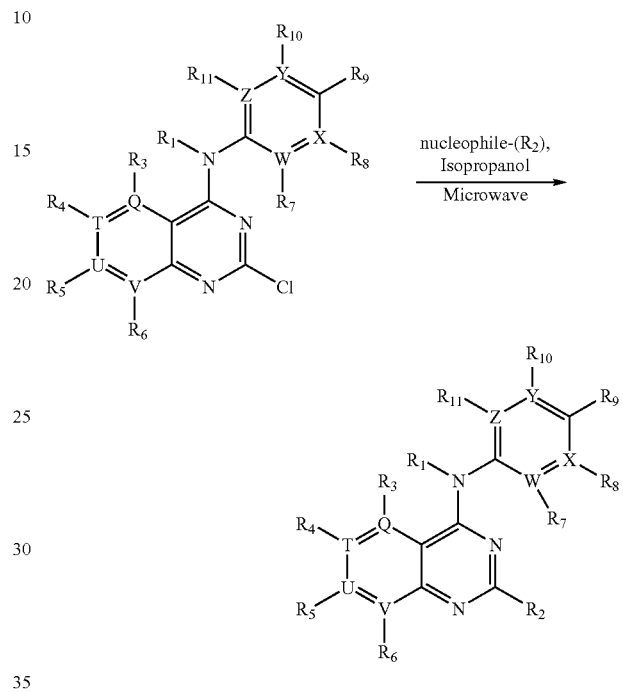

Compounds of this invention with Formulae I-VIb, wherein Ar is a substituted aryl or heteroaryl, could be prepared as illustrated by the exemplary reaction in Scheme 3. Reaction of 2,4-dichloroquinazoline with a substituted arylamine or heteroarylamine (Ar), such as a substituted pyridin-3-ylamine, produces the corresponding 4-Ar-amino substituted 2-chloro-quinazoline, which is alkylated with a haloalkyl, such as methylated by reaction with methyl iodide in the presence of a base such as NaH, to produce the corresponding 4-N-methyl-Ar-amino substituted 2-chloro-quinazoline.

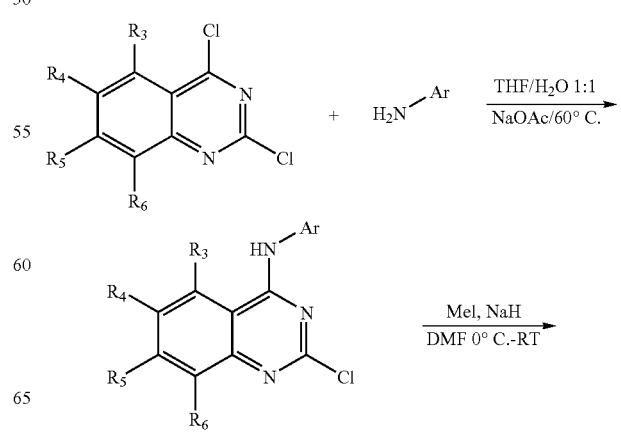

-continued

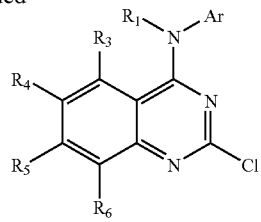

Alternatively, compounds of this invention with Formulae I-VIb also could be prepared as illustrated by the exemplary reaction in Scheme 4. The N-alkyl-arylamine or N-alkyl-heteroarylamine could be prepared by reaction of the arylamine or heteroarylamine with a ketone or aldehyde, such as acetone, in the presence of a reducing agent, such as NaCNBH$_3$. The N-alkyl-arylamine or N-alkyl-heteroarylamine is then reacted with optionally substituted 2,4-dichloroquinazoline to produce the corresponding 4-substituted 2-chloroquinazoline.

dichloroquinazoline by reaction with phosphorylchloride. Reaction of optionally substituted 2,4-dichloroquinazoline, such as 6-methyl-2,4-dichloroquinazoline with a substituted arylamine or heteroarylamine, such as N-methyl-4-methoxy-aniline, produces the corresponding 4-substituted 2-chloroquinazoline, such as substituted 2-chloro-4-anilino-quinazoline.

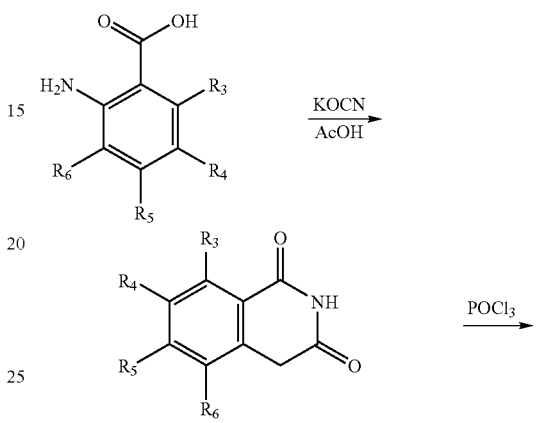

Scheme 5

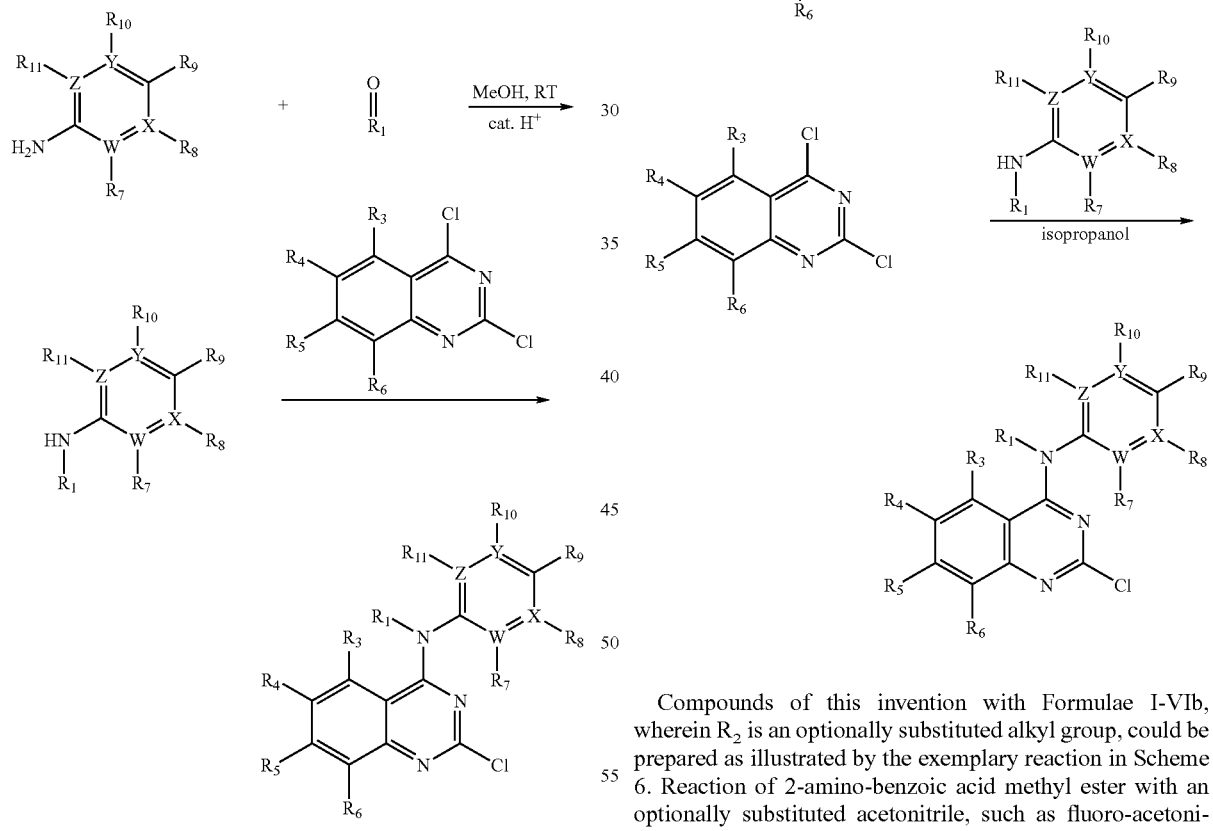

Scheme 4

Compounds of this invention with Formulae I-VIb also could be prepared as illustrated by the exemplary reaction in Scheme 5. Reaction of optionally substituted 2-amino-benzoic acid, such as 2-amino-5-methyl-benzoic acid, with potassium cyanate in the presence of an acid, such as acetic acid, produces the corresponding optionally substituted quinazoline-2,4-dione, such as 6-methyl-quinazoline-2,4-dione, which is converted to the corresponding optionally substituted 2,4-dichloroquinazoline, such as 6-methyl-2,4-

Compounds of this invention with Formulae I-VIb, wherein R$_2$ is an optionally substituted alkyl group, could be prepared as illustrated by the exemplary reaction in Scheme 6. Reaction of 2-amino-benzoic acid methyl ester with an optionally substituted acetonitrile, such as fluoro-acetonitrile, in the presence of HCl produces the corresponding 2-substituted quinazoline-4(3H)-one, such as 2-fluoromethyl-quinazoline-4-(3H)-one, which is converted to 2-substituted 4-chloro-quinazoline, such as 4-chloro-2-fluoromethyl-quinazoline by reaction with phosphorylchloride. Reaction of 2-substituted 4-chloro-quinazoline, such as 4-chloro-2-fluoromethyl-quinazoline with a substituted aniline, such as N-methyl-4-methoxy-aniline, produces the corresponding 2-substituted 4-anilino-quinazoline, such as 2-fluoromethyl-4-anilino-quinazoline. Other substituted acetonitriles that can be used for the reaction include chloro-acetonitrile and bromo-acetonitrile, as well as acetonitrile and propionitrile.

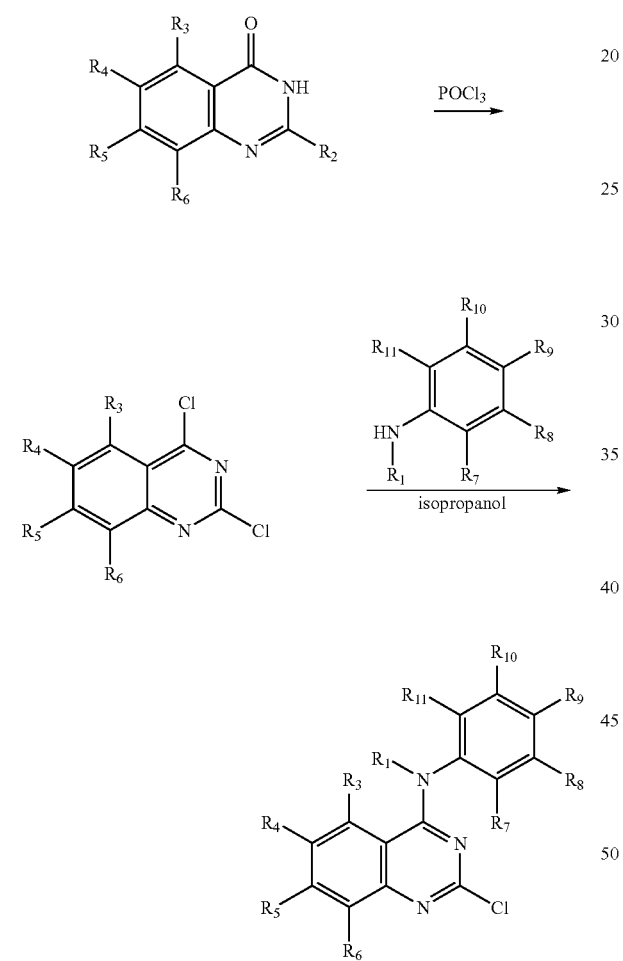

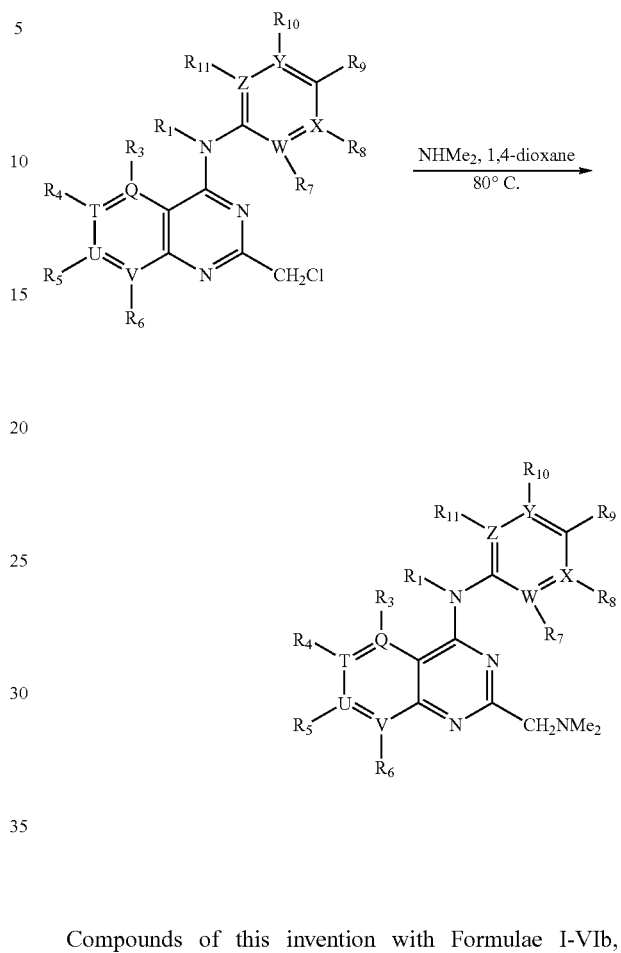

Compounds of this invention with Formulae I-VIb, wherein $R_2$ is a substituted alkyl group, could also be prepared as illustrated by the exemplary reaction in Scheme 7. Reaction of a substituted 2-chloroalkyl-4-(N-alkyl-arylamine or N-alkyl-heteroarylamine)-quinazoline, such as N-methyl-2-chloromethyl-4-anilino-quinazoline, with a nucleophile, such as NHMe$_2$, produces the substituted 2-dimethylaminomethyl-4-anilino-quinazoline. Other nucleophiles that can be used in the reaction include NaOMe, NaN$_3$, NaSMe, NH$_3$, NH$_2$Me, or NHMe$_2$, and the reaction can be run at room temperature and elevated temperature.

Compounds of this invention with Formulae I-VIb, wherein $R_1$ is a substituted alkyl, could be prepared as illustrated by the exemplary reaction in Scheme 8. For example, reaction of an optionally substituted 4-(arylamine or heteroarylamine)-quinazoline, such as 2-methyl-4-(6-methoxy-pyridin-3-ylamino)-quinazoline, with a substituted haloalkyl, such as difluoromethyl chloride, in the presence of a base such as NaH, produces the corresponding 4-(N-alkyl-arylamine or N-alkyl-heteroarylamine)-quinazoline, such as 2-methyl-N$^4$-difluoromethyl-4-(4-methoxy-pyridin-3-ylamino)-quinazoline.

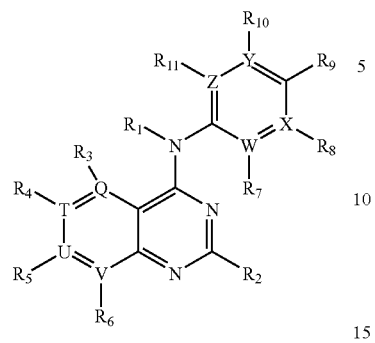

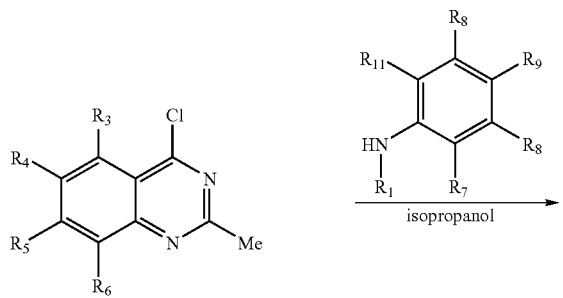

Compounds of this invention with Formula I-VIb, wherein $R_2$ is an alkyl group, could be prepared as illustrated by the exemplary reaction in Scheme 9. Reaction of a substituted 2-amino-benzoic acid, such as 2-amino-5-nitro-benzoic acid, with acetic anhydride, produces the corresponding substituted 2-methyl-4H-benzo[d][1,3]oxazine-4-one, such as 2-methyl-6-nitro-4H-benzo[d][1,3]oxazine-4-one, which is converted to the corresponding quinazoline-4(3H)-one, such as 2-methyl-6-nitro-quinazoline-4(3H)-one, by treatment with ammonia in dioxane. The compound is then converted to the corresponding 4-chloro-quinazoline, such as 4-chloro-2-methyl-6-nitro-quinazoline by reaction with phosphorylchloride. Reaction of the 4-chloro-quinazoline, such as 4-chloro-2-methyl-6-nitro-quinazoline with a substituted arylamine or heteroarylamine, such as N-methyl-4-methoxy-aniline, produces the corresponding 4-(arylamino or heteroarylamino)-quinazoline, such as substituted 2-methyl-6-nitro-4-anilino-quinazoline. Other substituted 2-amino-benzoic acid that can be used for the reaction include 2-amino-4-nitro-benzoic acid, 2-amino-5-chloro-benzoic acid.

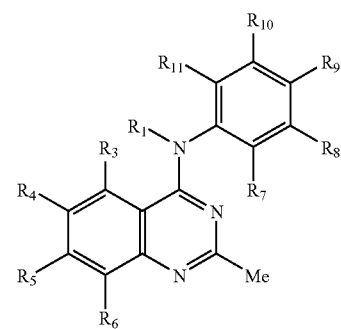

Compounds substituted with a nitro group can be reduced by hydrogenation under $H_2$ with Pd to produce the amino compound, which can be converted to the azido compounds by diazotization followed by treatment with $NaN_3$.

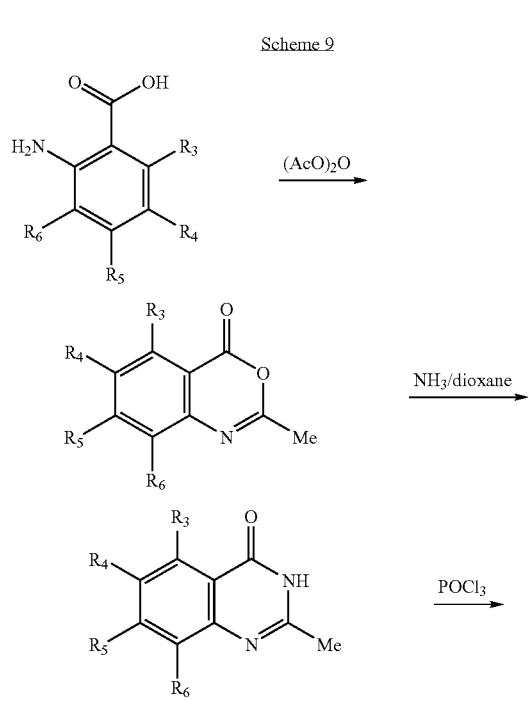

Scheme 9

-continued

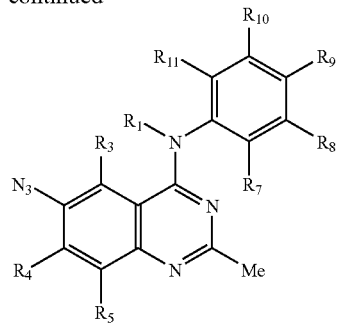

Compounds of this invention with Formula I-VIb, wherein ring A is a carbocycle, could be prepared as illustrated by the exemplary reaction in Scheme 10. Reaction of optionally substituted 5,6,7,8-tetrahydro-quinazoline-4(3H)-one with phosphorylchloride produces the corresponding optionally substituted 5,6,7,8-tetrahydro-4-chloroquinazoline, which is reacted with an optionally substituted N-alkyl-arylamine or N-alkyl-heteroarylamine, such as N-methyl-4-methoxy-aniline, to produce the corresponding optionally substituted 5,6,7,8-tetrahydro-4-(N-alkyl-arylamine or N-alkyl-heteroarylamine)-quinazoline.

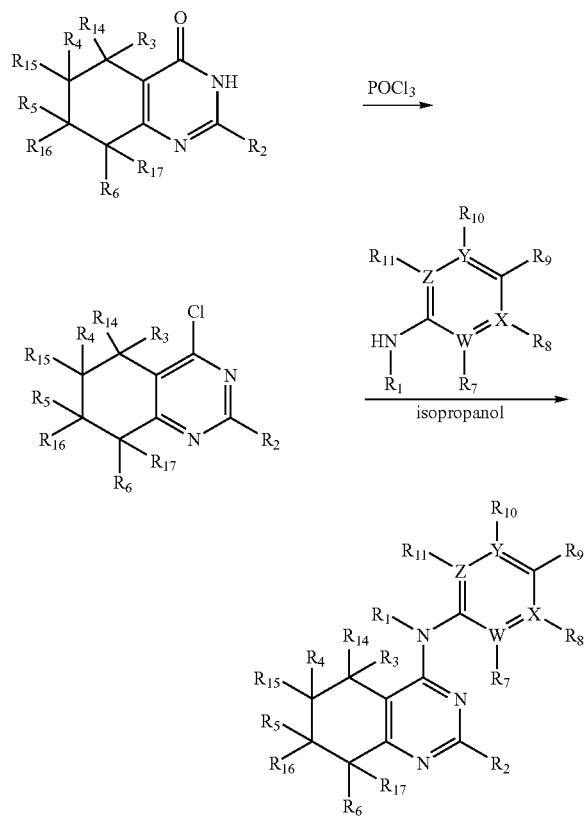

Compounds of this invention with Formula I-VIb, wherein ring A is a heteroaryl or heterocycle, such as pyrido, could be prepared as illustrated by the exemplary reaction in Scheme 11. Reaction of an amino-nicotinic acid, such as 2-amino-nicotinic acid, with acetyl chloride, in the presence of base, such as triethylamine, produces the corresponding amide, which is treated with ammonium acetate to produce the corresponding 2-methyl-pyrido[2,3-d](heteroaryl or heterocycle)-4-ol, such as 2-methyl-pyrido[2,3-d]pyrimidin-4-ol. The resulting compound is then converted to the corresponding 4-chloro-2-methyl-pyrido[2,3-d](heteroaryl or heterocycle), such as 4-chloro-2-methyl-pyrido[2,3-d]pyrimidine by reaction with phosphorylchloride, which is treated with an optionally substituted arylamino or heteroarylamino, such as N-methyl-4-methoxy-aniline to produce the corresponding optionally substituted 4-(arylamino or heteroarylamino)-2-methyl-pyrido[2,3-d](heteroaryl or heterocycle), such as substituted 4-anilino-2-methyl-pyrido[2,3-d]pyrimidine.

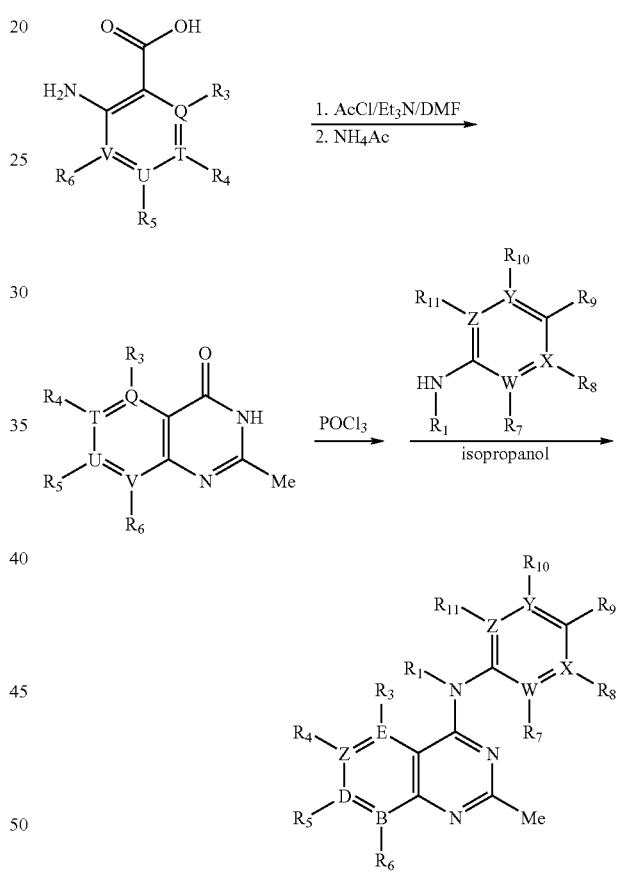

Additional exemplary compounds may be synthesized according to the synthesis schemes below:

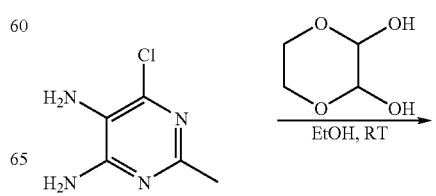

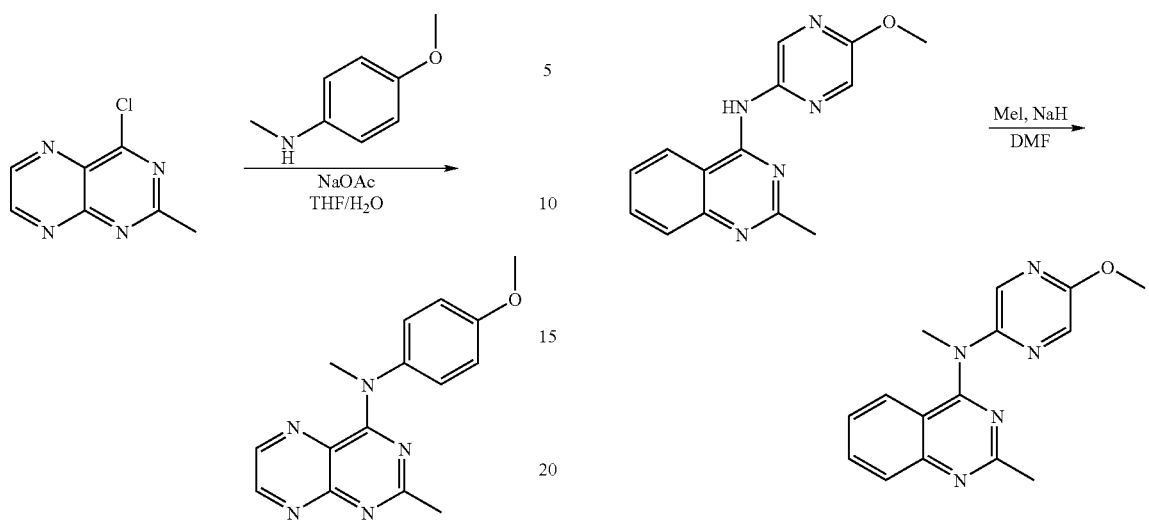
Scheme 13
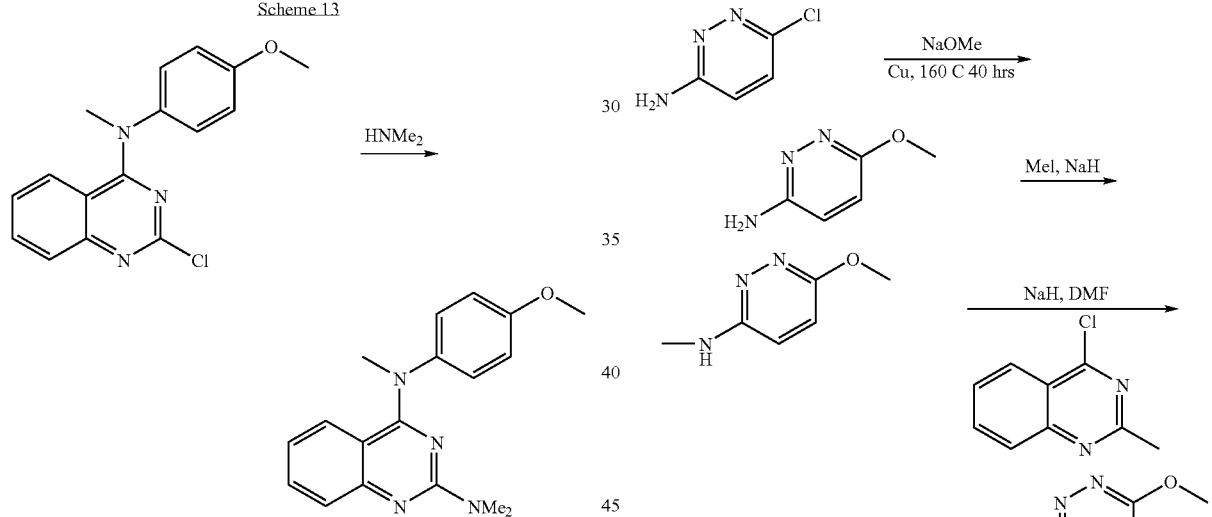
Scheme 14
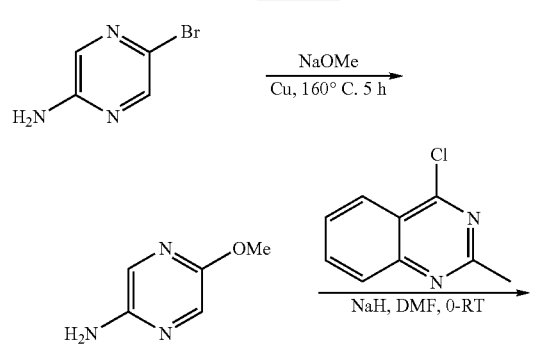
Scheme 15
Scheme 16
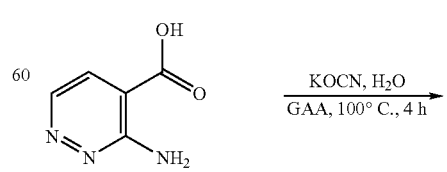

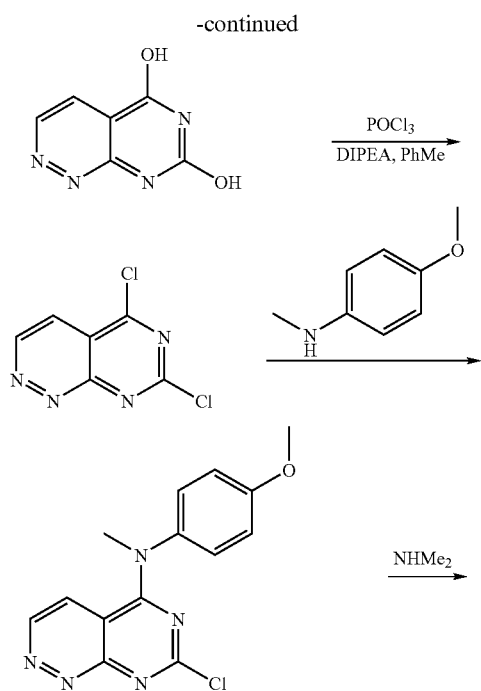
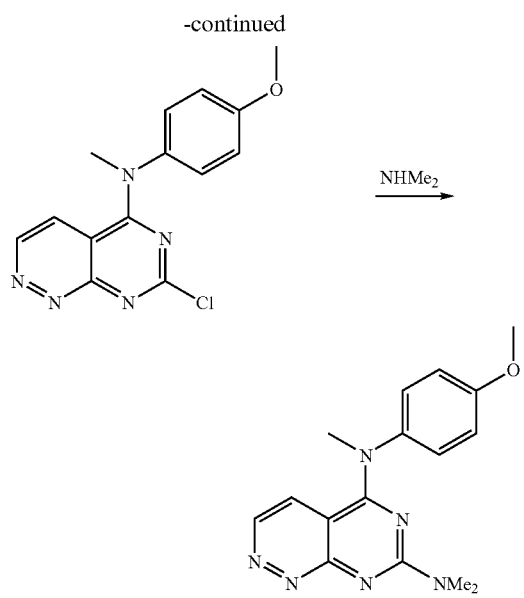
Scheme 17
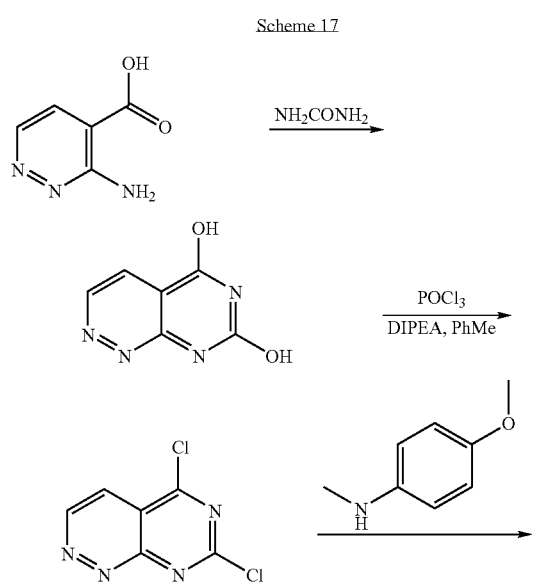
Scheme 18
Scheme 19
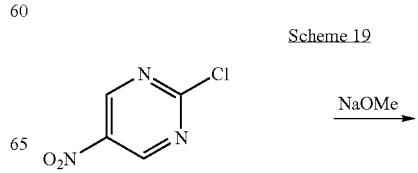

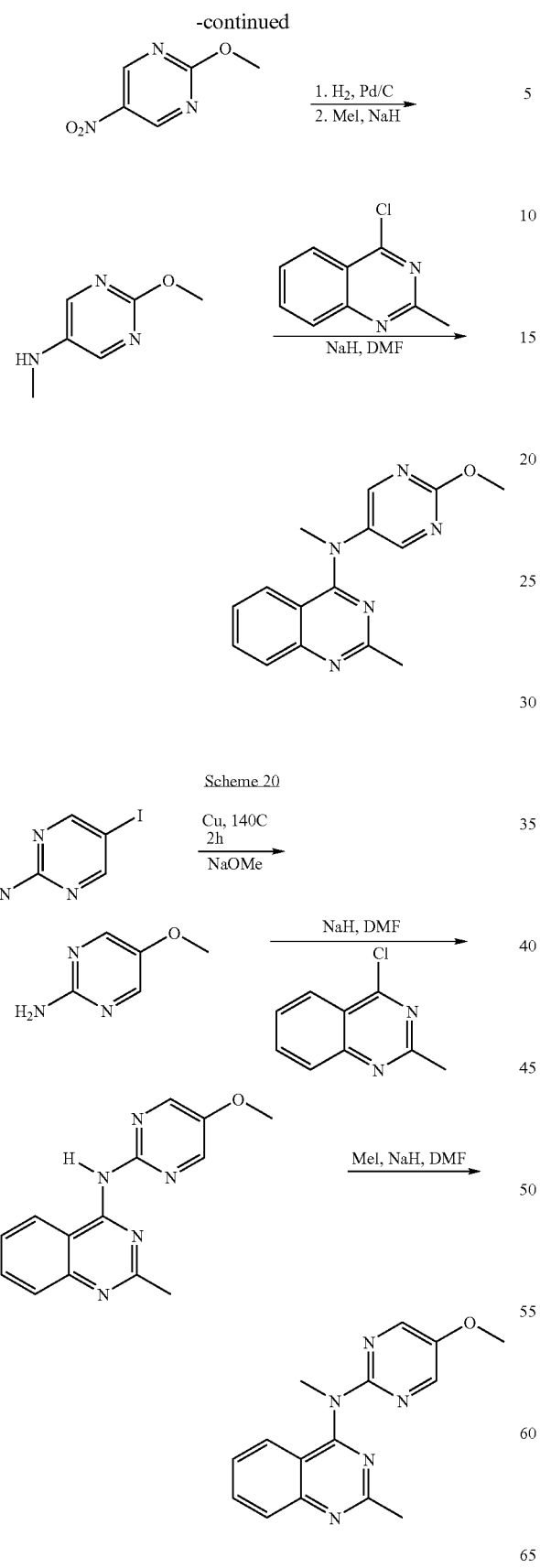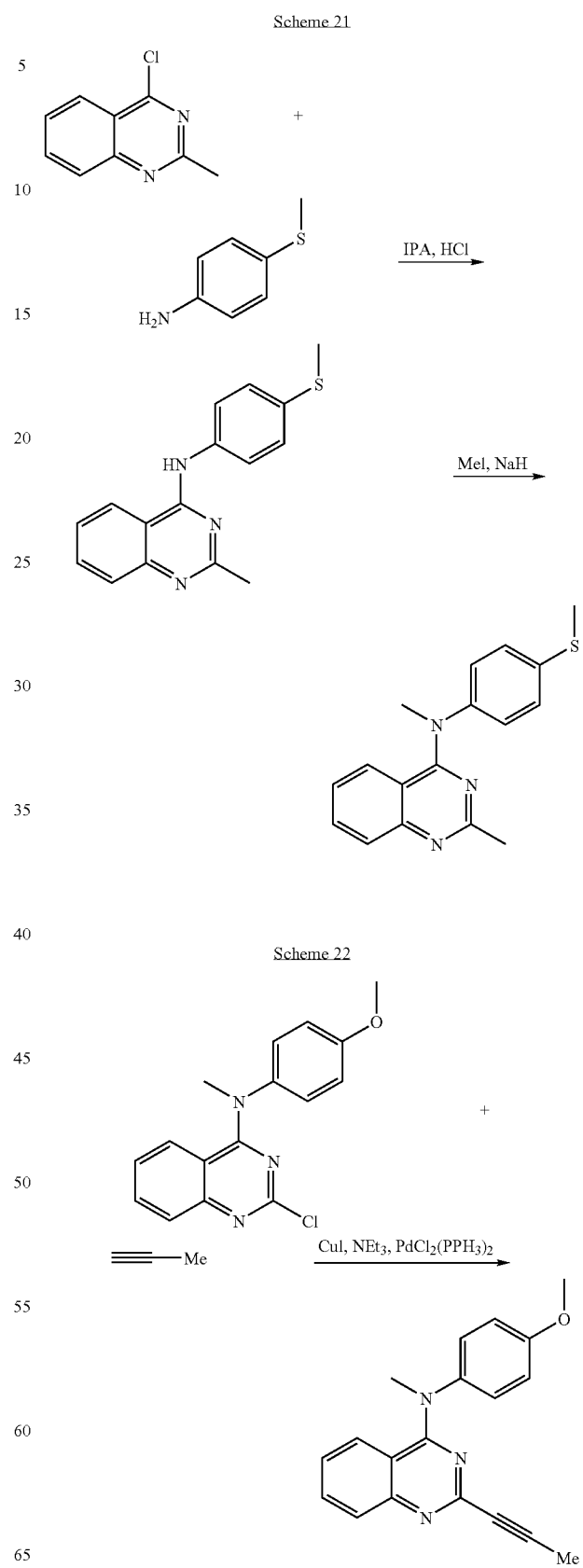

Scheme 23

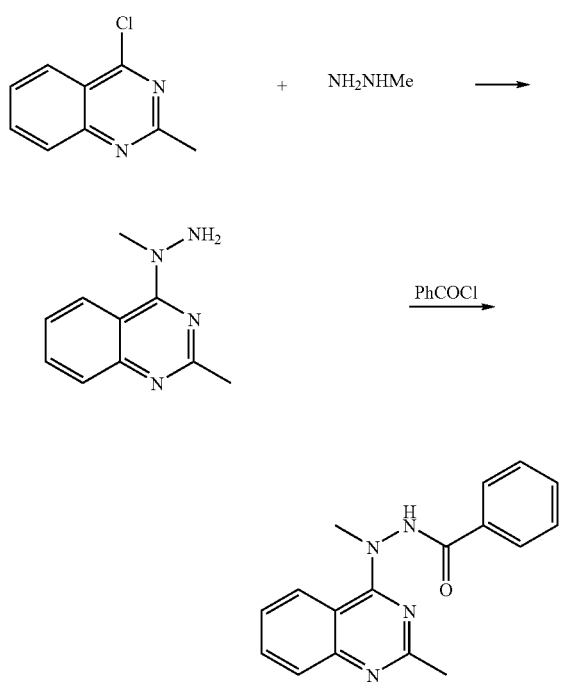

Scheme 24

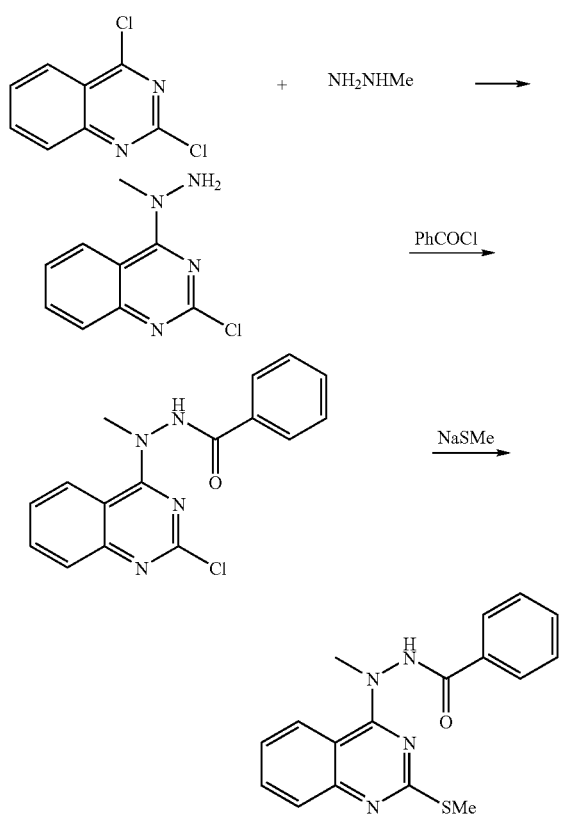

Scheme 25

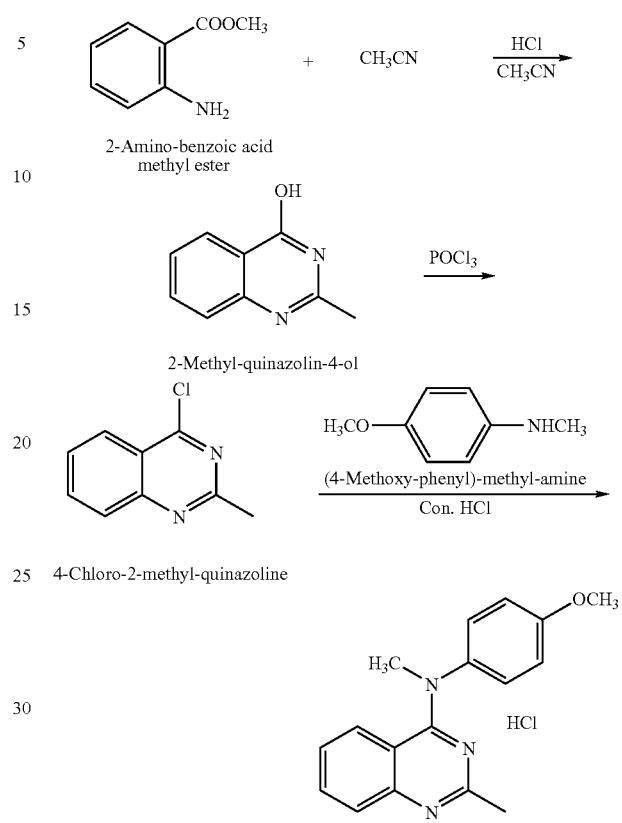

(4-Methoxy-phenyl)-methyl-(2-methyl-quinazolin-4-yl)-amine hydrochloride

An important aspect of the present invention is the discovery that compounds having Formulae I-VIb are activators of caspases and inducers of apoptosis. Another important aspect of the invention is the discovery that compounds having Formulae I-Vc are inhibitors of tubulin polymerization. Therefore, these compounds are useful in treating diseases that are responsive to activating caspases, inducing apoptosis, or inhibiting tubulin. For example, these compounds are useful in a variety of clinical conditions in which there is uncontrolled cell growth and spread of abnormal cells, such as in the case of cancer.

The present invention also includes a therapeutic method comprising administering to an animal an effective amount of a compound, or a pharmaceutically acceptable salt or prodrug of said compound of Formulae I-Vc, wherein said therapeutic method is useful to treat cancer, which is a group of diseases characterized by the uncontrolled growth and spread of abnormal cells. Such diseases include, but are not limited to, Hodgkin's disease, non-Hodgkin's lymphoma, acute lymphocytic leukemia, chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoides, head or neck carcinoma, osteogenic sarcoma, pancreatic carcinoma, acute granulocytic leukemia, hairy cell leukemia, neuroblastoma, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma.

In practicing the therapeutic methods, effective amounts of compositions containing therapeutically effective concentrations of the compounds formulated for oral, intravenous, local and topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptoms.

Another aspect of the present invention is to provide a pharmaceutical composition, containing an effective amount of a compound of Formulae I-VIb, or a pharmaceutically acceptable salt of said compound, in admixture with one or more pharmaceutically acceptable carriers or diluents.

In one embodiment, a pharmaceutical composition comprising a compound of Formulae I-Vc disclosed herein, or a pharmaceutically acceptable salt of said compound, in combination with a pharmaceutically acceptable vehicle is provided.

Preferred pharmaceutical compositions comprise compounds of Formulae I-VIb, and pharmaceutically acceptable salts, esters, or prodrugs thereof, that are able to induce caspase activation as determined by the method described in Example 145, preferably at an $EC_{50}$ no greater than 1,000 nM, more preferably at an $EC_{50}$ no greater than 500 nM, more preferably at an $EC_{50}$ no greater than 200 nM, more preferably at an $EC_{50}$ no greater than 100, and most preferably at an $EC_{50}$ no greater than 10 nM. Other preferred compositions comprise compounds of Formula I-VIb, and pharmaceutically acceptable salts, esters, or prodrugs thereof, that are able to inhibit tubulin polymerization as determined by the method described in Example 147.

Another embodiment of the present invention is directed to a composition effective to inhibit neoplasia comprising a compound, or a pharmaceutically acceptable salt or prodrug of said compound of Formulae I-VIb, which functions as a caspase cascade activator and inducer of apoptosis or inhibitor of tubulin polymerization, in combination with at least one known cancer chemotherapeutic agent, or a pharmaceutically acceptable salt of said agent. Examples of known cancer chemotherapeutic agents which may be used for combination therapy include, but not are limited to alkylating agents, such as busulfan, cis-platin, mitomycin C, and carboplatin; antimitotic agents, such as colchicine, vinblastine, paclitaxel, and docetaxel; topo I inhibitors, such as camptothecin and topotecan; topo II inhibitors, such as doxorubicin and etoposide; RNA/DNA antimetabolites, such as 5-azacytidine, 5-fluorouracil and methotrexate; DNA antimetabolites, such as 5-fluoro-2'-deoxy-uridine, ara-C, hydroxyurea and thioguanine; EGFR inhibitors, such as Iressa® (gefitinib) and Tarceva® (erlotinib); proteosome inhibitors; antibodies, such as campath, Herceptin® (trastuzumab), Avastin® (bevacizumab), or Rituxan® (rituximab). Other known cancer chemotherapeutic agents which may be used for combination therapy include melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine.

In practicing the methods of the present invention, the compound of the invention may be administered together with at least one known chemotherapeutic agent as part of a unitary pharmaceutical composition. Alternatively, the compound of the invention may be administered apart from at least one known cancer chemotherapeutic agent. In one embodiment, the compound of the invention and at least one known cancer chemotherapeutic agent are administered substantially simultaneously, i.e. the compounds are administered at the same time or one after the other, so long as the compounds reach therapeutic levels in the blood at the same time. On another embodiment, the compound of the invention and at least one known cancer chemotherapeutic agent are administered according to their individual dose schedule, so long as the compounds reach therapeutic levels in the blood.

It has been reported that alpha-1-adrenoceptor antagonists, such as doxazosin, terazosin, and tamsulosin can inhibit the growth of prostate cancer cell via induction of apoptosis (Kyprianou, N., et al., Cancer Res 60:4550-4555, (2000)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known alpha-1-adrenoceptor antagonists, or a pharmaceutically acceptable salt of said agent. Examples of known alpha-1-adrenoceptor antagonists, which can be used for combination therapy include, but are not limited to, doxazosin, terazosin, and tamsulosin.

It has been reported that sigma-2 receptors are expressed in high densities in a variety of tumor cell types (Vilner, B. J., et al., Cancer Res. 55: 408-413 (1995)) and that sigma-2 receptor agonists, such as CB-64D, CB-184 and haloperidol activate a novel apoptotic pathway and potentiate antineoplastic drugs in breast tumor cell lines. (Kyprianou, N., et al., Cancer Res. 62:313-322 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known sigma-2 receptor agonist, or a pharmaceutically acceptable salt of said agonist. Examples of known sigma-2 receptor agonists which can be used for combination therapy include, but are not limited to, CB-64D, CB-184 and haloperidol.

It has been reported that combination therapy with lovastatin, a HMG-CoA reductase inhibitor, and butyrate, an inducer of apoptosis in the Lewis lung carcinoma model in mice, showed potentiating antitumor effects (Giermasz, A., et al., Int. J. Cancer 97:746-750 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HMG-CoA reductase inhibitor, or a pharmaceutically acceptable salt of said agent. Examples of known HMG-CoA reductase inhibitors, which can be used for combination therapy include, but are not limited to, lovastatin, simvastatin, pravastatin, fluvastatin, atorvastatin and cerivastatin.

It has been reported that HIV protease inhibitors, such as indinavir or saquinavir, have potent anti-angiogenic activities and promote regression of Kaposi sarcoma (Sgadari, C., et al., Nat. Med. 8:225-232 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known HIV protease inhibitor, or a pharmaceutically acceptable salt of said agent. Examples of known HIV protease inhibitors, which can be used for combination therapy include, but are not limited to, amprenavir, abacavir, CGP-73547, CGP-61755, DMP-450, indinavir, nelfinavir, tipranavir, ritonavir, saquinavir, ABT-378, AG 1776, and BMS-232,632.

It has been reported that synthetic retinoids, such as fenretinide (N-(4-hydroxyphenyl)retinamide, 4HPR), have good activity in combination with other chemotherapeutic agents, such as cisplatin, etoposide or paclitaxel in small-cell lung cancer cell lines (Kalemkerian, G. P., et al., Cancer Chemother. Pharmacol. 43:145-150 (1999)). 4HPR also was reported to have good activity in combination with gamma-radiation on bladder cancer cell lines (Zou, C., et al., Int. J. Oncol. 13:1037-1041 (1998)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known retinoid and synthetic retinoid, or a pharmaceutically acceptable salt of said agent. Examples of known retinoids and synthetic retinoids, which can be used for combination therapy include, but are not limited to, bexarotene, tretinoin, 13-cis-retinoic acid, 9-cis-retinoic acid, α-difluoromethylornithine, ILX23-7553, fenretinide, and N-4-carboxyphenyl retinamide.

It has been reported that proteasome inhibitors, such as lactacystin, exert anti-tumor activity in vivo and in tumor cells in vitro, including those resistant to conventional chemotherapeutic agents. By inhibiting NF-kappaB transcriptional activity, proteasome inhibitors may also prevent angiogenesis and metastasis in vivo and further increase the sensitivity of cancer cells to apoptosis (Almond, J. B., et al., Leukemia 16:433-443 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known proteasome inhibitor, or a pharmaceutically acceptable salt of said agent. Examples of known proteasome inhibitors, which can be used for combination therapy include, but are not limited to, lactacystin, MG-132, and PS-341.

It has been reported that tyrosine kinase inhibitors, such as STI571 (Gleevec® (imatinib mesylate)), have potent synergetic effect in combination with other anti-leukemic agents, such as etoposide (Liu, W. M., et al. Br. J. Cancer 86:1472-1478 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known tyrosine kinase inhibitor, or a pharmaceutically acceptable salt of said agent. Examples of known tyrosine kinase inhibitors, which can be used for combination therapy include, but are not limited to, Gleevec® (imatinib mesylate), ZD1839 Iressa® (gefitinib), SH268, genistein, CEP2563, SU6668, SU11248, and EMD121974.

It has been reported that prenyl-protein transferase inhibitors, such as farnesyl protein transferase inhibitor R115777, possess preclinical antitumor activity against human breast cancer (Kelland, L. R., et. al., Clin. Cancer Res. 7:3544-3550 (2001)). Synergy of the protein farnesyltransferase inhibitor SCH66336 and cisplatin in human cancer cell lines also has been reported (Adjei, A. A., et al., Clin. Cancer. Res. 7:1438-1445 (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis, in combination with at least one known prenyl-protein transferase inhibitor, including farnesyl protein transferase inhibitor, inhibitors of geranylgeranyl-protein transferase type I (GGPTase-I) and geranylgeranyl-protein transferase type-II, or a pharmaceutically acceptable salt of said agent. Examples of known prenyl-protein transferase inhibitors, which can be used for combination therapy include, but are not limited to, R115777, SCH66336, L-778, 123, BAL9611 and TAN-1813.

It has been reported that cyclin-dependent kinase (CDK) inhibitors, such as flavopiridol, have potent synergetic effect in combination with other anticancer agents, such as CPT-11, a DNA topoisomerase I inhibitor in human colon cancer cells (Motwani, M., et al., Clin. Cancer Res. 7:4209-4219, (2001)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known cyclin-dependent kinase inhibitor, or a pharmaceutically acceptable salt of said agent. Examples of known cyclin-dependent kinase inhibitor, which can be used for combination therapy include, but are not limited to, flavopiridol, UCN-01, roscovitine and olomoucine.

It has been reported that in preclinical studies COX-2 inhibitors were found to block anigiogenesis, suppress solid tumor metastases, and slow the growth of implanted gastrointestinal cancer cells (Blanke, C. D., Oncology (Huntingt) 16(No. 4 Suppl. 3):17-21 (2002)). Therefore, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with at least one known COX-2 inhibitor, or a pharmaceutically acceptable salt of said inhibitor. Examples of known COX-2 inhibitors which can be used for combination therapy include, but are not limited to, celecoxib, valecoxib, and rofecoxib.

Another embodiment of the present invention is directed to a composition effective to inhibit neoplasia comprising a bioconjugate of a compound described herein, which functions as a caspase cascade activator and inducer of apoptosis or inhibitor of tubulin polymerization, in bioconjugation with at least one known therapeutically useful antibody, such as Herceptin® (trastuzumab) or Rituxan® (rituximab), growth factors, such as DGF, NGF; cytokines, such as IL-2, IL-4, or any molecule that binds to the cell surface. The antibodies and other molecules will deliver a compound described herein to its targets and make it an effective anticancer agent. The bioconjugates could also enhance the anticancer effect of therapeutically useful antibodies, such as Herceptin® (trastuzumab) or Rituxan® (rituximab).

Similarly, another embodiment of the present invention is directed to a composition effective to inhibit neoplasia comprising a compound, or a pharmaceutically acceptable salt or prodrug of a compound described herein, which functions as a caspase cascade activator and inducer of apoptosis or inhibitor of tubulin polymerization, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound, or a pharmaceutically acceptable salt or prodrug of a compound described herein, which functions as a caspase cascade activator and inducer of apoptosis or inhibitor of tubulin polymerization. The invention also relates to a method of treating cancer by surgically removing the cancer and then treating the animal with one of the pharmaceutical compositions described herein.

A wide range of immune mechanisms operate rapidly following exposure to an infectious agent. Depending on the type of infection, rapid clonal expansion of the T and B lymphocytes occurs to combat the infection. The elimination of the effector cells following an infection is one of the major mechanisms for maintaining immune homeostasis. The elimination of the effector cells has been shown to be regulated by apoptosis. Autoimmune diseases have lately been determined to occur as a consequence of deregulated cell death. In certain autoimmune diseases, the immune system directs its powerful cytotoxic effector mechanisms against specialized cells, such as oligodendrocytes in multiple sclerosis, the beta cells of the pancreas in diabetes mellitus, and thyrocytes in Hashimoto's thyroiditis (Ohsako, S. & Elkon, K. B., *Cell Death Differ.* 6:13-21 (1999)). Mutations of the gene encoding the lymphocyte apoptosis receptor Fas/APO-1/CD95 are reported to be associated with defective lymphocyte apoptosis and autoimmune lymphoproliferative syndrome (ALPS), which is characterized by chronic, histologically benign splenomegaly, generalized lymphadenopathy, hypergammaglobulinemia, and autoantibody formation. (Infante, A. J., et al., *J. Pediatr.* 133:629-633 (1998) and Vaishnaw, A. K., et al., *J. Clin. Invest.* 103:355-363 (1999)). It was reported that overexpression of Bcl-2, which is a member of the bcl-2 gene family of programmed cell death regulators with anti-apoptotic activity, in developing B cells of transgenic mice, in the presence of T cell dependent costimulatory signals, results in the generation of a modified B cell repertoire and in the production of pathogenic autoantibodies (Lopez-Hoyos, M., et al., Int. *J. Mol. Med.* 1:475-483 (1998)). It is therefore evident that many types of autoimmune disease are caused by defects of the apoptotic process. One treatment strategy for such diseases is to turn on apoptosis in the lymphocytes that are causing the autoimmune disease (O'Reilly, L. A. & Strasser, A., *Inflamm. Res.* 48:5-21 (1999)).

Fas-Fas ligand (FasL) interaction is known to be required for the maintenance of immune homeostasis. Experimental autoimmune thyroiditis (EAT), characterized by autoreactive T and B cell responses and a marked lymphocytic infiltration of the thyroid, is a good model to study the therapeutic effects of FasL. Batteux, F., et al., (*J. Immunol.* 162:603-608 (1999)) reported that by direct injection of DNA expression vectors encoding FasL into the inflamed thyroid, the development of lymphocytic infiltration of the thyroid was inhibited and induction of infiltrating T cells death was observed. These results show that FasL expression on thyrocytes may have a curative effect on ongoing EAT by inducing death of pathogenic autoreactive infiltrating T lymphocytes.

Bisindolylmaleimide VIII is known to potentiate Fas-mediated apoptosis in human astrocytoma 1321N1 cells and in Molt-4T cells; both of which were resistant to apoptosis induced by anti-Fas antibody in the absence of bisindolylmaleimide VIII. Potentiation of Fas-mediated apoptosis by bisindolylmaleimide VIII was reported to be selective for activated, rather than non-activated, T cells, and was Fas-dependent. Zhou T., et al., (*Nat. Med.* 5:42-48 (1999)) reported that administration of bisindolylmaleimide VIII to rats during autoantigen stimulation prevented the development of symptoms of T cell-mediated autoimmune diseases in two models, the Lewis rat model of experimental allergic encephalitis and the Lewis adjuvant arthritis model. Therefore, the application of a Fas-dependent apoptosis enhancer, such as bisindolylmaleimide VIII, may be therapeutically useful for the more effective elimination of detrimental cells and inhibition of T cell-mediated autoimmune diseases. Therefore, an effective amount of a compound, or a pharmaceutically acceptable salt or prodrug of the compound of Formulae I-Vc, which functions as a caspase cascade activator and inducer of apoptosis, is an effective treatment for autoimmune diseases.

Psoriasis is a chronic skin disease that is characterized by scaly red patches. Psoralen plus ultraviolet A (PUVA) is a widely used and effective treatment for psoriasis vulgaris. Coven, et al., *Photodermatol. Photoimmunol. Photomed.* 15:22-27 (1999), reported that lymphocytes treated with psoralen 8-MOP or TMP and UVA, displayed DNA degradation patterns typical of apoptotic cell death. Ozawa, et al., *J. Exp. Med.* 189:711-718 (1999) reported that induction of T cell apoptosis could be the main mechanism by which 312-nm UVB resolves psoriasis skin lesions. Low doses of methotrexate may be used to treat psoriasis to restore a clinically normal skin. Heenen, et al., *Arch. Dermatol. Res.* 290:240-245 (1998), reported that low doses of methotrexate may induce apoptosis and that this mode of action could explain the reduction in epidermal hyperplasia during treatment of psoriasis with methotrexate. Therefore, an effective amount of a compound, or a pharmaceutically acceptable salt or prodrug of the compound of Formulae I-Vc, which functions as a caspase cascade activator and inducer of apoptosis, is an effective treatment for hyperproliferative skin diseases, such as psoriasis.

Synovial cell hyperplasia is a characteristic of patients with rheumatoid arthritis (RA). It is believed that excessive proliferation of RA synovial cells, as well as defects in synovial cell death, may be responsible for synovial cell hyperplasia. Wakisaka, et al., *Clin. Exp. Immunol.* 114:119-128 (1998), found that although RA synovial cells could die via apoptosis through a Fas/FasL pathway, apoptosis of synovial cells was inhibited by proinflammatory cytokines present within the synovium. Wakisaka, et al. also suggested that inhibition of apoptosis by the proinflammatory cytokines may contribute to the outgrowth of synovial cells, and lead to pannus formation and the destruction of joints in patients with RA. Therefore, an effective amount of a compound, or a pharmaceutically acceptable salt or prodrug of the compound of Formulae I-Vc, which functions as a caspase cascade activator and inducer of apoptosis, is an effective treatment for rheumatoid arthritis.

There has been an accumulation of convincing evidence that apoptosis plays a major role in promoting resolution of the acute inflammatory response. Neutrophils are constitutively programmed to undergo apoptosis, thus limiting their pro-inflammatory potential and leading to rapid, specific, and non-phlogistic recognition by macrophages and semi-professional phagocytes (Savill, J., *J. Leukoc. Biol.* 61:375-380 (1997)). Boirivant, et al., *Gastroenterology* 116:557-565 (1999), reported that lamina propria T cells, isolated from areas of inflammation in Crohn's disease, ulcerative colitis, and other inflammatory states, manifest decreased CD2 pathway-induced apoptosis. In addition, studies of cells from inflamed Crohn's disease tissue indicate that this defect is accompanied by elevated Bcl-2 levels. Therefore, an effective amount of a compound, or a pharmaceutically acceptable salt or prodrug of the compound of Formulae I-Vc, which functions as a caspase cascade activator and inducer of apoptosis, is an effective treatment for inflammation.

Caspase cascade activators and inducers of apoptosis may also be a desirable therapy in the elimination of pathogens, such as HIV, Hepatitis C and other viral pathogens. The long lasting quiescence, followed by disease progression, may be explained by an anti-apoptotic mechanism of these pathogens leading to persistent cellular reservoirs of the virions. It has been reported that HIV-1 infected T leukemia cells or peripheral blood mononuclear cells (PBMCs) underwent enhanced viral replication in the presence of the caspase inhibitor Z-VAD-fmk. Furthermore, Z-VAD-fmk also stimulated endogenous virus production in activated PBMCs derived from HIV-1-infected asymptomatic individuals (Chinnaiyan, A., et al., *Nat. Med.* 3:333 (1997)). Therefore, apoptosis serves as a beneficial host mechanism to limit the spread of HIV and new therapeutics using caspase/apoptosis activators are useful to clear viral reservoirs from the infected individuals. Similarly, HCV infection also triggers anti-apoptotic mechanisms to evade the host's immune surveillance leading to viral persistence and hepatocarcinogenesis (Tai, D. I., et al. *Hepatology* 3:656-64 (2000)). Therefore, apoptosis inducers are useful as therapeutics for HIV, HCV, HBV, and other infectious disease.

Stent implantation has become the new standard angioplasty procedure. However, in-stent restenosis remains the major limitation of coronary stenting. New approaches have been developed to target pharmacological modulation of local vascular biology by local administration of drugs. This allows for drug applications at the precise site and time of vessel injury. Numerous pharmacological agents with antiproliferative properties are currently under clinical investigation, including actinomycin D, rapamycin or paclitaxel coated stents (Regar E., et al., *Br. Med. Bull.* 59:227-248 (2001)). Therefore, apoptosis inducers, which are antiproliferative, are useful as therapeutics for the prevention or reduction of in-stent restenosis.

Another important aspect of the present invention is the surprising discovery that compounds of the present invention are potent and highly efficacious activators of caspase-3, inhibitors of tubulin polymerization, and inhibitors of topoisomerase even in drug resistant cancer cells, which enables these compounds to inhibit the growth and proliferation of drug resistant cancer cells, and to cause apoptosis and cell death in the drug resistant cancer cells. Specifically, the compounds of the present invention are not substrates for the MDR transporters such as Pgp-1 (MDR-1), MRP-1 and BCRP. This is particularly surprising in view of the fact that almost all of the commercially available tubulin-interacting chemotherapeutics are substrates for multidrug resistance transporters (MDRs).

Multidrug resistance is the major cause of chemotherapy failure. Drug resistance is typically caused by ATP-dependent efflux of drug from cells by ATP-binding cassette (ABC) transporters. In particular, the ABC transporters ABCB1 (MDR-1, P glycoprotein); ABCC1 (MRP1); and ABCG2 (BCRP, MXR) are typically over-expressed in drug resistant tumors and thus are implicated in drug resistance. In comparison to most standard anti-cancer drugs, which are not effective in killing drug resistant cancer cells, the compounds of the present invention are effective in killing drug resistant cancer cells. Therefore, compounds of this invention are useful for the treatment of drug resistant cancer.

Thus, another aspect of the present invention is the application of the methods and compounds of the present invention as described above to tumors that have acquired resistance to other anticancer drugs. In one embodiment, a compound of the present invention is administered to a cancer patient who has been treated with another anti-cancer drug. In another embodiment, a compound of the present invention is administered to a patient who has been treated with and is not responsive to another anti-cancer drug or developed resistance to such other anti-cancer compound. In another embodiment, a compound of the present invention is administered to a patient who has been treated with another anti-cancer drug and is refractory to said other anti-cancer drug. The compounds of the present invention can be used in treating cancer in a patient who is not responsive or is resistant to any other anti-cancer agent. Examples of such other anti-cancer agent may include alkylating agents, antimitotic agents, topo I inhibitors, topo II inhibitors, RNA/DNA antimetabolites, EGFR inhibitors, angiogenesis inhibitors, tubulin inhibitors (e.g., vinblastine, Taxol® (paclitaxel), and analogues thereof), proteosome inhibitors, etc., some of the exemplary compounds of which are provided above and are general known in the art, e.g., melphalan, chlorambucil, cyclophosamide, ifosfamide, vincristine, mitoguazone, epirubicin, aclarubicin, bleomycin, mitoxantrone, elliptinium, fludarabine, octreotide, retinoic acid, tamoxifen, Gleevec® (imatinib mesylate) and alanosine. The compounds can be used in treating patients having any type of diseases responsive to the inhibition of tubulin or inhibition of topoisomerase (including but not limited to the types of cancer described above) who are not responsive or become resistant to another therapeutic agent, e.g., another anti-cancer agent.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to animals, e.g., mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. For intramuscular injection, the dose is generally approximately one-half of the oral dose. For example, a suitable intramuscular dose would be approximately 0.0025 to approximately 25 mg/kg of body weight, and most preferably, from approximately 0.01 to approximately 5 mg/kg of body weight. If a known cancer chemotherapeutic agent is also administered, it is administered in an amount that is effective to achieve its intended purpose. The amounts of such known cancer chemotherapeutic agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 10 mg, conveniently approximately 0.25 to 50 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, and also preparations that may be administered rectally, such as suppositories, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Basic salts are formed by mixing a solution of the compounds of the present invention with a solution of a pharmaceutically acceptable non-toxic base, such as sodium hydroxide, potassium hydroxide, choline hydroxide, sodium carbonate, Tris, N-methyl-glucamine and the like.

The pharmaceutical compositions of the invention may be administered to any animal, which may experience the beneficial effects of the compounds of the invention. Foremost among such animals are mammals, e.g., humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular: fillers, such as saccharides, e.g. lactose or sucrose, mannitol or sorbitol; cellulose preparations and/or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropymethyl-cellulose phthalate, are used. Dye stuffs or pigments may be added to the tablets or dragee coatings, e.g., for identification or in order to characterize combinations of active compound doses.

Other pharmaceutical preparations, which may be used orally include push-fit capsules made of gelatin, as well as soft, sealed capsules made of gelatin and a plasticizer, such as glycerol or sorbitol. The push-fit capsules may contain the active compounds in the form of: granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which may be used rectally include, e.g., suppositories, which consist of a combination of one or more of the active compounds with a suppository base. Suitable suppository bases are, e.g., natural or synthetic triglycerides, or paraffin hydrocarbons. In addition, it is also possible to use gelatin rectal capsules, which consist of a combination of the active compounds with a base. Possible base materials include, e.g., liquid triglycerides, polyethylene glycols, or paraffin hydrocarbons.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate or triglycerides or polyethylene glycol-400 (the compounds are soluble in PEG-400), or cremophor, or cyclodextrins. Aqueous injection suspensions may contain substances which increase the viscosity of the suspension include, e.g., sodium carboxymethyl cellulose, sorbitol, and/or dextran. Optionally, the suspension may also contain stabilizers.

In accordance with one aspect of the present invention, compounds of the invention are employed in topical and parenteral formulations and are used for the treatment of skin cancer.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

Example 1

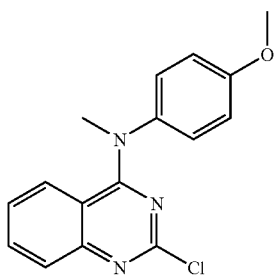

(2-Chloro-quinazolin-4-yl)-(4-methoxy-phenyl)-methyl-amine a) 2,4-Dichloroquinazoline: A suspension of 2,4-quinazolinedione (5.0 g, 30.8 mmol) in neat phosphorylchloride (50 mL) was heated under reflux for 18 h. The reaction mixture was concentrated under vacuum. The crude product was purified by chromatography (Silica gel) using ethyl acetate and hexane (1:4) to give 2,4-dichloroquinazoline as white solid (4.8 g, 96%). $^1$H NMR (CDCl$_3$): 8.29 (ddd, J=8.4, 2.1 and 0.9 Hz, 1H), 8.04-8.00 (m, 2H), 7.75 (ddd, J=8.1, 4.8 and 3.0 Hz, 1H).

b) (2-Chloro-quinazolin-4-yl)-(4-methoxy-phenyl)-methyl-amine: A solution of 2,4-dichloroquinazoline (300 mg, 1.51 mmol) and 4-methoxy-N-methylaniline (248 mg, 1.81 mmol) in 5 ml isopropanol with a drop of concentrated HCl was stirred at room temperature for 8 h. White precipitates were observed in the reaction mixture. The reaction was filtered, and the solid was washed with isopropanol, and dried under vacuum to give white powder (260 mg, 87%). $^1$H NMR (CDCl$_3$): 8.66 (dd, J=8.4 and 0.9 Hz, 1H), 7.75 (ddd, J=8.1, 7.5 and 0.9 Hz, 1H), 7.26-7.19 (m, 3H), 7.14 (ddd, J=8.1, 7.5, 0.9 Hz, 1H), 7.06 (dd, J=6.9 and 2.4 Hz, 2H), 6.75 (d, J=8.7 Hz, 1H), 3.91 (s, 3H), 3.81 (s, 3H).

Example 2

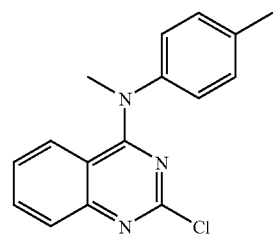

(2-Chloro-quinazolin-4-yl)-(4-methyl-phenyl)-methyl-amine

The title compound was prepared from 2,4-dichloroquinazoline (250 mg, 1.25 mmol) and 4-methyl-N-methylaniline (196 mg, 1.43 mmol) by a procedure similar to example 1b and was isolated as white powder (210 mg, 84%). $^1$H NMR (CDCl$_3$): 8.69 (d, J=8.4 Hz, 1H), 7.75 (dd, J=8.1 and 7.5 Hz, 1H), 7.39 (d, J=7.8 Hz, 2H), 7.25 (d, J=7.8 Hz, 2H), 7.13 (d, J=8.2 Hz, 1H), 6.74 (d, J=8.7 Hz, 1H), 3.81 (s, 3H), 2.49 (s, 3H).

Example 3

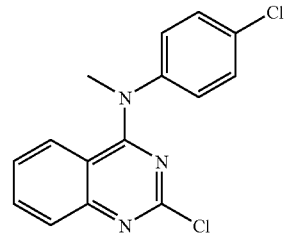

(2-Chloro-quinazolin-4-yl)-(4-chloro-phenyl)-methyl-amine

The title compound was prepared from 2,4-dichloroquinazoline (60 mg, 0.302 mmol) and 4-chloro-N-methylaniline (50 mg, 0.332 mmol) by a procedure similar to example 1b and was isolated as white powder (30 mg, 50%). $^1$H NMR (CDCl$_3$): 8.66 (d, J=8.4 Hz, 1H), 7.78 (ddd, J=8.1, 7.5 and 2.4

Hz, 1H), 7.57 (d, J=8.7 Hz, 2H), 7.28 (d, J=8.7 Hz, 2H), 7.19 (ddd, J=8.1, 7.5 and 2.4 Hz, 1H), 6.79 (d, J=8.4 Hz, 1H), 3.83 (s, 3H).

Example 4

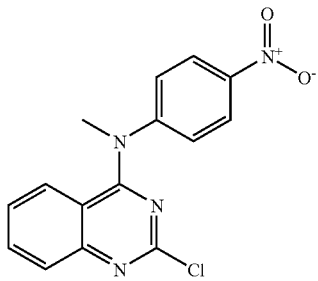

(2-Chloro-quinazolin-4-yl)-(4-nitro-phenyl)-methyl-amine

The title compound was prepared from 2,4-dichloro-quinazoline (50 mg, 0.251 mmol) and 4-nitro-N-methylaniline (46 mg, 0.302 mmol) by a procedure similar to example 1b and was isolated as yellow powder (6 mg, 12%). $^1$H NMR (CDCl$_3$): 8.24 (d, J=8.7 Hz, 2H), 7.81 (dd, J=8.1, and 2.4 Hz, 1H), 7.68 (ddd, J=8.1, 7.5 and 2.4 Hz, 1H), 7.28 (d, J=8.7 Hz, 2H), 7.18 (ddd, J=8.1, 7.5 and 2.4 Hz, 1H), 7.07 (d, J=7.8 Hz, 1H), 3.75 (s, 3H).

Example 5

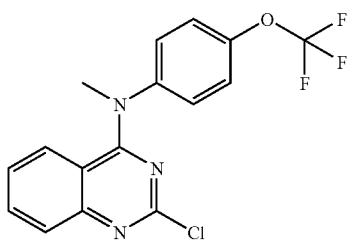

(2-Chloro-quinazolin-4-yl)-(4-trifluoromethoxy-phenyl)-methyl-amine

The title compound was prepared from 2,4-dichloro-quinazoline (50 mg, 0.251 mmol) and 4-trifluoromethoxy-N-methylaniline (20 μL, 0.302 mmol) by a procedure similar to example 1b and was isolated as white powder (22 mg, 44%). $^1$H NMR (CDCl$_3$): 7.93 (dd, J=8.4, and 0.6 Hz, 1H), 7.61 (ddd, J=8.4, 4.5 and 1.2 Hz, 1H), 7.29-7.22 (m, 4H), 7.06 (ddd, J=8.4, 4.5 and 1.2 Hz, 1H), 6.91 (d, J=8.7 Hz, 1H), 3.65 (s, 3H).

Example 6

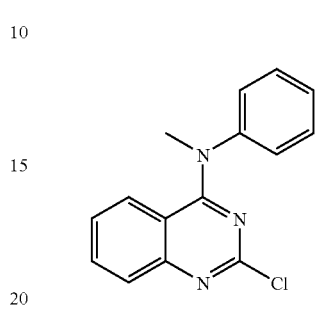

(2-Chloro-quinazolin-4-yl)-phenyl-methyl-amine

The title compound was prepared from 2,4-dichloro-quinazoline (50 mg, 0.251 mmol) and N-methylaniline (20 μL, 0.301 mmol) by a procedure similar to example 1b and was isolated as white powder (40 mg, 80%). $^1$H NMR (CDCl$_3$): 7.76 (dd, J=8.7, and 1.5 Hz, 1H), 7.56 (ddd, J=8.1, 6.6 and 1.5 Hz, 1H), 7.46-7.35 (m, 3H), 7.24-7.20 (m, 2H), 6.98 (ddd, J=8.7, 6.6 and 1.5 Hz, 1H), 6.90 (dd, J=8.7 and 1.5 Hz, 1H), 3.65 (s, 3H).

Example 7

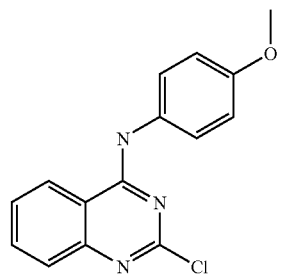

(2-Chloro-quinazolin-4-yl)-(4-methoxy-phenyl)-amine

The title compound was prepared from 2,4-dichloro-quinazoline (50 mg, 0.251 mmol) and 4-methoxyaniline (45 mg, 0.326 mmol) by a procedure similar to example 1b and was isolated as off white powder (55 mg, 77%). $^1$H NMR (CDCl$_3$): 10.25 (s, 1H), 8.58 (d, J=8.4 Hz, 1H), 7.88 (t, J=7.2 Hz, 1H), 7.71-7.63 (m, 4H), 7.03-6.99 (m, 2H), 3.79 (s, 3H).

Example 8

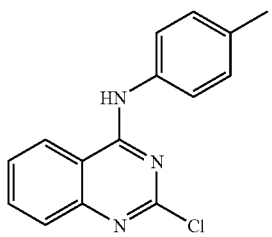

(2-Chloro-quinazolin-4-yl)-(4-methyl-phenyl)-amine

The title compound was prepared from 2,4-dichloroquinazoline (50 mg, 0.251 mmol) and 4-methylaniline (32 mg, 0.30 mmol) by a procedure similar to example 1b and was isolated as white powder (15 mg, 30%). $^1$H NMR (CDCl$_3$): 7.97-7.89 (m, 3H), 7.71 (d, J=6.6 Hz, 2H), 7.64 (ddd, J=8.4, 6.6 and 2.1 Hz, 1H), 7.33 (d, J=6.6 Hz, 2H), 2.47 (s, 3H).

Example 9

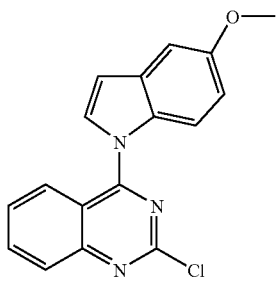

2-Chloro-4-(5-methoxyindol-1-yl)quinazoline

The title compound was prepared from 2,4-dichloroquinazoline (50 mg, 0.251 mmol) and 5-methoxyindole (40 mg, 0.302 mmol) similar to example 1b and was isolated as white powder (14 mg, 28%). $^1$H NMR (CDCl$_3$): 8.91 (s, 1H), 8.70 (ddd, J=8.4, 2.8 and 1.5 Hz, 1H), 8.01 (ddd, J=8.4, 2.8 and 1.5 Hz, 1H), 7.92 (dd, J=6.9 and 1.5 Hz, 1H), 7.87 (m, 1H), 7.74 (d, J=2.4 Hz, 1H), 7.61 (ddd, J=8.4, 6.9 and 1.2 Hz, 1H), 7.37 (d, J=9.0 Hz, 1H), 6.97 (dd, J=9.0 and 2.4 Hz, 1H), 3.88 (s, 3H).

Example 10

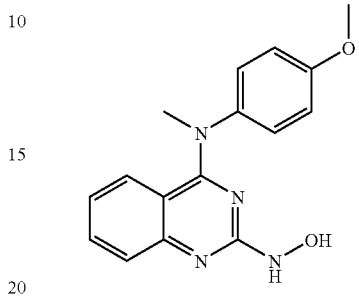

N$^2$-Hydroxyl-N$^4$-(4-methoxy-phenyl)-N$^4$-methyl-quinazoline-2,4-diamine

A mixture of (2-chloro-quinazolin-4-yl)-(4-methoxy-phenyl)-methyl-amine (15 mg, 0.050 mmol) and hydroxylamine hydrochloride (6.7 mg, 0.10 mmol) in isopropanol was heated by microwave at 130° C. for 20 min. The solvent was evaporated under reduced pressure. The product was isolated by preparative TLC as white solid (6 mg, 40%) using acetone:hexane (1:1) as eluent. $^1$H NMR (CDCl$_3$): 7.65 (d, J=8.4 Hz, 1H), 7.47 (ddd, J=8.4, 6.9 and 1.8 Hz, 1H), 7.08 (d, J=8.7 Hz, 2H), 6.94 (d, J=8.7 Hz, 2H), 6.88-6.75 (m, 2H), 3.86 (s, 3H), 3.48 (s, 3H).

Example 11

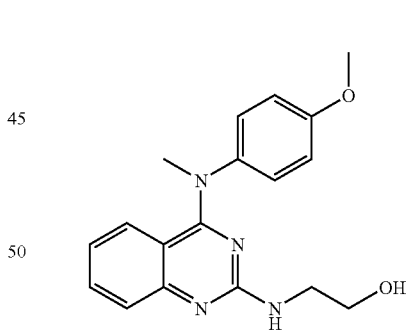

N$^2$-(2-Hydroxylethyl)-N$^4$-(4-methoxy-phenyl)-N$^4$-methyl-quinazoline-2,4-diamine The title compound was prepared from (2-chloro-quinazolin-4-yl)-(4-methoxy-phenyl)-methyl-amine (15 mg, 0.050 mmol) and 2-hydroxylethylamine (20 μL) by a procedure similar to example 10 and was isolated as white solid (12 mg, 80%). $^1$H NMR (CDCl$_3$): 7.43 (ddd, J=8.4, 1.5 and 0.9 Hz, 1H), 7.35 (ddd, J=7.8, 3.3 and 1.5 Hz, 1H), 7.12-7.06 (m, 2H), 6.92-6.90 (m, 2H), 6.84 (dd, J=8.4 and 1.5 Hz, 1H), 6.66 (ddd, J=7.2, 6.3 and 1.5 Hz, 1H), 3.91-3.89 (m, 2H), 3.83 (s, 3H), 3.69-3.65 (m, 2H), 3.48 (s, 3H).

Hz, 1H), 4.15 (d, J=6.9 Hz, 2H), 3.85 (s, 3H), 3.50 (s, 3H), 2.12-2.03 (m, 4H), 1.75 (s, 3H), 1.70 (s, 3H), 1.61 (s, 3H).

Example 12

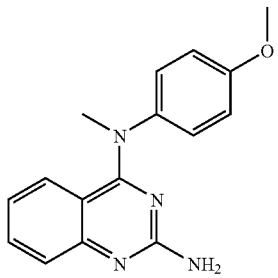

N$^4$-(4-Methoxy-phenyl)-N$^4$-methyl-quinazoline-2,4-diamine

Title compound was prepared from (2-chloro-quinazolin-4-yl)-(4-methoxy-phenyl)-methyl-amine (10 mg, 0.033 mmol) and 7 M ammonia in methanol (1 mL) by a procedure similar to example 10 (5 mg, 50%). $^1$H NMR (CDCl$_3$): 7.44 (m, 2H), 7.16 (m, 2H), 6.96-6.95 (m, 2H), 6.88 (dd, J=8.4 and 1.5 Hz, 1H), 6.72 (ddd, J=8.7, 6.6 and 1.8 Hz, 1H), 3.86 (s, 3H), 3.72 (s, 3H).

Example 13

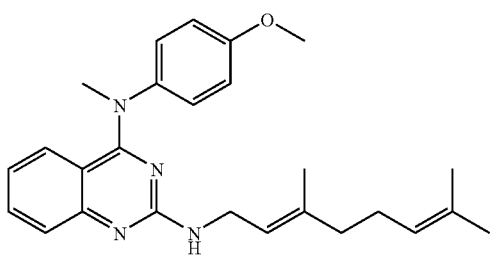

N$^2$-(3,7-Dimethyl-octa-2,6-dienyl)-N$^4$-(4-methoxy-phenyl)-N$^4$-methyl-quinazoline-2,4-diamine The title compound was prepared from (2-chloro-quinazolin-4-yl)-(4-methoxy-phenyl)-methyl-amine (45 mg, 0.151 mmol) and 3,7-dimethyl-2,6-diene-octamine (60 μL, 0.301 mmol) by a procedure similar to example 10 and was isolated as white powder (15 mg, 33%). $^1$H NMR (CDCl$_3$): 7.42 (d, J=8.1 Hz, 1H), 7.32 (ddd, J=8.7, 6.6 and 1.5 Hz, 1H), 7.12-7.07 (m, 2H), 6.91-6.85 (m, 3H), 6.65 (ddd, J=8.7, 6.6 and 1.5 Hz, 1H), 5.41 (t, J=7.5 Hz, 1H), 5.11 (ddd, J=6.6, 5.1 and 1.2

Example 14

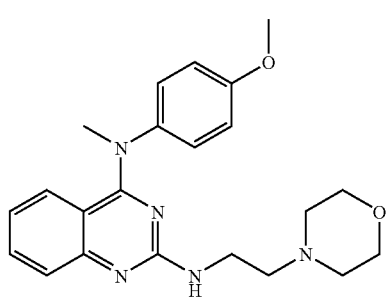

N$^4$-(4-Methoxy-phenyl)-N$^4$-methyl-N$^2$-(2-morpholin-4-yl-ethyl)-quinazoline-2,4-diamine The title compound was prepared from (2-chloro-quinazolin-4-yl)-(4-methoxy-phenyl)-methyl-amine (10 mg, 0.033 mmol) and 2-morpholin-4-yl-ethylamine (30 μL) by a procedure similar to example 10 and was isolated as white powder (10 mg, 100%). $^1$H NMR (CDCl$_3$): 7.42 (dd, J=8.7 and 1.2 Hz, 1H), 7.36 (ddd, J=8.1, 6.6 and 1.5 Hz, 1H), 7.10-7.09 (m, 2H), 6.92-6.86 (m, 3H), 6.67 (ddd, J=8.1, 6.6 and 1.4 Hz, 1H), 3.82 (s, 3H), 3.75-3.62 (m, 6H), 3.52 (s, 3H), 2.55-2.44 (m, 6H).

Example 15

4-Methoxy-phenyl)-methyl-(2-morpholin-4-yl-quinazolin-4-yl)-amine

The title compound was prepared from (2-chloro-quinazolin-4-yl)-(4-methoxy-phenyl)-methyl-amine (15 mg, 0.050 mmol) and morpholine (30 μL) by a procedure similar to example 10 and was isolated as white powder (10 mg, 66%). $^1$H NMR (CDCl$_3$): 7.46 (d, J=8.4 Hz, 1H), 7.35 (ddd, J=8.4, 6.6 and 1.5 Hz, 1H), 7.13-7.07 (m, 2H), 6.91-6.85 (m, 3H), 6.67 (ddd, J=8.4, 6.6 and 1.5 Hz, 1H), 3.94-3.90 (m, 4H), 3.85-3.81 (m, 7H), 3.52 (s, 3H).

Example 16

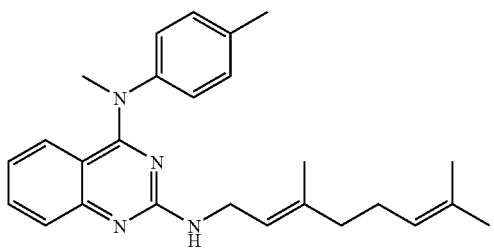

N²-(3,7-Dimethyl-octa-2,6-dienyl)-N⁴-(4-methyl-phenyl)-N⁴-methyl-quinazoline-2,4-diamine The title compound was prepared from (2-chloro-quinazolin-4-yl)-(4-methyl-phenyl)-methyl-amine (50 mg, 0.177 mmol) and 3,7-dimethyl-2,6-diene-octamine (50 µL, 0.265 mmol) by a procedure similar to example 10 and was isolated as white powder (7 mg, 14%). ¹H NMR (CDCl₃): 7.45 (d, J=8.1 Hz, 1H), 7.35 (ddd, J=8.1, 6.6 and 1.5 Hz, 1H), 7.16 (d, J=7.8 Hz, 2H), 7.06 (d, J=7.8 Hz, 2H), 6.91 (d, J=8.4 Hz, 1H), 6.66 (ddd, J=8.1, 6.6 and 1.5 Hz, 1H), 5.41 (dd, J=6.9 and 5.7 Hz, 1H), 5.11 (dd, J=5.7 and 4.2 Hz, 1H), 4.15 (t, J=6.9 Hz, 2H), 3.50 (s, 3H), 2.36 (s, 3H), 2.12-2.03 (m, 4H), 1.75 (s, 3H), 1.68 (s, 3H), 1.61 (s, 3H).

Example 17

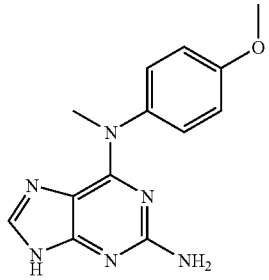

N⁶-(4-Methoxy-phenyl)-N-6-methyl-9H-purine-2,6-diamine

The title compound was prepared from 2-amino-6-chloro-9H-purine (100 mg, 0.546 mmol) and 4-methoxy-N-methyl-aniline (127 mg, 0.656 mmol) by a procedure similar to example 1b and was isolated as white powder (5 mg, 5%). ¹H NMR (CDCl₃): 7.54 (s, 1H), 7.25 (d, J=8.7 Hz, 2H), 6.98 (d, J=8.7 Hz, 2H), 3.86 (s, 3H), 3.66 (s, 3H).

Example 18

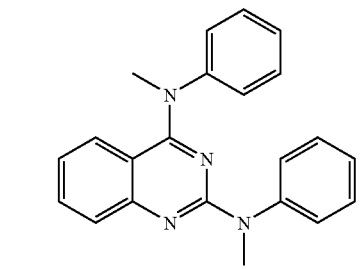

N²,N⁴-Dimethyl-N²,N⁴-diphenyl-quinazoline-2,4-diamine

The title compound was prepared from 2,4-dichloro-quinazoline (50 mg, 0.251 mmol) and N-methylaniline (40 µL, 0.401 mmol) by a procedure similar to example 1b and was isolated as white powder (33 mg, 66%). ¹H NMR (CDCl₃): 7.54 (dd, J=8.2 and 0.6 Hz, 1H), 7.45 (dd, J=8.4 and 1. Hz, 1H), 7.44-7.29 (m, 6H), 7.21-7.10 (m, 4H), 6.86 (dd, J=8.4 and 0.9 Hz, 1H), 6.67 (ddd, J=8.4, 7.2 and 1.1 Hz, 1H), 3.69 (s, 3H), 3.33 (s, 3H).

Example 19

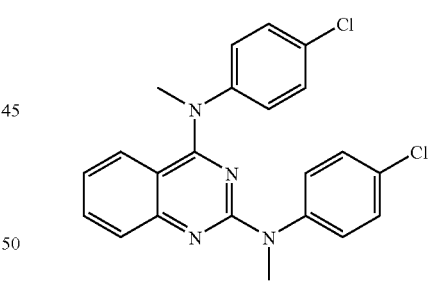

N²,N⁴-Bis(4-chloro-phenyl)-N²,N⁴-dimethyl-quinazoline-2,4-diamine

The title compound was prepared from 2,4-dichloro-quinazoline (60 mg, 0.3.02 mmol) and 4-chloro-N-methyla-niline (72 mg, 0.513 mmol) by a procedure similar to example 1b and was isolated as white powder (50 mg, 83%). ¹H NMR (CDCl₃): 8.93 (d, J=8.4 Hz, 1H), 7.56 (t, J=7.5 Hz, 1H), 7.47-7.44 (m, 4H), 7.32-7.27 (m, 2H), 7.18-7.14 (m, 2H), 6.95 (t, J=7.5 Hz, 1H), 6.67 (d, J=8.4 Hz, 1H), 4.02 (s, 3H), 3.25 (s, 3H).

Example 20

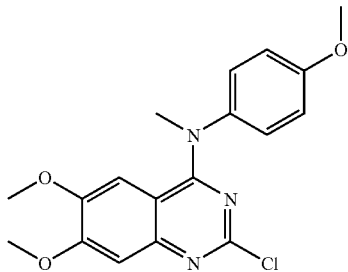

(2-Chloro-6,7-dimethoxyquinazolin-4-yl)-(4-methoxy-phenyl)-methyl-amine

A mixture of 2,4-dichloro-6,7-dimethoxyquinazoline (100 mg, 0.386 mmol), 4-methoxy-N-methylaniline (55 mg, 0.401 mmol) and sodium acetate (60 mg, 0.732 mmol) in tetrahydrofuran (5 mL) and water (2.5 mL) was stirred at room temperature for 48 h. The reaction mixture was evaporated to dryness and the residue was crystallized using ethanol/water and isolated as white solid (60 mg, 60%). $^1$H NMR (CDCl$_3$): 8.19 (s, 1H), 7.32-7.26 (m, 2H), 7.09-7.07 (m, 2H), 6.16 (s, 1H), 4.03 (s, 3H), 3.87 (s, 3H), 3.75 (s, 3H), 3.32 (s, 3H).

Example 21

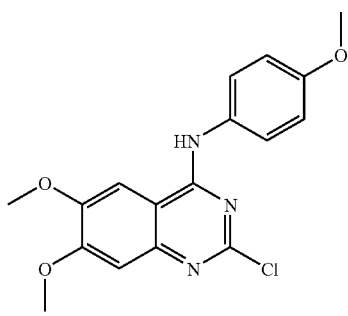

(2-Chloro-6,7-dimethoxyquinazolin-4-yl)-(4-methoxy-phenyl)-amine

The title compound was prepared from 2,4-dichloro-6,7-dimetoxyquinazoline (100 mg, 0.386 mmol) and 4-methoxyaniline (49 mg, 0.386 mmol) by a procedure similar to example 1b and was isolated as white powder (10 mg, 10%).

$^1$H NMR (CDCl$_3$): 8.10 (s, 1H), 7.70-7.68 (m, 2H), 7.23 (s, 1H), 6.96-6.94 (m, 2H), 4.07 (s, 3H), 3.99 (s, 3H), 3.85 (s, 3H).

Example 22

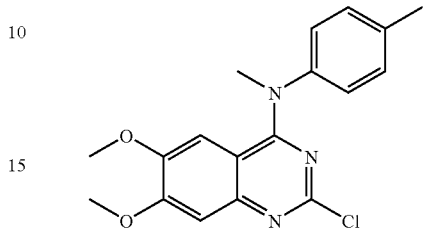

(2-Chloro-6,7-dimethoxyquinazolin-4-yl)-(4-methyl-phenyl)-methyl-amine

The title compound was prepared from 2,4-dichloro-6,7-dimetoxyquinazoline (100 mg, 0.386 mmol) and N-methyl-p-tolylamine (49 mg, 0.386 mmol) by a procedure similar to example 1b and was isolated as white powder (8 mg, 8%). $^1$H NMR (CDCl$_3$): 7.27 (d, J=8.4 Hz, 2H), 7.15 (d, J=8.4 Hz, 2H), 7.08 (s, 1H), 6.26 (s, 1H), 3.92 (s, 3H), 3.61 (s, 3H), 3.28 (s, 3H), 2.37 (s, 3H).

Example 23

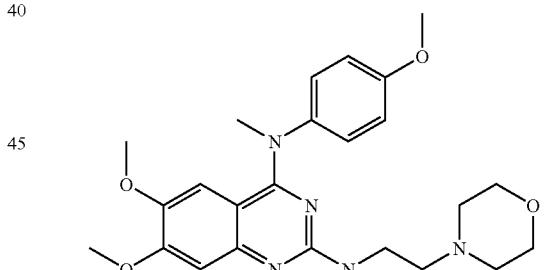

6,7-Dimethoxy-N$^4$-(4-methoxy-phenyl)-N$^4$-methyl-N$^2$-(2-morpholin-4-yl-ethyl)-quinazoline-2,4-diamine The title compound was prepared from (2-chloro-6,7-dimethoxyquinazolin-4-yl)-(4-methoxy-phenyl)-methyl-amine (50 mg, 0.139 mmol) and 2-morpholin-4-yl-ethylamine (25 μL, 0.167 mmol) by a procedure similar to example 10 and was isolated as white powder (27 mg, 54%). $^1$H NMR (CDCl$_3$): 7.21 (d, J=8.4 Hz, 2H), 7.00 (d, J=8.4 Hz, 2H), 6.93 (s, 1H), 6.13 (s, 1H), 3.95 (s, 3H), 3.84 (s, 3H), 3.77-3.74 (m, 4H), 3.71-3.66 (m, 2H), 3.60 (s, 3H), 3.25 (s, 3H), 2.70 (t, J=7.2 Hz, 2H), 2.59-2.56 (m, 4H).

Example 24

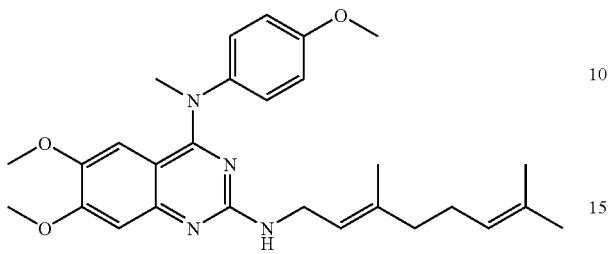

6,7-Dimethoxy-$N^2$-(3,7-dimethyl-octa-2,6-dienyl)-$N^4$-(4-methoxy-phenyl)-$N^4$-methyl-quinazoline-2,4-diamine The title compound was prepared from (2-chloro-6,7-dimethoxyquinazolin-4-yl)-(4-methoxy-phenyl)-methyl-amine (60 mg, 0.167 mmol) and 3,7-dimethyl-2,6-diene-octamine (50 mg, 0.424 mmol) by a procedure similar to example 10 and was isolated as white powder (68 mg, 85%). $^1$H NMR (CDCl$_3$): 7.15 (d, J=8.4 Hz, 2H), 6.91 (d, J=8.4 Hz, 2H), 6.85 (s, 1H), 6.29 (s, 1H), 5.41 (dd, J=6.9 and 6.0 Hz, 1H), 5.12 (ddd, J=6.9, 5.1 and 4.2 Hz, 1H), 4.69 (t, J=4.5 Hz, 1H), 4.12 (t, J=5.7 Hz, 2H), 3.91 (s, 3H), 3.79 (s, 3H), 3.49 (s, 3H), 3.30 (s, 3H), 2.13-2.05 (m, 4H), 1.75 (s, 3H), 1.69 (s, 3H), 1.61 (s, 3H).

Example 25

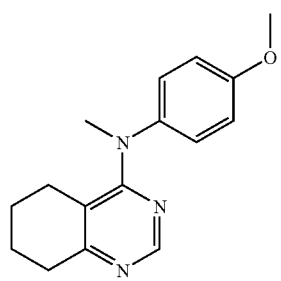

5,6,7,8-Tetrahydro-quinazolin-4-yl)-(4-methoxy-phenyl)-methyl-amine a) 4-Chloro-5,6,7,8-tetrahydroquinazoline: The title compound was prepared from 5,6,7,8-tetrahydro-4-quinazolinone (50 mg, 0.301 mmol) and phosphorylchloride (5 mL) by a procedure similar to example 1a and was isolated as off white solid (20 mg, 40%). $^1$H NMR (CDCl$_3$): 8.60 (s, 1H), 2.75 (m, 2H), 1.76 (m, 4H), 1.53 (m, 2H).

b) (5,6,7,8-Tetrahydro-quinazolin-4-yl)-(4-methoxy-phenyl)-methyl-amine: The title compound was prepared from 4-chloro-5,6,7,8-tetrahydroquinazoline (20 mg, 0.099 mmol) and 4-methoxy-N-methylaniline (16 mg, 0.111 mmol) by a procedure similar to example 1b and was isolated as white powder (25 mg, 83%). $^1$H NMR (CDCl$_3$): 8.60 (s, 1H), 7.02-6.96 (m, 2H), 6.87-6.82 (m, 2H), 3.83 (s, 3H), 3.39 (s, 3H), 2.75 (t, J=6.6 Hz, 2H), 1.76 (m, 4H), 1.53 (m, 2H).

Example 26

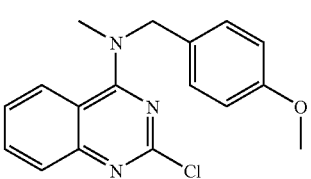

(2-Chloro-quinazolin-4-yl)-(4-methoxy-benzyl)-methyl-amine

The title compound was prepared from 2,4-dichloroquinazoline (50 mg, 0.251 mmol) and N-methyl-4-methoxybenzylamine (45 mg, 0.302 mmol) by a procedure similar to example 1b and was isolated as white powder (30 mg, 60%). $^1$H NMR (CDCl$_3$): 7.93 (dd, J=8.4 and 1.2 Hz, 1H), 7.78 (dd, J=8.4 and 1.5 Hz, 1H), 7.68 (ddd, J=8.4, 7.5 and 1.5 Hz, 1H), 7.34-7.26 (m, 3H), 6.96-6.92 (m, 2H), 4.94 (s, 2H), 3.83 (s, 3H), 3.31 (s, 3H).

Example 27

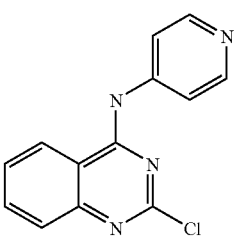

(2-Chloro-quinazolin-4-yl)-pyridin-4-yl-amine

To a stirred suspension of 2,4-dichloroquinazoline (42 mg, 0.21 mmol) and 4-aminopyridine (21 mg, 0.22 mmol) in 3 mL of anhydrous isopropanol was added a drop of concentrated HCl and the mixture was stirred overnight. Solid precipitates were observed and the mixture was filtered. The solid was washed with cold isopropanol and dried to give the title compound as white solid (38 mg, 0.13 mmol, 61%). $^1$H NMR (DMSO-d$_6$): 8.60 (d, J=7.5 Hz, 2H), 8.18-8.20 (m, 2H), 8.07-8.10 (m, 1H), 7.90-7.96 (m, 1H), 7.18 (d, J=7.8 Hz, 2H).

Example 28

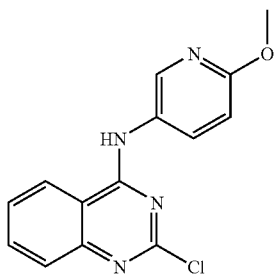

(2-Chloro-quinazolin-4-yl)-(6-methoxy-pyridin-3-yl)-amine

A mixture of 2,4-dichloroquinazoline (61 mg, 0.31 mmol), 5-amino-2-methoxy pyridine (40 mg, 0.32 mmol) and sodium acetate (38 mg, 0.46 mmol) in 3 mL of solvent (THF:water/1:1) was stirred at 60° C. for 45 min. The reaction mixture was diluted with 25 mL of ethyl acetate. It was washed with saturated NaCl, dried over anhydrous MgSO$_4$, filtered and concentrated. The crude product was purified by chromatography (40% ethyl acetate/hexanes) on silica gel to give the title compound (86 mg, 0.30 mmol, 98%). $^1$H NMR (CDCl$_3$): 8.38 (d, J=3.0 Hz, 1H), 8.07 (dd, J=8.7 and 3.0 Hz, 1H), 7.89-7.79 (d, J=8.4 Hz, 1H), 7.86 (m, 2H), 7.59-7.53 (m, 2H), 6.84 (d, J=8.7 Hz, 1H), 3.96 (s, 3H).

Example 29

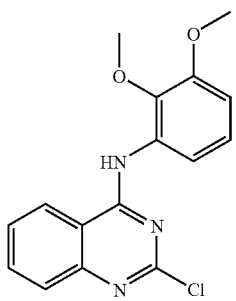

(2-Chloro-quinazolin-4-yl)-(2,3-dimethoxy-phenyl)-amine

The title compound was prepared from 2,4-dichloroquinazoline and 2,3-dimethoxyaniline by a procedure similar to example 28 (84% yield). $^1$H NMR (CDCl$_3$): 8.57 (s, broad, 1H), 8.38 (d, J=8.4 Hz, 1H), 7.77-7.86 (m, 3H), 7.55-7.61 (m, 1H), 7.15 (t, J=8.7 Hz, 1H), 6.73-6.75 (m, 1H), 4.00 (s, 3H), 3.91 (s, 3H).

Example 30

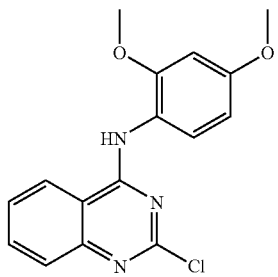

(2-Chloro-quinazolin-4-yl)-(2,4-dimethoxy-phenyl)-amine

The title compound was prepared from 2,4-dichloroquinazoline and 2,4-dimethoxyaniline by a procedure similar to example 28 (92% yield). $^1$H NMR (CDCl$_3$): 8.59 (d, J=8.7 Hz, 1H), 8.22 (s, broad, 1H), 7.75-7.81 (m, 3H), 7.52 (ddd, J=8.4, 6.6 and 2.1 Hz, 1H), 6.52-6.59 (m, 2H), 3.95 (s, 3H), 3.82 (s, 3H).

Example 31

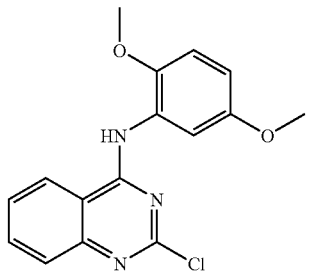

(2-Chloro-quinazolin-4-yl)-(2,5-dimethoxy-phenyl)-amine

The title compound was prepared from 2,4-dichloroquinazoline and 2,5-dimethoxyaniline by a procedure similar to example 28 (98% yield). $^1$H NMR (CDCl$_3$): 8.59 (d, J=3.0 Hz, 1H), 8.53 (s, broad, 1H), 7.78-7.87 (m, 3H), 7.57 (ddd, J=8.4, 6.6 and 1.8 Hz, 1H), 6.88 (d, J=9.0 Hz, 1H), 6.60 (dd, J=8.7 and 3.0 Hz, 1H), 3.97 (s, 3H), 3.87 (s, 3H).

Example 32

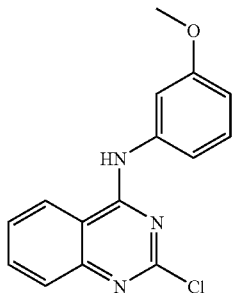

(2-Chloro-quinazolin-4-yl)-(3-methoxy-phenyl)-amine

The title compound was prepared from 2,4-dichloro-quinazoline and 3-methoxyaniline by a procedure similar to example 28 (80% yield). $^1$H NMR (CDCl$_3$): 7.79-7.87 (m, 3H), 7.54-7.62 (m, 3H), 7.20-7.35 (m, 3H), 6.76 (dd, J=8.4 and 2.1 Hz, 1H), 3.87 (s, 3H).

Example 33

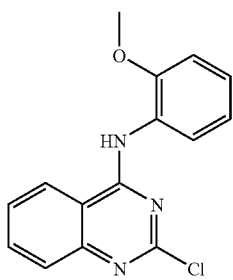

(2-Chloro-quinazolin-4-yl)-(2-methoxy-phenyl)-amine

The title compound was prepared from 2,4-dichloro-quinazoline and 2-methoxyaniline by a procedure similar to example 28 (35% yield). $^1$H NMR (CDCl$_3$): 8.76-8.79 (m, 1H), 8.50 (s, broad, 1H), 7.77-7.88 (m, 3H), 7.54-7.59 (m, 1H), 7.09-7.13 (m, 2H), 6.95-6.99 (m, 2H), 4.00 (s, 3H).

Example 34

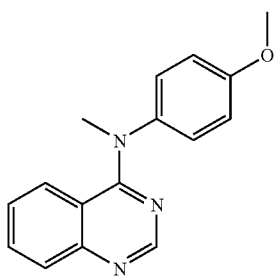

(4-Methoxy-phenyl)-methyl-quinazolin-4-yl-amine

The title compound was prepared from 4-chloroquinazoline and 4-methoxy-N-methylaniline by a procedure similar to example 28 (79% yield). $^1$H NMR (CDCl$_3$): 8.81 (s, 1H), 7.81 (d, J=8.1 Hz, 1H), 7.57 (ddd, J=8.1, 5.4 and 2.7 Hz, 1H), 7.09-7.14 (m, 2H), 7.03-7.06 (m, 2H), 6.9-6.93 (m, 2H).

Example 35

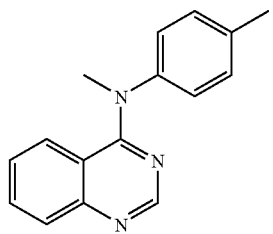

(4-Methyl-phenyl)-methyl-quinazolin-4-yl-amine

The title compound was prepared from 4-chloroquinazoline and 4-methyl-N-methylaniline by a procedure similar to example 28 (80% yield). $^1$H NMR (CDCl$_3$): 8.23 (s, 1H), 7.82 (d, J=8.4 Hz, 1H), 7.57 (ddd, J=8.4, 6.3 and 1.8 Hz, 1H), 7.17-7.20 (m, 2H), 7.00-7.10 (m, 4H), 3.61 (s, 3H), 2.39 (s, 3H).

Example 36

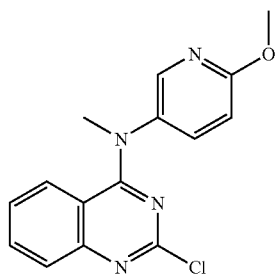

(2-Chloro-quinazolin-4-yl)-(6-methoxy-pyridin-3-yl)-methyl-amine

To a solution of (2-chloro-quinazolin-4-yl)-(6-methoxy-pyridin-3-yl)-amine (19.4 mg, 0.068 mmol) in 1 mL of DMF cooled at 0° C. was added methyl iodide (100 uL, 1.61 mmol), followed by sodium hydride (60% oil suspension, 5 mg, 0.13 mmol). The mixture was stirred at 0° C. for 1 h, then allowed to warm to room temperature and stirred for 1 h. The reaction mixture was quenched by adding 50 uL of water, diluted with 25 mL of ethyl acetate, washed with water (25 mL×3), saturated NaCl, dried over anhydrous MgSO$_4$, filtered and concentrated. The residue was purified by chromatography (20% ethyl acetate/hexanes) to give the title compound (14.3 mg, 0.048 mmol, 70%). $^1$H NMR (CDCl$_3$) 8.06 (d, J=2.7 Hz, 1H), 7.57-7.79 (m, 1H), 7.60 (ddd, J=8.1, 6.6 and 1.2 Hz, 1H), 7.44

(dd, J=8.7 and 2.7 Hz, 1H), 7.09 (ddd, J=8.1, 6.6 and 1.2 Hz, 1H), 6.99-7.02 (m, 1H), 6.82 (dd, J=8.7 and 0.6 Hz, 1H), 3.97 (s, 3H), 3.61 (s, 3H).

Example 37

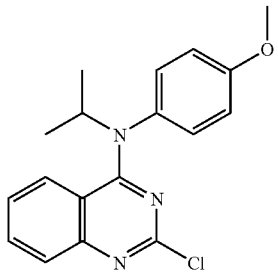

(2-Chloro-quinazolin-4-yl)-isopropyl-(4-methoxy-phenyl)-amine a) Isopropyl-(4-methoxy-phenyl)-amine: To a stirred solution of p-methoxy-aniline (443 mg, 3.60 mmol) and acetone (265 uL, 3.61 mmol) in 10 mL of anhydrous methanol at room temperature was added a drop of glacial acetic acid followed by NaCNBH$_3$ (226 mg, 3.60 mmol) portion wise over 0.5 h. The reaction mixture was then stirred for 3 h at room temperature. The solvents were removed under vacuum, and the residue was dissolved in 50 mL of ethyl acetate. The solution was washed with 5% NaHCO$_3$, saturated NaCl, dried over anhydrous MgSO4, filtered and concentrated. The crude was purified by chromatography (10% ethyl acetate/hexanes) to give the title compound (287 mg, 1.92 mmol, 48%). $^1$H NMR (CDCl$_3$): 6.77 (d, J=8.7 Hz, 2H), 6.57 (d, J=6.7 Hz, 2H), 3.74 (s, 3H), 3.54 (m, 1H, J=6.3), 2.94 (s, broad, 1H), 1.92 (d, J=6.3 Hz, 6H).

b) (2-Chloro-quinazolin-4-yl)-isopropyl-(4-methoxy-phenyl)-amine: The title compound was prepared from isopropyl-(4-methoxy-phenyl)-amine and 2,4-dichloroquinazoline by a procedure similar to example 27 (51% yield). $^1$H NMR (DMSO-d$_6$): 8.30-8.34 (m, 1H), 8.17-8.22 (m, 1H), 8.05-8.08 (m, 1H), 7.90-7.96 (m, 1H), 7.77 (d, J=8.1 Hz, 2H), 1.09 (d, J=8.4 Hz, 2H), 3.62 (m, 1H), 3.79 (s, 3H), 1.24 (d, J=6.0 Hz, 6H).

Example 38

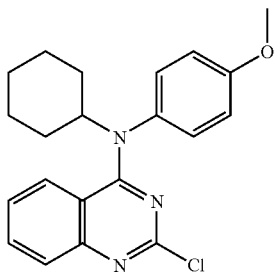

(2-Chloro-quinazolin-4-yl)-cyclohexyl-(4-methoxy-phenyl)-amine a) Cyclohexyl-(4-methoxy-phenyl)-amine: The title compound was prepared from cyclohexanone and p-methoxy aniline by a procedure similar to example 37a (60% yield). $^1$H NMR (CDCl$_3$): 6.76 (d, J=9.0 Hz, 2H), 6.57 (d, J=9.0 Hz, 2H), 3.75 (s, 3H), 3.16 (m, 1H), 2.34 (m, 1H), 1.61-1.89 (m, 5H), 1.05-1.42 (m, 5H).

b) (2-Chloro-quinazolin-4-yl)-cyclohexyl-(4-methoxy-phenyl)-amine: The title compound was prepared from cyclohexyl-(4-methoxy-phenyl)-amine and 2,4-dichloroquinazoline by a procedure similar to example 27 (93% yield). $^1$H NMR (DMSO-d$_6$): 8.32 (dd, J=8.4 and 1.5 Hz, 1H), 8.22 (ddd, J=8.4, 7.5 and 1.5 Hz, 1H), 8.05-8.09 (m, 1H), 7.93 (ddd, J=8, 6.9, 0.9 Hz, 1H), 7.45 (d, J=8.7 Hz, 2H), 7.08 (d, J=8.7 Hz, 2H), 3.27-3.34 (m, 1H), 1.89-1.92 (m, 2H), 1.73-1.76 (m, 2), 1.36-1.62 (m, 3H), 1.07-1.28 (m, 3H).

Example 39

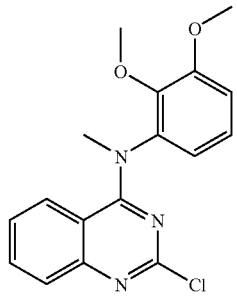

(2-Chloro-quinazolin-4-yl)-(2,3-dimethoxy-phenyl)-methyl-amine

The title compound was prepared from (2-chloro-quinazolin-4-yl)-(2,3-dimethoxy-phenyl)-amine and methyl iodide by a procedure similar to example 36 (71% yield). $^1$H NMR (CDCl$_3$): 7.74 (d, J=8.4 Hz, 1H), 7.53-7.59 (m, 1H), 7.12 (t, J=8.4 Hz, 1H), 6.94-7.01 (m, 3H), 6.87 (dd, J=8.1 and 1.5 Hz, 1H), 3.89 (s, 3H), 3.56 (s, 3H).

Example 40

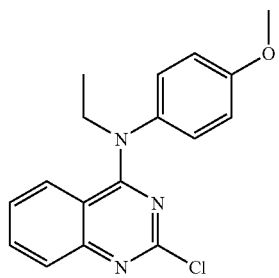

(2-Chloro-quinazolin-4-yl)-ethyl-(4-methoxy-phenyl)-amine

The title compound was prepared from (2-chloro-quinazolin-4-yl)-(4-methoxy-phenyl)-amine and ethyl iodide by a procedure similar to example 36 (58% yield). ¹H NMR (CDCl₃): 7.69-7.72 (m, 1H), 7.53 (ddd, J=8.1, 6.9 and 1.5 Hz, 1H), 7.09-7.14 (m, 2H), 6.94-6.70 (m, 3H), 6.83-6.87 (m, 1H), 4.13 (q, J=7.2 Hz, 2H), 3.87 (s, 1H), 1.30 (t, J=6.9 Hz, 3H).

Example 41

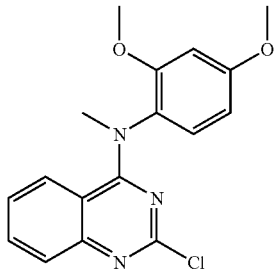

(2-Chloro-quinazolin-4-yl)-(2,4-dimethoxy-phenyl)-methyl-amine

The title compound was prepared from (2-chloro-quinazolin-4-yl)-(2,4-dimethoxy-phenyl)-amine and methyl iodide by a procedure similar to example 36 (91% yield). ¹H NMR (CDCl₃): 7.70-7.73 (m, 1H), 7.54 (ddd, J=8.7, 6.3 and 2.1 Hz, 1H), 7.10 (d, J=8.7 Hz, 1H), 6.93-7.23 (m, 2H), 6.50-6.57 (m, 2H), 3.87 (s, 3H), 3.67 (s, 3H), 3.52 (s, 3H).

Example 42

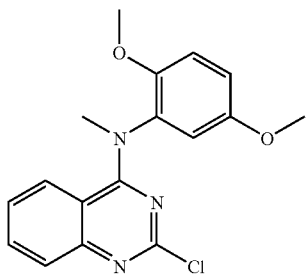

(2-Chloro-quinazolin-4-yl)-(2,5-dimethoxy-phenyl)-methyl-amine

The title compound was prepared from (2-chloro-quinazolin-4-yl)-(2,5-dimethoxy-phenyl)-amine and methyl iodide by a procedure similar to example 36 (78% yield). ¹H NMR (CDCl₃): 7.72-7.75 (m, 1H), 7.56 (ddd, J=8.4, 5.7 and 2.1 Hz, 1H), 6.98-7.00 (m, 2H), 6.92-6.92 (m, 2H), 6.78-6.79 (m, 1H), 3.75 (s, 3H), 3.58 (s, 3H), 3.56 (s, 3H).

Example 43

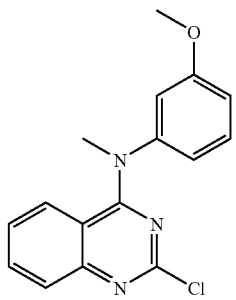

(2-Chloro-quinazolin-4-yl)-(3-methoxy-phenyl)-methyl-amine

The title compound was prepared from (2-chloro-quinazolin-4-yl)-(3-methoxy-phenyl)-amine and methyl iodide by a procedure similar to example 36 (60% yield). ¹H NMR (CDCl₃): 7.74-7.76 (m, 1H), 7.57 (ddd, J=8.4, 6.0 and 1.8 Hz, 1H), 7.32 (t, J=7.8 Hz, 1H), 6.98-7.03 (m, 2H), 6.89 (dd, J=8.1 and 2.4 Hz, 1H), 6.75-6.81 (m, 2H), 3.65 (s, 3H), 3.37 (s, 3H).

Example 44

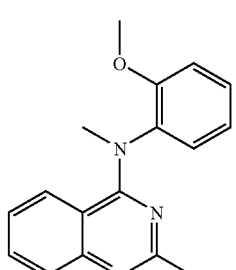

(2-Chloro-quinazolin-4-yl)-(2-methoxy-phenyl)-methyl-amine

The title compound was prepared from (2-chloro-quinazolin-4-yl)-(2-methoxy-phenyl)-amine and methyl iodide by a procedure similar to example 36 (72% yield). ¹H NMR (CDCl$_3$): 7.72 (d, J=8.1 Hz, 1H), 7.54 (ddd, J=8.4, 6.6 and 1.5 Hz, 1H), 7.20 (dd, J=8.4 and 1.8 Hz, 1H), 6.87-7.04 (m, 4H), 3.67 (s, 3H), 3.56 (s, 3H).

Example 45

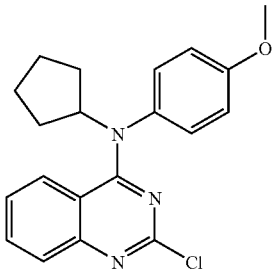

(2-Chloro-quinazolin-4-yl)-cyclopentyl-(4-methoxy-phenyl)-amine a) Cyclopentyl-(4-methoxy-phenyl)-amine: The title compound was prepared from cyclopentanone and p-methoxy aniline by a procedure similar to example 37a (68% yield). $^1$H NMR (CDCl$_3$): 6.78 (d, J=8.7 Hz, 2H), 6.57 (d, J=8.7 Hz, 2H), 3.74 (s, 3H), 3.18 (m, 1H), 2.23 (m, 1H), 1.82-2.01 (m, 2H), 1.52-1.73 (m, 4H), 1.38-1.49 (m, 2H).

b) (2-Chloro-quinazolin-4-yl)-cyclopentyl-(4-methoxy-phenyl)-amine: The title compound was prepared from cyclopentyl-(4-methoxy-phenyl)-amine and 2,4-dichloroquinazoline by a procedure similar to example 27 (39% yield). $^1$H NMR (CDCl$_3$): 8.31 (dd, J=8.7 and 1.3 Hz, 1H), 8.12 (ddd, J=8.4, 7.2 and 1.3 Hz, 1H), 8.12-8.08 (m, 1H), 7.93 (ddd, J=8.3, 7.2 and 1.3 Hz, 1H), 7.41 (d, J=8.4 Hz, 1H), 7.11 (d, J=8.7 Hz, 2H), 3.24-3.33 (m, 1H), 2.22-2.01 (m, 2H), 1.51-1.75 (m, 4H), 1.32-1.49 (m, 2H).

Example 46

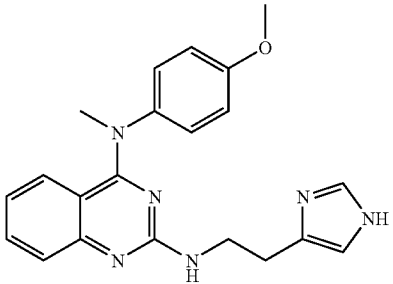

N$^2$-[2-(1H-Imidazol-4-yl)-ethyl]-N$^4$-(4-methoxy-phenyl)-N$^4$-methyl-quinazoline-2,4-diamine The title compound was prepared from (2-chloro-quinazolin-4-yl)-(4-methoxy-phenyl)-methylamine (10 mg, 0.033 mmol) and histamine hydrochloride (16 mg, 0.10) by a procedure similar to example 10 and was isolated as white solid (7 mg, 70%). $^1$H NMR (CDCl$_3$): 7.52 (s, 1H), 7.49 (brd, J=3.9 Hz, 2H), 7.20-7.15 (m, 2H), 7.03-6.96 (m, 3H), 6.83 (ddd, J=8.4, 4.5 and 3.9 Hz, 1H), 6.66 (d, J=8.7 Hz, 1H), 3.88 (s, 3H), 3.85 (t, J=6.6 Hz, 2H), 3.63 (s, 3H), 3.03 (t, J=6.6 Hz, 2H).

Example 47

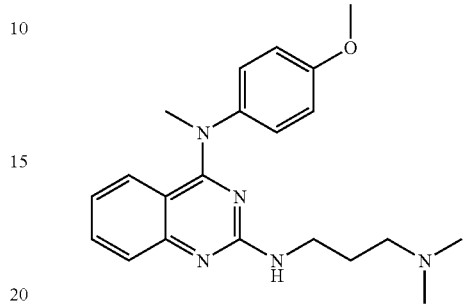

N$^2$-(3-Dimethylamino-propyl)-N$^4$-(4-methoxy-phenyl)-N$^4$-methyl-quinazoline-2,4-diamine The title compound was prepared from (2-chloro-quinazolin-4-yl)-(4-methoxy-phenyl)-methyl-amine (15 mg, 0.050 mmol) and N$^1$,N$^1$-dimethyl-propane-1,3-diamine (16 µl, 0.070 mmol) by a procedure similar to example 10 and was isolated as white powder (11 mg, 73%). $^1$H NMR (CDCl$_3$): 7.43 (dd, J=8.4 and 1.2 Hz, 1H), 7.34 (ddd, J=7.8, 6.6 and 1.2 Hz, 1H), 7.11-7.07 (m, 2H), 6.89-6.86 (m, 3H), 6.65 (ddd, J=8.1, 6.6 and 1.2 Hz, 1H), 3.82 (s, 3H), 3.61 (t, J=6.9 Hz, 2H), 3.49 (s, 3H), 2.41 (t, J=6.9 Hz, 2H), 2.28 (s, 6H), 1.89 (m, 2H).

Example 48

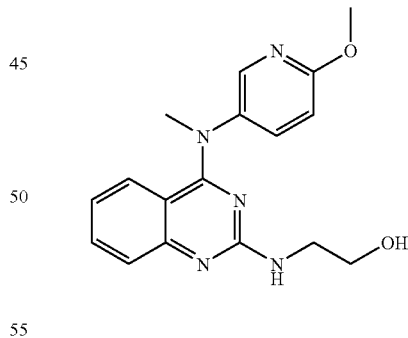

N$^2$-(2-Hydroxyethyl)-N$^4$-(6-methoxypyridin-3-yl)-N$^4$-methyl-quinazoline-2,4-diamine The title compound was prepared from (2-chloro-quinazolin-4-yl)-(6-methoxy-pyridin-3-yl)-methyl-amine (12 mg, 0.040 mmol) and ethanolamine (28 µl) by a procedure similar to example 10 and was isolated as off white solid (8 mg, 66%). $^1$H NMR (CDCl$_3$): 8.03 (brd, J=3.0 Hz, 1H), 7.47-7.35 (m, 3H), 6.91 (brd, J=8.7 Hz, 1H), 6.78-6.73 (m, 2H), 5.56 (brs, 1H), 3.94 (s, 3H), 3.93-3.90 (m, 2H), 3.70-3.56 (m, 2H), 3.48 (s, 3H).

Example 49

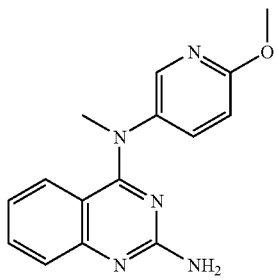

$N^4$-(6-methoxypyridin-3-yl)-$N^4$-methyl-quinazoline-2,4-diamine

The title compound was prepared from (2-chloro-quinazolin-4-yl)-(6-methoxy-pyridin-3-yl)-methylamine (10 mg, 0.030 mmol) and 7 M ammonia in methanol (1 mL) by a procedure similar to example 10 (3 mg, 30%). $^1$H NMR (CDCl$_3$): 8.04 (dd, J=2.9, 0.6 Hz, 1H), 7.49-7.43 (m, 2H), 7.39 (dd, J=5.7 and 2.7 Hz, 1H), 6.92 (brd, J=8.4 Hz, 1H), 6.85-6.78 (m, 2H), 5.65 (s, 2H), 3.96 (s, 3H), 3.54 (s, 3H).

Example 50

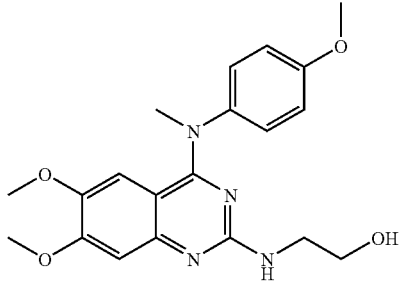

$N^2$-(2-Hydroxyethyl)-$N^4$-(4-methoxy-phenyl)-$N^4$-methyl-6,7-dimethoxyquinazoline-2,4-diamine The title compound was prepared from (2-Chloro-6,7-dimethoxyquinazolin-4-yl)-(4-methoxy-phenyl)-amine (26 mg, 0.079 mmol) and ethanolamine (30 µl) by a procedure similar to example 10 and was isolated as white powder (14 mg, 54%). $^1$H NMR (CDCl$_3$): 7.14 (dd, J=6.6 and 2.1 Hz, 2H), 6.91 (d, J=6.6 and 2.1 Hz, 2H), 6.81 (s, 1H), 6.25 (s, 1H), 3.90 (s, 3H), 3.92-3.88 (m, 2H), 3.80 (s, 3H), 3.69-3.65 (m, 2H), 3.49 (s, 3H), 3.28 (s, 3H).

Example 51

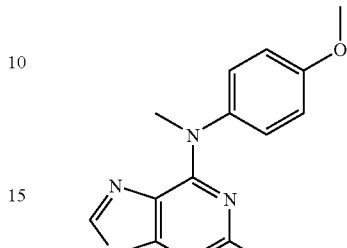

(2-Chloro-9H-purin-6-yl)-(4-methoxy-phenyl)-methyl-amine

The title compound was prepared from 2,6-dichloro-9H-purine (50 mg, 0.265) and 4-methoxy-N-methylaniline (40 mg, 0.291 mmol) by a procedure similar to example 1b and was isolated as off white powder (10 mg, 20%). $^1$H NMR (CDCl$_3$): 7.81 (s, 1H), 7.37 (d, J=8.4 Hz, 2H), 7.04 (d, J=8.4 Hz, 2H), 3.93 (s, 3H), 3.77 (s, 3H).

Example 52

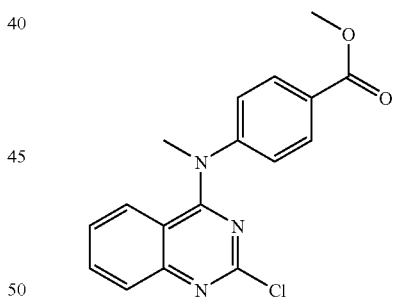

(2-Chloro-quinazolin-4-yl)-(4-methylcarboxyphenyl)-methyl-amine

The title compound was prepared from 2,4-dichloro-quinazoline (30 mg, 0.152 mmol) and 4-methylamino-benzoic acid methyl ester (27 mg, 0.167 mmol) by a procedure similar to example 1b and was isolated as off white powder (25 mg, 83%). $^1$H NMR (CDCl$_3$): 8.08-8.04 (m, 2), 7.81 (ddd, J=8.4, 5.4 and 1.2 Hz, 1H), 7.62 (ddd, J=8.7, 3.9 and 1.8 Hz, 1H), 7.26-7.21 (m, 2H), 7.06 (ddd, J=8.4, 7.8 and 0.9 Hz, 1H), 6.99 (ddd, J=7.5, 1.2 and 0.9 Hz, 1H), 3.94 (s, 3H), 3.70 (s, 3H).

Example 53

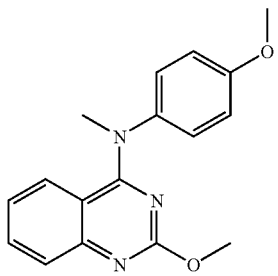

(2-methoxy-quinazolin-4-yl)-(4-methoxyphenyl)-methylamine

To a solution of (2-chloro-quinazolin-4-yl)-(4-methoxyphenyl)-methyl-amine (50 mg, 0.167 mmol) in 2 ml methanol was added sodium methoxide (500 μl, 25% by wt. in methanol). The solution was stirred at 80° C. for 1 h, and it was diluted with 50 ml ethylacetate. The solution was washed with water, dried and concentrated. The product was purified using small silica column and isolated as off white solid (22 mg, 54%). $^1$H NMR (CDCl$_3$): 7.89 (d, J=8.4 Hz, 1H), 7.53 (ddd, J=8.7, 5.4 and 2.4 Hz, 1H), 7.19-7.14 (m, 2H), 6.99-6.93 (m, 2H), 6.90-6.85 (m, 2H), 4.14 (s, 3H), 3.86 (s, 3H), 3.64 (s, 3H).

Example 54

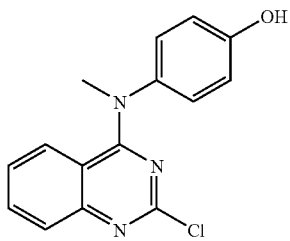

(2-Chloro-quinazolin-4-yl)-(4-hydroxyphenyl)-methylamine

To a solution of (2-chloro-quinazolin-4-yl)-(4-methoxyphenyl)-methyl-amine (100 mg, 0.334 mmol) in 30 ml dichloromethane cooled at −20° C. was added slowly 60 μl of BBr$_3$ (0.668 mmol). The reaction mixture was stirred at −20° C. for 2 h then it was warmed to room temperature. It was stirred another 2 h at this temperature. The reaction mixture was diluted with ethyl acetate (50 ml) and washed with cold 5% sodium bicarbonate. The organic phase was dried and concentrated. The residue was purified by a small silica column using ethyl acetate and hexane (1:3) as eluents to give the product (57 mg, 57%). $^1$H NMR (CDCl$_3$): 7.65-7.56 (m, 2H), 7.04-6.87 (m, 5H), 3.59 (s, 3H).

Example 55

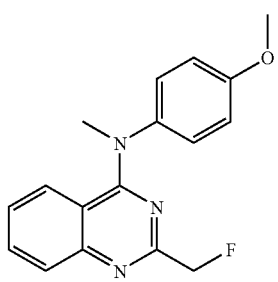

(2-Fluoromethyl-quinazolin-4-yl)-(4-methoxy-phenyl)-methyl-amine a) 2-Fluoromethyl-quinazolin-4(3H)-one: To a solution of 2-amino-benzoic acid methyl ester (151 mg, 1 mmol) and fluoro-acetonitrile (0.14 ml, 2.5 mmol) in dioxane (5 ml) at room temperature was added concentrated HCl (0.05 ml) dropwise. The mixture was heated at 80° C. for 24 h and then cooled to room temperature. The resulting solid was collected and dissolved in water (10 ml), and the solution was neutralized with saturated aqueous NaHCO$_3$ to pH 7. The solution was extracted by ethyl acetate. The extracts were evaporated, and the residue was purified by column chromatography on silica gel with ethyl acetate and hexane (1:1) as eluent, yielding 70 mg (39%) of the title compound.

b) (2-Fluoromethyl-quinazolin-4-yl)-(4-methoxy-phenyl)-methyl-amine: A suspension of 2-fluoromethyl-quinazolin-4(3H)-one (70 mg, 0.39 mmol) in phosphoryl chloride (2 ml) and N,N-dimethylaniline (0.035 ml, 0.27 mmol) was heated under reflux for 12 hours. The reaction mixture was poured onto ice and the precipitate was collected by filtration, then washed and dried to give 4-chloro-2-fluoromethyl-quinazoline, which was used directly for the next reaction. To a solution of 4-chloro-2-fluoromethyl-quinazoline with (4-methoxy-phenyl)-methylamine (160 mg, 1.2 mmol) in isopropyl alcohol (5 ml) was added concentrated HCl (0.05 ml) and the solution was stirred at room temperature overnight. The solution was neutralized with saturated aqueous NaHCO$_3$, and was extracted by ethyl acetate. The extracts were evaporated, and the residue was purified by column chromatography on silica gel with ethyl acetate and hexane (1:1) as eluent, yielding 11 mg (9.5%) of the title compound. $^1$H NMR (CDCl$_3$): 7.87-7.84 (m, 1H), 7.60-7.54

(m, 1H), 7.14-7.10 (m, 2H), 7.04-7.01 (m, 2H), 6.95-6.91 (m, 2H), 5.60 (s, 1H), 5.44 (s, 1H), 3.85 (s, 3H), 3.60 (s, 3H).

Example 56

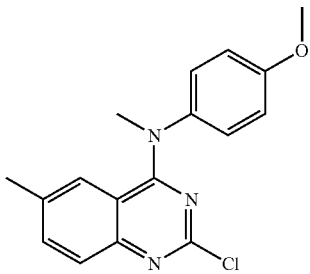

(2-Chloro-6-methyl-quinazolin-4-yl)-(4-methoxy-phenyl)-methyl-amine a) 6-Methyl-quinazoline-2,4-dione: To a suspension of 2-amino-5-methyl benzoic acid (0.758 g, 5 mmol) and potassium cyanate (0.673 g, 8.3 mmol) in water (20 mL) was added acetic acid (0.5 mL). The mixture was stirred at room temperature for 24 h. A white solid was collected by vacuum filtration, washed with water, and dried in vacuo (0.736 g, 84%): $^1$H NMR (DMSO-$d_6$) 9.90 (br s, 1H), 8.27 (d, J=8.4 Hz, 1H), 7.70 (d, J=1.8 Hz, 1H), 7.29 (dd, J=2.4, 8.7 Hz, 1H), 6.50 (br s, 1H), 2.25 (s, 3H).

b)(2-Chloro-6-methyl-quinazolin-4-yl)-(4-methoxy-phenyl)-methyl-amine: The above 6-methyl-quinazoline-2,4-dione (201 mg, 1.14 mmol) and N,N-dimethylaniline (0.2 mL) were refluxed in phosphorus oxychloride (5 mL) under argon overnight. The solvent was removed by distillation under reduced pressure. The purple residue was dissolved in isopropanol (10 mL). N-methyl-p-anisidine (201 mg, 1.465 mmol) was added. The mixture was stirred at room temperature overnight. The solvent was evaporated and the residue was purified by column chromatography (SiO$_2$, EtOAc:hexanes 5-25%) to give the product as a light yellow solid (62 mg, 17%): $^1$H NMR (CDCl$_3$) 7.62 (d, J=8.7 Hz, 1H), 7.38 (dd, J=1.8, 8.7 Hz, 1H), 7.16-7.10 (m, 2H), 6.89-6.86 (m, 2H), 6.63 (s, 1H), 3.86 (s, 3H), 3.60 (s, 3H), 2.09 (s, 3H).

Compounds of EXAMPLE 57-64 were prepared similar to Example 56.

Example 57

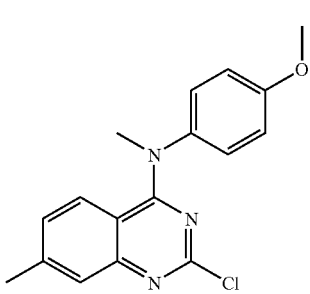

(2-Chloro-7-methyl-quinazolin-4-yl)-(4-methoxy-phenyl)-methyl-amine a) 7-Methyl-quinazoline-2,4-dione: White solid: $^1$H NMR (DMSO-$d_6$) 10.07 (br s, 1H), 8.24 (s, 1H), 7.79 (d, J=8.1 Hz, 1H), 6.78 (dd, J=0.6, 9.0 Hz, 1H), 6.54 (br s, 1H), 2.30 (s, 3H).

b) (2-Chloro-7-methyl-quinazolin-4-yl)-(4-methoxy-phenyl)-methyl-amine: Light yellow solid: $^1$H NMR (CDCl$_3$) 7.51 (m, 1H), 7.16-7.10 (m, 2H), 6.96-6.91 (m, 2H), 6.83 (dd, J=1.8, 8.7 Hz, 1H), 6.78 (d, J=8.7 Hz, 1H), 3.85 (s, 3H), 3.59 (s, 3H), 2.38 (s, 3H).

Example 58

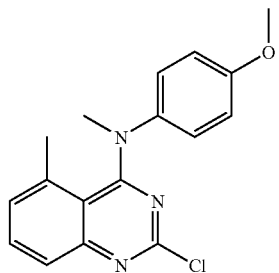

(2-Chloro-5-methyl-quinazolin-4-yl)-(4-methoxy-phenyl)-methyl-amine a) 5-Methyl-quinazoline-2,4-dione: Off-white solid: $^1$H NMR (CDCl$_3$) 11.04 (s, 2H), 7.45 (t, J=7.8 Hz, 1H), 7.01 (d, J=7.8 Hz, 1H), 6.94 (d, J=7.5 Hz, 1H), 2.65 (s, 3H).

b) (2-Chloro-5-methyl-quinazolin-4-yl)-(4-methoxy-phenyl)-methyl-amine: Light yellow solid: $^1$H NMR (CDCl$_3$) 7.64-7.61 (m, 1H), 7.54 (dd, J=7.2, 8.4 Hz, 1H), 6.99-6.96 (m, 1H), 6.75-6.68 (m, 4H), 3.75 (s, 3H), 3.63 (s, 3H), 2.11 (s, 3H).

Example 59

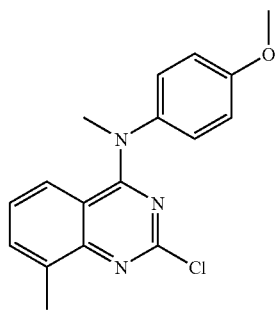

(2-Chloro-8-methyl-quinazolin-4-yl)-(4-methoxy-phenyl)-methyl-amine a) 8-Methyl-quinazoline-2,4-dione: Light brown solid: $^1$H NMR (DMSO-$d_6$) 11.43 (s, 1H), 10.50 (s, 1H), 7.86 (d, J=8.1 Hz, 1H), 7.58 (d, J=7.2 Hz, 1H), 7.19 (t, J=7.8 Hz, 1H), 2.43 (s, 3H).

b) (2-Chloro-8-methyl-quinazolin-4-yl)-(4-methoxy-phenyl)-methyl-amine:

$^1$H NMR (CDCl$_3$) 7.42-7.39 (m, 1H), 7.14-7.04 (m, 2H), 6.94-6.87 (m, 3H), 6.84 (dd, J=1.5, 8.4 Hz, 1H), 3.84 (s, 3H), 3.60 (s, 3H), 2.63 (s, 3H).

Example 60

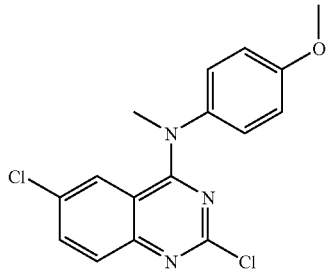

(2,6-Dichloro-quinazolin-4-yl)-(4-methoxy-phenyl)-methyl-amine a) 6-Chloro-quinazoline-2,4-dione: white solid: $^1$H NMR (DMSO-d$_6$) 11.44 (s, 1H), 11.28 (s, 1H), 7.81 (d, J=2.1 Hz, 1H), 7.69 (dd, J=9.0, 2.1 Hz, 1H), 7.19 (d, J=9.0 Hz, 1H).

b) (2,6-Dichloro-quinazolin-4-yl)-(4-methoxy-phenyl)-methyl-amine: Yellow solid: $^1$H NMR (CDCl$_3$) 7.66 (d, J=8.7 Hz, 1H), 7.49 (dd, J=2.1, 8.7 Hz, 1H), 7.18-7.12 (m, 2H), 7.02-6.96 (m, 2H), 6.78 (dd, J=0.6, 2.1 Hz, 1H), 3.88 (s, 3H), 3.61 (s, 3H).

Example 61

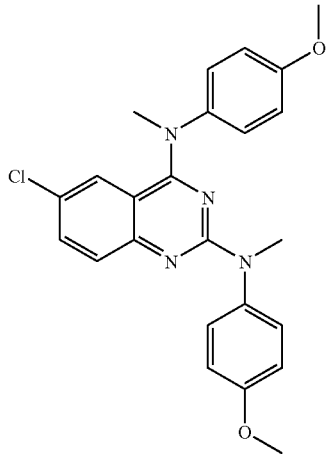

6-Chloro-N$^2$N$^4$-bis-(4-methoxy-phenyl)-N$^2$,N$^4$-dimethyl-quinazoline-2,4-diamine The title compound was isolated from the reaction of Example 60. Yellow solid: $^1$H NMR (CDCl$_3$) 7.41 (d, J=9.0 Hz, 1H), 7.35-7.30 (m, 2H), 7.29 (d, J=2.4 Hz, 1H), 7.26 (t, J=1.5 Hz, 1H), 7.09-7.04 (m, 2H), 6.94-6.80 (m, 5H), 6.72 (d, J=2.4 Hz, 1H), 3.84 (s, 3H), 3.83 (s, 3H), 3.62 (s, 3H), 3.27 (s, 3H).

Example 62

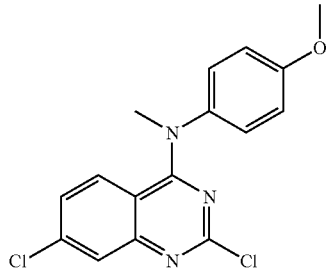

(2,7-Dichloro-quinazolin-4-yl)-(4-methoxy-phenyl)-methyl-amine a) 7-Chloro-quinazoline-2,4-dione: White solid: $^1$H NMR (DMSO-d$_6$) 11.42 (s, 1H), 11.26 (s, 1H), 7.88 (d, J=8.7 Hz, 1H), 7.22 (dd, J=1.2, 8.1 Hz, 1H), 7.18 (d, J=2.1 Hz, 1H).

b) (2,7-Dichloro-quinazolin-4-yl)-(4-methoxy-phenyl)-methyl-amine: Light yellow solid: $^1$H NMR (CDCl$_3$) 7.70 (d, J=2.4 Hz, 1H), 7.16-7.11 (m, 2H), 6.98-6.92 (m, 3H), 6.80 (d, J=9.3 Hz, 1H), 3.86 (s, 3H), 3.60 (s, 3H).

Example 63

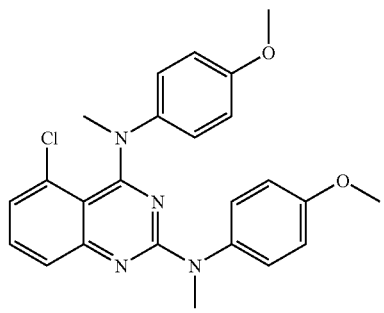

5-Chloro-N$^2$,N$^4$-bis-(4-methoxy-phenyl)-N$^2$,N$^4$-dimethyl-quinazoline-2,4-diamine a) 5-Chloro-quinazoline-2,4-dione: White solid: $^1$H NMR (DMSO-d$_6$) 11.28 (s, 2H), 7.55 td (td, J=8.4, 0.6 Hz, 1H), 7.19 (d, J=7.8 Hz, 1H), 7.12 (d, J=8.4 Hz, 1H).

b) 5-Chloro-N$^2$,N$^4$-bis-(4-methoxy-phenyl)-N$^2$,N$^4$-dimethyl-quinazoline-2,4-diamine: Yellow solid: $^1$H NMR (CDCl$_3$) 7.43 (d, J=8.4 Hz, 1H), 7.32-7.26 (m, 3H), 6.93-6.88

(m, 2H), 6.81 (dd, J=1.2, 7.2 Hz, 1H), 6.75-6.65 (m, 4H), 3.83 (s, 3H), 3.73 (s, 3H), 3.61 (s, 3H), 3.33 (s, 3H).

Example 64

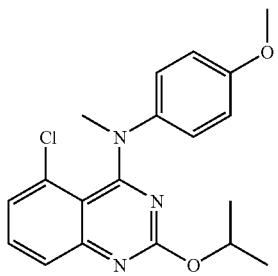

(5-Chloro-2-isopropoxy-quinazolin-4-yl)-(4-methoxy-phenyl)-methyl-amine

The title compound was isolated from the reaction of Example 63. White solid: $^1$H NMR (CDCl$_3$) 7.45-7.36 (m, 2H), 7.26-7.21 (m, 2H), 7.13 (dd, J=2.1, 6.9 Hz, 1H), 6.94-6.89 (m, 2H), 5.09 (m, 1H), 3.85 (s, 3H), 3.57 (s, 3H), 1.30 (d, J=6.3 Hz, 6H).

Example 65

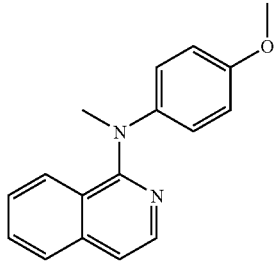

(Isoquinolin-1-yl)-(4-methoxy-phenyl)-methylamine

A mixture of 1-chloroisoquinoline (50 mg, 0.31 mmol) and (4-methoxy-phenyl)-methyl amine (300 mg, 2.2 mmol) was heated in a sealed tube at 140° C. overnight. The crude product was purified by chromatography (5-6% ethyl acetate/hexanes) on silica gel to give the title compound (46 mg, 0.17 mmol, 57%). $^1$H NMR (CDCl$_3$): 8.22 (d, 1H, 5.7), 7.68 (d, 1H, J=8.1), 7.62 (d, 1H, J=8.7), 7.47 (ddd, 1H, J=0.9, 6.9, 8.1), 7.24 (d, 1H, J=6.0), 7.19 (ddd, 1H, J=1.5, 6.9, 8.7), 6.94 (m, 2H), 6.79 (m, 2H), 3.76 (s, 3H), 3.52 (s, 3H).

Example 66

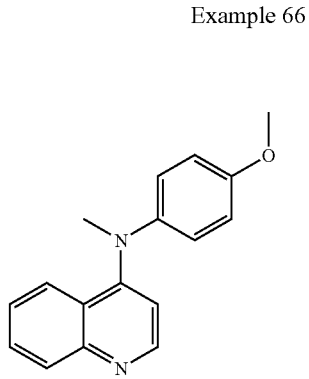

(4-Methoxy-phenyl)-methyl-(quinolin-4-yl)-amine

A mixture of 4-chloroquinoline (50 mg, 0.31 mmol) and (4-methoxy-phenyl)-methyl amine (300 mg, 2.2 mmol) was heated in a sealed tube at 140° C. overnight. The crude product was purified by chromatography (20-40% ethyl acetate/hexanes) on silica gel to give the title compound (60 mg, 0.23 mmol, 74%). $^1$H NMR (CDCl$_3$): 8.77 (d, 1H, J=5.1), 8.00-8.04 (m, 1H), 7.61-7.64 (m, 1H), 7.55 (ddd, 1H, J=1.5, 6.9, 8.4), 7.22 (ddd, 1H, J=1.5, 6.9, 8.1), 6.99 (d, 1H, J=4.8), 6.92 (m, 2H), 6.89 (m, 2H), 3.77 (s, 3H), 3.43 (s, 3H).

Example 67

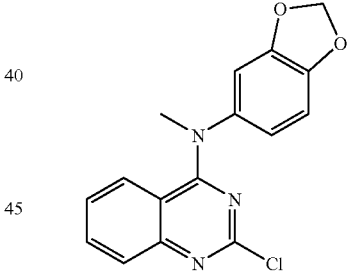

(2-Chloro-quinazolin-4-yl)-(3,4-methylenedioxyphenyl)-methyl-amine a) (2-Chloro-quinazolin-4-yl)-(3,4-methylenedioxyphenyl)-amine: The title compound was prepared from 3,4-methylenedioxyphenylamine and 2,4-dichloroquinazoline by a procedure similar to example 1b and was isolated as solids (45% yield). $^1$H NMR (CDCl$_3$): 7.81-7.83 (m, 3H), 7.51-7.56 (m, 2H), 7.44 (d, 1H, J=2.1), 6.98 (dd, 1H, J=2.1, 8.1), 6.82 (d, 1H, J=8.1), 6.01 (s, 2H).

b). (2-Chloro-quinazolin-4-yl)-(3,4-methylenedioxyphenyl)-methyl-amine: The title compound was prepared from (2-chloro-quinazolin-4-yl)-(3,4-methylenedioxyphenyl)-amine by a procedure similar to example 36 and was isolated as solids (66% yield). $^1$H NMR (CDCl$_3$): 7.73-7.76 (m, 1H), 7.58 (m, 1H), 7.07 (m, 2H), 6.82 (d, 1H, J=8.4), 6.72 (m, 1H), 6.68 (m, 1H), 6.06 (s, 2H), 3.59 (s, 3H).

Compounds of EXAMPLE 68-70 were prepared similar to Example 67.

Example 68

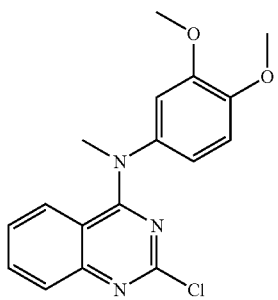

(2-Chloro-quinazolin-4-yl)-(3,4-dimethoxy-phenyl)-methyl-amine a) (2-Chloro-quinazolin-4-yl)-(3,4-dimethoxy-phenyl)-amine: $^1$H NMR (CDCl$_3$): 7.77-7.86 (m, 3H), 7.51-7.60 (m, 3H), 7.12 (dd, 1H, J=2.4, 8.4), 6.90 (d, 1H, J=8.4), 3.94 (s, 3H), 3.91 (s, 3H).

b). (2-Chloro-quinazolin-4-yl)-(3,4-dimethoxy-phenyl)-methyl-amine: $^1$H NMR (CDCl$_3$): 7.72-7.75 (m, 1H), 7.57 (ddd, 1H, J=1.5, 6.6, 8.4), 7.01 (ddd, 1H, J=1.2, 6.9, 8.7), 6.88-6.96 (m, 2H), 6.73-6.81 (m, 2H), 3.94 (s, 3H), 3.80 (s, 3H), 3.63 (s, 3H).

Example 69

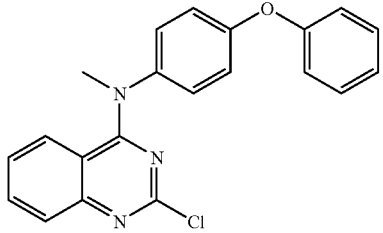

(2-Chloro-quinazolin-4-yl)-(4-phenoxy-phenyl)-methyl-amine a) (2-Chloro-quinazolin-4-yl)-(4-phenoxy-phenyl)-amine: $^1$H NMR (CDCl$_3$): 7.78-7.87 (m, 3H), 7.68-7.74 (m, 2H), 7.60 (s, broad, 1H), 7.56 (ddd, 1H, J=3.3, 9.9, 12.0), 7.33-7.39 (m, 2H), 7.03-7.16 (m, 5H).

b) (2-Chloro-quinazolin-4-yl)-(4-phenoxy-phenyl)-methyl amine: $^1$H NMR (CDCl$_3$): 7.74-7.77 (m, 1H), 7.59 (ddd, 1H, J=1.5, 6.6, 8.4), 7.36-7.42 (m, 2H), 7.10-7.20 (m, 3H), 7.03-7.10 (m, 5H), 6.97-7.00 (m, 1H), 3.64 (s, 3H).

Example 70

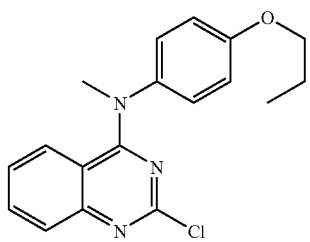

(2-Chloro-quinazolin-4-yl)-(4-propoxy-phenyl)-methyl-amine a) (2-Chloro-quinazolin-4-yl)-(4-propoxy-phenyl)-amine: $^1$H NMR (CDCl$_3$): 7.76-7.84 (m, 3H), 7.52-7.62 (m, 4H), 6.95 (m, 2H), 3.94 (t, 2H, J=6.6), 1.83 (hex, 2H, J=7.2), 1.05 (t, 3H, J=7.5)

b) (2-Chloro-quinazolin-4-yl)-(4-propoxy-phenyl)-methyl-amine: $^1$H NMR (CDCl$_3$): 7.71-7.74 (m, 1H), 7.55 (ddd, 1H, J=1.5, 6.9, 8.4), 7.10-7.16 (m, 2H), 7.00 (ddd, 1H, J=1.5, 6.9, 8.4), 6.91-6.96 (m, 3H), 3.96 (t, 2H, J=6.6), 1.84 (hex, 2H, J=7.5), 1.08 (t, 3H, J=7.5).

Example 71

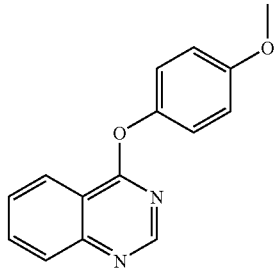

4-(4-Methoxy-phenoxy)-quinazoline

To a stirred solution of 4-methoxyphenol (75 mg, 0.60 mmol) and 4-chloro-quinazoline (125 mg, 76 mmol) in 3 mL of DMF was added sodium hydride (60% oil suspension, 30 mg, 0.75 mmol) at 0° C., then the reaction mixture was allowed to warm to room temperature and stirred for 5 h. The reaction was quenched by adding 50 uL of water and diluted with 25 mL of ethyl acetate. It was washed with water (25 mL×3), saturated NaCl, dried over anhydrous MgSO$_4$, filtered and concentrated. The residue was purified by chromatography (25% ethyl acetate/hexanes) to give the title compound (134 mg, 0.53 mmol, 89%). $^1$H NMR (CDCl$_3$): 8.78 (s, 1H), 8.38 (m, 1H), 7.89-8.02 (m, 2H), 7.67 (m, 1H), 7.19 (m, 1H), 7.00 (m, 1H), 3.86 (s, 3H).

Example 72

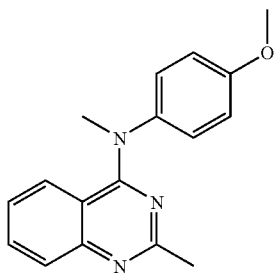

(4-Methoxy-phenyl)-methyl-(2-methyl-quinazolin-4-yl)-amine hydrochloride a) 4-Chloro-2-methyl-quinazoline: A stirred suspension of 2-methyl-4(3H)-quinazolinone (5 g, 31.2 mmol) in POCl₃ (100 mL) was heated at 120° C. for 3 h. The excess POCl₃ was removed under vacuum, then to the residue was added crushed ice and 200 mL of saturated NaHCO₃, and the mixture was extracted with ethyl acetate (200 mL×2). The combined extracts were washed with water, saturated NaCl, dried over anhydrous MgSO₄, filtered and concentrated. The crude product was purified by column chromatography (5-8% ethyl acetate/hexane) to give the title compound (2.5 g, 14.0 mmol, 45%). ¹H NMR (CDCl₃): 8.21-8.25 (m, 1H), 7.89-7.99 (m, 2H), 7.66 (ddd, 1H, J=1.8, 6.6, 8.7), 2.87 (s, 3H).

b) (4-Methoxy-phenyl)-methyl-(2-methyl-quinazolin-4-yl)-amine hydrochloride: The title compound was prepared from 4-chloro-2-methyl-quinazoline (2.31 g, 12.9 mmol) and (4-methoxy phenyl)-methyl-amine (2.0 g, 14.6 mmol) by a procedure similar to example 1b and was isolated as solids (2.90 g, 9.18 mmol, 71%). ¹H NMR (CDCl₃): 8.53 (dd, 1H, J=0.6, 8.1), 7.7 (ddd, 1H, J=1.2, 7.2, 8.4), 7.22 (m, 2H), 7.13 (ddd, 1H, J=1.2, 7.2, 8.7), 7.05 (m, 2H), 6.76 (d, 1H, J=8.7), 3.91 (s, 3H), 3.78 (s, 3H), 2.96 (s, 3H).

Example 73

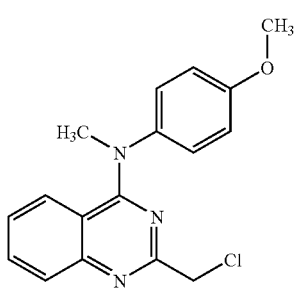

(2-Chloromethyl-quinazolin-4-yl)-(4-methoxy-phenyl)-methyl-amine a) 2-Chloromethyl-quinazolin-4(3H)-one: To a solution of 2-amino-benzoic acid methyl ester (0.26 ml, 2 mmol) and chloro-acetonitrile (0.16 ml, 4.0 mmol) in dioxane (8 ml) at room temperature was added concentrated HCl (1.0 ml) dropwise. The mixture was heated at 80° C. for 24 h and then cooled to room temperature. The resulting solid was collected and dissolved in water (10 ml), and the solution was neutralized with 2 N NaOH aqueous to pH 7. The precipitation was collected by filtration, then washed with water and dried to give 309 mg (79.6%) of the title compound.

b) (2-Chloromethyl-quinazolin-4-yl)-(4-methoxy-phenyl)-methyl-amine: A mixture of 2-chloromethyl-quinazolin-4(3H)-one (256 mg, 1.32 mmol), phosphoryl chloride (1.23 ml, 13.2 mmol) and N,N-dimethylaniline (0.34 ml, 2.64 mmol) in chloroform (10 ml) was heated under reflux for 4 h. The reaction mixture was poured onto ice and extracted by ethyl acetate. The solvent was evaporated, and the residue was purified by column chromatography on silica gel with acetate and hexane (1:1) as eluent, yielding 180 mg of 4-chloro-2-chloromethyl-quinazoline. The intermediate (170 mg, 0.80 mmol) and (4-methoxy-phenyl)-methylamine (131.7 mg, 0.96 mmol) in isopropyl alcohol (5 ml) with concentrated HCl (0.05 ml) was stirred at room temperature overnight. The precipitation was formed and collected by filtration, then washed and dried to give 231 mg (92%) of the title compound. ¹H NMR (CDCl₃): 7.82 (d, J=8.7 Hz, 1H), 7.59-7.53 (m, 1H), 7.15-7.12 (m, 2H), 7.03-7.00 (m, 2H), 6.95-6.91 (m, 2H), 4.73 (s, 2H), 3.85 (s, 3H), 3.62 (s, 3H).

Example 74

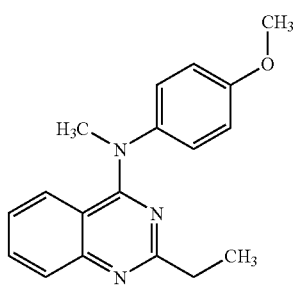

(2-Ethyl-quinazolin-4-yl)-(4-methoxy-phenyl)-methyl-amine

The title compound was prepared in three steps by a procedure similar to Example 73. ¹H NMR (CDCl₃): 7.76 (d, J=8.4 Hz, 1H), 7.55-7.49 (m, 1H), 7.13-7.09 (m, 2H), 7.03-6.89 (m, 4H), 3.83 (s, 3H), 3.60 (s, 3H), 2.97 (q, J=7.5 Hz, 2H), 1.44 (t, J=7.8 Hz, 3H).

Example 75

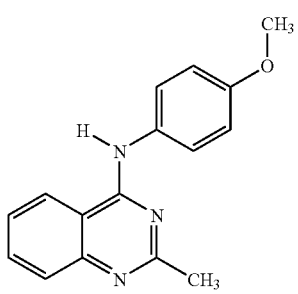

(2-Methyl-quinazolin-4-yl)-(4-methoxy-phenyl)-amine

The title compound was prepared from 4-chloro-2-methyl-quinazoline (108 mg, 0.605 mmol) and 4-methoxy-phenylamine (89.4 mg, 0.73 mmol) by a procedure similar to Example 72b. $^1$H NMR (DMSO-$d_6$): 11.28 (brs, 1H), 8.73 (d, J=8.4 Hz, 1H), 8.06 (t, J=7.5 Hz, 1H), 7.85-7.78 (m, 2H), 7.66 (d, J=9 Hz, 2H), 7.06 (d, J=8.7 Hz, 2H), 3.81 (s, 3H), 2.60 (s, 3H).

Example 76

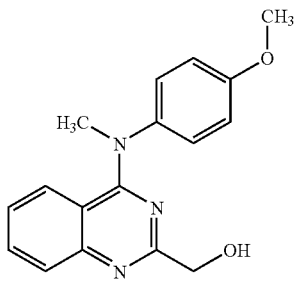

(2-Hydroxymethyl-quinazolin-4-yl)-4-methoxy-phenyl)-methyl-amine

To a solution of (2-chloromethyl-quinazolin-4-yl)-(4-methoxy-phenyl)-methyl-amine hydrochloride salt (67 mg, 0.19 mmol) in 1,4-dioxane (3 ml) was added 2 N NaOH aqueous (1 ml). The mixture was heated at 80° C. for 24 h and then was cooled to room temperature. The reaction mixture was diluted with ethyl acetate, then was washed with water and dried with NaSO$_4$. The solvent was evaporated, and the residue was purified by column chromatography on silica gel with acetate and hexane (1:1) as eluent, yielding 25 mg of title compound (44%). $^1$H NMR (CDCl$_3$): 7.78-7.75 (m, 1H), 7.59-7.53 (m, 1H), 7.15-7.12 (m, 2H), 7.02-7.00 (m, 2H), 6.94-6.91 (m, 2H), 4.79 (s, 2H), 3.85 (s, 3H), 3.59 (s, 3H).

Example 77

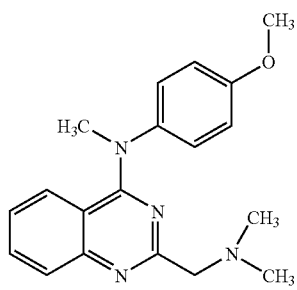

(2-Dimethylaminomethyl-quinazolin-4-yl)-(4-methoxy-phenyl)-methyl-amine

The title compound was prepared from (2-chloromethyl-quinazolin-4-yl)-(4-methoxy-phenyl)-methyl-amine and dimethylamine by a procedure similar to Example 76. $^1$H NMR (DMSO-$d_6$): 7.71 (d, J=8.7 Hz, 1H), 7.60 (t, J=8.4 Hz, 1H), 7.20 (d, J=8.4 Hz, 2H), 7.09 (t, J=8.1 Hz, 1H), 7.00-6.96 (m, 3H), 3.78 (s, 3H), 3.63 (s, 2H), 3.50 (s, 3H), 2.33 (s, 6H).

Example 78

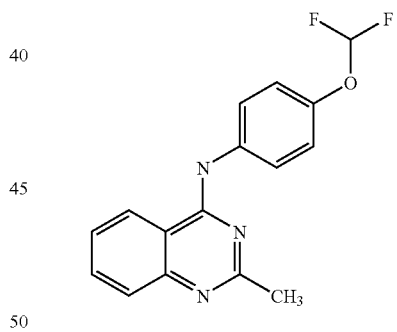

(4-Difluoromethoxy-phenyl)-(2-methyl-quinazolin-4-yl)-amine

A mixture of 4-chloro-2-methyl-quinazoline (450 mg, 2.52 mmol), 4-difluoromethoxy-phenylamine (0.32 ml, 2.52 mmol) and sodium acetate (248.07 mg, 3.02 mmol) in 6 mL of solvent (THF:water=1:1) was stirred at 70° C. for 1 h. The reaction mixture was diluted with 30 mL of ethyl acetate. It was washed with brine, dried over anhydrous Na$_2$SO$_4$, filtered and concentrated. The crude product was purified by chromatography on silica gel with acetate and hexane (1:5) as eluent, yielding 713 mg of title compound (94%). $^1$H NMR (CDCl$_3$): 7.87-7.76 (m, 5H), 7.51 (t, J=8.4 Hz, 1H)), 7.40 (brs, 1H), 7.19 (d, J=8.7 Hz, 2H), 6.76-6.27 (three single peaks, 1H), 2.71 (s, 3H).

Example 79

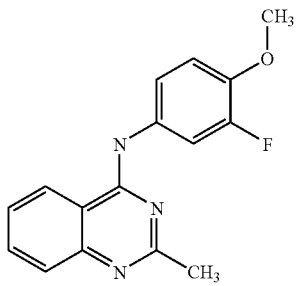

(3-Fluoro-4-methoxy-phenyl)-(2-methyl-quinazolin-4-yl)-amine

The title compound was prepared from 4-chloro-2-methyl-quinazoline (150 mg, 0.84 mmol), 3-fluoro-4-methoxy-phenylamine (118.5 mg, 0.84 mmol) by a procedure similar to example 78. $^1$H NMR (CDCl$_3$): 7.89-7.75 (m, 4H), 7.53-7.48 (m, 1H)), 7.38-7.34 (m, 2H), 7.0 (t, J=8.7 Hz, 1H), 3.92 (s, 3H), 2.71 (s, 3H).

Example 80

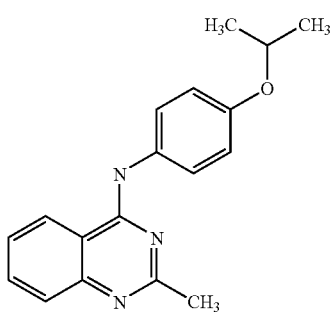

(4-Isopropoxy-phenyl)-(2-methyl-quinazolin-4-yl)-amine

The title compound was prepared from 4-chloro-2-methyl-quinazoline (100 mg, 0.56 mmol), 4-isopropoxy-phenylamine (84.66 mg, 0.56 mmol) by a procedure similar to example 78. $^1$H NMR (CDCl$_3$): 7.84-7.72 (m, 3H), 7.70-7.66 (m, 2H)), 7.50-7.45 (m, 1H), 7.30 (brs, 1H), 6.96-6.93 (m, 2H), 4.59-4.51 (m, 1H), 2.68 (s, 3H), 1.36 (d, J=6.3 Hz, 6H).

Example 81

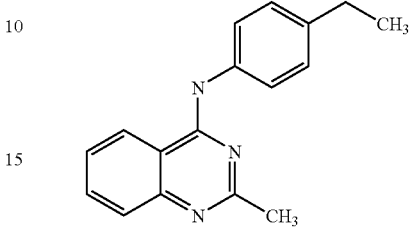

(4-Ethyl-phenyl)-(2-methyl-quinazolin-4-yl)-amine

The title compound was prepared from 4-chloro-2-methyl-quinazoline (100 mg, 0.56 mmol), 4-ethyl-phenylamine (0.07 ml, 0.56 mmol) by a procedure similar to example 78. $^1$H NMR (CDCl$_3$): 7.85-7.78 (m, 2H), 7.76-7.71 (m, 3H)), 7.49 (t, J=7.5 Hz, 1H), 7.36 (brs, 1H), 7.24 (s, 2H), 2.70-2.69 (m, 5H), 1.26 (t, J=7.5 Hz, 3H).

Example 82

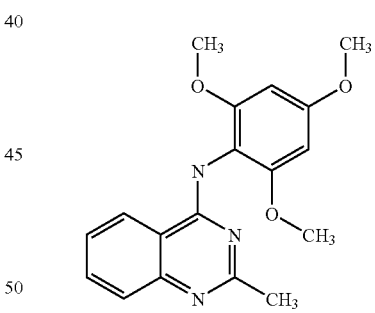

(2-Methyl-quinazolin-4-yl)-(2,4,6-trimethoxy-phenyl)-amine

The title compound was prepared from 4-chloro-2-methyl-quinazoline (89.3 mg, 0.5 mmol), 2,4,6-trimethoxy-phenylamine (91.6 mg, 0.5 mmol) by a procedure similar to example 78. $^1$H NMR (CDCl$_3$): 7.86 (d, J=8.4 Hz, 1H), 7.80

(d, J=8.4 Hz, 1H), 7.71 (t, J=6.6 Hz, 1H), 7.41 (t, J=8.1 Hz, 1H), 6.81 (brs, 1H), 6.25 (s, 2H), 3.87 (s, 3H), 3.79 (s, 6H), 2.57 (s, 3H).

Example 83

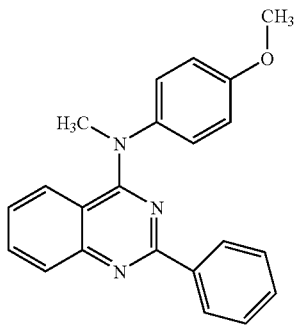

(4-Methoxy-phenyl)-(2-phenyl-quinazolin-4-yl)-methyl-amine

The title compound was prepared from (4-methoxy-phenyl)-(2-phenyl-quinazolin-4-yl)-amine (51 mg, 0.16 mmol) and methyl iodide (0.07 ml, 1.09 mmol) by a procedure similar to Example 36. $^1$H NMR (CDCl$_3$): 8.64-8.61 (m, 2H), 7.90 (d, J=8.4 Hz, 1H), 7.59-7.48 (m, 4H), 7.18-7.14 (m, 2H), 7.08-6.98 (m, 2H), 6.94-6.91 (m, 2H), 3.85 (s, 3H), 3.73 (s, 3H).

Example 84

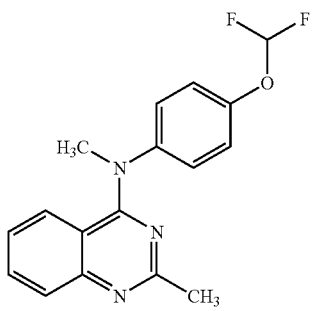

(4-Difluoromethoxy-phenyl)-(2-methyl-quinazolin-4-yl)-methyl-amine

The title compound was prepared from (4-difluoromethoxy-phenyl)-(2-methyl-quinazolin-4-yl)-amine (710 mg, 2.36 mmol) and methyl iodide (1.03 ml, 16.52 mmol), by a procedure similar to Example 36 (40.8% yield). $^1$H NMR (CDCl$_3$): 7.77 (dd, J=8.4 Hz, J=0.9 Hz, 1H), 7.59-7.53 (m, 1H), 7.17-7.10 (m, 4H), 7.06-6.99 (m, 2H), 6.78 (d, J=0.6 Hz, 0.25H), 6.54 (d, J=0.9 Hz, 0.5H), 6.29 (d, J=0.9 Hz, 0.25H), 3.62 (s, 3H), 2.75 (s, 3H).

Example 85

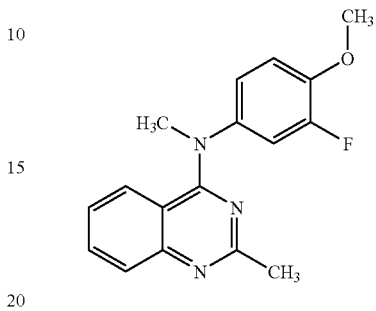

(3-Fluoro-4-methoxy-phenyl)-(2-methyl-quinazolin-4-yl)-methyl-amine

The title compound was prepared from (3-fluoro-4-methoxy-phenyl)-(2-methyl-quinazolin-4-yl)-amine (250 mg, 0.88 mmol) and methyl iodide (0.39 ml, 6.18 mmol) by a procedure similar to example 36. $^1$H NMR (CDCl$_3$): 7.76 (d, J=8.4 Hz, 1H), 7.59-7.53 (m, 1H), 7.09-6.82 (m, 5H), 3.91 (s, 3H), 3.58 (s, 3H), 2.73 (s, 3H).

Example 86

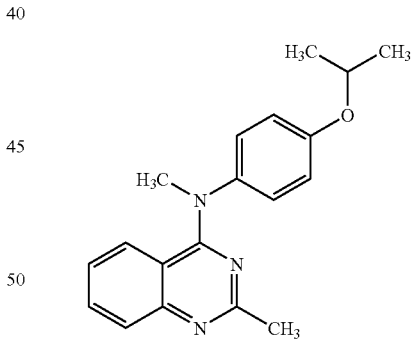

(4-Isopropoxy-phenyl)-(2-methyl-quinazolin-4-yl)-methyl-amine

The title compound was prepared from (4-isopropoxy-phenyl)-(2-methyl-quinazolin-4-yl)-amine (164.3 mg, 0.56 mmol) and methyl iodide (0.25 ml, 3.92 mmol) by a procedure similar to example 36. $^1$H NMR (CDCl$_3$): 7.73 (d, J=7.8

Hz, 1H), 7.54-7.49 (m, 1H), 7.10-6.86 (m, 6H), 4.57-4.52 (m, 1H), 3.58 (s, 3H), 2.72 (s, 3H), 1.36 (d, J=6 Hz, 6H).

Example 87

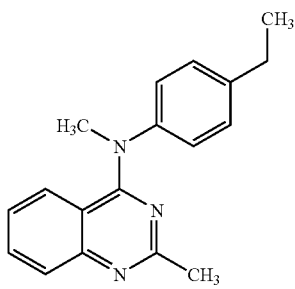

(4-Ethyl-phenyl)-(2-methyl-quinazolin-4-yl)-methyl-amine

The title compound was prepared from (4-ethyl-phenyl)-(2-methyl-quinazolin-4-yl)-amine (122 mg, 0.46 mmol) and methyl iodide (0.2 ml, 3.25 mmol) by a procedure similar to example 36. $^1$H NMR (CDCl$_3$): 7.74 (d, J=8.1 Hz, 1H), 7.54-7.49 (m, 1H), 7.19 (d, J=8.4 Hz, 2H), 7.09-6.92 (m, 4H), 3.61 (s, 3H), 2.73-2.63 (m, 5H), 1.26 (d, J=7.5 Hz, 3H).

Example 88

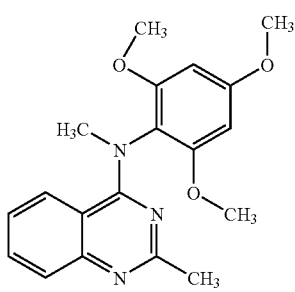

(2-Methyl-quinazolin-4-yl)-(2,4,6-trimethoxy-phenyl)-methyl-amine

The title compound was prepared from (2-methyl-quinazolin-4-yl)-(2,4,6-trimethoxy-phenyl)-amine (56 mg, 0.17 mmol) and methyl iodide (0.1 ml, 1.6 mmol) by a procedure similar to example 36. $^1$H NMR (CDCl$_3$): 7.70 (d, J=8.4 Hz, 1H), 7.49 (t, J=7.8 Hz, 1H), 7.09 (d, J=8.7 Hz, 1H), 6.93 (t, J=8.1 Hz, 1H), 6.18 (s, 2H), 3.86 (s, 3H), 3.63 (s, 6H), 3.44 (s, 3H), 2.70 (s, 3H).

Compounds of Example 89-90 were prepared by a procedure similar to Example 56.

Example 89

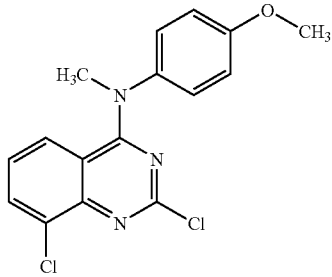

(2,8-Dichloro-quinazolin-4-yl)-(4-methoxy-phenyl)-methyl-amine a) 8-Chloro-1H-quinazoline-2,4-dione: White solid: $^1$H NMR (DMSO-d$_6$) 11.47 (s, 1H), 10.77 (s, 1H), 7.88 (m, 1H), 7.78 (m, 1H), 7.18 (m, 1H).

b) (2,8-Dichloro-quinazolin-4-yl)-(4-methoxy-phenyl)-methyl-amine: Off-white solid: $^1$H NMR (CDCl$_3$) 7.66 (dd, J=2.7, 6.3 Hz, 1H), 7.14-7.10 (m, 2H), 6.97-6.89 (m, 4H), 3.86 (s, 3H), 3.62 (s, 3H).

Example 90

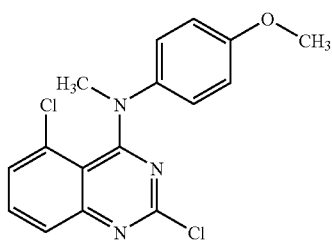

(2,5-Dichloro-quinazolin-4-yl)-(4-methoxy-phenyl)-methyl-amine a) 5-Chloro-1H,3H-quinazoline-2,4-dione: White solid: $^1$H NMR (DMSO-d$_6$) 11.28 (s, 2H), 7.55 (m, 1H), 7.19 (d, J=7.8 Hz, 1H), 7.12 (d, J=8.4 Hz, 1H).

b) (2,5-Dichloro-quinazolin-4-yl)-(4-methoxy-phenyl)-methyl-amine: Yellow solid: $^1$H NMR (CDCl$_3$) 7.67 (m, 1H), 7.52 (m, 1H), 7.16 (m, 1H), 6.80-6.69 (m, 4H), 3.76 (s, 3H), 3.65 (s, 3H).

Example 91

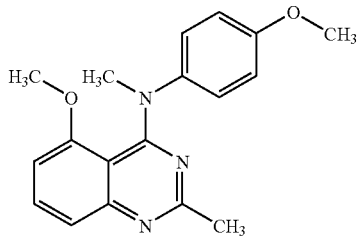

(5-Methoxy-2-methyl-quinazolin-4-yl)-(4-methoxy-phenyl)-methyl-amine a) 5-Methoxy-2-methyl-quinazolin-4-ol: To a suspension of 2-amino-6-methoxy-benzoic acid (305 mg, 1.82 mmol) and 4-N,N-dimethylaminopyridine (20 mg, 0.16 mmol) in DMF/toluene (2:6 mL) at 0° C. was added triethylamine (1.1 mL, 7.9 mmol) followed by slow addition of acetyl chloride (0.40 mL, 5.6 mmol) under argon. The suspension was stirred at rt for 19 h. Ammonium acetate (0.62 g, 8.0 mmol) was added and the reaction mixture was further stirred at 90° C. for 5 h. The solid was collected by filtration, washed with water, and dried to give an off-white solid (103 mg, 30%): $^1$H NMR (CDCl$_3$) 10.69 (s, 1H), 7.66 (t, J=8.4 Hz, 1H), 7.25 (d, J=8.4 Hz, 1H), 6.49 (d, J=8.4 Hz, 1H), 4.01 (s, 3H), 2.53 (s, 3H).

b) (5-Methoxy-2-methyl-quinazolin-4-yl)-(4-methoxy-phenyl)-methyl-amine: The title compound was prepared by a procedure similar to that of Example 56b as white solid: $^1$H NMR (CDCl$_3$) 7.51 (t, J=8.4 Hz, 1H), 7.35 (dd, J=0.9, 8.4 Hz, 1H), 6.85-6.80 (m, 2H), 6.85-6.72 (m, 2H), 6.56 (dd, J=0.9, 7.8 Hz, 1H), 3.75 (s, 3H), 3.60 (s, 3H), 3.25 (s, 3H), 2.68 (s, 3H).

Example 92

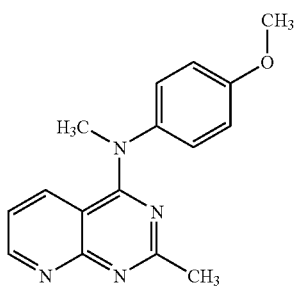

(4-Methoxy-phenyl)-(2-methyl-pyrido[2,3-d]pyrimidin-4-yl)-methyl-amine a) 2-Methyl-pyrido[2,3-d]pyrimidin-4-ol: To a solution of 2-amino-nicotinic acid (277 mg, 2 mmol), 4-N,N-dimethylaminopyridine (20 mg, 0.16 mmol), triethylamine (1.1 mL, 7.9 mmol) in DMF (2 mL) was added acetyl chloride (0.35 mL, 4.9 mmol) slowly at 0° C. under argon. The white precipitate was formed immediately. The mixture was then heated at 90° C. for 3.5 h, then ammonium acetate (0.601 g, 7.8 mmol) was added. The mixture was stirred for 1 h, cooled to rt and diluted with water (20 mL). It was extracted with EtOAc (2×50 mL), and the extracts were dried over MgSO$_4$, and evaporated. The crude was purified by column chromatography (SiO$_2$, EtOAc:MeOH/0-10%) to give an off-white solid (47 mg, 16%): $^1$H NMR (DMSO-d$_6$) 11.40 (s, 1H), 9.01 (dd, J=2.1, 4.8 Hz, 1H), 8.61 (dd, J=2.4, 8.1 Hz, 1H), 7.44 (dd, J=4.8, 8.1 Hz, 1H), 2.66 (s, 3H).

b) (4-Methoxy-phenyl)-(2-methyl-pyrido[2,3-d]pyrimidin-4-yl)-methyl-amine: To a solution of 2-methyl-pyrido[2,3-d]pyrimidin-4-ol (47 mg, 0.32 mmol) in toluene (2 mL) was added phosphorus oxychloride (0.05 mL, 0.55 mmol) and diisopropylethyl amine (0.12 mL, 0.69 mmol). The solution was stirred at rt for 25 h, then (4-methoxy-phenyl)-methylamine (45 mg, 0.33 mmol) was added. The reaction mixture was stirred at rt for 22 h. The solvent was evaporated and the crude was purified by column chromatography (SiO$_2$, EtOAc:hexanes/30-100%). The product was collected as an off-white solid (6 mg, 7%): $^1$H NMR (CDCl$_3$) 8.22 (dd, J=2.1, 4.5 Hz, 1H), 7.24 (d, J=2.1 Hz, 1H), 7.15-7.10 (m, 2H), 6.96-6.92 (m, 2H), 6.88 (dd, J=4.2, 8.4 Hz, 1H), 3.85 (s, 3H), 3.60 (s, 3H), 2.05 (s, 3H).

Example 93

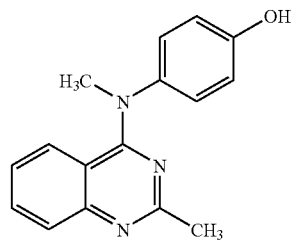

(4-Hydroxy-phenyl)-(2-methyl-quinazolin-4-yl)-methyl-amine

To a solution of (4-methoxy-phenyl)-(2-methyl-quinazolin-4-yl)-methyl-amine hydrochloride salt (106 mg, 0.336 mmol) in dichloromethane (10 mL) at −78° C. was added slowly boron tribromide (1M in CH$_2$Cl$_2$, 0.75 mL) under argon. The cold bath was removed and the reaction mixture was allowed to warm up slowly to 10° C. in 1.5 h. The reaction mixture was quenched with water (10 mL), basified with 2N NaOH to pH=10, and extracted with EtOAc (2×25 mL). The EtOAc extracts were dried and evaporated to give a light brown residue. The crude was purified by column chromatography (SiO$_2$, EtOAc:hexanes/15-50%) to give the product as a white solid, which was further purified by recrystallization from MeOH: $^1$H NMR (acetone-d$_6$) 8.74 (s, 1H), 7.75

(m, 1H), 7.67 (m, 1H), 7.20-7.18 (m, 3H), 7.12 (m, 1H), 7.04-6.99 (m, 2H), 3.64 (s, 3H), 2.79 (s, 3H).

Example 94

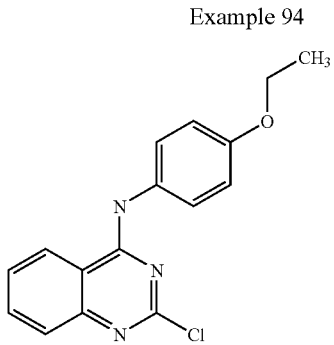

(2-Chloro-quinazolin-4-yl)-(4-ethoxy-phenyl)-amine

The title compound was prepared from 2,4-dichloroquinazoline and 4-ethoxyaniline by a procedure similar to example 28 (32%). $^1$H NMR (CDCl$_3$): 7.81 (m, 1H), 7.65 (m, 1H), 7.32 (m, 2H), 7.03 (m, 1H), 6.73 (m, 3H), 4.09 (q, J=7.2, 2H), 1.49 (t, J=7.2, 3H).

Example 95

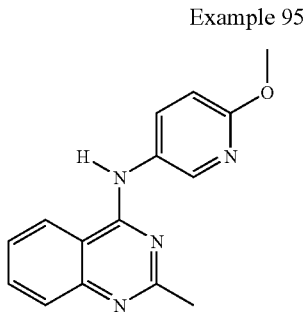

(2-Methyl-quinazolin-4-yl)-(6-methoxy-pyridin-3-yl)-amine

The title compound was prepared from 4-chloro-2-methylquinazoline and 3-amino-5-methoxypyridine by a procedure similar to example 28 (32%). $^1$H NMR (CDCl$_3$): 8.51 (d, J=1.8, 1H), 8.12 (m, 1H), 7.72-7.89 (m, 3H), 7.49 (m, 2H), 6.81 (d, J=8.7, 1H), 3.89 (s, 3H), 2.68 (s, 3H).

Example 96

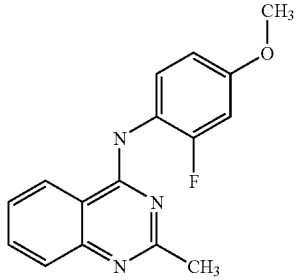

(2-Fluoro-4-methoxy-phenyl)-(2-methyl-quinazolin-4-yl)-amine

The title compound was prepared from 4-chloro-2-methylquinazoline and 2-fluoro-4-methoxyaniline by a procedure similar to example 28 (79%). $^1$H NMR (CDCl$_3$): 8.54 (m, 1H), 7.83 (m, 2H), 7.65 (m, 1H), 7.50 (m, 1H), 7.47 (s, broad, 1H), 6.74-6.81 (m, 2H), 3.83 (s, 3H), 2.70 (s, 3H).

Example 97

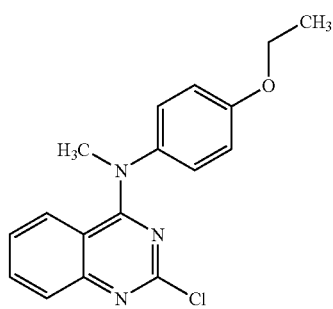

(2-Chloro-quinazolin-4-yl)-(4-ethoxy-phenyl)-methylamine

The title compound was prepared from (2-chloro-quinazolin-4-yl)-(4-ethoxy-phenyl)-amine by a procedure similar to example 36 (28%). $^1$H NMR (CDCl$_3$): 7.73 (m, 1H), 7.55 (m, 1H), 7.12 (m, 2H), 7.00 (m, 1H), 6.93 (m, 3H), 4.07 (q, J=7.2, 2H), 3.61 (s, 3H), 1.46 (t, J=7.2, 3H).

Example 98

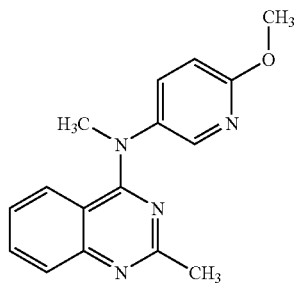

(2-Methyl-quinazolin-4-yl)-(6-methoxy-pyridin-3-yl)-methyl-amine

The title compound was prepared from (2-methyl-quinazolin-4-yl)-(6-methoxy-pyridin-3-yl)-amine by a procedure similar to example 36 (28%). $^1$H NMR (CDCl$_3$): 8.03 (d, J=2.7, 1H), 7.77 (m, 1H), 7.56 (ddd, J=8.1, 6.3, 1.8, 1H), 7.38

(dd, J=8.7, 3.0, 1H), 7.01 (m, 2H), 6.76 (d, J=9.0, 1H), 3.96 (s, 3H), 3.59 (s, 3H), 2.73 (s, 3H).

Example 99

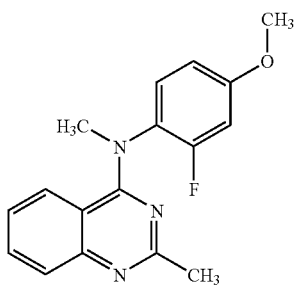

(2-Fluoro-4-methoxy-phenyl)-(2-methyl-quinazolin-4-yl)-methyl-amine

The title compound was prepared from (2-methyl-quinazolin-4-yl)-(2-fluoro-4-methoxy-phenyl)-amine by a procedure similar to example 36 (51%). $^1$H NMR (CDCl$_3$): 7.76 (d, J=8.1, 1H), 7.55 (ddd, J=8.1, 6.3, 1.8, 1H), 6.98-7.11 (m, 3H), 6.66-6.76 (m, 2H), 3.83 (s, 3H), 3.54 (s, 3H), 2.73 (s, 3H).

Example 100

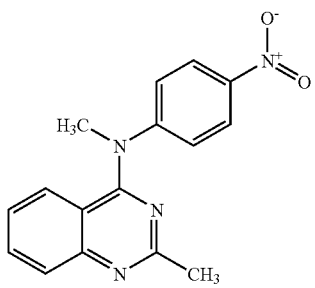

(2-Methyl-quinazolin-4-yl)-(4-nitro-phenyl)-methyl-amine

To a solution of 4-chloro-2-methylquinazoline (1.4 g, 7.84 mmol) and (4-nitro-phenyl)-methylamine (1.09 g, 7.16 mmol) in 20 mL of dimethylformamide cooled to 0° C. was added sodium hydride (0.6 g, 60 oil suspension, 15 mmol). The reaction mixture was stirred at 0° C. for 1 h and quenched by adding 200 uL of water. It was diluted with 150 mL of ethyl acetate, washed with water (100 mL×3), saturated NaCl, dried over anhydrous MgSO$_4$, filtered and concentrated. The residue was purified by chromatography (30% ethyl acetate/hexanes) to give the title compound (1.41 g, 4.78 mmol, 67%). $^1$H NMR (CDCl$_3$): 8.14 (m, 2H), 7.91 (m, 1H), 7.71 (ddd, J=8.4, 6.6, 1.8, 1H), 7.19-7.32 (m, 2H), 7.05 (m, 2H), 3.76 (s, 3H), 2.82 (s, 3H).

Example 101

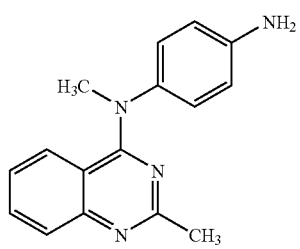

(4-Amino-phenyl)-(2-methyl-quinazolin-4-yl)-methyl-amine

A mixture of (2-methyl-quinazolin-4-yl)-(4-nitro-phenyl)-methylamine (200 mg, 0.68 mmol) in 25 mL of ethyl acetate was hydrogenated over Palladium on carbon (70 mg) at 50 psi for 4 h, and the reaction mixture was filtered through a pad of celite and concentrated. The resulting crude product was purified by chromatography (50% ethyl acetate/hexane) to obtain the title compound (140 mg, 78%). $^1$H NMR (CDCl$_3$): 7.71 (m, 1H), 7.51 (ddd, J=8.4, 6.9, 1.5, 1H), 7.09 (m, 1H), 6.93-7.05 (m, 3H), 6.68 (m, 2H), 3.74 (s, broad, 2H), 3.56 (s, 3H), 2.71 (s, 3H).

Example 102

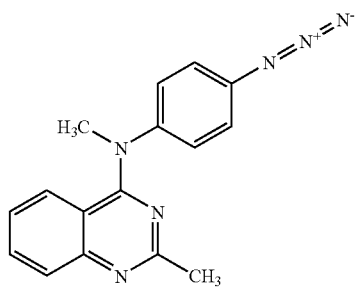

(4-Azido-phenyl)-(2-methyl-quinazolin-4-yl)-methyl-amine

To a solution of (2-methyl-quinazolin-4-yl)-(4-amino-phenyl)-methylamine (20 mg, 0.076 mmol) in 1.2 mL of 1N HCl was added 100 uL of methanol and it was cooled 0° C. One drop of concentrated HCl was added and the solution was stirred at 0° C. for 0.25 h. To the solution was added dropwise a solution of sodium nitrite (25 mg, 0.36 mmol) in 200 uL of water. The reaction mixture was stirred for 0.5 h, then was added a solution of sodium azide (25 mg, 0.38 mmol) in 300 uL of water followed by another batch of sodium azide (25 mg, 0.38 mmol). The reaction mixture was stirred at the 0° C. for 1 h. The reaction mixture was diluted with 50 mL of ethyl acetate, washed with saturated sodium bicarbonate followed by saturated sodium chloride. The organic layer was dried over anhydrous Na₂SO₄, filtered and concentrated. The residue was purified by column chromatography (20-25% ethyl acetate/hexanes) on silica gel to give the title compound (19.8 mg, 0.068 mmol, 90%). $^1$H NMR (CDCl₃): 7.76 (m, 1H), 7.56 (ddd, J=8.1, 6.3, 1.8, 1H), 7.13 (m, 2H), 6.98-7.13 (m, 4H), 3.61 (s, 3H), 2.74 (s, 3H).

Example 103

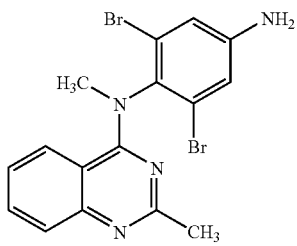

(4-Amino-2,6-dibromo-phenyl)-(2-methyl-quinazolin-4-yl)-methyl-amine and

Example 104

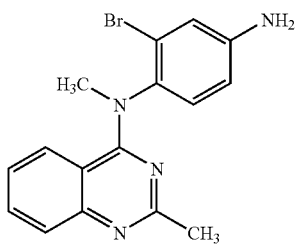

(4-Amino-2-bromo-phenyl)-(2-methyl-quinazolin-4-yl)-methyl-amine

To a mixture of (2-methyl-quinazolin-4-yl)-(4-amino-phenyl)-methylamine (53 mg, 0.20 mmol) in 1.8 mL of glacial acetic acid cooled at 12° C. was added dropwise a solution of Bromine (64 mg, 0.40 mmol) in 1 mL of glacial acetic acid. The mixture was stirred for 1 min and the reaction mixture was quenched by adding 1 mL of saturated sodium thiosulfate. The reaction mixture was diluted with 50 mL of ethyl acetate, and the organic layer was washed with saturated sodium bicarbonate. The organic layer was dried over anhydrous MgSO₄, filtered and concentrated. The residue was purified by chromatography (25-30% ethyl acetate/hexanes) to give the two compounds. (2-Methyl-quinazolin-4-yl)-(4-amino-2,6-dibromo-phenyl)-methyl-amine (17.5 mg, 0.041 mmol, 21%). $^1$H NMR (CDCl₃): 7.78 (m, 1H), 7.58 (ddd, J=8.1, 6.6, 1.2, 1H), 7.24-7.27 (m, 2H), 7.15-7.19 (m, 1H), 7.09 (m, 1H), 4.62 (s, broad, 2H), 3.54 (s, 3H), 2.72 (s, 3H) and (2-methyl-quinazolin-4-yl)-(4-amino-2-bromo-phenyl)-methyl-amine. (15 mg, 0.045 mmol, 22%). $^1$H NMR (CDCl₃): 7.75 (m, 1H), 7.55 (ddd, J=8.4, 6.9, 1.5, 1H), 7.31 (d, J=2.7, 1H), 7.13 (m, 1H), 7.03 (ddd, J=8.1, 6.9, 1.2, 1H), 6.91 (dd, J=8.1, 2.1, 1H), 6.74 (d, J=8.7, 1H), 4.18 (s, broad, 2H), 3.55 (s, 3H), 2.72 (s, 3H).

Example 105

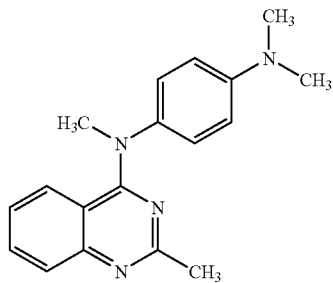

(4-Dimethylamino-phenyl)-(2-methyl-quinazolin-4-yl)-methyl-amine

To a solution of (2-methyl-quinazolin-4-yl)-(4-amino-phenyl)-methylamine (14 mg, mmol) in 1.5 mL of 37% aqoues formaldehyde solution and 10 uL of glacial acetic was added Sodium cyanoborohydride (15 mg, 0.24 mmol) and the mixture was stirred at room temperature for 2 h. The reaction mixture was quenched by adding 50 uL of 1N HCl. It was diluted with 50 mL of ethyl acetate, washed with saturated sodium bicarbonate, and followed by saturated sodium chloride. The organic layer was dried over anhydrous Na₂SO₄, filtered and concentrated. The residue was purified by column chromatography (25% ethyl acetate/hexanes) on silica gel to give the title compound (12.4 mg, 0.042 mmol, 80%). $^1$H NMR (CDCl₃): 7.71 (m, 1H), 7.50 (ddd, J=8.4, 6.9, 1.5, 1H), 7.03-7.09 (m, 3H), 6.95 (ddd, J=8.1, 6.6, 0.9, 1H), 6.70 (m, 2H), 3.57 (s, 3H), 2.99 (s, 6H), 2.71 (s, 3H).

Example 106

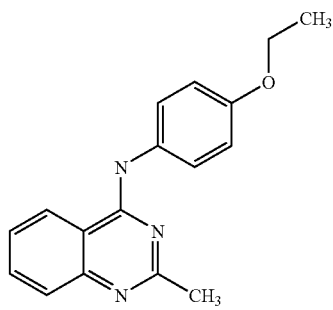

(4-Ethoxy-phenyl)-(2-methyl-quinazolin-4-yl)-amine

The title compound was prepared from 4-chloro-2-methylquinazoline and 4-ethoxyaniline by a procedure similar to example 28 (93%). $^1$H NMR (CDCl₃): 7.83 (m, 1H), 7.81 (m, 1H), 7.42 (m, 1H), 7.65-7.71 (m, 2H), 7.46 (ddd, J=8.4, 6.9, 1.5, 1H), 7.37 (s, broad, 1H), 6.92-6.97 (m, 2H), 4.06 (q, J=6.9, 2H), 2.68 (s, 3H), 1.43 (t, J=6.9, 3H).

Example 107

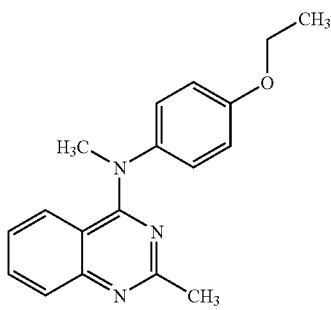

(4-Ethoxy-phenyl)-(2-methyl-quinazolin-4-yl)-methyl-amine

The title compound was prepared from (2-methyl-quinazolin-4-yl)-(4-ethoxy-phenyl)-amine by a procedure similar to example 36 (67%). $^1$H NMR (CDCl$_3$): 7.71-7.74 (m, 1H), 7.51 (ddd, J=8.1, 6.6, 1.5, 1H), 7.09 (m, 2H), 6.95-7.04 (m, 2H), 6.86-6.92 (m, 2H), 4.04 (q, J=6.9, 2H), 3.58 (s, 3H), 2.72 (s, 3H), 1.44 (t, J=6.9, 3H).

Example 108

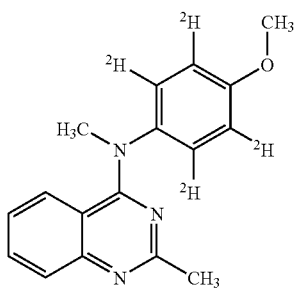

4-Methoxy-phenyl-2,3,5,6-d$_4$)-(2-methyl-quinazolin-4-yl)-methyl-amine a) (4-Methoxy-phenyl-2,3,5,6-d$_4$)-methylacetamide. To a solution of (4-hydroxy-phenyl-2,3,5,6-d$_4$)-acetamide (0.410 g, 2.46 mmol) in 15 mL of dimethylformamide was added methyl iodide (1 mL, 16.1 mmol) and the solution was cooled to 0° C., then sodium hydride (0.25 g, 60% oil suspension, 6.3 mmol) was added, and the mixture was stirred for 2 h at 0° C. The reaction mixture was quenched by addition of 100 uL of water, and diluted with 100 mL of ethyl acetate. It was washed with water (100 mL×3), saturated NaCl, dried over anhydrous MgSO$_4$, filtered and concentrated. The residue was purified by chromatography (50% ethyl acetate/hexanes) to give the title compound (0.380 g, 1.93 mmol, 78%). $^1$H NMR (CDCl$_3$): 3.83 (s, 3H), 3.23 (s, 3H), 1.86 (s, 3H).

b) (4-Methoxy-phenyl-2,3,5,6-d$_4$)-methylamine. A mixture of (4-methoxy-phenyl-2,3,5,6-d$_4$)-methylacetamide (280 mg, 1.41 mmol) in 15 mL of 2N HCl was refluxed for 4 h. The reaction mixture was cooled to 0° C., basified using cold 2N NaOH and extracted with ethyl acetate (50 mL×2). The combined organic extracts were washed with saturated NaCl, dried over anhydrous MgSO$_4$, filtered and concentrated. The residue was purified by chromatography (20% ethyl acetate/hexanes) to give the title compound (199 mg, 1.28 mmol, 90%). $^1$H NMR (CDCl$_3$): 3.75 (s, 3H), 3.22 (s, broad, 1H), 2.80 (s, 3H).

c) (4-Methoxy-phenyl-2,3,5,6-d$_4$)-(2-methyl-quinazolin-4-yl)-methyl-amine. The title compound was prepared from 4-chloro-2-methylquinazoline and (4-methoxy-phenyl-2,3,5,6-d$_4$)-methylamine by a procedure similar to example 28 (65%). $^1$H NMR (CDCl$_3$): 7.73 (m, 1H), 7.52 (ddd, J=8.4, 6.3, 1.8, 1H), 6.93-7.03 (m, 2H), 3.84 (s, 3H), 3.59 (s, 3H), 2.71 (s, 3H).

Example 109

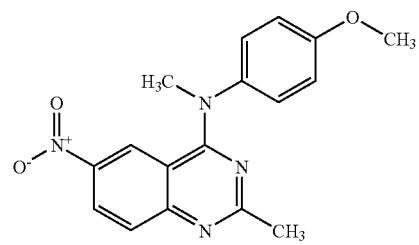

(4-Methoxy-phenyl)-(2-methyl-6-nitro-quinazolin-4-yl)-methyl-amine a) 2-Methyl-6-nitro-4H-benzo[d][1,3]oxazin-4-one. A mixture of 2-amino-5-nitrobenzoic acid (2.0 g, 10.9 mmol) in 20 mL of acetic anhydride was refluxed for 2 h. The reaction mixture was cooled to room temperature and the resulting precipitate was collected and washed with cold diethylether and dried under vacuum to obtain the title compound (1.45 g, 7.01 mmol, 64%). $^1$H NMR (CDCl$_3$): 9.05 (d, J=2.4, 1H), 8.61 (dd, J=9.0, 2.7, 1H), 7.71 (d, J=7.9, 1H), 2.55 (s, 3H).

b) 2-Methyl-6-nitro-quinazoline-4-one. A solution of 2-methyl-6-nitro-4H-benzo[d][1,3]oxazin-4-one (200 mg, 0.97 mmol) in a solution of ammonia in dioxane (0.5 M, 2.5 mL, 1.25 mmol) was heated at 70° C. for 4 h in a sealed tube. The reaction mixture was cooled to room temperature, and the resulting precipitate was collected and washed with cold diethylether and dried. The crude product was used for the next step.

c) 4-Chloro-2-methyl-6-nitro-quinazoline. A mixture of 2-methyl-6-nitro-quinazoline-4-one (100 mg, 0.49 mmol) and diisopropylethylamine (250 uL) in 3 mL of toluene was heated to 120° C. for 1 h, then phosphorylchloride (50 uL, 0.54 mmol) was added and the mixture was heated at 80° C. for 3 h. The reaction mixture was cooled to room temperature and poured into ice (about 15 g), basified with saturated NaHCO$_3$ and extracted with 75 mL of ethyl acetate. The organic layer was washed with water (50 mL), 1N citric acid (50 mL), water (50 mL) and saturated NaCl, dried over anhydrous Na$_2$SO$_4$, filtered and concentrated. The residue was purified by column chromatography (15% ethyl acetate/hexanes) on silica gel to give the title compound (65.5 mg, 0.29 mmol, 60%). $^1$H NMR (CDCl$_3$): 9.17 (d, J=2.4, 1H), 8.69 (dd, J=9.3, 2.4, 1H), 8.13 (d, J=9.3, 1H), 2.93 (s, 3H).

d) (4-Methoxy-phenyl)-(2-methyl-6-nitro-quinazolin-4-yl)-methyl-amine. The title compound was prepared from 4-chloro-2-methyl-6-nitro-quinazoline and (4-methoxy-phenyl)-methylamine by a procedure similar to example 28 (87% yield). $^1$H NMR (CDCl$_3$): 8.27 (dd, J=9.3, 2.7, 1H), 7.82 (d, J=2.4, 1H), 7.75 (d, J=9.0, 1H), 7.18 (m, 2H), 7.01 (m, 1H), 3.88 (s, 3H), 3.65 (s, 3H), 2.73 (s, 3H).

Example 110

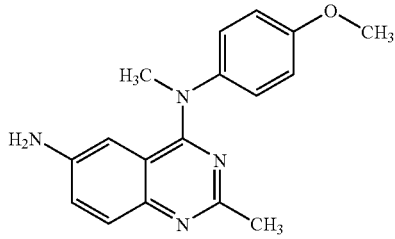

(6-Amino-2-methyl-quinazolin-4-yl)-(4-methoxy-phenyl)-methyl-amine

The title compound was prepared from (4-methoxy-phenyl)-(2-methyl-6-nitro-quinazolin-4-yl)-methyl-amine by a procedure as described in example 101 (70%). $^1$H NMR (CDCl$_3$): 7.59 (d, J=9.0, 1H), 7.07 (m, 2H), 6.99 (dd, J=8.7, 2.4, 1H), 6.88 (m, 2H), 6.16 (d, J=2.1, 1H), 3.48 (s, broad, 2H), 3.82 (s, 3H), 3.55 (s, 3H), 2.68 (s, 3H).

Example 111

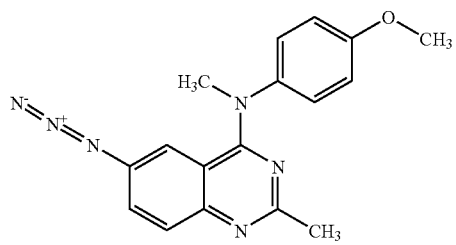

(6-Azido-2-methyl-quinazolin-4-yl)-(4-methoxy-phenyl)-methyl-amine

The title compound was prepared from (6-amino-2-methyl-quinazolin-4-yl)-(4-methoxy-phenyl)-methyl-amine by a procedure described for example 102 (83%). $^1$H NMR (CDCl$_3$): 7.69 (d, J=9.0, 1H), 7.10-7.18 (m, 3H), 6.95 (m, 2H), 6.62 (d, J=2.4, 1H), 3.84 (s, 3H), 3.59 (s, 3H), 2.760 (s, 3H).

Example 112

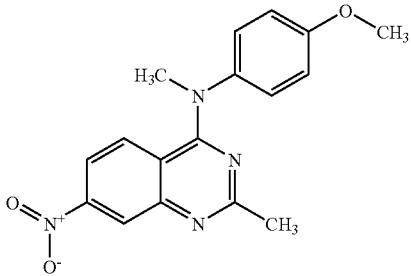

(4-Methoxy-phenyl)-methyl-(2-methyl-7-nitro-quinazolin-4-yl)-amine

The title compound was prepared from 2-amino-4-nitrobenzoic acid by a procedure similar to example 109. $^1$H NMR (CDCl$_3$): 8.56 (d, J=2.4, 1H), 7.68 (dd, J=9.3, 2.7, 1H), 7.08-7.14 (m, 3H), 6.92-6.97 (m, 2H), 3.86 (s, 3H), 3.61 (s, 3H), 2.73 (s, 3H).

Example 113

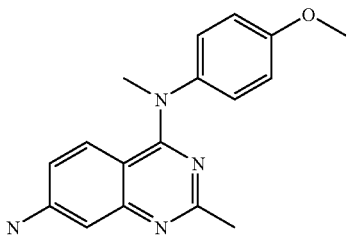

(7-Amino-2-methyl-quinazolin-4-yl)-(4-methoxy-phenyl)-methyl-amine

The title compound was prepared from (4-methoxy-phenyl)-(2-methyl-7-nitro-quinazolin-4-yl)-methyl-amine by a procedure as described in example 101. $^1$H NMR (CDCl$_3$/d$_4$-methanol): 7.11-7.15 (m, 2H), 6.93-6.96 (m, 2H), 6.86 (m, 1H), 6.63 (d, J=9.3, 1H), 6.35 (dd, J=9.3, 2.4, 1H), 3.86 (s, 3H), 3.60 (s, 3H), 2.65 (s, 3H).

Example 114

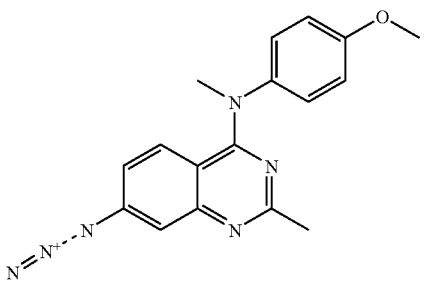

(7-Azido-2-methyl-quinazolin-4-yl)-(4-methoxy-phenyl)-methyl-amine

The title compound was prepared from (7-amino-2-methyl-quinazolin-4-yl)-(4-methoxy-phenyl)-methyl-amine by a procedure as described for example 102. $^1$H NMR (CDCl$_3$): 7.36 (d, J=2.4, 1H), 7.08-7.13 (m, 2H), 6.88-6.96 (m, 3H), 6.59 (dd, J=9.0, 2.4, 1H), 3.84 (s, 3H), 3.57 (s, 3H), 2.69 (s, 3H).

Example 115

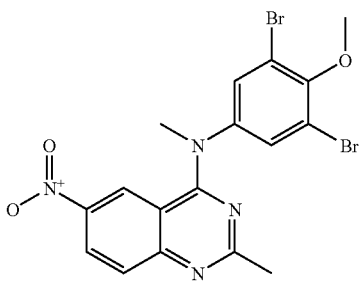

(3,5-Dibromo-4-methoxy-phenyl)-(2-methyl-6-nitro-quinazolin-4-yl)-methyl-amine a) N-(3,5-dibromo-4-hydroxyphenyl)acetamide: To a solution of N-(4-hydroxyphenyl)acetamide (0.50 g, 3.03 mmol) in glacial acetic acid (1 mL), methanol (1 mL) and methylene chloride (5 mL) cooled at 0° C. was added a solution of bromine (1 g, 6.25 mmol) in 1 mL of glacial acetic acid, and the mixture was stirred at 0° C. for 2 h. Additional bromine (1 g, 6.25 mmol) in 1 mL of glacial acetic acid was added and the mixture was stirred for 0.75 h at 0° C. The reaction mixture was diluted with 100 mL of ethyl acetate, washed with 1M Na$_2$SO$_3$ (100 mL), water, half saturated NaHCO$_3$ (100 mL) and saturated NaCl (100 mL). The organic layer was dried over Na$_2$SO$_4$, filtered and concentrated. The crude product was purified by column chromatography (40-45% ethyl acetate/hexanes) on silica gel to give the title compound (0.52 g, 1.61 mmol, 53%). $^1$H NMR (CDCl$_3$): 9.96 (s, broad, 1H), 9.64 (s, broad, 1H), 7.77 (s, 2H), 2.01 (s, 3H).

b) N-(3,5-dibromo-4-methoxyphenyl)-N-methylacetamide: The title compound was prepared from N-(3,5-dibromo-4-hydroxyphenyl)acetamide (510 mg, 1.58 mmol) by a procedure similar to Example 108a (460 mg, 1.36 mmol, 86%). $^1$H NMR (CDCl$_3$): 7.39 (s, 2H), 3.92 (s, 3H), 3.22 (s, 3H), 1.92 (s, 3H).

c) (3,5-dibromo-4-methoxy-phenyl)-methylamine: The title compound was prepared from N-(3,5-dibromo-4-methoxyphenyl)-N-methylacetamide (426 mg, 1.26 mmol) by a procedure similar to Example 108b (323 mg, 1.09 mmol, 87%). $^1$H NMR (CDCl$_3$): 6.72 (s, 2H), 3.80 (s, 3H), 3.67 (s, broad, 1H), 2.78 (d, J=5.1, 3H).

d) (3,5-Dibromo-4-methoxy-phenyl)-(2-methyl-6-nitroquinazolin-4-yl)-methyl-amine. The title compound was prepared from 4-chloro-2-methyl-5-nitroquinazoline and (3,5-dibromo-4-methoxy-phenyl)-methylamine by a procedure similar to example 28 (61% yield). $^1$H NMR (CDCl$_3$): 8.35 (dd, J=9.3, 2.4, 1H), 7.86 (d, J=2.1, 1H), 7.84 (d, J=9.0, 1H), 7.47 (m, 1H), 7.44 (s, 2H), 3.98 (s, 3H), 3.66 (s, 3H), 2.75 (s, 3H).

Example 116

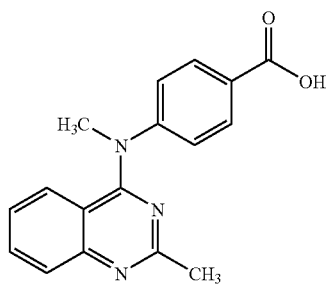

4-(N-Methyl-N-(2-methylquinazolin-4-yl)amino) benzoic Acid

The title compound was prepared from 4-chloro-2-methylquinazoline and 4-(methylamino)benzoic acid by a procedure described for example 1b. $^1$H NMR (CDCl$_3$): 8.42-8.39 (m, 1H), 8.28 (m, 2H), 7.84 (m, 1H), 7.45 (m, 2H), 7.37 (m, 1H), 7.22 (m, 1H), 6.84 (d, J=1H, 8.4), 3.91 (s, 3H), 3.01 (s, 3H).

Example 117

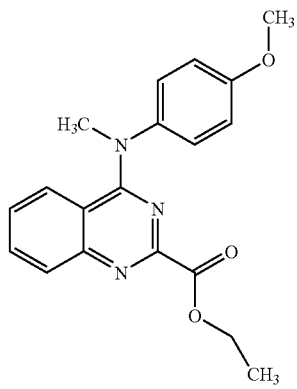

Ethyl 4-(N-(4-Methoxy-phenyl)-N-methylamino) quinazoline-2-carboxylate

The title compound was prepared from ethyl 4-chloroquinazoline-2-carboxylate and (4-methoxy-phenyl)-methylamine by using the procedure described for example 1b. $^1$H NMR (CDCl$_3$): 7.98-8.02 (m, 1H), 7.61 (ddd, J=1H, 8.1, 6.9, 1.5), 7.08-7.17 (m, 3H), 7.01-7.05 (m, 1H), 6.91-6.96 (m, 2H), 4.56 (q, J=2H, 7.2), 3.84 (s, 3H), 3.71 (s, 3H), 1.50 (t, J=2H, 7.2).

Example 118

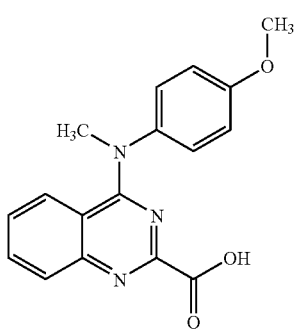

4-(N-(4-Methoxy-phenyl)-N-methylamino)quinazoline-2-carboxylic Acid

A mixture of ethyl 4-(N-(4-methoxy-phenyl)-N-methylamino)quinazoline-2-carboxylate (560 mg, 1.66 mmol) and sodium hydroxide (126 mg, 3.15 mmol) in 25 mL of methanol and water (1:3) was stirred at room temperature for 5 h. The solvents were removed under vaccum, and the residue was dissolved in 50 mL of water and acidified to pH 3. The white precipitate was collected and washed with water and dried (380 mg, 1.23 mmol, 74%). $^1$H NMR (CDCl$_3$): 8.02-8.05 (m, 1H), 7.68 (ddd, J=1H, 8.4, 6.9, 1.5), 7.14-7.20 (m, 3H), 7.02-7.05 (m, 1H), 6.94-6.99 (m, 2H), 3.87 (s, 3H), 3.74 (s, 3H).

Example 119

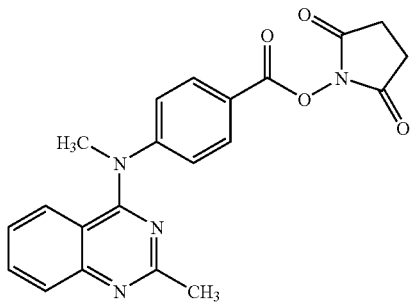

Succinimidyl 4-(N-Methyl-N-(2-methylquinazolin-4-yl)amino)benzoic Acid Ester

A solution of 4-(N-methyl-N-(2-methylquinazolin-4-yl)amino)benzoic acid (250 mg, 0.852 mmol), N-hydroxysuccinimide (75 mg, 0.653 mmol) and dicyclohexylcarbodiimide (135 mg, 0.653 mmol) in 50 mL of methylene chloride was refluxed overnight. The reaction mixture was cooled to room temperature and diluted with 100 mL of ethyl acetate, washed with water (3×100 mL), saturated NaCl and the organic layer was dried over Na$_2$SO$_4$, filtered and concentrated. The crude product was purified by chromatography (75% ethyl acetate/hexanes) on silica gel to give the title compound (170 mg, 0.435 mmol, 51%). $^1$H NMR (CDCl$_3$): 8.06 (m, 2H), 7.95 (m, 1H), 7.71 (m, 1H), 7.11-7.22 (m, 4H), 3.76 (s, 3H), 2.84 (s, 3H), 2.81-2.92 (m, 4H).

Example 120

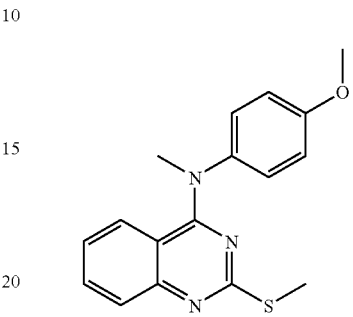

(2-Methylthio-quinazolin-4-yl)-(4-methoxy-phenyl)-methyl-amine

A mixture of (2-chloro-quinazolin-4-yl)-(4-methoxy-phenyl)-methyl-amine (150 mg, 0.5 mmol), sodium methanethiolate (105 mg, 1.5 mmol) in 5 mL of solvent (THF:MeOH:water=3:1:1) was stirred at 70° C. for 4 h. The reaction mixture was diluted with 30 mL of ethyl acetate and it was washed with brine, dried over anhydrous Na$_2$SO$_4$, filtered and concentrated. The crude product was purified by chromatography on silica gel with acetate and hexane (1:5) as eluent, yielding 11 mg of title compound (7%). $^1$H NMR (CDCl$_3$): 7.65 (d, J=8.4 Hz, 1H), 7.51-7.45 (m, 1H), 7.14-7.10 (m, 2H), 6.93-6.89 (m, 4H), 3.84 (s, 3H), 3.58 (s, 3H), 2.67 (s, 3H).

Example 121

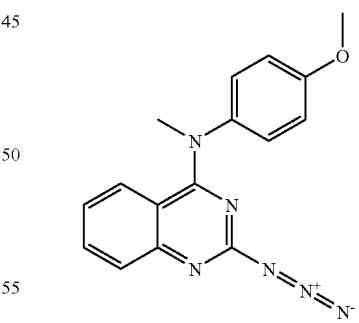

(2-Azido-quinazolin-4-yl)-(4-methoxy-phenyl)-methyl-amine

The title compound was prepared from (2-chloro-quinazolin-4-yl)-(4-methoxy-phenyl)-methyl-amine (150 mg, 0.5 mmol), sodium azide (97.5 mg, 1.5 mmol) in 5 mL of solvent (THF:MeOH:water=0.3:1:1) by a procedure similar to that of example 120 (4%). $^1$H NMR (CDCl$_3$): 8.45 (d, J=8.4 Hz, 1H), 7.78-7.72 (m, 1H), 7.27-7.22 (m, 2H), 7.19-7.14 (m, 2H), 6.95 (d, J=8.7 Hz, 2H), 3.86 (s, 3H), 3.69 (s, 3H).

Example 122

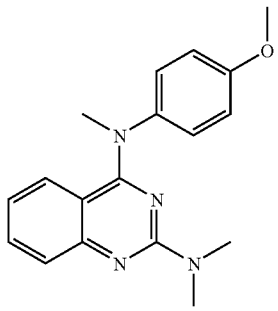

(2-Dimethylamino-quinazolin-4-yl)-(4-methoxy-phenyl)-methyl-amine

A mixture of (2-chloro-quinazolin-4-yl)-(4-methoxy-phenyl)-methyl-amine (150 mg, 0.5 mmol), 2.0 M dimethylamine in methanol (2.0 ml, 4 mmol) in a sealed tube was stirred at 70-80° C. overnight. The mixture was filled and the filtration was concentrated by vacuum. The residue was extracted with ethyl acetate and was washed with brine, dried over anhydrous $Na_2SO_4$, filtered and concentrated. The crude product was purified by chromatography on silica gel with acetate and hexane (1:9) as eluent, yielding 128 mg of title compound (83%). $^1$H NMR ($CDCl_3$): 7.44 (d, J=7.8 Hz, 1H), 7.36-7.30 (m, 1H), 7.11-7.08 (m, 2H), 6.90-6.85 (m, 3H), 6.65-6.59 (m, 1H), 3.82 (s, 3H), 3.51 (s, 3H), 3.30 (s, 6H).

Example 123

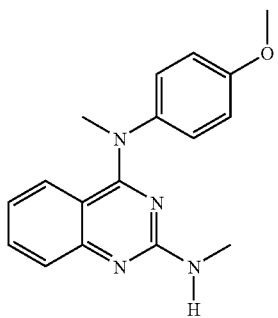

(2-Methylamino-quinazolin-4-yl)-(4-methoxy-phenyl)-methyl-amine

The title compound was prepared from (2-chloro-quinazolin-4-yl)-(4-methoxy-phenyl)-methyl-amine (150 mg, 0.5 mmol), 2.0 M methylamine in THF (2.0 ml, 4 mmol) by a procedure similar to that of example 122 (53.7%). $^1$H NMR ($CDCl_3$): 7.45 (d, J=7.8 Hz, 1H), 7.39-7.33 (m, 1H), 7.11-

7.07 (m, 2H), 6.90-6.87 (m, 3H), 6.69-6.64 (m, 1H), 4.95 (brs, 1H), 3.82 (s, 3H), 3.50 (s, 3H), 3.11 (d, J=5.1 Hz, 3H).

Example 124

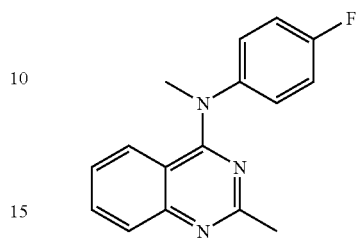

(4-Fluoro-phenyl)-(2-methyl-quinazolin-4-yl)-methyl-amine

The title compound was prepared from 4-chloro-2-methyl-quinazoline (178.6 mg, 1.0 mmol) and (4-fluoro-phenyl)-methyl-amine (125 mg, 2.52 mmol) by a procedure similar to example 28 (46.8%). $^1$H NMR ($CDCl_3$): 7.76 (dd, J=0.9 Hz, J=8.3 Hz, 1H), 7.58-7.52 (m, 1H), 7.16-7.00 (m, 6H), 3.60 (s, 3H), 2.73 (s, 3H), Example 125

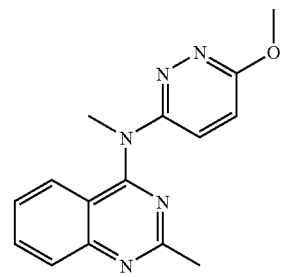

(6-Methoxy-pyridazin-3-yl)-(2-methyl-quinazolin-4-yl)-methyl-amine a) 3-Amino-6-methoxy-pyridazine: A mixture of 3-amino-6-chloro-pyridazine (500 mg, 3.86 mmol), sodium methoxide (1.0 ml, 4.4 mmol, 25% w/w) and copper powder (331 mg, 5.17 mmol) in methanol (3 ml) was heated in a sealed tube at 160° C. for 24 h. After cooling, the reaction mixture was diluted with methanol (10 ml) and filtered, and the filtrate was concentrated by vacuum. The residue was purified by chromatography on silica gel with acetate and hexane (1:2) as eluent, yielding 413 mg of title compound (85.7%). $^1$H NMR ($CDCl_3$): 6.81 (m, 2H), 4.62 (brs, 2H), 4.00 (s, 3H).

b) (6-Methoxy-pyridazin-3-yl)-methyl-amine: To a solution of 3-amino-6-methoxy-pyridazine (90 mg, 0.72 mmol) in THF (2 ml) at 0° C. was added sodium hydride (44 mg, 1.08 mmol, 60% oil dispersion), followed by methyl iodide (0.07 ml, 1.08 mmol). The mixture was stirred at 0° C. for 1 h, then allowed to warm to room temperature and stirred for another 2 h. The reaction mixture was diluted with EtOAc (10 ml), washed with saturated $NaHCO_3$ aq., brine, dried over $Na_2SO_4$, filtered and concentrated by vacuum. The residue was purified by chromatography on silica gel with acetate and hexane (1:2 to 1:1) as eluent, yielding 6.0 mg of title compound (6.0%). $^1$H NMR (CDCl$_3$): 6.79 (d, J=9.0 Hz, 1H), 6.68 (d, J=10.5 Hz, 1H), 4.29 (brs, 1H), 4.01 (s, 3H), 3.01 (d, J=4.8 Hz, 3H).

c) (6-Methoxy-pyridazin-3-yl)-(2-methyl-quinazolin-4-yl)-methyl-amine: To a solution of (6-methoxy-pyridazin-3-yl)-methyl-amine (10 mg, 0.072 mmol) in DMF (1 ml) at 0° C. was added sodium hydride (4.3 mg, 0.11 mmol, 60% oil dispersion), followed by 4-chloro-2-methyl-quinazoline (12.9 mg, 0.072 mmol). The mixture was stirred at 0° C. for 1 h, then allowed to warm to room temperature and stirred for another 2 h. The reaction mixture was diluted with EtOAc (10 ml), washed with saturated NaHCO$_3$ aq., brine, dried over Na$_2$SO$_4$, filtered and concentrated by vacuum. The residue was purified by chromatography on silica gel with acetate and hexane (1:2 to 1:1) as eluent, yielding 2.0 mg of title compound (10%). $^1$H NMR (CDCl$_3$): 7.90 (d, J=8.1 Hz, 1H), 7.73 (t, J=8.4 Hz, 1H), 7.48 (d, J=8.7 Hz, 1H), 7.34-7.31 (m, 1H), 6.94 (d, J=9.3 Hz, 1H), 6.81 (d, J=9.6 Hz, 1H), 4.12 (s, 3H), 3.85 (s, 3H), 2.78 (s, 3H).

Example 126

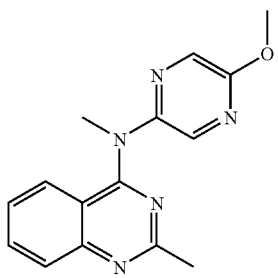

(5-Methoxy-pyrazin-2-yl)-(2-methyl-quinazolin-4-yl)-methyl-amine a) 2-Amino-5-methoxy-pyrazine: The title compound was prepared from 2-amino-5-bromo-pyrazine (500 mg, 2.87 mmol) and sodium methoxide (1.0 ml, 4.4 mmol, 25% w/w) by a procedure similar to example 125a (29%). $^1$H NMR (CDCl$_3$): 7.76 (s, 1H), 7.56 (s, 1H), 4.20 (brs, 2H), 3.88 (s, 3H).

b) (5-Methoxy-pyrazin-2-yl)-(2-methyl-quinazolin-4-yl)-amine: The title compound was prepared from 2-amino-5-methoxy-pyrazine (105 mg, 0.84 mmol) and 4-chloro-2-methyl-quinazoline (150 mg, 0.84 mmol) by a procedure similar to example 125c, yielding 106 mg of the title product.

c) (5-Methoxy-pyrazin-2-yl)-(2-methyl-quinazolin-4-yl)-methyl-amine: The title compound was prepared from (5-methoxy-pyrazin-2-yl)-(2-methyl-quinazolin-4-yl)-amine (106 mg, 0.40 mmol) by a procedure similar to example 36 (56%). $^1$H NMR (CDCl$_3$): 8.06 (d, J=1.2 Hz, 1H), 7.85-7.81 (m, 1H), 7.74 (d, J=1.5 Hz, 1H), 7.65-7.60 (m, 1H), 7.17-7.05 (m, 2H), 3.94 (s, 3H), 3.70 (s, 3H), 2.78 (s, 3H).

Example 127

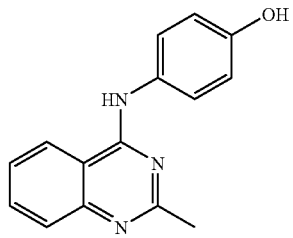

(4-hydroxy-phenyl)-(2-methyl-quinazolin-4-yl)-amine

The title compound was prepared from 4-chloro-2-methyl-quinazoline (818 mg, 4.58 mmol), 4-hydroxy-aniline (500 mg, 4.58 mmol) by a procedure similar to example 1b to give 498 mg (43%) of off white solids. $^1$H NMR (DMSO-d$_6$): 9.51 (s, 1H), 9.34 (s, 1H), 8.44 (d, J=7.8 Hz, 1H), 7.77 (t, J=8.4 Hz, 1H), 7.67-7.48 (m, 4H), 6.79 (d, J=7.8 Hz, 2H), 2.45 (s, 3H).

Example 128

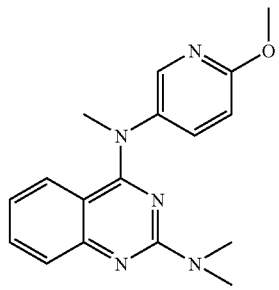

(2-Dimethylamino-quinazolin-4-yl)-(6-methoxy-pyridin-3-yl)-methyl-amine

The title compound was prepared from (2-chloro-quinazolin-4-yl)-(6-methoxy-pyridin-3-yl)-methyl-amine (69 mg, 0.23 mmol) and 2.0 M dimethylamine in methanol (4 ml, 8 mmol) by a procedure similar to example 122 (51%). $^1$H NMR (CDCl$_3$): 8.02 (d, J=2.7 Hz, 1H), 7.47 (d, J=8.1 Hz, 1H), 7.38-7.34 (m, 2H), 6.93 (d, J=8.4 Hz, 1H), 6.75-6.66 (m, 2H), 3.94 (s, 3H), 3.51 (s, 3H), 3.30 (s, 6H).

Example 129

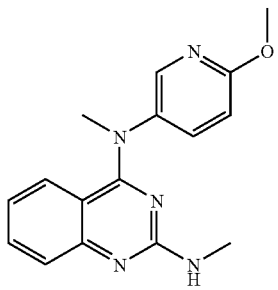

(2-Methylamino-quinazolin-4-yl)-(6-methoxy-pyridin-3-yl)-methyl-amine

The title compound was prepared from (2-chloro-quinazolin-4-yl)-(6-methoxy-pyridin-3-yl)-methyl-amine (69 mg, 0.23 mmol) and 2.0 M methylamine in THF (4 ml, 8 mmol) by a procedure similar to example 122 to give 20 mg (30%) of yellow solids. $^1$H NMR (CDCl$_3$): 8.02-8.01 (m, 1H), 7.48 (d, J=8.1 Hz, 1H), 7.42-7.34 (m, 2H), 6.97-6.94 (m, 1H), 6.76-6.70 (m, 2H), 5.01 (brs, 1H), 3.95 (s, 3H), 3.50 (s, 3H), 3.12 (d, J=5.1 Hz, 3H).

Example 130 and 131

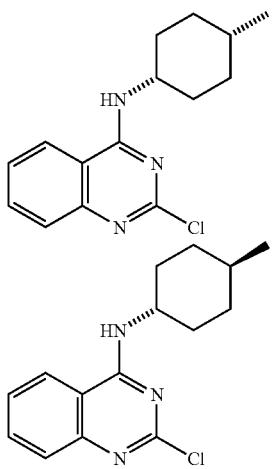

(2-Chloro-quinazolin-4-yl)-(cis-4-methylcyclohexyl)-amine and (2-chloro-quinazolin-4-yl)-(trans-4-methylcyclohexyl)-amine The title compounds were prepared from 2,4-dichloroquinazoline and 4-methylcyclohexyl-amine by a procedure similar to example 28. The isomers were separated by chromatography (10-12% ethyl acetate/hexane). (2-Chloroquinazolin-4-yl)-(cis-4-methylcyclohexyl)-amine. $^1$H NMR (CDCl$_3$): 7.66-7.79 (m, 3H), 7.46 (ddd, J=1.8, 6.3, 8.4, 1H), 5.96 (d, broad, J=6.6, 1H), 4.49 (m, 1H), 1.68-1.87 (m, 7H), 1.25 (m, 2H), 0.99 (d, J=6.6, 3H). (2-Chloro-quinazolin-4-yl)-(trans-4-methylcyclohexyl)-amine. $^1$H NMR (CDCl$_3$): 7.67-7.78 (m, 3H), 7.43 (ddd, J=1.8, 6.6, 8.4, 1H), 5.78 (d, broad, J=7.5, 1H), 4.22 (m, 1H), 2.15-2.21 (m, 2H), 1.76-1.82 (m, 2H), 1.11-1.46 (m, 5H), 0.94 (d, J=6.6, 3H).

Example 132

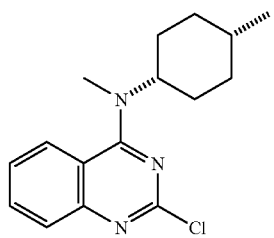

(2-Chloro-quinazolin-4-yl)-(cis-4-methylcyclohexyl)-methyl-amine

The title compound was prepared from (2-chloro-quinazolin-4-yl)-(cis-4-methylcyclohexyl)-amine by a procedure similar to example 36. $^1$H NMR (CDCl$_3$): 7.88 (m, 1H), 7.75-7.78 (m, 1H), 7.68 (ddd, J=1.5, 6.9, 8.4, 1H), 7.37 (ddd, J=1.5, 6.9, 8.4, 1H), 4.36 (m, 1H), 3.24 (s, 3H), 1.86-2.00 (m, 3H), 1.61-1.75 (m, 6H), 1.05 (d, J=7.2, 3H).

Example 133

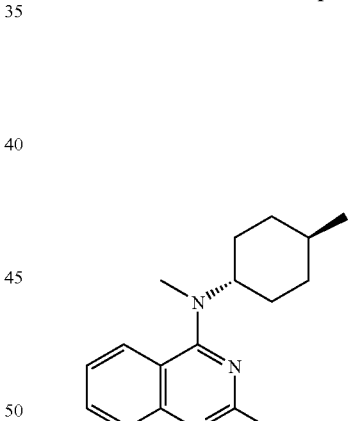

(2-Chloro-quinazolin-4-yl)-(trans-4-methylcyclohexyl)-methyl-amine

The title compound was prepared from (2-chloro-quinazolin-4-yl)-(trans-4-methylcyclohexyl)-amine by a procedure similar to example 36. $^1$H NMR (CDCl$_3$): 7.89 (m, 1H), 7.74-7.78 (m, 1H), 7.68 (ddd, 0.9, 6.6, 8.1, 1H), 7.37 (ddd, J=1.2, 6.6, 8.1, 1H), 4.38 (m, 1H), 3.21 (s, 3H), 1.67-1.95 (m, 6H), 1.39 (m, 1H), 1.4-1.25 (m, 2H), 0.93 (d, J=6.3, 3H).

Example 134

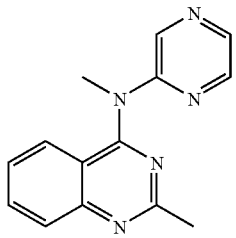

(2-Methyl-quinazolin-4-yl)-(pyrazin-2-yl)-methyl-amine

The title compound was prepared from 4-chloro-2-methyl-quinazoline and 2-amino-pyrazine in two steps by a procedure similar to examples 100 and 36. $^1$H NMR (CDCl$_3$): 8.27 (dd, J=1.5, 2.4, 1H), 8.13-8.14 (m, 2H), 7.95 (d, J=8.4, 1H), 7.77 (ddd, J=1.5, 6.6, 8.4, 1H), 7.45-7.48 (m, 1H), 7.34 (ddd, J=0.9, 6.6, 8.1, 1H), 3.78 (s, 3H), 2.83 (s, 3H).

Example 135

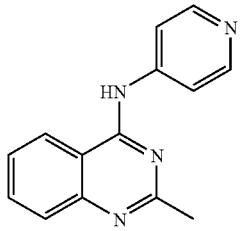

(2-Methyl-quinazolin-4-yl)-(pyridin-4-yl)-amine

The title compound was prepared from 4-chloro-2-methyl-quinazoline and 4-amino-pyridine by a procedure similar to examples 100. $^1$H NMR (CDCl$_3$): 8.58 (m, 1H), 7.79-7.93 (m, 5H), 7.70 (s, broad, 1H), 7.55 (ddd, J=1.2, 6.9, 8.1, 1H), 2.79 (s, 3H).

Example 136

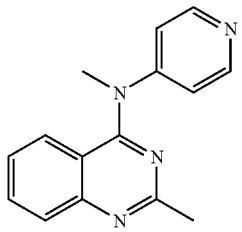

(2-Methyl-quinazolin-4-yl)-(pyridin-4-yl)-methyl-amine

The title compound was prepared from 4-chloro-2-methyl-quinazoline (0.178 g, 2.13 mmol) and (pyridin-4-yl)-methyl-amine (0.108 g, 1.84 mmol) by a procedure similar to examples 125c (0.224 g, 49%). $^1$H NMR (CDCl$_3$): 8.39 (m, 2H), 7.91 (d, J=8.4, 1H), 7.73 (ddd, J=1.2, 6.6, 8.4, 1H), 7.41 (m, 1H), 7.23-7.29 (m, 1H), 6.79-6.82 (m, 2H), 3.70 (s, 3H), 2.83 (s, 3H).

Example 137

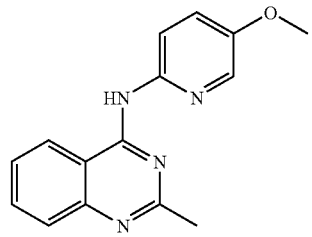

(5-Methoxy-pyridin-2-yl)-(2-methyl-quinazolin-4-yl)-amine a) 2-Amino-5-methoxy-pyridine. A mixture of 2-amino-5-iodo-pyridine (1 g, 4.54 mmol) in 20 mL of absolute methanol with 400 mg of copper powder and sodium methoxide (6 mmol) was heated at 160° C. overnight in a seal tube. The reaction mixture was cooled to room temperature, diluted with 80 mL of methanol and filtered through a pad of celite. The filtrate was concentrated and the residue was purified by chromatography (80% ethyl acetate/hexane) to give the title compound (174 mg, 31%). $^1$H NMR (CDCl$_3$): 7.78 (d, J=2.7, 1H), 7.09 (dd, J=3.0, 9.0, 1H), 6.48 (d, J=9.0, 1H), 3.78 (s, 3H).

b) (5-Methoxy-pyridin-2-yl)-(2-methyl-quinazolin-4-yl)-amine: The title compound was prepared from 4-chloro-2-methyl-quinazoline and 2-amino-5-methoxy-pyridine by a procedure similar to example 28.

Example 138

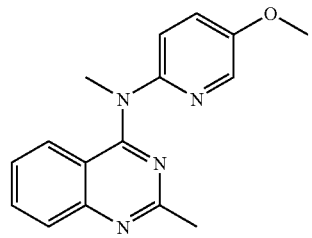

(5-Methoxy-pyridin-2-yl)-(2-methyl-quinazolin-4-yl)-methyl-amine

The title compound was prepared from (5-methoxy-pyridin-2-yl)-(2-methyl-quinazolin-4-yl)-amine by a procedure similar to example 36. $^1$H NMR (CDCl$_3$): 8.31 (d, 3.3, 1H), 7.80 (d, J=8.4, 1H), 7.58 (ddd, J=1.5, 6.6, 8.4, 1H), 7.13 (dd, J=3.3, 9.0, 1H), 6.99-7.10 (m, 2H), 6.82 (d, J=9.0, 1H), 3.87 (s, 3H), 3.70 (s, 3H), 2.76 (s, 3H).

Example 139

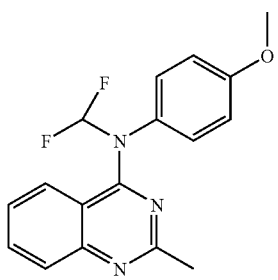

Difluoromethyl-(4-methoxy-phenyl)-(2-methyl-quinazolin-4-yl)-amine

A solution of (4-methoxy-phenyl)-(2-methyl-quinazolin-4-yl)-amine (100 mg, 0.35 mmol) in 3 mL of dimethylformamide in a 15 mL high pressure reaction vessel was cooled to −78° C. Diflurochloromethane (about 0.8 mL) was condensed into the solution, then cesium carbonate (160 mg, 0.49 mmol) was added. The reaction vessel was capped and heated at 80° C. overnight. The reaction mixture was cooled to room temperature and cooled to −78° C. and the seal tube was uncapped, warm to room temperature and allowed to stand for 2 h. The reaction mixture was diluted with 50 mL of ethyl acetate and the organic layer was washed with water (50 mL×3), followed by saturated aqueous NaCl. The organic layer was dried over anhydrous sodium sulfate, filtered and concentrated. The residue was purified by chromatography (30% ethyl acetate/hexane, 6 drops triethylamine/500 mL of solvent) to give the title compound (35 mg, 0.111 mmol, 32%). $^1$H NMR (CDCl$_3$): 8.35 (dd, J=1.8, 8.1, 1H), 7.35-(m, 3H), 7.25 (t, J=72.1, 1H), 7.21-7.25 (m, 2H), 6.86-6.91 (m, 2H), 3.82 (s, 3H), 2.48 (s, 3H).

Example 140

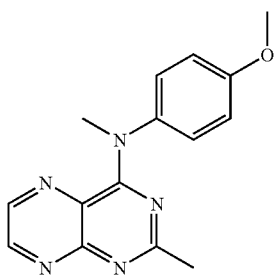

(4-Methoxy-phenyl)-(2-methyl-pteridin-4-yl)-methyl-amine a) 4-Chloro-2-methyl-pteridine. A mixture of 6-chloro-2-methyl-pyrimidine-4,5-diamine (37 mg, 0.233 mmol) and 1,4-dioxane-2,3-diol (32 mg, 0.266 mmol) in 0.8 mL of absolute ethanol was stirred at room temperature for 2 h. The reaction mixture was evaporated to dryness and the residue was purified by column chromatography (50% ethyl acetate/hexane) to give the title compound (41 mg, 0.227 mmol, 97%). $^1$H NMR (CDCl$_3$): 9.24 (d, J=1.8, 1H), 9.05 (d, J=1.5, 1H), 2.99 (s, 3H).

b) (4-Methoxy-phenyl)-(2-methyl-pteridin-4-yl)-methyl-amine. The title compound was prepared from 4-chloro-2-methyl-pteridine and (4-methoxy-phenyl)-methyl-amine by a procedure similar to example 28 (67%). $^1$H NMR (CDCl$_3$): 8.73 (d, J=1.8, 1H), 8.22 (d, J=1.8, 1H), 7.07-7.10 (m, 2H), 6.86-6.92 (m, 2H), 3.85 (s, 3H), 3.69 (s, 3H), 2.73 (s, 3H).

Example 141

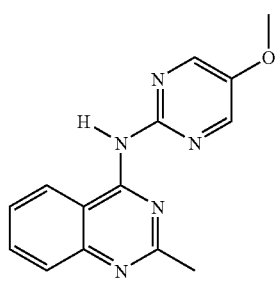

(5-Methoxy-pyrimidin-2-yl)-(2-methyl-quinazolin-4-yl)-amine a) 2-Amino-5-methoxy-pyrimidine: The title compound was prepared from 2-amino-5-iodo-pyrimidine (2.0 g, 9.0 mmol) and sodium methoxide (10 ml, 44 mmol, 25% w/w) by a procedure similar to example 125a (21%). $^1$H NMR (CDCl$_3$): 8.05 (s, 2H), 4.78 (brs, 2H), 3.81 (s, 3H).

b) (5-Methoxy-pyrimidin-2-yl)-(2-methyl-quinazolin-4-yl)-amine: The title compound was prepared from 2-amino-5-methoxy-pyrimidine (240 mg, 1.92 mmol) and 4-chloro-2-methyl-quinazoline (343 mg, 1.92 mmol) by a procedure similar to example 125c, yielding 283 mg of the title product (55%). $^1$H NMR (CDCl$_3$): 8.69 (dd, J=1.5 Hz, J=8.1 Hz, 1H), 8.43 (s, 2H), 7.73-7.67 (m, 1H), 7.60 (d, J=7.2 Hz, 1H), 7.49-7.43 (m, 1H), 3.95 (s, 3H), 2.58 (s, 3H).

Example 142

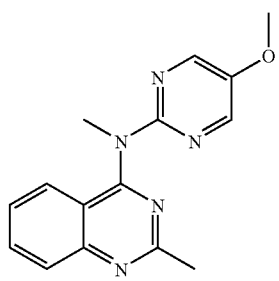

(5-Methoxy-pyrimidin-2-yl)-(2-methyl-quinazolin-4-yl)-methyl-amine

The title compound was prepared from (5-methoxy-pyrimidin-2-yl)-(2-methyl-quinazolin-4-yl)-amine (0.170 mg, 0.64 mmol) by a procedure similar to example 36 (50%). $^1$H NMR (CDCl$_3$): 8.12 (s, 2H), 7.91 (d, J=8.4 Hz, 1H), 7.74-7.69 (m, 1H), 7.38-7.34 (m, 1H), 7.30-7.24 (m, 1H), 3.85 (s, 3H), 3.78 (s, 3H), 2.83 (s, 3H).

Example 143

Identification of (2-Chloro-quinazolin-4-yl)-(4-methoxy-phenyl)-methyl-amine and Analogs as Caspase Cascade Activators and Inducers of Apoptosis in Solid Tumor Cells Human breast cancer cell lines T-47D and DLD-1 were grown according to media component mixtures designated by American Type Culture Collection+10% FCS (Invitrogen Corporation), in a 5% CO$_2$-95% humidity incubator at 37° C. T-47D and DLD-1 cells were maintained at a cell density between 50 and 80% confluency at a cell density of 0.1 to 0.6×10$^6$ cells/mL. Cells were harvested at 600×g and resuspended at 0.65×10$^6$ cells/mL into appropriate media+10% FCS. An aliquot of 22.5 µL of cells was added to a well of a 384-well microtiter plate containing 2.5 µL of a 10% DMSO in RPMI-1640 media solution containing 0.16 to 100 µM of (2-chloro-quinazolin-4-yl)-(4-methoxy-phenyl)-methyl-amine or other test compound (0.016 to 10 µM final). An aliquot of 22.5 µL of cells was added to a well of a 384-well microtiter plate containing 2.5 µL of a 10% DMSO in RPMI-1640 media solution without test compound as the control sample. The samples were mixed by agitation and then incubated at 37° C. for 48 h in a 5% CO$_2$-95% humidity incubator. After incubation, the samples were removed from the incubator and 25 mL of a solution containing 14 µM of N-(Ac-DEVD)-N'-ethoxycarbonyl-R110 fluorogenic substrate (Cytovia, Inc.; WO99/18856), 20% sucrose (Sigma), 20 mM DTT (Sigma), 200 mM NaCl (Sigma), 40 mM Na PIPES buffer pH 7.2 (Sigma), and 500 µg/mL lysolecithin (Calbiochem) was added. The samples were mixed by agitation and incubated at room temperature. Using a fluorescent plate reader (Model SPECTRAfluor Plus, Tecan), an initial reading (T=0) was made approximately 1-2 min after addition of the substrate solution, employing excitation at 485 nm and emission at 530 nm, to determine the background fluorescence of the control sample. After the 3 h incubation, the samples were read for fluorescence as above (T=3 h).

Calculation:
The Relative Fluorescence Unit values (RFU) were used to calculate the sample readings as follows:

$RFU_{(T=3h)}$ − Control $RFU_{(T=0)}$ = Net $RFU_{(T=3h)}$

The activity of caspase cascade activation was determined by the ratio of the net RFU value for (2-chloro-quinazolin-4-yl)-(4-methoxy-phenyl)-methyl-amine or other test compounds to that of control samples. The EC$_{50}$ (nM) was determined by a sigmoidal dose-response calculation (Prism 3.0, GraphPad Software Inc.).

The caspase activity (Ratio) and potency (EC$_{50}$) are summarized in Table I:

TABLE I

| | Caspase Activity and Potency | | | |
|---|---|---|---|---|
| | T-47D (24 hr) | | T-47D (48 hr) | |
| Exa. Cmpd. | Ratio | EC$_{50}$ (nM) | Ratio | EC$_{50}$ (nM) |
| 1 | 8.7 | 2 | NA | NA |
| 2 | 6.7 | 31 | NA | NA |
| 3 | 8.1 | 79 | NA | NA |
| 4 | 7.1 | 872 | NA | NA |
| 5 | 10.3 | 24 | NA | NA |
| 6 | 6.7 | 219 | NA | NA |
| 7 | 1.2 | >10000 | 1.0 | >10000 |
| 8 | 1.0 | >10000 | NA | NA |
| 9 | NA | NA | 1.8 | >10000 |
| 10 | NA | NA | 12.8 | 48 |
| 11 | 9.0 | 8 | 12.5 | 10 |
| 12 | 5.3 | 8 | 12.8 | 9 |
| 13 | 8.9 | 260 | NA | NA |
| 14 | 9.7 | 1345 | 12.3 | 1326 |
| 15 | 5.7 | 56 | 11.5 | 89 |
| 16 | 7.6 | 296 | NA | NA |
| 17 | 3.0 | 7945 | NA | NA |
| 18 | 1.0 | >10000 | 1.0 | >10000 |
| 19 | 1.0 | >10000 | 1.0 | >10000 |
| 20 | 13.1 | 161 | NA | NA |
| 21 | 1.0 | >10000 | 1.0 | >10000 |
| 22 | 1.0 | >10000 | 1.0 | >10000 |
| 23 | 1.0 | >10000 | 1.0 | >10000 |
| 24 | 1.0 | >10000 | 2.4 | 9460 |
| 25 | NA | NA | 5.8 | 42 |
| 26 | NA | NA | 15.7 | 178 |
| 27 | NA | NA | 1.0 | >10000 |
| 28 | 1.0 | >10000 | 1.0 | >10000 |
| 29 | NA | NA | 1.0 | >10000 |
| 30 | NA | NA | 1.0 | >10000 |
| 31 | 8.0 | 317 | 14.7 | 563 |
| 32 | NA | NA | 1.0 | >10000 |
| 33 | NA | NA | 1.0 | >10000 |
| 34 | 7.5 | 7 | NA | NA |
| 35 | 7.2 | 141 | NA | NA |
| 36 | 6.7 | 6 | NA | NA |
| 37 | 3.3 | 2693 | NA | NA |
| 38 | 3.4 | 2933 | NA | NA |
| 39 | 4.5 | 693 | NA | NA |
| 40 | NA | NA | 6.1 | 47 |
| 41 | NA | NA | 12.4 | 20 |
| 42 | 8.6 | 282 | 14.6 | 265 |
| 43 | NA | NA | 14.7 | 34 |
| 44 | NA | NA | 14.3 | 501 |
| 45 | NA | NA | 1.0 | >10000 |
| 46 | 12.8 | 2184 | 9.4 | 2272 |
| 47 | NA | NA | 11.5 | 187 |
| 48 | NA | NA | 12.5 | 137 |
| 49 | 7.5 | 29 | 13.4 | 22 |
| 50 | NA | NA | 1.0 | >10000 |
| 51 | NA | NA | 0.9 | >10000 |
| 52 | NA | NA | 10.8 | 6 |
| 53 | 8.3 | 5 | 11.4 | 11 |
| 54 | NA | NA | 12.5 | 46 |
| 55 | NA | NA | 9.0 | 1 |
| 56 | NA | NA | 4.9 | 5 |
| 57 | NA | NA | 6.2 | 432 |
| 58 | NA | NA | 10.8 | 1 |
| 59 | NA | NA | 7.1 | 11 |
| 60 | NA | NA | 6.5 | 13 |
| 61 | NA | NA | 9.2 | 4046 |
| 62 | NA | NA | 12.7 | 316 |
| 63 | NA | NA | 10.9 | 427 |
| 64 | NA | NA | 1 | >10000 |
| 65 | NA | NA | 13.7 | 599 |
| 66 | 7.2 | 18 | 12.5 | 22 |
| 67 | NA | NA | 12.5 | 38 |
| 68 | NA | NA | 13.1 | 4 |
| 69 | NA | NA | 1 | >1000 |
| 70 | NA | NA | 11.3 | 42 |
| 71 | NA | NA | 6.9 | 2265 |
| 72 | 9.0 | 2 | 7.4 | 2 |
| 73 | 6.2 | 679 | 5.7 | 543 |
| 74 | 6.6 | 15 | 5.3 | 36 |
| 75 | 1.5 | >10000 | NA | NA |

TABLE I-continued

Caspase Activity and Potency

| Exa. Cmpd. | T-47D (24 hr) Ratio | T-47D (24 hr) EC$_{50}$ (nM) | T-47D (48 hr) Ratio | T-47D (48 hr) EC$_{50}$ (nM) |
|---|---|---|---|---|
| 76 | 5.6 | 7 | 14.1 | 8 |
| 77 | 5.7 | 700 | 12.3 | 2107 |
| 78 | 0.6 | >10000 | NA | NA |
| 79 | 0.7 | >10000 | NA | NA |
| 80 | 8.3 | 5752 | NA | NA |
| 81 | 1.9 | >10000 | NA | NA |
| 82 | 1.0 | >10000 | NA | NA |
| 83 | NA | NA | 10.8 | 168 |
| 84 | 6.7 | 8 | NA | NA |
| 85 | 7.6 | 2 | NA | NA |
| 86 | 6.2 | 41 | NA | NA |
| 87 | 6.3 | 25 | NA | NA |
| 88 | 7.6 | 556 | NA | NA |
| 89 | NA | NA | 7.8 | 24 |
| 90 | 10.6 | 2 | NA | NA |
| 91 | 8.3 | 4 | NA | NA |
| 92 | 10.1 | 16 | NA | NA |
| 93 | 11.3 | 65 | NA | NA |
| 94 | NA | NA | 1.0 | >10000 |
| 95 | 1.0 | >10000 | NA | NA |
| 96 | 1.0 | >10000 | NA | NA |
| 97 | NA | NA | 9.0 | 5 |
| 98 | 5.4 | 14 | 12.9 | 8 |
| 99 | 6.9 | 4 | NA | NA |
| 100 | 8.9 | 474 | NA | NA |
| 101 | 9.5 | 175 | NA | NA |
| 102 | 8.8 | 5 | 11.3 | 16 |
| 103 | 9.3 | 552 | NA | NA |
| 104 | 8.6 | 134 | NA | NA |
| 105 | 8.5 | 2 | NA | NA |
| 106 | 1.1 | >10000 | NA | NA |
| 107 | 5.2 | 5 | NA | NA |
| 108 | 4.8 | 1 | NA | NA |
| 109 | 4.6 | 274 | NA | NA |
| 110 | 8.8 | 7 | NA | NA |
| 111 | 9.4 | 32 | NA | NA |
| 112 | 1.0 | >10000 | NA | NA |
| 113 | 3.7 | 735 | NA | NA |
| 114 | 7.2 | 130 | NA | NA |
| 115 | 1.0 | >10000 | NA | NA |
| 116 | 1.0 | >10000 | NA | NA |
| 117 | 7.4 | 134 | NA | NA |
| 118 | 1.0 | >10000 | NA | NA |
| 119 | 11.8 | 4288 | NA | NA |
| 120 | 5.2 | 8 | NA | NA |
| 121 | 8.8 | 30 | NA | NA |
| 122 | 8.2 | 16 | NA | NA |
| 123 | 8.2 | 8 | NA | NA |
| 124 | 5.2 | 408 | NA | NA |
| 125 | 8.3 | 385 | NA | NA |
| 126 | 7.6 | 55 | NA | NA |
| 127 | 1.2 | >10000 | NA | NA |
| 128 | 10 | 58 | NA | NA |
| 129 | 10 | 27 | NA | NA |
| 130 | 1.2 | >10000 | NA | NA |
| 131 | 1.2 | >10000 | NA | NA |
| 132 | 1.2 | >10000 | NA | NA |
| 133 | 1.2 | >10000 | NA | NA |
| 134 | 1.2 | >10000 | NA | NA |
| 135 | 1.2 | >10000 | NA | NA |
| 136 | 1.2 | >10000 | NA | NA |
| 137 | 1.2 | >10000 | NA | NA |
| 138 | 5.0 | 15 | NA | NA |
| 139 | 5.6 | 4662 | NA | NA |
| 140 | 7.0 | 27 | NA | NA |
| 141 | 1.2 | >10000 | NA | NA |
| 142 | 7.5 | 141 | NA | NA |

NA = Not available

The following substituted N'-methyl-N'-(quinazolin-4-yl)benzohydrazides and analogs also are identified as potent caspase cascade activators and inducers of apoptosis and are thus useful in treating the various diseases and disorders discussed above.

| Compound | T-47D (24 hr) Ratio | T-47D (24 hr) EC$_{50}$ (nM) | T-47D (48 hr) Ratio | T-47D (48 hr) EC$_{50}$ (nM) |
|---|---|---|---|---|
| 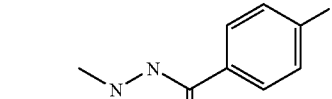 4-chloro-N'-methyl-N'-(2-(methylthio)quinazolin-4-yl)benzohydrazide | NA | NA | 14.4 | 138 |
| 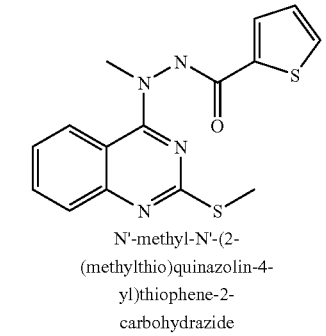 N'-methyl-N'-(2-(methylthio)quinazolin-4-yl)thiophene-2-carbohydrazide | NA | NA | 10.1 | 737 |
| 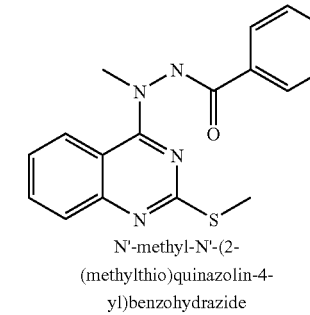 N'-methyl-N'-(2-(methylthio)quinazolin-4-yl)benzohydrazide | NA | NA | 14.7 | 149 |
| 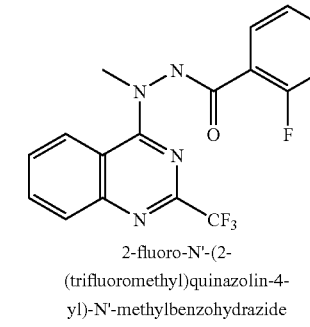 2-fluoro-N'-(2-(trifluoromethyl)quinazolin-4-yl)-N'-methylbenzohydrazide | NA | NA | 13.7 | 184 |

-continued

| Compound | T-47D (24 hr) Ratio | T-47D (24 hr) EC$_{50}$ (nM) | T-47D (48 hr) Ratio | T-47D (48 hr) EC$_{50}$ (nM) |
|---|---|---|---|---|
| 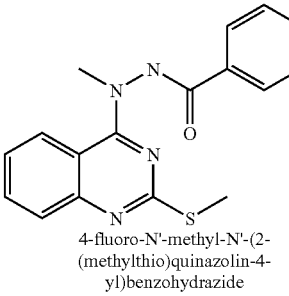<br>4-fluoro-N'-methyl-N'-(2-(methylthio)quinazolin-4-yl)benzohydrazide | NA | NA | 13.8 | 290 |
| 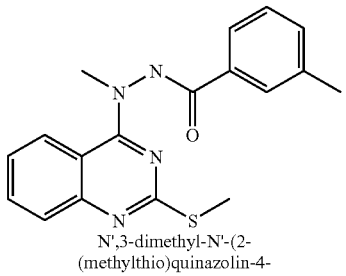<br>N',3-dimethyl-N'-(2-(methylthio)quinazolin-4-yl)benzohydrazide | NA | NA | 12.7 | 46 |
| 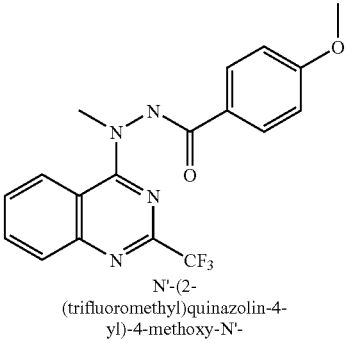<br>N'-(2-(trifluoromethyl)quinazolin-4-yl)-4-methoxy-N'-methylbenzohydrazide | NA | NA | 13.1 | 39 |

Thus, (2-chloro-quinazolin-4-yl)-(4-methoxy-phenyl)-methyl-amine (Example 1) and analogs are identified as potent caspase cascade activators and inducers of apoptosis and are thus useful in treating the various diseases and disorders discussed above.

Example 144

Identification of (2-Chloro-quinazolin-4-yl)-(4-methoxy-phenyl)-methyl-amine and Analogs as Antineoplastic Compounds that Inhibit Cell Proliferation ($GI_{50}$)

T-47D, DLD, H1299, MX-1 and SW620 cells were grown and harvested as in Example 143. An aliquot of 90 μL of cells ($4.4 \times 10^4$ cells/mL) was added to a well of a 96-well microtiter plate containing 5 μL of a 10% DMSO in RPMI-1640 media solution containing 10 nM to 100 μM of (2-chloro-quinazolin-4-yl)-(4-methoxy-phenyl)-methyl-amine (1 nM to 10 μM final). An aliquot of 45 μL of cells was added to a well of a 96-well microtiter plate containing 5 μL of a 10% DMSO in RPMI-1640 media solution without compound as the control sample for maximal cell proliferation ($L_{Max}$). The samples were mixed by agitation and then incubated at 37° C. for 48 h in a 5% $CO_2$-95% humidity incubator. After incubation, the samples were removed from the incubator and 25 μL of CellTiter-Glo™ reagent (Promega) was added. The samples were mixed by agitation and incubated at room temperature for 10-15 min. Plates were then read using a luminescent plate reader (Model SPECTRAfluor Plus, Tecan) to give $L_{test}$ values.

Baseline for $GI_{50}$ (dose for 50% inhibition of cell proliferation) of initial cell numbers was determined by adding an aliquot of 45 μL of cells or 45 μL of media, respectively, to wells of a 96-well microtiter plate containing 5 μL of a 10% DMSO in RPMI-1640 media solution. The samples were mixed by agitation and then incubated at 37° C. for 0.5 h in a 5% $CO_2$-95% humidity incubator. After incubation, the samples were removed from the incubator and 25 μL of CellTiter-Glo™ reagent (Promega) was added. The samples were mixed by agitation and incubated at 37° C. for 10-15 min at room temperature in a 5% $CO_2$-95% humidity incubator. Fluorescence was read as above, ($L_{Start}$) defining luminescence for initial cell number used as baseline in $GI_{50}$ determinations.

Calculation:

$GI_{50}$(dose for 50% inhibition of cell proliferation) is the concentration where $[(L_{Test}-L_{Start})/(L_{Max}-L_{Start})]=0.5$.

The $GI_{50}$ (nM) are summarized in Table II:

TABLE II

| | $GI_{50}$ in Cancer Cells | | | |
|---|---|---|---|---|
| | $GI_{50}$ (nM) | | | |
| Cell lines | Example 1 | Example 7 | Example 34 | Example 36 |
| T-47D | 8 | >10000 | 503 | 111 |
| DLD | 8 | >10000 | 76 | 89 |
| H1299 | 6 | >10000 | 59 | 53 |
| MX-1 | 5 | >10000 | 73 | 73 |
| SW620 | 3 | >10000 | 55 | 70 |

Example 145 Identification of (2-Chloro-quinazolin-4-yl)-(4-methoxy-phenyl)-methyl-amine and Analogs as Inhibitors of Tubulin Polymerization Lyophilized tubulin (Cytoskeleton #ML113, 1 mg, MAP-rich) was assayed for the effect of the test compound on tubulin polymerization as measured by change in fluorescence for 4',6-diamidino-2-phenylindole (DAPI) (Barron, D. M. et al. *Analytical Biochem.*, 2003, 315, 49-56.). 1 μl of serial dilutions of each test compound (from 100×DMSO stock) was added in 96 well plate format and preincubated for 30 minutes with 94 ul of the non-GTP supplemented tubulin supernatant. 5 μl of DAPI/GTP solution was added to initiate polymerization and incubated for 30 minutes at 37° C. Fluorescence was read with excitation 350 nm, emission wavelength 485 nm on a Tecan Spectraflour Plus. Polymerized tubulin (DMSO and with the tubulin stabilizer Taxol® (paclitaxel)) gives a higher DAPI fluorescence as compared to non-polymerized tubulin (vinblastine and colchicine used to determine baseline). The $IC_{50}$ for tubulin inhibition was the concentration found to decrease the fluorescence of DAPI by 50% as calculated with Prism 3.0. The $IC_{50}$ are summarized in Table III.

TABLE III

Inhibition of Tubulin Polymerization Activity

| Example | Caspase activation (EC$_{50}$ nM) | Inhibition of tubulin polymerization (IC$_{50}$, nM) |
|---|---|---|
| 1 | 2 | <500 |
| 2 | 31 | 3000 |
| 6 | 219 | 4000 |
| 7 | >10000 | >50000 |
| 12 | 8 | 2000 |
| 13 | 260 | 6000 |
| 20 | 161 | 3000 |
| 25 | 42 | 2000 |
| 31 | 317 | 10000 |
| 34 | 7 | 1000 |
| 35 | 141 | 4000 |
| 36 | 6 | <1000 |
| 41 | 20 | <1000 |
| 42 | 282 | 5000 |
| 43 | 34 | 2000 |
| 44 | 501 | 10000 |
| 65 | 599 | 10000 |
| 72 | 2 | <1000 |

Thus, (2-chloro-quinazolin-4-yl)-(4-methoxy-phenyl)-methyl-amine (Example 1) and analogs are identified as potent inhibitors of tubulin polymerization and are thus useful in treating diseases and disorders discussed above.

Example 146

Identification of (2-Chloro-quinazolin-4-yl)-(4-methoxy-phenyl)-methyl-amine as a Cytotoxic Compound in Multidrug Resistant Cells Cytotoxicity of compounds in multidrug resistant cells can be determined by administering compounds to cell lines that overexpress the multidrug resistance pump MDR-1 and determining the viability of the cell lines. NCI-ADR/Res and P388/ADR cell lines are known to over-express the multidrug resistance pump MDR-1 (also known as P-glycoprotein-1; Pgp-1); whereas MCF-7 and P388 cell lines do not overexpress the multidrug resistance pumps MDR-1, MRP-1, or BCRP.

NCI-ADR/Res, MCF-7, P388, and P388/ADR cell lines were obtained from American Type Culture Collection (Manassas, Va.) and maintained in RPMI-1640 media supplemented with 10% FCS, 10 units/ml penicillin and streptomycin, 2 mM Glutamax and 1 mM sodium pyruvate (Invitrogen Corporation, Carlsbad, Calif.). For compound testing, cells were plated in 96 well dishes at a concentration of 1.5×10$^4$ cells/well. Cells were allowed to adhere to the plate overnight and then incubated with compounds at final concentrations ranging from 0.13 nM to 10 uM for 72 hours. Cell viability was then assessed using the ATP-lite reagent (Perkin Elmer, Foster City, Calif.). Plates were read on a Wallac Topcount luminescence reader (Perkin Elmer, Foster City, Calif.) and the results graphed in Prism software (Graphpad Software, Inc., San Diego, Calif.). Non-linear regression with variable slope analysis was performed to obtain IC$_{50}$ concentration values.

Example 1 compound, docetaxel, and vinblastine were tested for their ability to kill multidrug resistant cells by administering the compounds to NCI-ADR/Res, MCF-7 cells, P388 and P388/ADR cells and determining the viability of the cells. Example 1 compound maintained nearly equal potency in all four cell lines, whereas known MDR-1 substrates vinblastine and docetaxel showed a loss of potency in the MDR-1 over-expressing cell lines as shown in Table IV below:

TABLE IV

Cytotoxicity of Exa 1 Cmpd in MDR-1 over-expressing cell lines

| | IC$_{50}$ (nM) | | |
|---|---|---|---|
| Cell Line | Exa 1 Cmpd | Vinblastine | Docetaxel |
| MCF-7 | 2.9 | 0.5 | 2 |
| NCI/ADR-RES | 1.3 | 3 | 410 |
| P388 | 1.1 | 2.6 | 7 |
| P388/ADR | 2.7 | 2.8 | 127 |

Thus, (2-chloro-quinazolin-4-yl)-(4-methoxy-phenyl)-methyl-amine is identified as a cytotoxic compound in multidrug resistant cells and is thus useful in treating diseases and disorders discussed above.

Example 147

Propidium Iodide and Annexin V Flow Cytometer-Based Assay to Detect Apoptosis Necrotic versus apoptotic killing of human cell lines by compounds can be determined using dual annexin V-FITC and propidium iodide (PI) staining. Flipping of phosphatidylserine to the outer leaflet of the plasma membrane is a characteristic of all apoptotic cells. AnnexinV is a serum protein that binds to phosphatidylserine in the presence of the divalent cations (calcium). PI is a DNA stain that is excluded from live cells and is used to discriminate between cells with intact or damaged plasma membranes.

Cells are plated at varying densities in 6 well plates and treated with varying concentrations of compounds for 18-72 hours. Cells are grown in RPMI-1640 media supplemented with 10% FCS. DMSO concentrations do not exceed 0.1% v:v in any assay. All cells in the wells are harvested and rinsed 1× with cold Hanks buffered saline solution (HBSS) containing calcium and magnesium (Invitrogen, Carlsbad Calif.). Carefully aspirate supernatant after the wash and resuspend in 100 μl Annexin V-FITC (Annexin V/PI Apoptosis Detection Kit; R & D Systems TA4638; Minneapolis, Minn.) in binding buffer (10 mM HEPES pH 7.4, 150 mM NaCl, 5 mM KCl, 1 mM MgCl$_2$, 1.8 mM CaCl$_2$ and 2% bovine serum albumin w:v). Incubate in dark for 15 minutes on ice. Prior to analyzing samples, the volume is adjusted to 500 μl with 1× Binding Buffer and 25 μl PI is added per sample. Staining can be quantified on a flow cytometer (Becton-Dickenson, Franklin Lake, N.J.).

Example 148

Injection Formulation

| Excipients | Amount |
|---|---|
| Active Compound | 5 mg |
| PEG-400 | 5 grams |
| TPGS | 10 grams |
| Benzyl alcohol | 0.5 gram |

-continued

Injection Formulation

| Excipients | Amount |
|---|---|
| Ethanol | 2 grams |
| D5W | Add to make 50 mL |

An injection formulation of a compound selected from Formula IV (the "Active Compound") can be prepared according to the following method. 5 mg of the Active Compound is dissolved into a mixture of the d-α-tocopheryl polyethylene glycol 1000 succinate (TPGS), PEG-400, ethanol, and benzyl alcohol. D5W is added to make a total volume of 50 mL and the solution is mixed. The resulting solution is filtered through a 0.2 μm disposable filter unit and is stored at 25° C. Solutions of varying strengths and volumes are prepared by altering the ratio of Active Compound in the mixture or changing the total amount of the solution.

Example 149

Tablet Formulation

| Active Compound | 100.0 mg |
|---|---|
| Lactose | 100.0 mg |
| Corn Starch | 50.0 mg |
| Hydrogenated Vegetable Oil | 10.0 mg |
| Polyvinylpyrrolidone | 10.0 mg |
| | 270.0 mg |

A formulation of tablets of a compound selected from Formulae I-VIb (e.g. Example 1 compound) (the "Active Compound") can be prepared according to the following method. 100 mg of Active Compound is mixed with 100 mg lactose. A suitable amount of water for drying is added and the mixture is dried. The mixture is then blended with 50 mg of corn starch, 10 mg hydrogenated vegetable oil, and 10 mg polyvinylpyrrolidinone. The resulting granules are compressed into tablets. Tablets of varying strengths are prepared by altering the ratio of Active Compound in the mixture or changing the total weight of the tablet.

Example 150

Capsule Formulation

| Active Compound | 100.0 mg |
|---|---|
| Microcrystalline Cellulose | 200.0 mg |
| Corn Starch | 100.0 mg |
| Magnesium Stearate | 400.0 mg |
| | 800.0 mg |

A formulation of capsules containing 100.0 mg of a compound selected from Formulae I-VIb (e.g. Example 1 compound) (the "Active Compound") can be prepared according to the following method. 100 mg of Active Compound is mixed with 200 mg of microcrystalline cellulose and 100 mg of corn starch. 400 mg of magnesium stearate is then blended into the mixture and the resulting blend is encapsulated into a gelatin capsule. Doses of varying strengths can be prepared by altering the ratio of the Active Compound to pharmaceutically acceptable carriers or changing the size of the capsule.

Example 151

Identification of (2-Chloro-quinazolin-4-yl)-(4-methoxy-phenyl)-methyl-amine as an Inhibitor of Topoisomerase The ability of compounds to inhibit Topoisomerase II activity in relaxing supercoiled DNA can be determined by adding compounds to DNA samples and measuring the formation of topoisomers. The addition of Topoisomerase II to DNA samples results in the formation of topoisomers, which migrate faster than open circular DNA and slower than supercoiled DNA substrate when run on a gel. Ethidium Bromide, a known intercalator, and etoposide (VP16), a known topoisomerase II inhibitor, are used as controls.

Assay reagents were obtained from TopoGEN, Inc. (Columbus, Ohio). Samples were prepared by combining 10 μl of D/W, 2 μl of 10×TOPO II assay buffer, and 1 μl (0.25 μg) pRYG DNA. 5 μl of (2-Chloro-quinazolin-4-yl)-(4-methoxy-phenyl)-methyl-amine (Example 1 Compound), Ethidium Bromide, or VP16 were added to samples at varying concentrations. 2 μl of TOPO II (4 units in 20 μl reaction) was added to the samples and the samples were incubated at 37° C. in a water bath for 50 minutes. 2 μl of 10% SDS was added and 0. Proteinase K (500 μg/ml) was added and the samples were incubated again at 37° C. in a water bath for 50 minutes. Half of the reaction was loaded on a 1% gel without ethidium bromide and run in 1×TAE buffer at 20 volts/cm for 2 hours. The gel was stained with 0.5 μg/ml Ethidium Bromide for 10 seconds and destained in D/W for 30 seconds. The resulting gel image is shown in FIG. 1.

Inspection of the amount of supercoiled DNA present in the sample with 100 μM of Example 1 Compound indicates that inhibition of DNA relaxation is substantial. The results are consistent with topoisomerase II inhibition as well as with an effect of the compound not on topoisomerase II, but rather on the DNA itself, such as intercalation of the compound into the DNA substrate. In order to distinguish between direct inhibition of topoisomerase II activity and intercalation, the effect of Example 1 Compound is determined on topoisomerase I-mediated relaxation of supercoiled DNA.

Samples were prepared by combining 10 μl of D/W, 2 μl of 10×TOPO II assay buffer, and 1 μl (0.25 μg) Form I DNA. 5 μl of (2-Chloro-quinazolin-4-yl)-(4-methoxy-phenyl)-methyl-amine (Example 1 Compound), Ethidium Bromide, or VP16 were added to samples at varying concentrations. 1 μl of TOPO I (5 units in 20 μl reaction) was added to the samples and the samples were incubated at 37° C. in a water bath for 50 minutes. 2 μl of 10% SDS was added and 0. Proteinase K (500 μg/ml) was added and the samples were incubated again at 37° C. in a water bath for 50 minutes. Half of the reaction was loaded on a 1% gel without ethidium bromide and run in 1×TAE buffer at 20 volts/cm for 2 hours. The gel was stained with 0.5 μg/ml Ethidium Bromide for 10 seconds and destained in D/W for 30 seconds. The resulting gel image is shown in FIG. 2.

Figure 2:
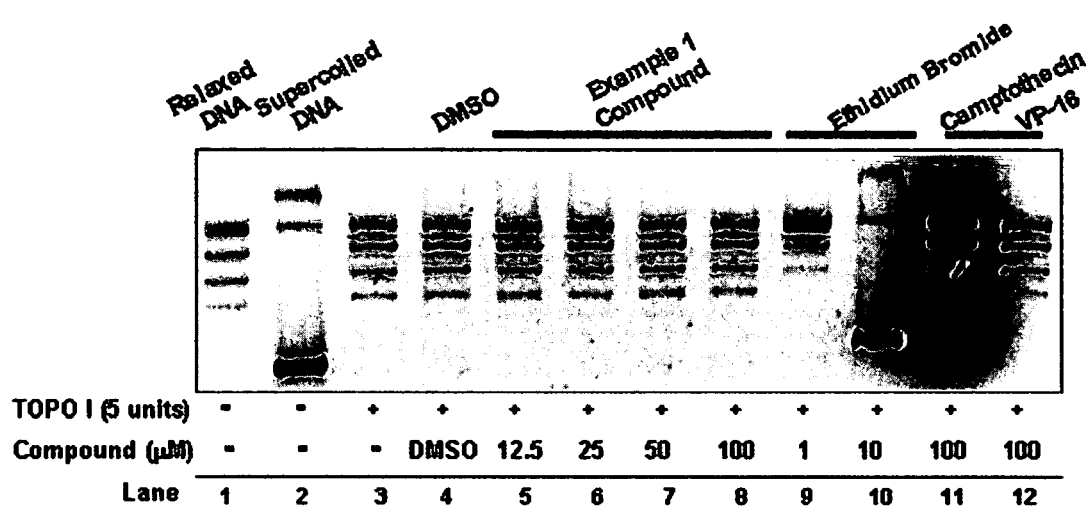
FIG. 2 shows the results of a Topoisomere I activity assay testing Example 1 compound.

As shown in FIG. 2, the known intercalator, Ethidium Bromide, completely eliminated topoisomerase I-dependent relaxation of supercoiled DNA, just as it eliminated topoisomerase II-dependent relaxation of supercoiled DNA (see FIG. 1). In contrast, Example 1 Compound and the known topoisomerase II inhibitor, VP-16, have no apparent effect on topoisomerase I activity.

Example 152

Identification of Radiolabeled (4-Azido-phenyl)-(2-methyl-quinazolin-4-yl)-methyl-amine as an Inhibitor of Topoisomerase 30 Units (15 ul) Human Type II Topoisomerase (p170 Form) (from TopoGEN, Inc., Columbus, Ohio) was incubated with 50 nM radiolabeled Example 102 compound for 60 minutes at room temperature.

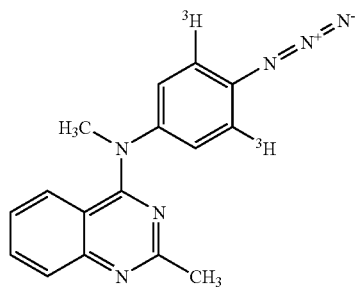

Figure 3:
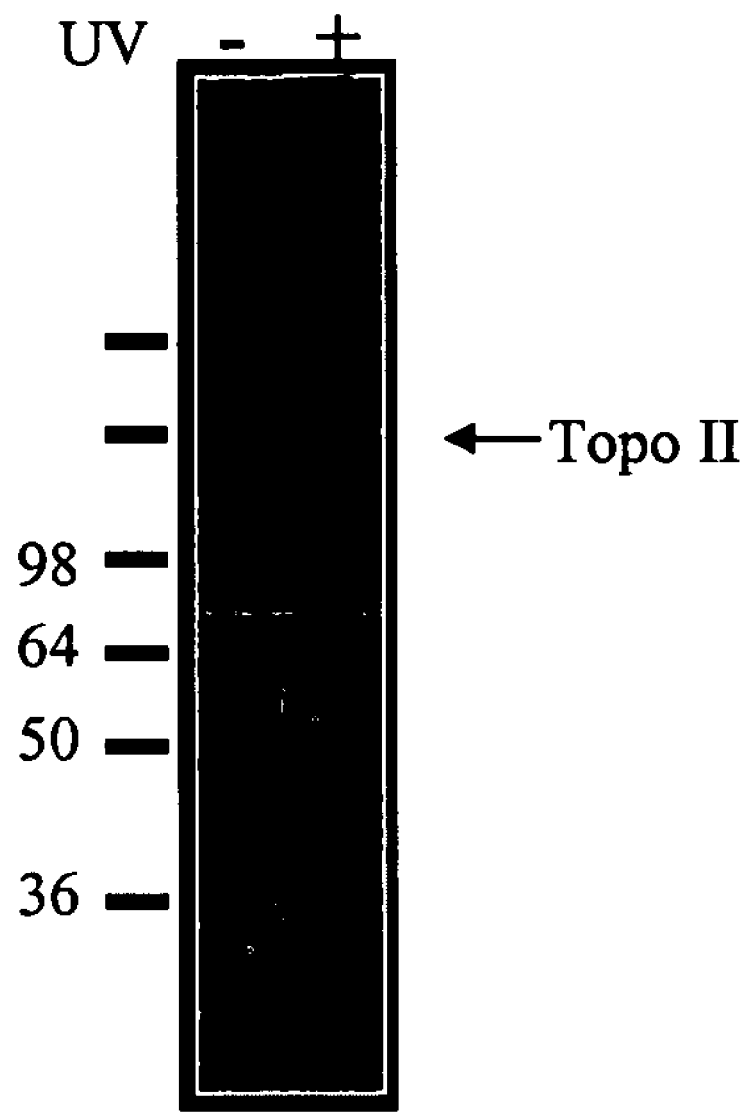
FIG. 3 depicts the binding of radiolabeled Example 102 compound to Topoisomerase II.

Radiolabeled Example 102 Compound (Radiolabeled Example 102 compound stock is 16.67 uM, 60 Ci/mmol, 1 Ci/ml American Radiolabeled Chemicals, Inc., St. Louis, Mo. Samples were either UV irradiated (+) with a short wavelength UV Source (254 nm) for 10 minutes at a distance of 3.5 cm or not irradiated (−). 8 ul of 5× sample buffer (150 mM Tris, pH 6.8, 50% glycerol, 1% SDS, 50 mM dithiothreitol, 62 mg/ml bromophenol blue) was added to the samples and boiled for 5 minutes. The entire sample was then loaded onto a 6% Tris-Glycine SDS-gel (10 well, 1.5 mm thickness) (Invitrogen, Carlsbad, Calif.). The gel was stained with 1% Coomassie Brilliant Blue in 40% methanol, 7.5% acetic acid for 2 hours then de-stained in several changes of de-stainer (40% methanol, 7.5% acetic acid). The gel was then incubated in Amplify (Amersham, Piscataway, N.J.) for 30 minutes at room temperature and then dried down on Whatman filter paper at 80° C. for 2 hours on a gel dryer. The dried gel was put on Hyperfilm (Amersham) in a film cassette and placed at −80° C. for 5-7 days. The resulting gel image is shown in FIG. 3. These results indicate that the compound binds sufficiently well to Topoisomerase II to crosslink to the enzyme when photoactivated.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound according to Formula VIb:

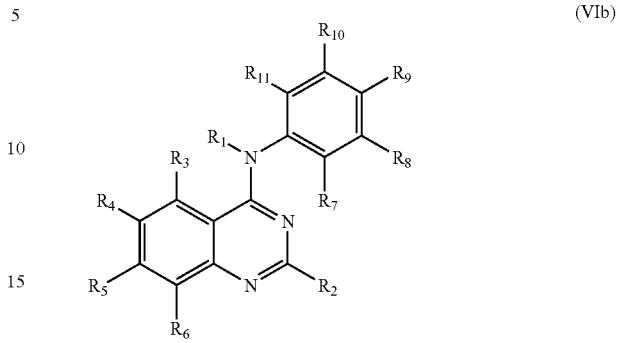

(VIb)

or pharmaceutically acceptable salts thereof, wherein:

$R_1$ is methyl or ethyl;

$R_5$ is H or F;

$R_2$ is halo, $N_3$, $NH_2$, $C_{1-6}$ alkyl, -thio-$C_{1-6}$ alkyl, $C_{2-8}$ alkynyl, $C_{1-6}$ alkoxy, halo-$C_{1-6}$ alkyl, hydroxy-$C_{1-6}$ alkyl, —C(O)O—$C_{1-6}$ alkyl, —N($R^a$)($R^b$), N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl, wherein when $R^a$ and/or $R^b$ are $C_{1-6}$ alkyl, then $R^a$ and $R^b$ are independently optionally substituted with $C_{2-8}$ alkenyl or —N($R^{aa}$)($R^{bb}$), wherein $R^{aa}$ and $R^{bb}$ are independently H, $C_{1-6}$ alkyl or $R^{aa}$ and $R^{bb}$ together with the nitrogen atom to which they are both linked form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl;

$R_3$, is H, halo, $C_{1-6}$ alkyl, or $C_{1-6}$ alkoxy;

$R_4$, is H, halo, $C_{1-6}$ alkyl, or $C_{1-6}$ alkoxy, $N_3$, nitro, or —N($R^a$)($R^b$), wherein $R^a$ and $R^b$ are independently H or $C_{1-6}$ alkyl;

$R_6$, is H, halo, or $C_{1-6}$ alkyl;

$R_7$, $R_8$, $R_{10}$, and $R_{11}$ are H, halo, or $C_{1-6}$ alkoxy; and $R_9$ is H, halo, $N_3$, OH, nitro, $NH_2$, $C_{1-6}$ alkyl, $C_{1-6}$ alkoxy optionally substituted with 1-3 halo substituents, thio-$C_{1-6}$ alkyl, —C(O)O—$C_{1-6}$ alkyl, —N($R^a$)($R^b$), wherein $R^a$ and $R^b$ are independently H or $C_{1-6}$ alkyl wherein optionally $R_9$ and $R_{10}$ together form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl;

provided that when $R_9$ is H then $R_8$ and $R_{10}$ are not both H or one H and the other halo.

2. The compound of claim 1, wherein when $R_9$ is H then at least one of $R_8$ and $R_{10}$ is not H or halo.

3. The compound of claim 1, wherein: $R_1$ is methyl or ethyl; $R_2$ it is methyl, ethyl, Cl, F, fluoromethyl, $C_{1-3}$ hydroxyalkyl, $NH_2$, $NH_2OH$, $NHCH_2CH_2OH$, $NHCH_3$, $N(CH_3)_2$, $N_3$, morpholino, $OCH_3$, $OC_2H_5$, or $SCH_3$; $R_3$ is H, $CH_3$, OCH₃, F, or Cl; R₄ is H, CH₃, NH₂, N₃, F, or Cl; R₅ is H; R₆ is H, CH₃, F, or Cl; R₇ and R₁₁ are independently H, F, or OCH₃; R₈ and R₁₀ are independently H, F, Cl, or OCH₃; and R₉ is selected from the group consisting of H, OH, N₃, Cl, C$_{1-3}$ alkyl, or —OR$_{9a}$ where R$_{9a}$ is C$_{1-3}$ alkyl or C$_{1-3}$ haloalkyl, —N(R$_{2b}$)(R$_{2c}$) wherein R$_{2b}$ and R$_{2c}$ are independently C$_{1-3}$ alkyl, or —COOR$_{9b}$ where R$_{9b}$ is C$_{1-3}$ alkyl, and optionally R₁₀ and R₉ together form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl; provided that when R₉ is H, at least one of R₈ and R₁₀ is OCH₃, and when R₉ is C$_{1-3}$ alkyl or C$_{1-3}$ haloalkyl or Cl, R₂ is Cl or methyl or ethyl.

4. The compound of claim 1, wherein R₉ is H; OH; Cl; N₃; C$_{1-3}$ alkyl; —OR$_{9a}$ where R$_{9a}$ is C$_{1-4}$ alkyl or C$_{1-3}$ haloalkyl; —NH(R$^a$) or —N(R$^a$)(R$^b$) where R$^a$ and R$^b$ are independently C$_{1-3}$ alkyl; or —COOR$_{9b}$ where R$_{9b}$ is C$_{1-3}$ alkyl; and optionally R₉ and R₁₀ together form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl.

5. The compound of claim 1, wherein R₂ is halo; N₃; C$_{1-6}$ alkyl optionally substituted with OH or halo; —XR$_{2a}$ wherein X is S or O, and R$_{2a}$ is C$_{1-6}$ alkyl; —CO₂R$^d$ wherein R$^d$ is C$_{1-3}$ alkyl; or —N(R$^a$)(R$^b$) wherein R$^a$ and R$^b$ are independently H, OH (R$^a$ and R$^b$ are not both OH), C$_{1-6}$ alkyl, C$_{1-6}$ hydroxyalkyl, or C$_{1-6}$ alkyl that is optionally substituted with —N(R$^e$)(R$^f$) wherein R$^e$ and R$^f$ are independently H, or C$_{1-3}$ alkyl, and wherein optionally R$^a$ and R$^b$ together with the nitrogen atom to which they are both linked may form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl.

6. The compound of claim 1, wherein R₂ is halo; C$_{1-3}$ alkyl optionally substituted with OH or halo; —XR$_{2a}$ wherein X is S or O and R$_{2a}$ is C$_{1-3}$ alkyl; or —N(R$^a$)(R$^b$) wherein R$^a$ and R$^b$ are independently H, OH (R$^a$ and R$^b$ are not both OH), C$_{1-3}$ alkyl, C$_{2-3}$ hydroxyalkyl.

7. The compound of claim 1, wherein R₂ is methyl, ethyl, Cl, F, fluoromethyl, C$_{1-3}$ hydroxyalkyl, NH₂, NHOH, —NHCH₂CH₂OH, NHCH₃, N(CH₃)₂, N₃, morpholino, OCH₃, OC₂H₅ or SCH₃.

8. The compound of claim 1, wherein R₂ is methyl, Cl, —CH₂OH, —NH₂, —NHCH₃, —NHCH₂CH₂OH, —OCH₃, —SCH₃, or —CH₂F.

9. The compound of claim 1, wherein when R₉ is H, then R₈ or R₁₀ or both are C$_{1-3}$ alkoxy.

10. The compound of claim 1, wherein when R₉ is C$_{1-6}$ alkyl or C$_{1-6}$ haloalkyl, then R₂ is methyl, ethyl, Cl, F, fluoromethyl, C$_{1-3}$ hydroxyalkyl, NH₂, NHOH, —NHCH₂CH₂OH, NHCH₃, N(CH₃)₂, N₃, morpholino, OCH₃, OC₂H₅, or SCH₃.

11. The compound of claim 1, wherein R₉ is N₃; —OR$_{9a}$, wherein R$_{9a}$ is C$_{1-3}$ alkyl optionally substituted with 1-3 F; —N(R$^a$)(R$^b$) where R$^a$ and R$^b$ are independently C$_{1-3}$ alkyl; or —COOR$_{9b}$ where R$_{9b}$ is C$_{1-3}$ alkyl.

12. The compound of claim 1, wherein R₉ is —OCH₃, —OC₂H₅, —N(CH₃)₂, —CO₂CH₃, —OCHF₂, or N₃.

13. The compound of claim 1, wherein R₁ is CH₃; R₂ is methyl, ethyl, Cl, F, fluoromethyl, CH₂OH, NH₂, NHCH₃, N(CH₃)₂, —NHCH₂CH₂OH, OCH₃, or SCH₃; R₃ is H, CH₃, OCH₃, F, or Cl; R₄ is H, CH₃, NH₂, F, or Cl; R₅ is H; R₆ is H, F or Cl; R₇ and R₁₁ are independently H, F, or OCH₃; R₈ and R₁₀ are independently H, F, Cl, or OCH₃; and R₉ is selected from the group consisting of —OR₁₂ where R₁₂ is methyl, ethyl, fluoromethyl or fluoroethyl, —NHCH₃, N(CH₃)₂, N₃, and —COOR₁₃ where R₁₃ is methyl or ethyl.

14. The compound of claim 1, wherein R₁ is CH₃; R₂ is methyl, Cl, —CH₂OH, —NH₂, —NHCH₃, —NHCH₂CH₂OH, —OCH₃, —SCH₃, or —CH₂F; R₃ is H, —CH₃, OCH₃, or Cl; R₄ is H, CH₃, or NH₂; R₅ is H; R₆ is H, or CH₃; R₇ and R₁₁ are independently H, or F; R₈ and R₁₀ are independently H, or F or OCH₃; and R₉ is —OCH₃ or —OC₂H₅, —N(CH₃)₂, —CO₂CH₃, —OCHF₂, or N₃.

15. The compound of claim 1, wherein R₁ is CH₃; R₂ is Cl, methyl or CH₂F; R₃ is H, CH₃, F or Cl; R₄, R₅ and R₆ are H; R₇, R₈, R₁₀ and R₁₁ are independently H or F; and R₉ is —OCH₃ or —N(CH₃)₂.

16. A compound selected from the group consisting of:
N²-Hydroxyl-N⁴-(4-methoxy-phenyl)-N⁴-methyl-quinazoline-2,4-diamine;
N²-(2-Hydroxylethyl)-N⁴-(4-methoxy-phenyl)-N⁴-methyl-quinazoline-2,4-diamine;
4-(4-methoxy-phenyl)-N⁴-methyl-quinazoline-2,4-diamine;
N²-(3,7-Dimethyl-octa-2,6-dienyl)-N⁴-(4-methoxy-phenyl)-N⁴-methyl-quinazoline-2,4-diamine;
4-(4-Methoxy-phenyl)-N⁴-methyl-N²-(2-morpholin-4-yl-ethyl)-quinazoline-2,4-diamine;
(4-Methoxy-phenyl)-methyl-(2-morpholin-4-yl-quinazolin-4-yl)-amine;
N²-[2-(1H-Imidazol-4-yl)-ethyl]-N⁴-(4-methoxy-phenyl)-N⁴-methyl-quinazoline-2,4-diamine;
N²-(3-Dimethylamino-propyl)-N⁴-(4-methoxy-phenyl)-N⁴-methyl-quinazoline-2,4-diamine;
5-Chloro-N²,N⁴-bis-(4-methoxy-phenyl)-N²,N⁴-dimethyl-quinazoline-2,4-diamine;
6-Chloro-N²,N⁴-bis-(4-methoxy-phenyl)-N²,N⁴-dimethyl-quinazoline-2,4-diamine;
(2-Dimethylamino-quinazolin-4-yl)-(4-methoxy-phenyl)-methyl-amine; and
(2-Methylamino-quinazolin-4-yl)-(4-methoxy-phenyl)-methyl-amine;
or a pharmaceutically acceptable salt thereof.

17. A compound selected from the group consisting of:
(2-Fluoromethyl-quinazolin-4-yl)-(4-methoxy-phenyl)-methyl-amine;
(4-Methoxy-phenyl)-methyl-(2-methyl-quinazolin-4-yl)-amine;
(2-Chloromethyl-quinazolin-4-yl)-(4-methoxy-phenyl)-methyl-amine;
(2-Ethyl-quinazolin-4-yl)-(4-methoxy-phenyl)-methyl-amine;
Ethyl 4-(N-(4-methoxy-phenyl)-N-methylamino)quinazoline-2-carboxylate;
(2-hydroxymethyl-quinazolin-4-yl)-(4-methoxy-phenyl)-methyl-amine;
(2-Dimethylaminomethyl-quinazolin-4-yl)-(4-methoxy-phenyl)-methyl-amine;
(4-Difluoromethoxy-phenyl)-(2-methyl-quinazolin-4-yl)-methyl-amine;
(3-Fluoro-4-methoxy-phenyl)-(2-methyl-quinazolin-4-yl)-methyl-amine;
(4-Isopropoxy-phenyl)-(2-methyl-quinazolin-4-yl)-methyl-amine;
(4-Ethyl-phenyl)-(2-methyl-quinazolin-4-yl)-methyl-amine;
(5-Methoxy-2-methyl-quinazolin-4-yl)-(4-methoxy-phenyl)-methyl-amine;
(4-Hydroxy-phenyl)-(2-methyl-quinazolin-4-yl)-methyl-amine;

(2-Fluoro-4-methoxy-phenyl)-(2-methyl-quinazolin-4-yl)-methyl-amine;
(2-Methyl-quinazolin-4-yl)-(4-nitro-phenyl)-methyl-amine;
(4-Amino-phenyl)-(2-methyl-quinazolin-4-yl)-methyl-amine;
(4-Azido-phenyl)-(2-methyl-quinazolin-4-yl)-methyl-amine;
(4-Amino-2,6-dibromo-phenyl)-(2-methyl-quinazolin-4-yl)-methyl-amine;
(4-Amino-2-bromo-phenyl)-(2-methyl-quinazolin-4-yl)-methyl-amine;
(4-Dimethylamino-phenyl)-(2-methyl-quinazolin-4-yl)-methyl-amine;
(4-Ethoxy-phenyl)-(2-methyl-quinazolin-4-yl)-methyl-amine;
(4-Methoxy-phenyl-2,3,5,6-$d_4$)-(2-methyl-quinazolin-4-yl)-methyl-amine;
(4-Methoxy-phenyl)-(2-methyl-6-nitro-quinazolin-4-yl)-methyl-amine;
(6-Amino-2-methyl-quinazolin-4-yl)-(4-methoxy-phenyl)-methyl-amine;
(6-Azido-2-methyl-quinazolin-4-yl)-(4-methoxy-phenyl)-methyl-amine;
(2,4,6-Trimethoxy-phenyl)-(2-methyl-quinazolin-4-yl)-methyl-amine; and
(4-Fluoro-phenyl)-(2-methyl-quinazolin-4-yl)-methyl-amine;
or a pharmaceutically acceptable salt thereof.

18. A compound selected from the group consisting of:
(2-Chloro-quinazolin-4-yl)-(4-methoxy-phenyl)-methyl-amine;
(2-Chloro-quinazolin-4-yl)-(4-methyl-phenyl)-methyl-amine;
(2-Chloro-quinazolin-4-yl)-(4-chloro-phenyl)-methyl-amine;
(2-Chloro-quinazolin-4-yl)-(4-nitro-phenyl)-methyl-amine;
(2-Chloro-quinazolin-4-yl)-(4-trifluoromethoxy-phenyl)-methyl-amine;
(2-Chloro-quinazolin-4-yl)-(2,3-dimethoxy-phenyl)-methyl-amine;
(2-Chloro-quinazolin-4-yl)-ethyl-(4-methoxy-phenyl)-amine;
(2-Chloro-quinazolin-4-yl)-(2,4-dimethoxy-phenyl)-methyl-amine;
(2-Chloro-quinazolin-4-yl)-(2,5-dimethoxy-phenyl)-methyl-amine;
(2-Chloro-quinazolin-4-yl)-(3-methoxy-phenyl)-methyl-amine;
(2-Chloro-quinazolin-4-yl)-(2-methoxy-phenyl)-methyl-amine;
(2-Chloro-quinazolin-4-yl)-(4-methylcarboxyphenyl)-methyl-amine;
(2-Chloro-quinazolin-4-yl)-(4-hydroxyphenyl)-methylamine;
(2-Chloro-6-methyl-quinazolin-4-yl)-(4-methoxy-phenyl)-methyl-amine;
(2-Chloro-5-methyl-quinazolin-4-yl)-(4-methoxy-phenyl)-methyl-amine;
(2-Chloro-8-methyl-quinazolin-4-yl)-(4-methoxy-phenyl)-methyl-amine;
(2,6-Dichloro-quinazolin-4-yl)-(4-methoxy-phenyl)-methyl-amine;
(2-Chloro-quinazolin-4-yl)-(3,4-methylenedioxyphenyl)-methyl-amine;
(2-Chloro-quinazolin-4-yl)-(3,4-dimethoxy-phenyl)-methyl-amine;
(2-Chloro-quinazolin-4-yl)-(4-propoxy-phenyl)-methyl-amine;
(2-Chloro-quinazolin-4-yl)-(4-ethoxy-phenyl)-methyl-amine;
(2,8-Dichloro-quinazolin-4-yl)-(4-methoxy-phenyl)-methyl-amine; and
(2,5-Dichloro-quinazolin-4-yl)-(4-methoxy-phenyl)-methyl-amine;
or a pharmaceutically acceptable salt thereof.

19. The compound (2-methoxy-quinazolin-4-yl)-(4-methoxyphenyl)-methylamine, or a pharmaceutically acceptable salt thereof.

20. The compound (2-methylthio-quinazolin-4-yl)-(4-methoxy-phenyl)-methyl-amine, or a pharmaceutically acceptable salt thereof.

21. The compound (2-azido-quinazolin-4-yl)-(4-methoxyphenyl)-methyl-amine, or a pharmaceutically acceptable salt thereof.

22. The compound (4-methoxy-phenyl)-methyl-(2-methyl-quinazolin-4-yl)-amine hydrochloride.

23. The compound (4-Dimethylamino-phenyl)-(2-methyl-quinazolin-4-yl)-methyl-amine, or a pharmaceutically acceptable salt thereof.

24. A compound according to Formula VIb:

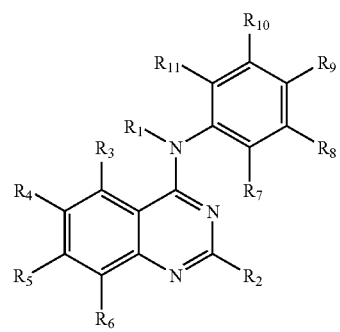

(VIb)

or pharmaceutically salts thereof, wherein:

$R_1$ is methyl or ethyl;

$R_5$ is H or F;

$R_2$ is H, halo, $N_3$, $NH_2$, $C_{1-6}$ alkyl, $C_{2-8}$ alkynyl, $C_{1-6}$ alkoxy, halo-$C_{1-6}$ alkyl, hydroxy-$C_{1-6}$ alkyl, —C(O)O—$C_{1-6}$ alkyl, N($R^a$)($R^b$)—$C_{1-6}$ alkyl-, wherein $R^a$ and $R^b$ are independently H, OH ($R^a$ and $R^b$ are not both OH), $C_{2-6}$ hydroxyalkyl, or $C_{1-6}$ alkyl, or $R^a$ and $R^b$ together with the nitrogen atom to which they are both linked form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl, wherein when $R^a$ and/or $R^b$ are $C_{1-6}$ alkyl, then $R^a$ and $R^b$ are independently optionally substituted with $C_{2-8}$ alkenyl or —N($R^{aa}$)($R^{bb}$), wherein $R^{aa}$ and $R^{bb}$ are independently H, $C_{1-6}$ alkyl or $R^{aa}$ and $R^{bb}$ together with the nitrogen atom to which they are both linked form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl;

$R_3$, is H, halo, $C_{1-6}$ alkyl, or $C_{1-6}$ alkoxy;

$R_4$, is H, halo, $C_{1-6}$ alkyl, or $C_{1-6}$ alkoxy, $N_3$, nitro, or —N($R^a$)($R^b$), wherein $R^a$ and $R^b$ are independently H or $C_{1-6}$ alkyl;

$R_6$ is H, halo, or $C_{1-6}$ alkyl;

$R_7$, $R_8$, $R_{10}$, $R_{11}$ are H, halo, or $C_{1-6}$ alkoxy; and provided that $R_9$ is H; OH; Cl; $N_3$; $C_{1-3}$ alkyl; $C_{1-3}$ haloalkyl; —$OR_{9a}$ where $R_{9a}$ is $C_{1-4}$ alkyl or $C_{1-3}$ haloalkyl; —NH($R^a$) or —N($R^a$)($R^b$) where $R^a$ and $R^b$ are independently $C_{1-3}$ alkyl; or —$COOR_{9b}$ where $R_{9b}$ is $C_{1-3}$ alkyl; and optionally $R_9$ and $R_{10}$ together form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl; and provided that when $R_9$ is H then $R_8$ and $R_{10}$ are not both H or one H and the other halo.

25. The compound of claim 24, wherein when $R_9$ is H then at least one of $R_8$ and $R_{10}$ is not H or halo.

26. The compound of claim 24, wherein $R_1$ is methyl or ethyl; $R_2$ is H, methyl, ethyl, Cl, F, fluoromethyl, $C_{1-3}$ hydroxyalkyl, $NH_2$, $NH_2OH$, $NHCH_2CH_2OH$, $NHCH_3$, $N(CH_3)_2$, $N_3$, morpholino, $OCH_3$, $OC_2H_5$, or $SCH_3$; $R_3$ is H, $CH_3$, $OCH_3$, F, or Cl; $R_4$ is H, $CH_3$, $NH_2$, $N_3$, F, or Cl; $R_5$ is H; $R_6$ is H, $CH_3$, F, or Cl; $R_7$ and $R_{11}$ are independently H, F, or $OCH_3$; $R_8$ and $R_{10}$ are independently H, F, Cl, or $OCH_3$; and $R_9$ is selected from the group consisting of H, OH, $N_3$, Cl, $C_{1-3}$ alkyl, $C_{1-3}$ haloalkyl, or —$OR_{9a}$ where $R_{9a}$ is $C_{1-3}$ alkyl or $C_{1-3}$ haloalkyl, —N($R_{2b}$)($R_{2c}$) wherein $R_{2b}$ and $R_{2c}$ are independently $C_{1-3}$ alkyl, or —$COOR_{9b}$ where $R_{9b}$ is $C_{1-3}$ alkyl, and optionally $R_{10}$ and $R_9$ together form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl; provided that when $R_9$ is H, at least one of $R_8$ and $R_{10}$ is $OCH_3$, and when $R_9$ is $C_{1-3}$ alkyl or Cl, $R_2$ is Cl or methyl or ethyl.

27. The compound of claim 24, wherein $R_2$ is H; halo; $N_3$; $C_{1-6}$ alkyl optionally substituted with OH or halo; —$XR_{2a}$ wherein X is S or O, and $R_{2a}$ is $C_{1-6}$ alkyl; —$CO_2R^d$ wherein $R^d$ is $C_{1-3}$ alkyl; or —N($R^a$)($R^b$) wherein $R^a$ and $R^b$ are independently H, OH ($R^a$ and $R^b$ are not both OH), $C_{1-6}$ alkyl, $C_{1-6}$ hydroxyalkyl, or $C_{1-6}$ alkyl that is optionally substituted with —N($R^e$)($R^f$) wherein $R^e$ and $R^f$ are independently H or $C_{1-3}$ alkyl, and wherein optionally $R^a$ and $R^b$ together with the nitrogen atom to which they are both linked may form a 5 or 6-membered heterocycle selected from the group consisting of: tetrahydrofuranyl, pyranyl, piperidinyl, piperazinyl, pyrrolidinyl, imidazolidinyl, imidazolinyl, morpholinyl, pyrazolidinyl, pyrazolinyl, tetronoyl, and tetramoyl.

28. The compound of claim 24, wherein $R_2$ is H; halo; $C_{1-3}$ alkyl optionally substituted with OH or halo; —$XR_{2a}$ wherein X is S or O and $R_{2a}$ is $C_{1-3}$ alkyl; or —N($R^a$)($R^b$) wherein $R^a$ and $R^b$ are independently H, OH ($R^a$ and $R^b$ are not both OH), $C_{1-3}$ alkyl, $C_{2-3}$ hydroxyalkyl.

29. The compound of claim 24, wherein $R_2$ is H, methyl, ethyl, Cl, F, fluoromethyl, $C_{1-3}$ hydroxyalkyl, $NH_2$, NHOH, —$NHCH_2CH_2OH$, $NHCH_3$, $N(CH_3)_2$, $N_3$, morpholino, $OCH_3$, $OC_2H_5$ or $SCH_3$.

30. The compound of claim 24, wherein $R_2$ is H, methyl, Cl, —$CH_2OH$, —$NH_2$, —$NHCH_3$, —$NHCH_2CH_2OH$, —$OCH_3$, —$SCH_3$, or —$CH_2F$.

31. The compound of claim 24, wherein when $R_9$ is H, then $R_8$ or $R_{10}$ or both are $C_{1-3}$ alkoxy.

32. The compound of claim 24, wherein $R_9$ is $N_3$; —$OR_{9a}$, wherein $R_{9a}$ is $C_{1-3}$ alkyl optionally substituted with 1-3 F; —N($R^a$)($R^b$) where $R^a$ and $R^b$ are independently $C_{1-3}$ alkyl; or —$COOR_{9b}$ where $R_{9b}$ is $C_{1-3}$ alkyl.

33. The compound of claim 24, wherein $R_9$ is —$OCH_3$, —$OC_2H_5$, —$N(CH_3)_2$, —$CO_2CH_3$, —$OCHF_2$, or $N_3$.

34. The compound of claim 24, wherein $R_1$ is $CH_3$; $R_2$ is H, methyl, ethyl, Cl, F, fluoromethyl, $CH_2OH$, $NH_2$, $NHCH_3$, $N(CH_3)_2$, —$NHCH_2CH_2OH$, $OCH_3$, or $SCH_3$; $R_3$ is H, $CH_3$, $OCH_3$, F, or Cl; $R_4$ is H, $CH_3$, $NH_2$, F, or Cl; $R_5$ is H; $R_6$ is H, $CH_3$, F, or Cl; $R_7$ and $R_{11}$ are independently H, F, or $OCH_3$; $R_8$ and $R_{10}$ are independently H, F, Cl, or $OCH_3$; and $R_9$ is selected from the group consisting of —$OR_{12}$ where $R_{12}$ is methyl, ethyl, fluoromethyl or fluoroethyl, —$NHCH_3$, $N(CH_3)_2$, $N_3$, and —$COOR_{13}$ where $R_{13}$ is methyl or ethyl.

35. The compound of claim 24, wherein $R_1$ is $CH_3$; $R_2$ is H, methyl, Cl, —$CH_2OH$, —$NH_2$, —$NHCH_3$, —$NHCH_2CH_2OH$, —$OCH_3$, —$SCH_3$, or —$CH_2F$; $R_3$ is H, —$CH_3$, $OCH_3$, or Cl; $R_4$ is H, $CH_3$, or $NH_2$; $R_5$ is H; $R_6$ is H, or $CH_3$; $R_7$ and $R_{11}$ are independently H, or F; $R_8$ and $R_{10}$ are independently H, or F or $OCH_3$; and $R_9$ is —$OCH_3$ or —$OC_2H_5$, —$N(CH_3)_2$, —$CO_2CH_3$, —$OCHF_2$, or $N_3$.

36. The compound of claim 24, wherein $R_1$ is $CH_3$; $R_2$ is Cl, methyl or $CH_2F$; $R_3$ is H, $CH_3$, F or Cl; $R_4$, $R_5$ and $R_6$ are H; $R_7$, $R_8$, $R_{10}$ and $R_{11}$ are independently H or F; and $R_9$ is —$OCH_3$ or —$N(CH_3)_2$.

37. A compound selected from the group consisting of:

(4-Methoxy-phenyl)-methyl-quinazolin-4-yl-amine; and (4-Methyl-phenyl)-methyl-quinazolin-4-yl-amine;

or a pharmaceutically acceptable salt thereof.

38. A pharmaceutical composition comprising a pharmaceutically acceptable carrier and an effective amount of a compound according to claim 1.

39. A pharmaceutical composition comprising a pharmaceutically acceptable carrier and an effective amount of a compound according to claim 24.

40. The compound (4-methoxy-phenyl)-methyl-(2-methyl-quinazolin-4-yl)-amine, or a pharmaceutically acceptable salt thereof.

41. A method of inhibiting tubulin in a mammal in need of such treatment, said method comprises treating the mammal with an effective amount of a compound according to claim 1.

42. A method of inhibiting tubulin in a mammal in need of such treatment, said method comprises treating the mammal with an effective amount of a compound according to claim 16.

43. A method of inhibiting tubulin in a mammal in need of such treatment, said method comprises treating the mammal with an effective amount of a compound according to claim 17.

44. A method of inhibiting tubulin in a mammal in need of such treatment, said method comprises treating the mammal with an effective amount of a compound according to claim 18.

45. A method of inhibiting tubulin in a mammal in need of such treatment, said method comprises treating the mammal with an effective amount of a compound according to claim 22.

46. A method of inhibiting tubulin in a mammal in need of such treatment, said method comprises treating the mammal with an effective amount of a compound according to claim 24.

47. A method of inhibiting tubulin in a mammal in need of such treatment, said method comprises treating the mammal with an effective amount of a compound according to claim 37.

48. A method of inhibiting tubulin in a mammal in need of such treatment, said method comprises treating the mammal with an effective amount of a compound according to claim 40.

* * * * *

UNITED STATES PATENT AND TRADEMARK OFFICE
CERTIFICATE OF CORRECTION

PATENT NO. : 7,618,975 B2  Page 1 of 1
APPLICATION NO. : 10/885903
DATED : November 17, 2009
INVENTOR(S) : Sui Xiong Cai et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 865 days.

should read (*) Notice: Subject to any disclaimer, the term of this patent is extended or adjusted under 35 U.S.C. 154(b) by 1,345 days.

In column 194, line 22, in claim 1, delete "$C_{2-8}$" and insert -- $C_{2-6}$ --, therefor.

In column 194, line 65, in claim 3, delete "it is" and insert -- is --, therefor.

In column 195, line 65 and 66, in claim 13, delete "$R_6$ is H, F or Cl;" and insert -- $R_6$ is H, $CH_3$, F, or Cl; --, therefor.

In column 196, line 20, in claim 16, delete "4" and insert -- $N^4$ --, therefor.

In column 196, line 24, in claim 16, delete "4" and insert -- $N^4$ --, therefor.

In column 198, line 48, in claim 24, delete "$C_{2-8}$" and insert -- $C_{2-6}$ --, therefor.

Signed and Sealed this

Twenty-fourth Day of August, 2010

David J. Kappos
*Director of the United States Patent and Trademark Office*